US011242563B2

(12) United States Patent
Hicks et al.

(10) Patent No.: US 11,242,563 B2
(45) Date of Patent: Feb. 8, 2022

(54) ANALYSIS OF AUTISM SPECTRUM DISORDER

(71) Applicants: QUADRANT BIOSCIENCES INC., Syracuse, NY (US); THE RESEARCH FOUNDATION FOR THE STATE UNIVERSITY OF NEW YORK, Syracuse, NY (US); PENN STATE RESEARCH FOUNDATION, University Park, PA (US)

(72) Inventors: Steven D. Hicks, Hershey, PA (US); Frank A. Middleton, Fayetteville, NY (US); Richard Uhlig, Ithaca, NY (US); Alexander Rajan, Syracuse, NY (US)

(73) Assignees: QUADRANT BIOSCIENCES INC., Syracuse, NY (US); THE RESEARCH FOUNDATION FOR THE STATE UNIVERSITY OF NEW YORK, Syracuse, NY (US); PENN STATE RESEARCH FOUNDATION, University Park, PA (US)

( * ) Notice: Subject to any disclaimer, the term of this patent is extended or adjusted under 35 U.S.C. 154(b) by 158 days.

(21) Appl. No.: 16/496,158

(22) PCT Filed: Mar. 22, 2018

(86) PCT No.: PCT/US2018/023821
§ 371 (c)(1),
(2) Date: Sep. 20, 2019

(87) PCT Pub. No.: WO2018/175759
PCT Pub. Date: Sep. 27, 2018

(65) Prior Publication Data
US 2020/0157625 A1    May 21, 2020

Related U.S. Application Data

(60) Provisional application No. 62/622,341, filed on Jan. 26, 2018, provisional application No. 62/590,446, filed on Nov. 24, 2017, provisional application No. 62/554,154, filed on Sep. 5, 2017, provisional application No. 62/502,124, filed on May 5, 2017, provisional application No. 62/484,332, filed on Apr. 11, 2017, provisional application No. 62/484,357, filed on Apr. 11, 2017, provisional application No. 62/474,339, filed on Mar. 21, 2017.

(51) Int. Cl.
| *C12Q 1/68* | (2018.01) |
| *C12Q 1/6883* | (2018.01) |
| *C12Q 1/689* | (2018.01) |
| *A61K 45/06* | (2006.01) |

(52) U.S. Cl.
CPC .......... *C12Q 1/6883* (2013.01); *C12Q 1/689* (2013.01); *A61K 45/06* (2013.01); *C12Q 2600/112* (2013.01); *C12Q 2600/178* (2013.01)

(58) Field of Classification Search
None
See application file for complete search history.

(56) References Cited

U.S. PATENT DOCUMENTS

| 2009/0209621 A1 | 8/2009 | Mendell et al. |
| 2013/0012403 A1 | 1/2013 | Hu |

FOREIGN PATENT DOCUMENTS

| WO | WO 2011/079299 A1 | 6/2011 | |
| WO | WO 2016/118662 A1 | 7/2016 | |
| WO | WO-2016118662 A1 * | 7/2016 | .......... C12Q 1/6883 |
| WO | WO 2017/019440 A1 | 2/2017 | |

OTHER PUBLICATIONS

Hicks et al. (BMC Pediatrics (2016) 16:52, 11 pages) (Year: 2016).*
International Search Report and Written Opinion dated Aug. 1, 2018 in PCT/US2018/23821 filed Mar. 22, 2018.
Schwarzenbach, H. et al., "Data Normalization Strategies for MicroRNA Quantification," Clinical Chemistry, vol. 61, No. 11, 2015, pp. 1333-1342.
Heegaard, N. H. H., et al., "Diurnal Variations of Human Circulating Cell-Free Micro-RNA," PLOS ONE, vol. 11, No. 8, Aug. 5, 2016, pp. 1-15.
Partial Supplementary European Search Report dated Dec. 8, 2020 in European Patent Application No. 18770882.1, citing documents AM and AV-AY therein, 18 pages.
He et al., "Bioinformatic Analysis of Potential microRNAs in Ischemic Stroke", Journal of Stroke and Cerebrovascular Diseases, vol. 25, No. 7, 2016, pp. 1753-1759, XP029600203, ISSN: 1052-3057, 7 total pages, DOI: 10.1016/J.JSTROKECEREBROVASDIS.2016.03.023.
N. N. Affymetrix, "Affymetrix miRNA array 3.0 comprises probes for hsa-miR-4705", Affymetrix NeAffx database, Jul. 2016, pp. 1, XP055749943, 1 total page, Retrieved from internet: URL: https://www.affymetrix.com/analysis/netaffx/mirna_probe_set.affx?pk=miRNA-3_0:hsa-miR-4705_st, retrieved on Nov. 12, 2020.

(Continued)

*Primary Examiner* — Juliet C Switzer
(74) *Attorney, Agent, or Firm* — Oblon, McClelland, Maier & Neustadt, L.L.P.

(57) ABSTRACT

This application provides methods to differentiate between subjects with autism spectrum disorder (ASD) and typically developing (TD) or developmentally delayed (DD) subjects using miRNA and/or microbiome levels detected in saliva samples and patient information. The method can be used to monitor the progress of ASD and guide its treatment. RNA-seq, qPCR, or other methods determine counts and abundance of miRNA or microbiomes. MicroRNA and/or microbiome sequencing data are refined by normalization to expression levels or abundance of time-invariant miRNAs and/or microbial RNAs to control for time of sample collection or to compensate for circadian fluctuations in these levels. Multivariate logistic regression and nonlinear classification techniques are further used to select a panel of miRNAs and microbiomes that accurately differentiate between subjects with ASD, DD, and TD in subjects with an unknown ASD status. These panels of miRNAs and microbiomes may be developed into a RNA assay kit.

19 Claims, 46 Drawing Sheets

(56) References Cited

OTHER PUBLICATIONS

Cheng et al., "microRNA modulation of circadian dock period and entrainment", Neuron, Jun. 2007, pp. 813-829, XP055544073, ISSN: 0896-6273, DOI: 10.1016/j.neuron.2007.05.017, 27 total pages.
Thaiss et al., "Microbiota Diurnal Rhythmicity Programs Host Transcriptome Oscillations", Cell, Elsevier, vol. 167, No. 6, Dec. 2016, pp. 1495-1510.e1-e5, XP029830921, ISSN: 0092-8674, 29 total pages, DOI: 10.1016/J.CELL.2016.11.003.
Extended European Search Report dated Mar. 12, 2021 in European Patent Application No. 18770882.1, 17 pages.
Vichithra Rasangi Batuwita Liyanage, "Role of RNA Methylation and Non-Coding RNAs in Pathobiology of Autism Spectrum Disorders" Biomedical Sciences, vol. 2, No. 4, 2016, pp. 24-33.

\* cited by examiner

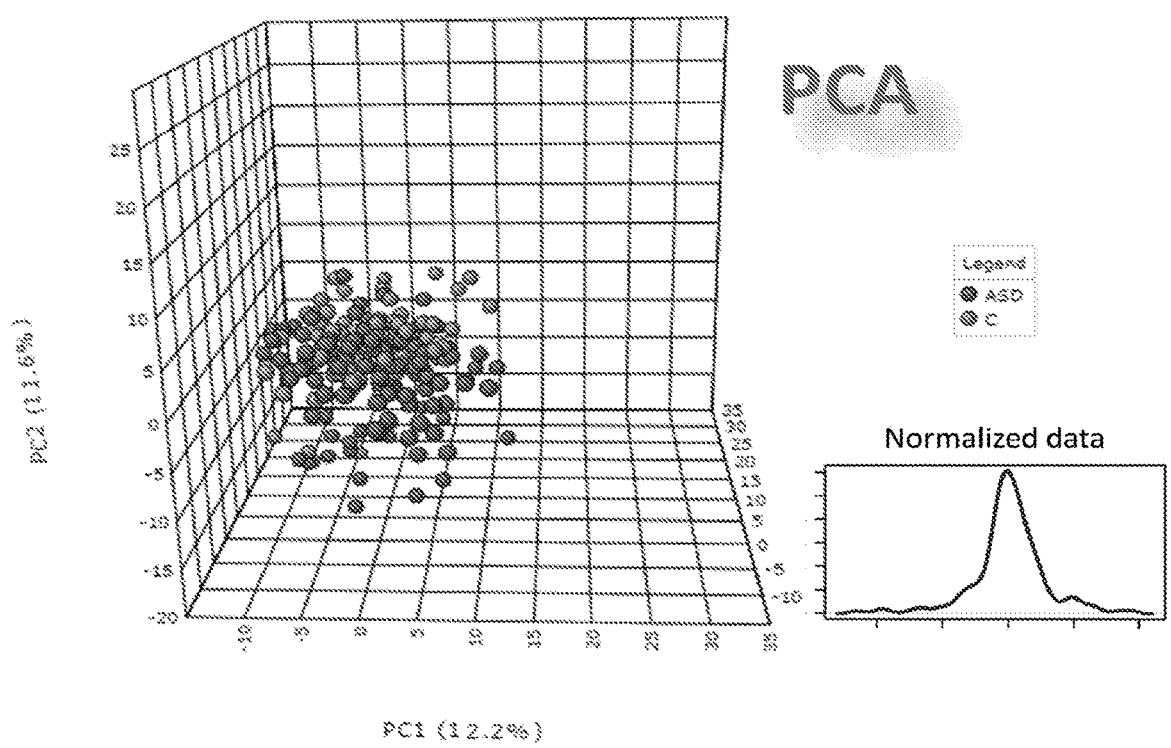
Fig. 1A                    Fig. 1B

Fig. 3A 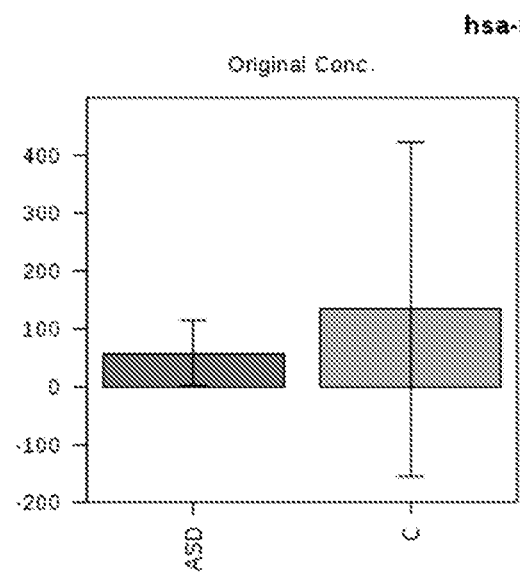 Fig. 3B 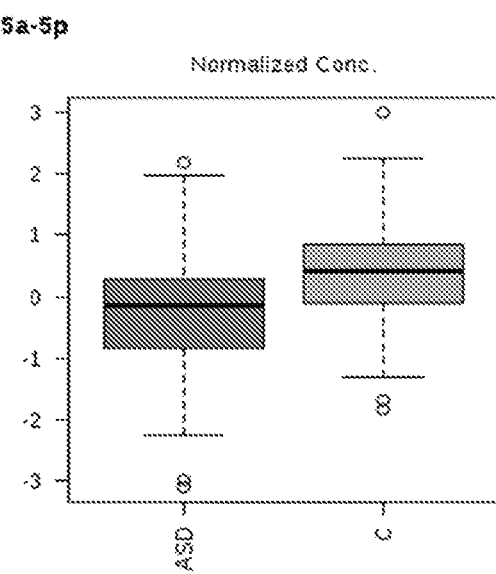
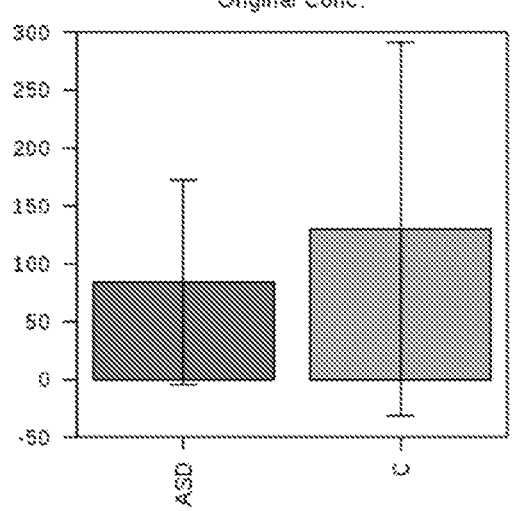 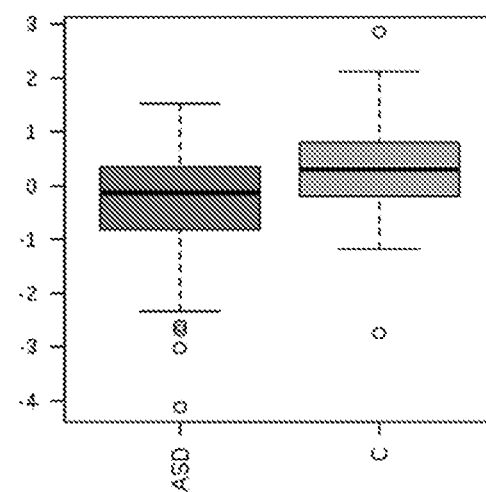
Fig. 3C Fig. 3D

Fig. 5A
Fig. 5B
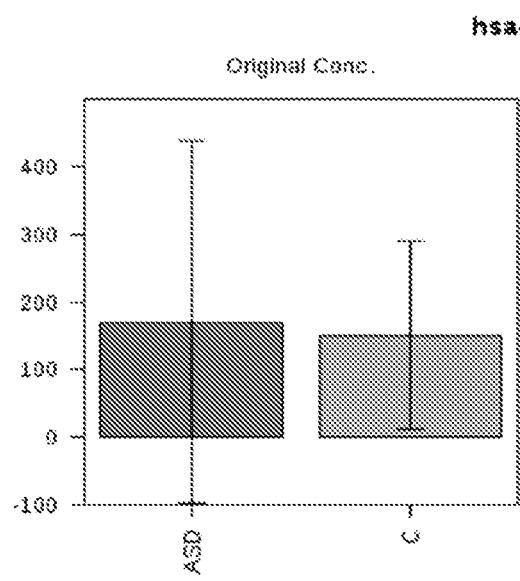
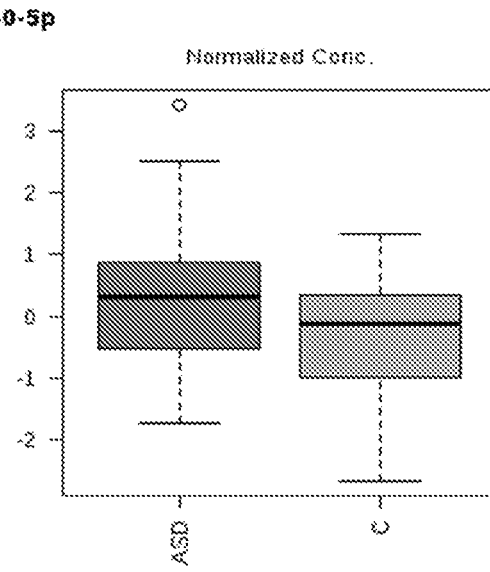
Fig. 5C
Fig. 5D
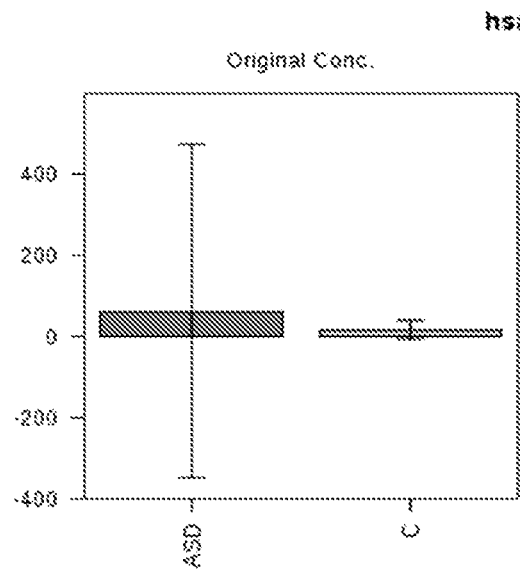
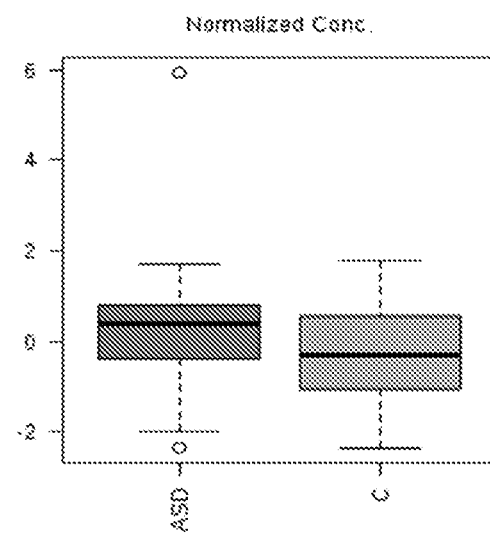

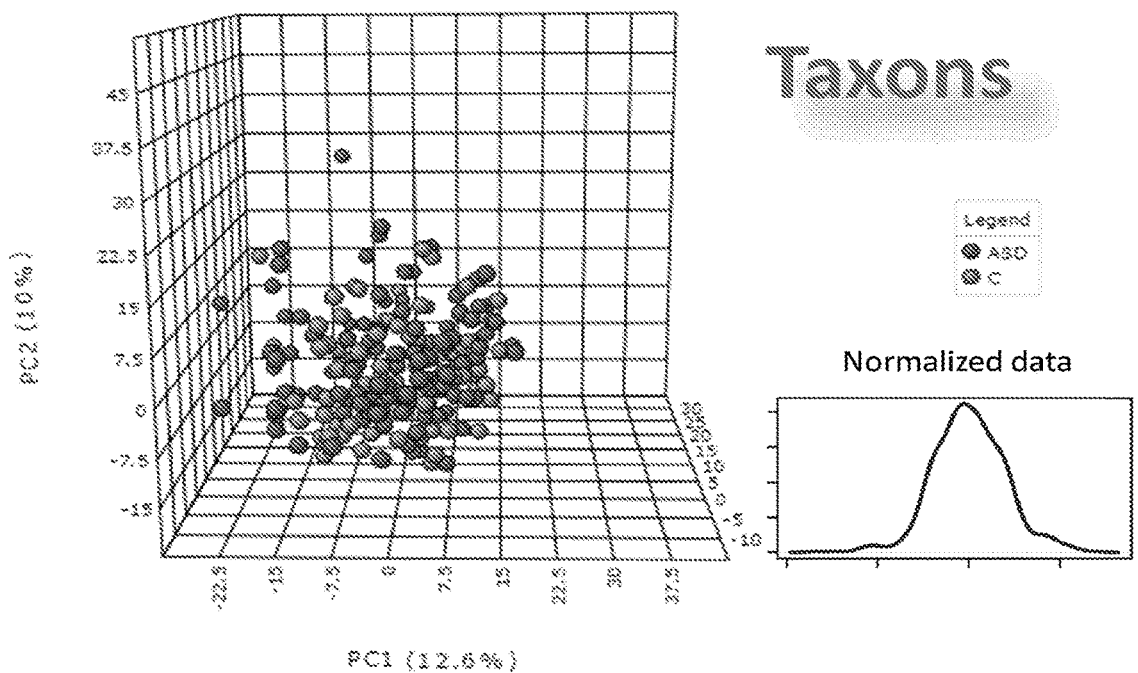
Fig. 6A  Fig. 6B
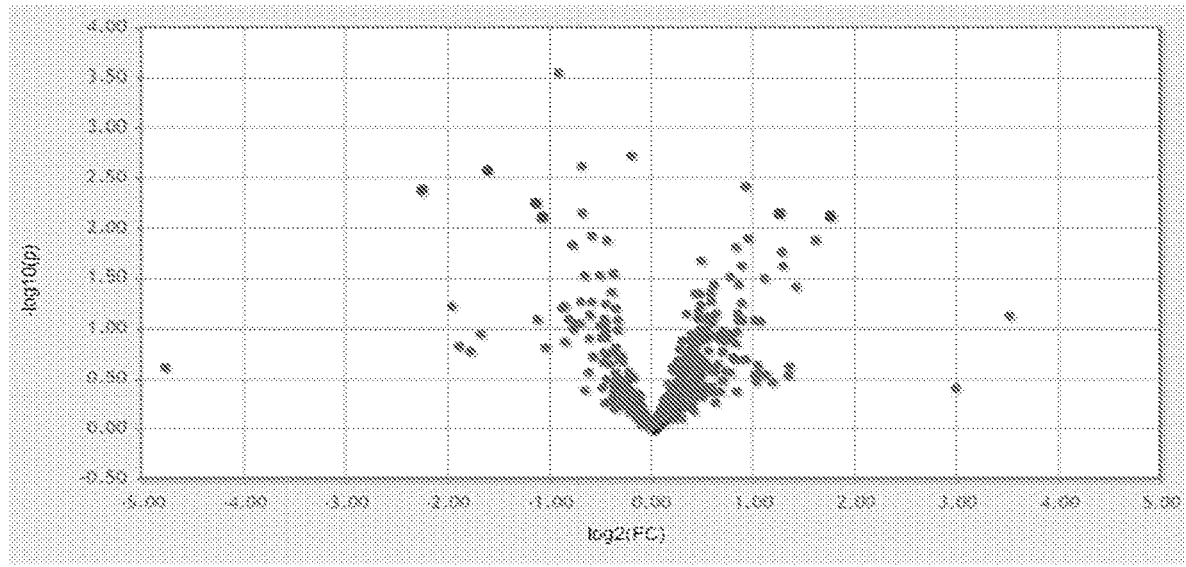
Fig. 6C

| Performance of Logistic Regression Model | | | |
|---|---|---|---|
| | AUC | Sensitivity | Specificity |
| Training/Discovery | 0.823 (0.804 – 0.842) | 0.841 (0.814 – 0.867) | 0.672 (0.643 – 0.700) |
| 10-fold Cross-Validation | 0.766 (0.700 – 0.832) | 0.783 (0.783 – 0.872) | 0.664 (0.577 – 0.751) |

| Performance of Logistic Regression Model: | | | |
|---|---|---|---|
| | AUC | Sensitivity | Specificity |
| Training/Discovery | 0.815 (0.797 – 0.834) | 0.828 (0.802 – 0.854) | 0.652 (0.623 – 0.680) |
| 10-fold Cross-Validation | 0.759 (0.694 – 0.823) | 0.742 (0.742 – 0.833) | 0.667 (0.582 – 0.751) |

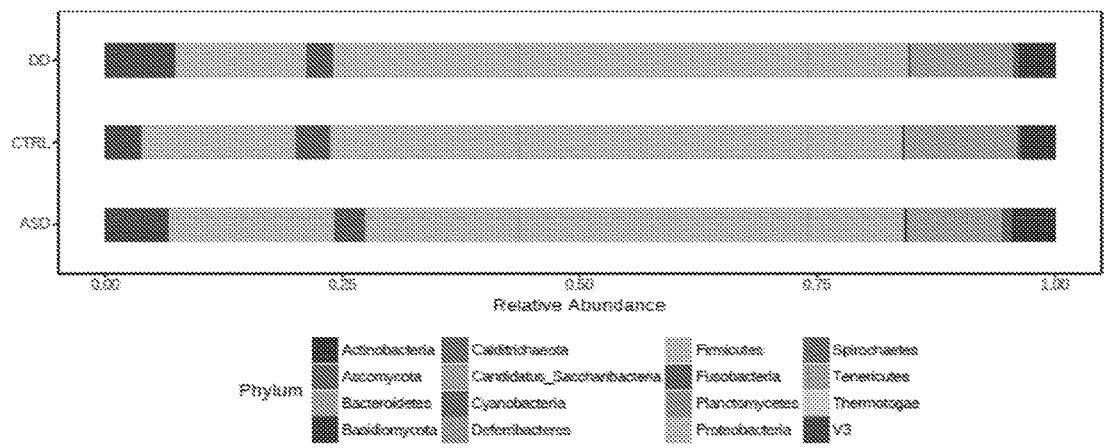
Fig. 31
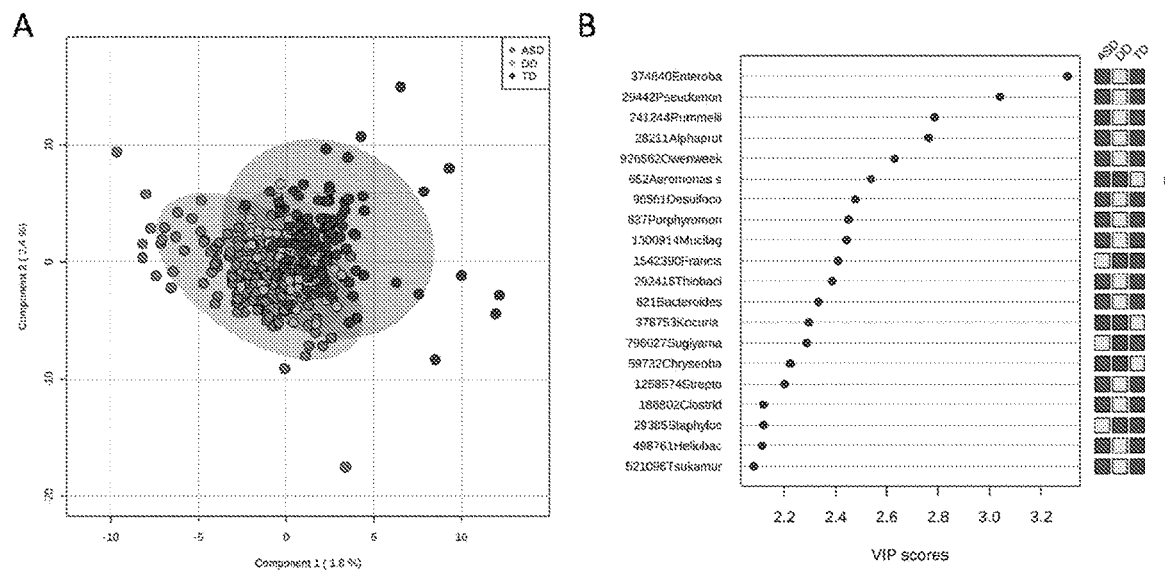
Fig. 32A                     Fig. 32B

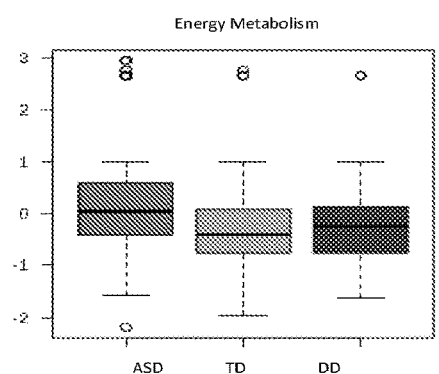
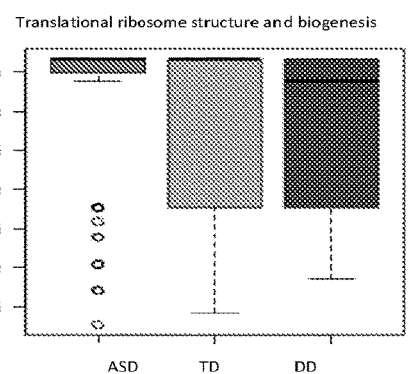
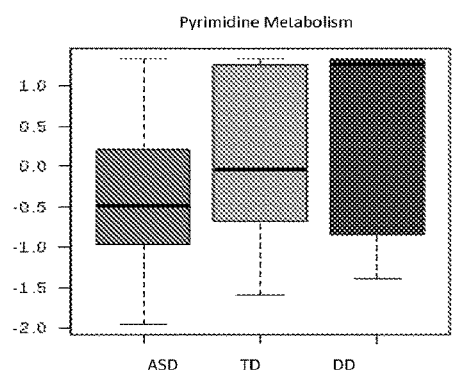
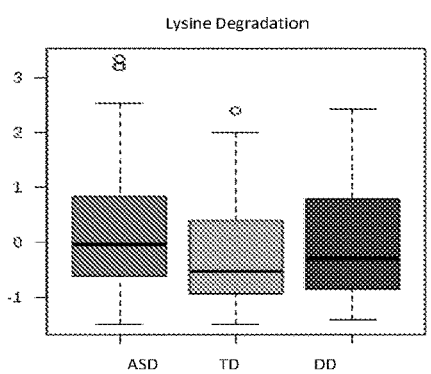
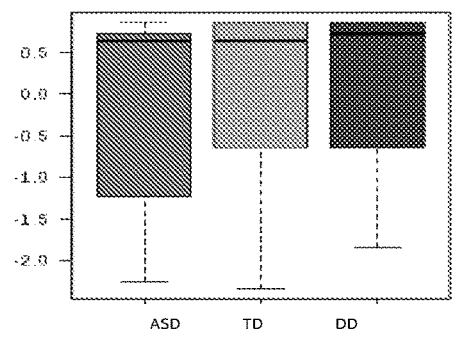
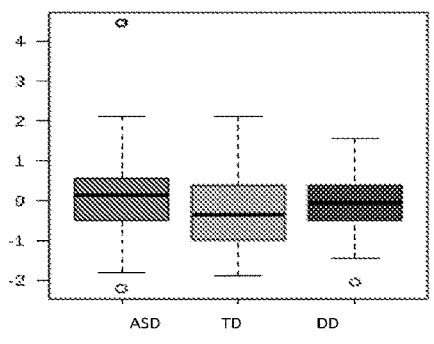
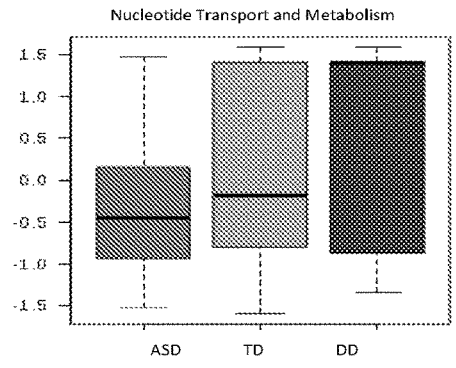
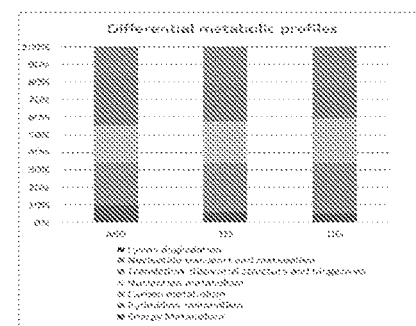
Fig. 34A-H

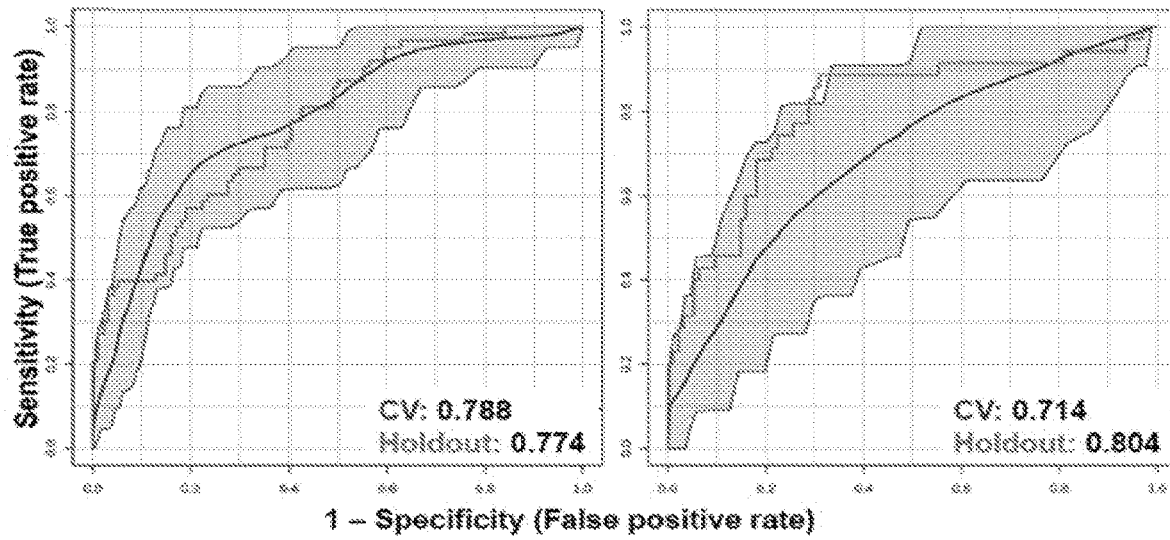
Fig. 37A     Fig. 37B
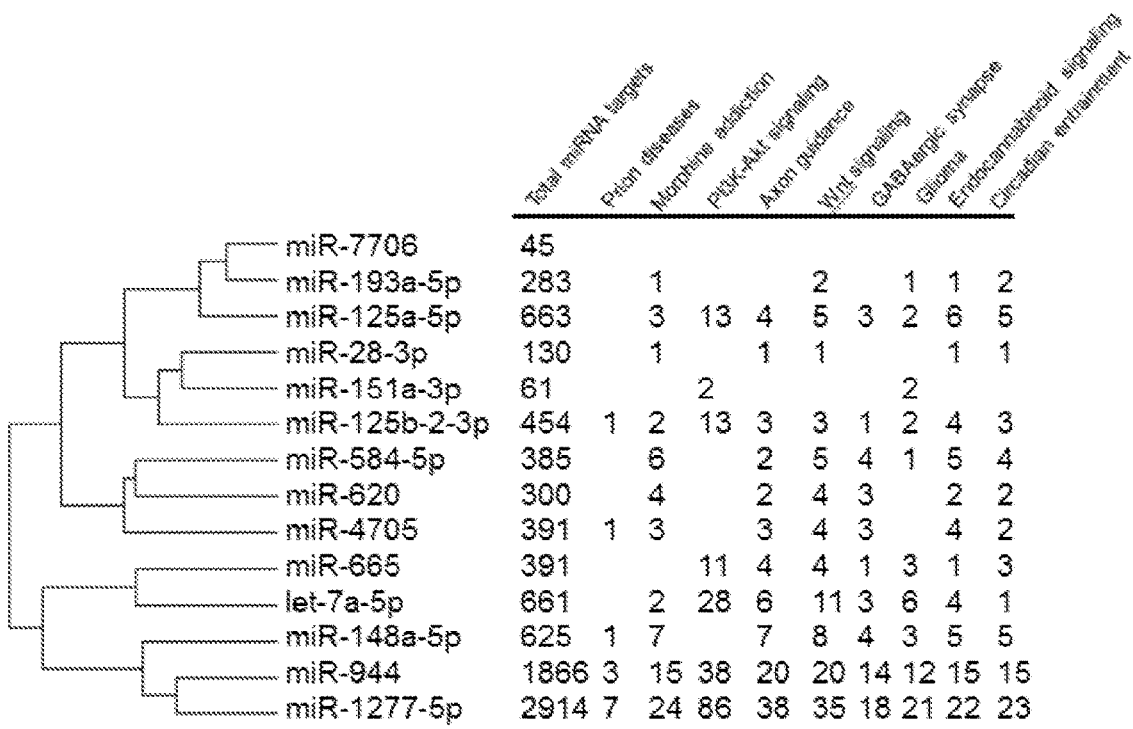
Fig. 38

| | hsa-miR-106b-3p | hsa-miR-128-3p | hsa-miR-130a-3p | hsa-miR-15a-5p | hsa-miR-192-5p | hsa-miR-199a-3p | hsa-miR-199b-3p | hsa-miR-203a-3p |
|---|---|---|---|---|---|---|---|---|
| hsa-miR-106b-3p | | 0.83 | 0.58 | 0.52 | 0.79 | 0.71 | 0.71 | 0.70 |
| hsa-miR-128-3p | 0.83 | | 0.75 | 0.61 | 0.81 | 0.70 | 0.70 | 0.83 |
| hsa-miR-130a-3p | 0.58 | 0.75 | | 0.58 | 0.63 | 0.51 | 0.51 | 0.65 |
| hsa-miR-15a-5p | 0.52 | 0.61 | 0.58 | | 0.73 | 0.72 | 0.72 | 0.68 |
| hsa-miR-192-5p | 0.79 | 0.81 | 0.63 | 0.73 | | 0.90 | 0.90 | 0.83 |
| hsa-miR-199a-3p | 0.71 | 0.70 | 0.51 | 0.72 | 0.90 | | | 0.76 |
| hsa-miR-199b-3p | 0.71 | 0.70 | 0.51 | 0.72 | 0.90 | | | 0.76 |
| hsa-miR-203a-3p | 0.70 | 0.83 | 0.65 | 0.68 | 0.83 | 0.76 | 0.76 | |
| hsa-miR-221-3p | 0.82 | 0.73 | 0.64 | 0.81 | 0.76 | 0.70 | 0.70 | 0.67 |
| hsa-miR-26a-5p | 0.67 | 0.87 | 0.73 | 0.45 | 0.58 | 0.48 | 0.48 | 0.57 |
| hsa-miR-26b-5p | 0.63 | 0.77 | 0.80 | 0.61 | 0.60 | 0.49 | 0.49 | 0.74 |
| hsa-miR-3074-5p | 0.71 | 0.84 | 0.64 | 0.60 | 0.72 | 0.56 | 0.56 | 0.77 |
| hsa-miR-30e-3p | 0.74 | 0.69 | 0.52 | 0.71 | 0.84 | 0.90 | 0.90 | 0.75 |
| hsa-miR-320a | 0.53 | 0.74 | 0.88 | 0.52 | 0.58 | 0.45 | 0.45 | 0.75 |
| hsa-miR-345-5p | 0.76 | 0.83 | 0.76 | 0.76 | 0.89 | 0.80 | 0.80 | 0.86 |
| hsa-miR-375 | 0.85 | 0.66 | 0.57 | 0.48 | 0.81 | 0.54 | 0.54 | 0.68 |
| hsa-miR-423-3p | 0.71 | 0.65 | 0.63 | 0.53 | 0.69 | 0.55 | 0.55 | 0.67 |
| hsa-miR-92a-3p | 0.86 | 0.85 | 0.76 | 0.81 | 0.86 | 0.75 | 0.75 | 0.67 |
| hsa-miR-93-5p | 0.94 | 0.79 | 0.52 | 0.64 | 0.85 | 0.69 | 0.69 | 0.73 |
| Mason-Pfizer monkey virus | 0.73 | 0.86 | 0.80 | 0.54 | 0.68 | 0.64 | 0.64 | 0.77 |
| Falconid herpesvirus 1 | 0.69 | 0.87 | 0.74 | 0.73 | 0.77 | 0.68 | 0.68 | 0.82 |
| Fusobacterium nucleatum subsp. Nucleatum | -0.29 | -0.60 | -0.55 | -0.52 | -0.50 | -0.45 | -0.45 | -0.54 |
| Campylobacter hominis | 0.07 | -0.21 | -0.38 | -0.33 | -0.18 | -0.18 | -0.18 | 0.29 |
| Macrococcus caseolyticus | 0.43 | 0.37 | -0.03 | 0.33 | 0.43 | 0.46 | 0.46 | -0.10 |
| Fusobacterium nucleatum subsp. Vincentii | -0.19 | -0.55 | -0.68 | -0.45 | -0.29 | -0.29 | -0.29 | -0.55 |
| Veillonella parvula | -0.53 | -0.57 | -0.51 | -0.44 | -0.45 | -0.44 | -0.44 | -0.55 |
| Prevotella melaninogenica | 0.61 | 0.73 | 0.74 | 0.54 | 0.54 | 0.51 | 0.51 | 0.68 |
| Haemophilus | 0.46 | 0.64 | 0.69 | 0.60 | 0.57 | 0.53 | 0.53 | 0.62 |
| Prevotella | 0.35 | 0.47 | 0.62 | 0.48 | 0.30 | -0.27 | -0.27 | 0.58 |
| Haemophilus parainfluenzae | 0.51 | 0.35 | 0.34 | 0.53 | 0.63 | 0.48 | 0.48 | 0.39 |

ANALYSIS OF AUTISM SPECTRUM DISORDER

CROSS-REFERENCE TO RELATED APPLICATIONS

This application claims priority Provisional Patent Application Nos. 62/474,339, filed Mar. 21, 2017; 62/484,357, filed Apr. 11, 2017; 62/484,332, filed Apr. 11, 2017; 62/502,124, filed May 5, 2017; 62/554,154, filed Sep. 5, 2017; 62/590,446, filed Nov. 24, 2017; and 62/622,341, filed Jan. 26, 2018, the contents of which are incorporated herein by reference in their entirety.

BACKGROUND

Field of the Disclosure

The present invention relates to the field of evaluation of autism and autism spectrum disorder (ASD) in young children involving detecting, measuring and analyzing oral microRNA and/or microbiome, including normalization of data to account for temporal variations, and diagnosing ASD, monitoring the progress of a disorder or disease and optionally treating a subject in need thereof.

Description of the Related Art

Autism spectrum disorder (ASD) affects 1 in 45 children and is characterized by a wide array of deficits in social interaction and communication, as well as restrictive, repetitive interests and behavior. Despite significant evidence for genetic contributions to ASD risk, no single gene variant has been discovered that can account for more than 1% of the overall incidence. Consequently, considerable interest has turned to the study of epigenetic mechanisms as potential contributing factors to the risk for ASD. MicroRNAs (miRNAs) are now well-recognized epigenetic regulators of human gene expression that influence numerous biological processes in all cell types. Moreover, miRNAs are released from the cells in which they are synthesized and circulate throughout the body in all extracellular fluids. Alterations in miRNA levels have been reported in postmortem brain, as well as in extracellular fluids of subjects with ASD. Our prior studies have focused on saliva due to the dense neural connections that exist between the brain and most tissues and structures within the oral cavity. Using next generation sequencing (NGS), the inventors have found that a small set of miRNAs demonstrated potential diagnostic utility for distinguishing a set of ASD subjects (average age 9 years) from a matched set of typically developing control children. In addition to the miRNA findings, the salivary microbiome of ASD children was distinctly different than that of the control children. Emerging evidence indicates that a strong relationship may exist between host miRNAs and the resident bacteria of the lower gastrointestinal (GI) tract or gut microbiome.

Healthcare providers have an opportunity to improve outcomes for children with ASD through early diagnosis and referral for evidence-based behavioral therapy (Zwaigenbaum et al., 2015; Dawson et al. 2010). Studies suggested earlier treatment initiation contributed to improved social and behavioral outcomes.

Accurate diagnosis of autism spectrum disorder (ASD) in young children is a key priority in autism research and clinical practice but extremely challenging due to broad heterogeneity in severity and variable patterns of symptom emergence (Macari et al., 2012). Compounding these difficulties, the definition of ASD has continued to change with each edition of the Diagnostic and Statistical Manual (DSM) of the American Psychiatric Association (APA). Current criteria for ASD in DSM-5 require "Persistent deficits in social communication and social interaction across multiple contexts," including deficits in social-emotional reciprocity, non-verbal communication, and developing, maintaining, and understanding relationships. DSM-5 also introduced a new diagnostic category termed Social Communication Disorder (SCD), which is not considered part of ASD. SCD applies to individuals with deficits in appropriate language use in social contexts, but otherwise lacking the restricted interests and repetitive behaviors seen in ASD. In this study, the inventors refer to children with diagnoses of any of DSM-5 recognized Communication Disorders (including SCD), and children with DSM-5 diagnoses of either Unspecified Intellectual Disability or Global Developmental Delay as simply Developmental Delay (DD). Inventors refer to children without suspicion of diagnosis of ASD or DD as Typically Developing (TD). Further, inventors refer to the cohort that is the union of TD children and children with DD as Control (C), non-ASD, or non-spectrum (NS) interchangeably.

Although assignment of DSM-5 diagnoses for ASD and DD is considered the clinical gold standard, the process of making the assignment is not specifically detailed, and is often therefore performed using somewhat subjective application of the criteria by individual practitioners. This is a less than ideal situation given the evidence for improved outcomes when appropriate behavioral interventions can be initiated in children with ASD. To help advance the process of identifying children with ASD, various screening tools have been developed. However, even the most widely-adopted screening tool, the Modified Checklist for Autism in Toddlers Revised (M-CHAT-R) (2015), lacks specificity and is only useful for children between the ages of 18 to 30 months (Robins et al., 2008). Several other adjunctive screening tools have also been proposed, including brain MRI, EEG, eye-tracking, and various measures of metabolites, DNA sequence alterations, oxidative stress and mitochondrial damage (Goldani et al., 2014). However, each of these has significant limitations and none are routinely utilized in clinical practice (Goldani et al., 2014), thus delaying referral for definitive diagnostic evaluation, and the initiation of interventional therapies (Dawson et al., 2010). Diagnostic tools, such as the Autism Diagnostic Observation Schedule (ADOS), also are used, but they are often used incorrectly and can lead to overdiagnosis (In: Monterey Bay Forum 2012; Wilkinson, 2012). Thus, development of accurate and objective diagnostic biomarkers for ASD would represent a valuable addition to the current standard of care.

Environmental factors that influence ASD include parental (especially paternal) age, maternal diet and health, and pre-pregnancy, prenatal, and postnatal exposure to pollutants and toxins (Durkin et al., 2008; Huang et al., 2015; Saeedi et al., 2015; Mohamed et al., 2015; Schmidt et al., 2012; Talbott et al., 2015; Liu et al., 2015). However, these do not explain the whole story because there is a strong genetic component of ASD (Geschwind, 2011). Concordance rates are as high as 88% in monozygotic twins and 31% in dizygotic twins (Rosenberg et al., 2009), while full siblings have a two-fold greater concordance rate than half siblings (Constantino et al., 2013). These figures suggest that ASD heritability could be as great as 50%. Yet nearly 2,000 individual genes have been implicated in ASD (Xu et al., 2012), and no single copy number variant explains more than 1% of ASD incidence (Chahrour et al., 2012). Indeed, ASD has been shown to be affected by genetic heterogeneity, where a single disorder is exhibited through multiple genetic and non-genetic factors (Hui et al., 2015) Fragile X, the most common form of inherited intellectual disability, is the leading known genetic cause of ASD. Other genetic mutations and variations influence ASD diagnosis, including mutations of the TBRI gene and polymorphisms of CACNA1A, a calcium channel (Huang et al., 2015; Wisniowiecka-Kowalniik et al., 2013; Li et al., 2015).

Given the multifactorial genetic and environmental risk facts that have been identified in ASD, it is possible that one or more epigenetic mechanisms might play a role in ASD pathogenesis (Hall et al., 2014). Among these potential mechanisms are microRNAs (miRNAs). MiRNAs are non-coding nucleic acids that can regulate expression of entire gene networks by repressing the transcription of mRNA into proteins, or by promoting the degradation of target mRNAs (Follert et al., 2014). Studies of microRNA (miRNA) in children with ASD have demonstrated differential expression patterns in post-mortem brain tissue (Abu-Elneel et al., 2008), serum (Ghahramani et al., 2011) and cultured peripheral lymphoblasts (Talebizadeh et al., 2008; Sarachana et al., 2010; Ghahramani et al., 2011; Hicks et al., 2016). Several of the miRNAs identified in these studies target genes known to be involved in ASD (Banerjee-Basu et al., 2014), but brain biopsy is simply too invasive to be a suitable model for ASD screening and physiologic relevance of miRNA expression in cultured lymphoblasts is a methodological concern (Baron et al., 2006). Furthermore, these studies were small in scale and failed to characterize subjects' clinical characteristics with validated measures of neurodevelopment (e.g., ADOS or ADI-R). This final point is an important one given that children with ASD exhibit a wide range of developmental problems including language delays, learning difficulties, and social problems. There is thus a need to establish reliable diagnostic criteria for ASD as early as possible and, at the same time, differentiate those subgroups with distinct developmental concerns.

MiRNAs are now known to be essential for normal brain development and function. Notably, miRNAs can be packaged within exosomes and other lipophilic carriers as a means of extracellular signaling. This feature allows non-invasive measurement of miRNA levels in extracellular biofluids such as saliva (Hicks et al., 2017), and renders them attractive biomarker candidates for disorders of the central nervous system (CNS) (Sun et al., 2015). Studies of miRNA in children with ASD have demonstrated differential expression patterns in post-mortem brain tissue (Ander et al., 2015; Mor et al., 2015), serum, and cultured peripheral lymphoblasts (Sarachana et al., 2010; Ghahramani et al., 2011). Several of the miRNAs identified in these studies target genes known to be involved in ASD (Hicks et al., 2016). Brain biopsy is clearly too invasive to be suitable for ASD screening and the physiologic relevance of miRNA expression in cultured lymphoblasts introduces methodological concerns. Given the robust cranial nerve innervation of the oropharynx, its proximity to glymphatic structures, and the sensorimotor pathology observed in children with ASD (food texture sensitivity (Schreck et al., 2004), taste aversions, and speech apraxia (Tierney et al., 2012) the inventors previously explored the potential of salivary miRNA to differentiate children with ASD from typically developing peers (Hicks, Ignacio, et al., 2016). A pilot study of 24 children with ASD demonstrated that salivary miRNAs are altered in ASD and broadly correlate with miRNAs reported to be altered in the brain of children with ASD.

One of the densest sources of innervation of the tongue and salivary glands derives from the facial nucleus, and striking abnormalities in this cranial nerve nucleus were reported more than 20 years ago in studies of postmortem brain tissue from subjects with idiopathic or thalidomide-induced ASD (Rodier et al., 1996), providing clear support for neurodevelopment theories of ASD. Thus, extracellular miRNA quantification in saliva provides an attractive and minimally-invasive technique for brain-related biomarker identification in children with ASD. Moreover, this method minimizes many of the limitations associated with analysis of post-mortem brain tissue (e.g., anoxic brain injury, RNA degradation, post-mortem interval, agonal state), or peripheral leukocytes (relevance of expression changes, painful blood draws) employed in previous studies (Abu-Elneel et al., 2008; Mundalil et al., 2014; Talebizadeh et al., 2008; Sarachana et al., 2010; Ghahramani et al., 2011).

Together, these studies support the utility of miRNA measurement in ASD screening. However, the clinical applicability of prior miRNA studies in ASD patients has been limited by several factors: 1) no miRNA study has employed more than 55 ASD participants (Mundalil et al., 2014), despite the broad, heterogeneous nature of the disorder; 2) no miRNA study has enrolled children at the ages (2-6 years) when ASD diagnosis first occurs (i.e. when a diagnostic biomarker panel would have the most clinical utility); 3) no miRNA study has compared children with ASD to peers with non-autistic developmental delay—a comparison required to develop a robust diagnostic toolset; and 4) no study has examined the ability of miRNA signatures to differentiate ASD phenotypes—a priority for the autism community.

The inventors sought to address these deficiencies and establish a diagnostic panel of salivary miRNAs for prospective validation. They hypothesized that characterization of salivary miRNA concentrations in children with ASD, non-autistic developmental delay (DD), and typical development (TD) would identify panels of miRNAs with the screening (ASD vs. TD) and diagnostic (ASD vs. DD) potential. They also posited that these miRNAs would exhibit brain-related targets on functional pathway analyses and display associations with specific autistic phenotypes (evaluated with standardized measures of communication, socialization, and repetitive behavior).

The microbiome of the gastrointestinal (GI) tract is essential for mammalian physiology, aiding digestion, synthesis, and absorption of important nutritional components such as amino acids, folate, and B vitamins. Accumulating evidence suggests that the GI microbiome also influences host behavior and neurodevelopment through the "microbial-gut-brain axis". This axis represents an evolving concept of microbial-mediated cross-talk between the central nervous system (CNS) and GI tract that occurs through several different modalities, including direct neural activation, immune modulation, and hormonal, peptidergic, and epigenetic signaling.

The gut microbiome is a new frontier in autism research (Current Psychiatry Reports, 15(2), 337). In support of this possibility, recent studies have found correlations between fecal microbiome elements and ASD symptoms (Mayer et al., 2014; Vuong et al., 2017; Adams et al., 2011; Kang et al., 2013). Most studies examining this phenomenon have looked at gut microbiomes using 16S rRNA sequencing (McElhanon et al., 2014). For example, one group found that *Haemophilus parainfluenzae* in the gut was associated with an increase in self-injurious behavior (Luna et al., 2016). Another study found four gut microbial genera whose increases were associated with ASD, and two genera whose increases were associated with neurotypical individuals (Strati et al., 2017). Moreover, some of these studies also provided evidence that the observed microbiome differences might underlie the gastrointestinal (GI) symptoms that often occur in ASD. For example, constipation in ASD was found to be associated with higher levels of *Escherichia/Shigella* and *Clostridium* cluster XVIII (Strati et al., 2017). Although it remains unclear whether such associations with GI symptoms are driven by restrictive diets common among ASD individuals, or whether these microbial shifts are causative of such ASD endophenotypes, the data are compelling since nearly 90% of children with ASD experience some feeding-related concern (Ledford et al., 2006) most often related to food selectivity or potentially GI intolerance (Sharp et al., 2012). These atypical nutrition patterns may increase the risk for medical issues such as gut inflammation, obesity (Hill et al., 2015), constipation (Pang et al., 2011), and poor bone growth (Hediger et al., 2008) in addition to contributing to altered behavior. A recent novel study in an ASD rodent model helped unify these possibilities by demonstrating that reconstitution of the gut with *Lactobacillus* restored oxytocin levels, ventral tegmental plasticity, and social behaviors (Buffington et al., 2016). Similar improvements in ASD symptoms have also been recently observed in human subjects treated by microbial transfer from the gut of healthy subjects (although the study was not double-blind or placebo-controlled) (Kang et al., 2017).

Although the exact mechanisms remain enigmatic, it is also now increasingly clear that alterations in the GI microbiome and gut-brain axis occur in a range of neuropsychiatric and neurodevelopmental disorders, including autism spectrum disorder (ASD). In fact, a disproportionate number of ASD patients suffer from GI comorbidities, including constipation, chronic diarrhea, abdominal pain, and gastroesophageal reflux. Although nearly 50% of ASD risk is attributable to genetic variations (such as nucleotide polymorphisms and copy number variants), it is possible that gene-environment interactions could act through the gut-brain axis (under the influence of the GI microbiome) and significantly modulate ASD risk. Microbial influence on serotonin levels provides a striking example of this.

Polymorphisms in the serotonin transporter gene contribute to the risk of ASD. However, the majority of serotonin synthesis occurs in intestinal enterochromaffin cells, through the conversion of tryptophan into serotonin via tryptophan hydroxylase. The GI microbiome enhances serotonin synthesis via the effects of short-chain fatty acids on enterochromaffin cells. Once synthesized, most serotonin acts within the gut to promote intestinal motility, although some of it passes into the peripheral circulation and can potentially impact the CNS, particularly during early brain development. Thus, disturbance of the gut microbiome could alter serotonin signaling, acting in concert with a child's genetic background.

Building on this idea of gene-environment interactions, there is accumulating evidence for disrupted gut-brain signaling in ASD. For example, a recent study of 13 children with regressive-onset autism and GT comorbidities identified increased levels of fecal *Clostridium* and non-spore-forming anaerobes compared to those seen in typically developing controls. Disturbances in fecal *Clostridium* abundance have also been reported in two additional ASD microbiome studies. Other investigations have noted alterations in the *Bacteroides*/Firmicutes ratio in children with ASD, though the directionality of those changes conflict. Additional reports also implicate *Lactobacillus, Prevotella,* *Coprococcus, Desulfovibrio*, and Veilonellaceae alterations in ASD. The lack of consensus between studies is challenging, but may be explained, in-part, by the relatively small sample sizes used to explore a highly heterogeneous disorder. The small size of these investigations has also prevented sub-division of ASD participants into phenotypic subtypes. A larger-scale approach could provide valuable insights into the relationship of the microbiome to autistic behavior, GI pathology, and immune function.

The potential role of the microbiome in ASD also gains strong support from several animal studies that have modulated social behaviors through dysbiosis, and ameliorated those symptoms with restoration of gut microbes. Parallel findings have even been reported in human ASD. For example, studies of antibiotic therapy with vancomycin or tetracyclines have been able to temporarily mitigate some of the behavioral symptoms in ASD patients. A recent study of fecal microbiota transfer therapy in 18 children with ASD also demonstrated improvements in bacterial diversity along alongside improvements in parent-reported GI and ASD symptoms. These effects persisted for eight weeks after intervention.

It is worth noting that nearly all studies of the ASD microbiome have focused on the lower GI tract. However, the oropharynx, which serves as the sole entry point to the GI tract, also represents a site of ASD pathology. Children with ASD suffer from increased rates of motor (speech) and sensory (food texture) pathology in the mouth and the inventors have previously described epi-transcriptomic changes in the saliva of children with ASD. This led the inventors to posit that perturbations in the oral microbiome might also occur in children with ASD.

The inventors have interrogated the human microbiome using high-throughput shotgun metatranscriptome data from the oropharynx of 180 children with ASD, 106 typically developing controls (TD), and 60 children with non-autistic developmental delay (DD). It has been hypothesized that organisms with altered abundance in the lower GI tract of ASD individuals would demonstrate similar changes in transcriptional activity in the oropharynx. Furthermore, it was posited that specific microbiome communities would differentiate ASD endophenotypes and correlate with abundance of mRNAs related to neurohormone signaling and metabolic regulation.

The proper regulation of sleep in humans is critical for normal mental and physical health. Many major organ systems exhibit fluctuations in their functional state related to sleep-wake cycles or circadian rhythm. Disturbances in sleep or disruption of circadian rhythm are a common problem in brain injuries and many chronic brain diseases or disorders, including autism, depression, Parkinson's disease and Alzheimer's disease.

During sleep-wake cycles there are numerous molecular, cellular, and physiological changes that occur. Many of these changes are driven by what are referred to as circadian regulatory genes, such as CLOCK and BMAL1. These, in turn, cause numerous changes in the expression of physiologically relevant genes, proteins, and hormones. Apart from light-dark cycles, the factors that influence expression of circadian genes are not fully understood. Taken together, the invenotrs' data suggest a previously unknown relationship between saliva miRNA and microbe content as well as temporal influences (i.e., temporal variations) on miRNAs (and/or microbes) themselves. The systems and methods described herein to normalize epigenetic data (sequencing data or other data) that experience temporal variations may be used in any suitable application where temporal variations may affect the data. The systems and methods describes herein may be used in applications to detect the onset of medical conditions and/or changes in medical conditions—more specifically, to detect onset and/or changes in neurological disorders such as autism, sleep disorders, and traumatic brain injury (TBI).

SUMMARY OF THE INVENTION

Clinical diagnosis of autism spectrum disorder (ASD) relies on time-consuming subjective assessments. An objective of the inventors was to investigate the utility of salivary microRNAs for differentiating children with ASD from peers with typical development (TD) and non-autistic developmental delay (DD). Another objective was to explore microRNA patterns among ASD phenotypes to use in the algorithm to achieve desired sensitivity and specificity. Another objective of the inventors was to investigate the utility of oral microbiome for differentiating children with ASD from peers with typical development (TD) and non-autistic developmental delay (DD).

Another objective of the inventors was to investigate strength of the relationships between miRNA and microbiome as a quick, accurate, and objective screening tool for ASD.

Other non-limiting objectives of the inventors were to determine a relationship of miRNA levels and microbiome levels to diurnal variations in the mouth saliva; to examine if any of the identified miRNAs with diurnal variations are known to regulate circadian genes; and to quantify the strength of the relationship between the miRNAs and microbes that show the greatest degree of circadian fluctuation.

These and other objects of the present invention will become more apparent in conjunction with the following detailed description of the preferred embodiments, either alone or in combinations thereof.

BRIEF DESCRIPTION OF THE DRAWINGS

A more complete appreciation of an object of the present disclosure and many of the advantages thereof will be readily obtained as the same becomes better understood by reference to the following detailed description when considered in connection with the accompanying drawings which are described below.

FIGS. 1A, B show sphericity and normalization of miRNA data in ASD and TD children assessed by PCA.

FIGS. 3A, B, C, D show box plots of selected miRNA differences between ASD and TD children.

FIGS. 5A, B, C, D show box plots of selected miRNA differences between ASD and TD children.

FIGS. 6A, B show sphericity and normalization of microbiome data assessed by PCA.

FIG. 6C shows a volcano plot of microbiome data with outliers indicated in red/gray scale.

FIG. 31 shows Oral phyla abundance across ASD, TD, and DD children. The relative abundance of 16 oral phyla is shown for children with autism spectrum disorder (ASD; n=180), typical development (TD; n=106), and non-autistic developmental delay (DD; n=60). Non-parametric Kruskal-Wallis testing revealed significant differences (FDR<0.05) among the three groups for Planctomycetes ($\chi2$=31.0, FDR=3.2E-06), Cyanobacteria ($\chi2$=14.8, FDR=0.005), and Calditrichaeota ($\chi2$=9.6, FDR=0.04).

FIGS. 32A-B show Oral taxonomic profiles distinguish ASD children from TD and DD peers. A partial least squares discriminant analysis was used to visualize differences in taxonomic profiles at the species level between ASD, TD, and DD groups in two dimensions (A). A model accounting for 4% of the variance between groups resulted in partial separation of ASD participants (red/gray scale) from TD (blue/gray scale) and DD (green/gray scale) peers. The 20 taxons most critical for group projection are shown, based on variable importance in projection score (B). The majority of these taxons (14) are reduced (green/gray scale boxes) in ASD samples relative to TD and DD groups. Three taxons are elevated in ASD participants (red gray scale boxes) and three demonstrated intermediate abundance patterns (yellow/gray scale boxes).

FIGS. 34A, B, C, D, E, F, G, H show: KEGG pathways with differential representation included Microbial Energy Metabolism (A), Translation Ribosome Structure and Biogenesis (B), Pyrimidine Metabolism (C), Lysine Degradation (D), Nucleotide Metabolism (E), Carbon Metabolism (F), Nucleotide Transport and Metabolism (G). (H) shows Differential metabolic profiles.

FIG. 37A-B. Salivary miRNAs identify ASD status. A logistic regression analysis was used to test the ability of 28 miRNAs for identifying ASD status. A panel of 5 miRNA ratios, that employed 4 miRNAs (miR-665, miR-28-3p, miR-148a-5p, miR-1277-5p) while controlling for sex and presence of GI disturbance demonstrated an area under the curve (AUC) of 0.788 (95% CI: 0.677-0.875) in the first 50% of the ASD and TD participants using a 100-fold cross validation (CV) approach (A). This panel maintained an AUC of 0.744 in the naïve hold-out set. A panel of 4 miRNA ratios that employed 4 miRNAs (miR-148a-5p, miR-125b-2-3p, miR-28-3p, miR-374c-5p) while controlling for age demonstrated an AUC of 0.714 (95% CT: 0.564-0.847) in the first 50% of the ASD and DD participants using a 100-fold CV approach (B). This panel displayed an AUC of 0.603 in the naïve hold-out set.

FIG. 38 shows Functional relationships of salivary miRNAs altered in ASD children. Hierarchical clustering of the 14 miRNAs of interest based on pathway union of their mRNA targets (identified in DIANA miRPath with microT-cds algorithm). The 14 miRNAs targeted mRNAs from 41 KEGG pathways with greater frequency than that expected by chance. The number of mRNAs targeted by each miRNA in 9 brain-related pathways is shown, along with the total number of mRNA targets for each miRNA. Note that three pairs of miRNAs which cluster here based on functional targets (miR-193a-5p/miR-125a-5p; miR-148a-5p/miR-944; and miR-620/miR-4705) were also clustered based on salivary concentration patterns among ASD, TD, and DD groups (FIG. 35).

DETAILED DESCRIPTION OF THE EMBODIMENTS

Figure 1C:
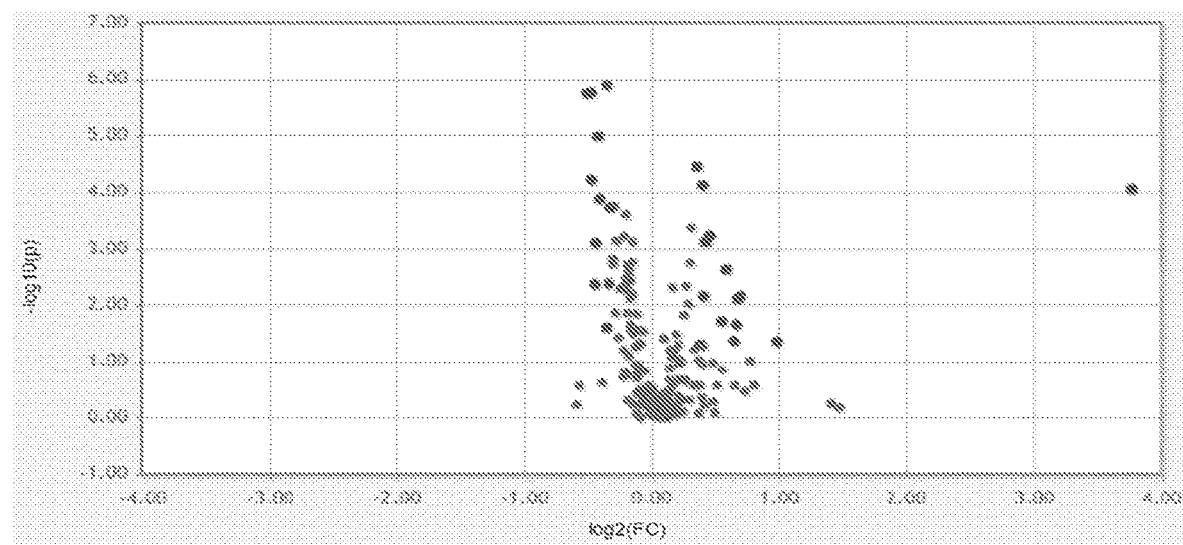
FIG. 1C shows a volcano plot of miRNA data with outliers indicated in red/gray scale.
Figure 2A:
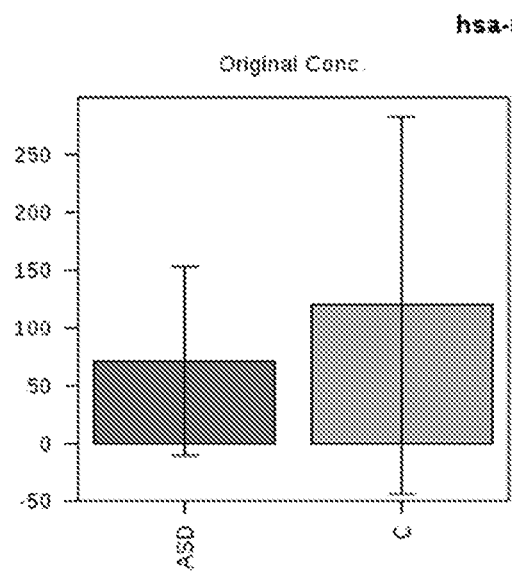
FIGS. 2A, B, C, D show box plots of selected miRNA differences between ASD and TD children.
Figure 2B:
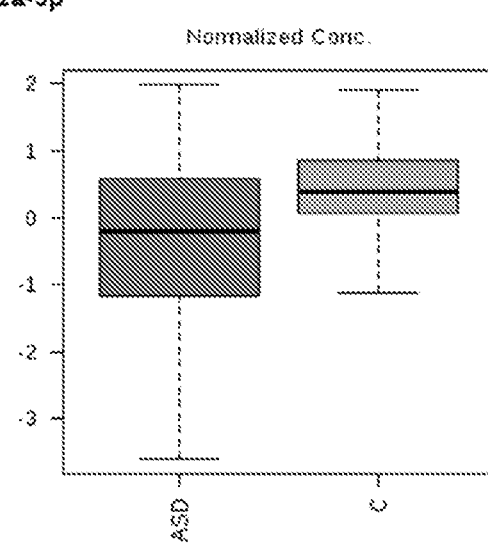
Figure 2C:
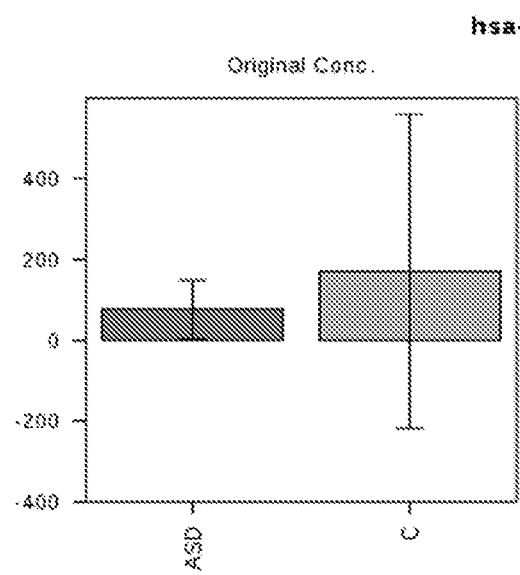
Figure 2D:
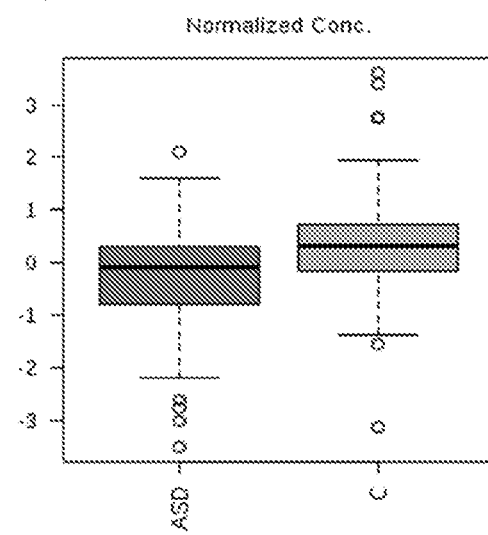
Figure 4A:
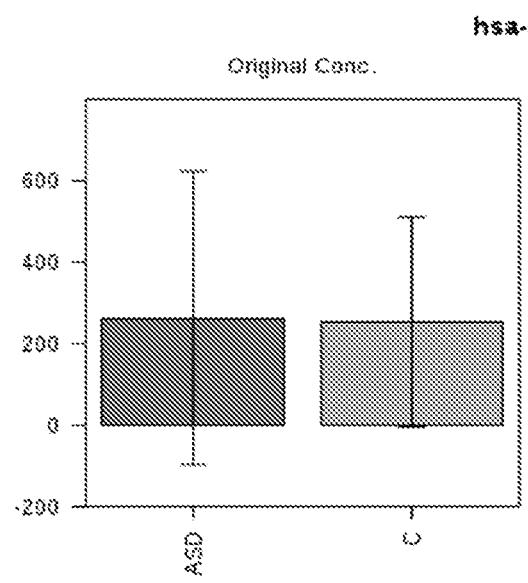
FIGS. 4A, B, C, D show box plots of selected miRNA differences between ASD and TD children.
Figure 4B:
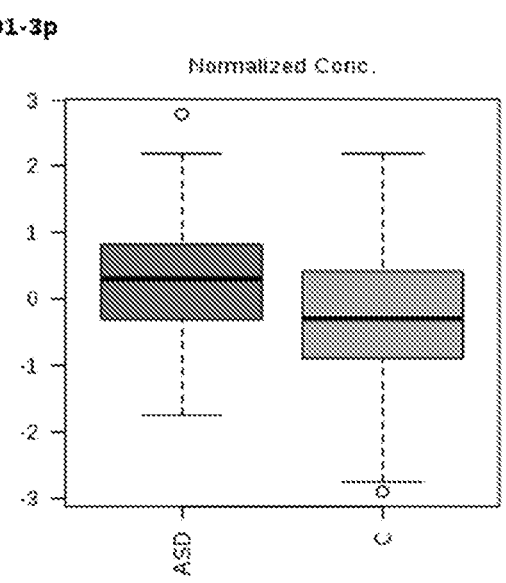
Figure 4C:
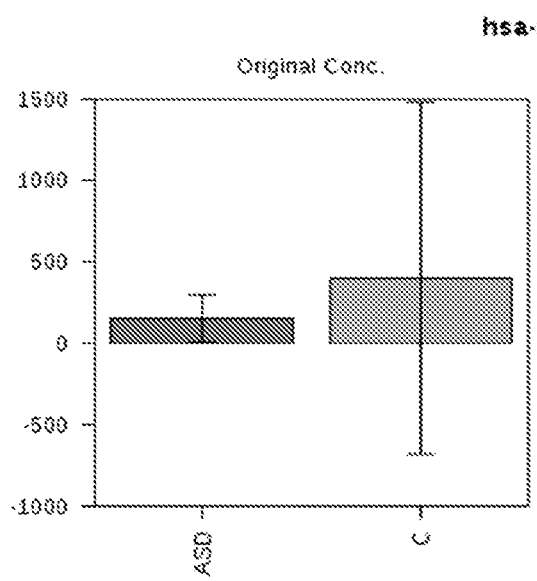
Figure 4D:
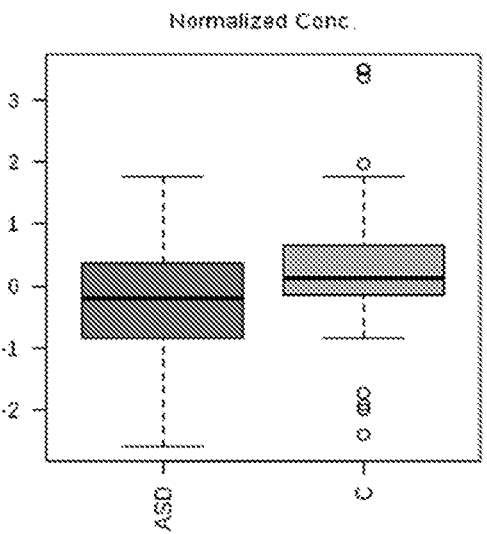
Figure 7A:
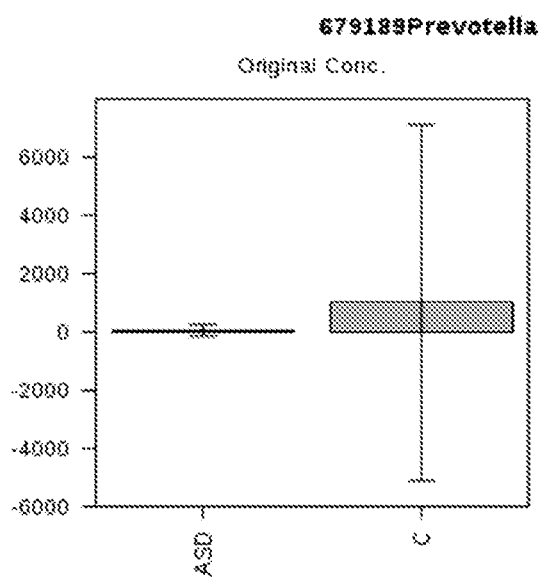
FIGS. 7A, B, C, D show box plots of selected taxon differences between ASD and TD children.
Figure 7B:
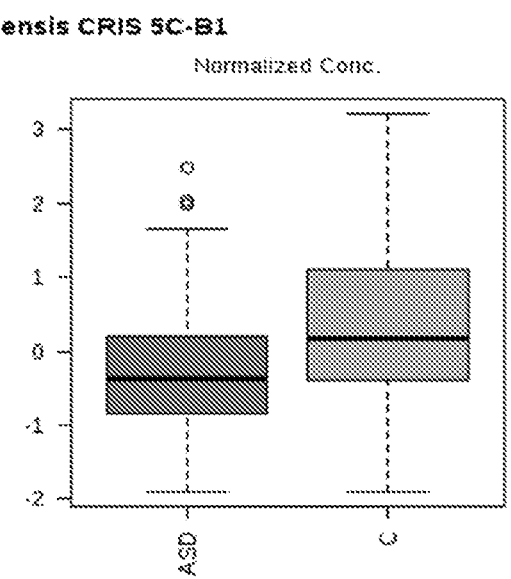
Figure 7C:
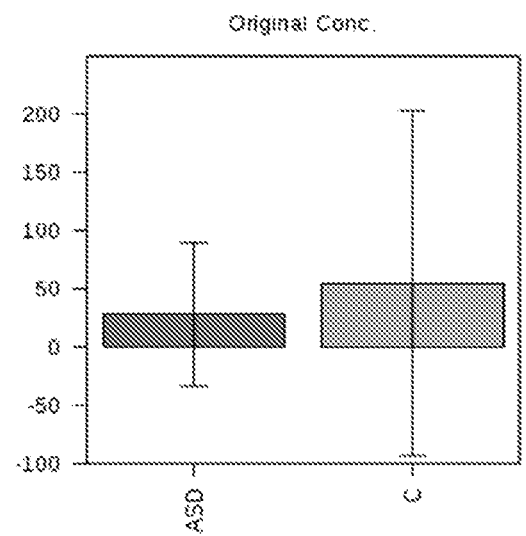
Figure 7D:
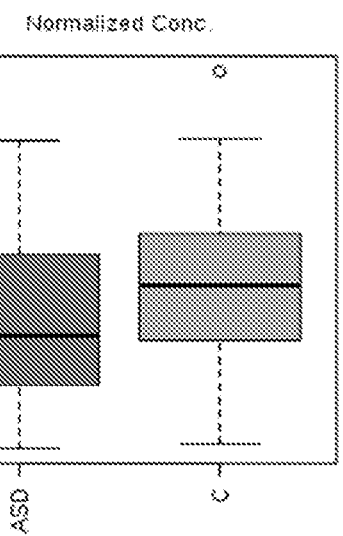
Figure 8A:
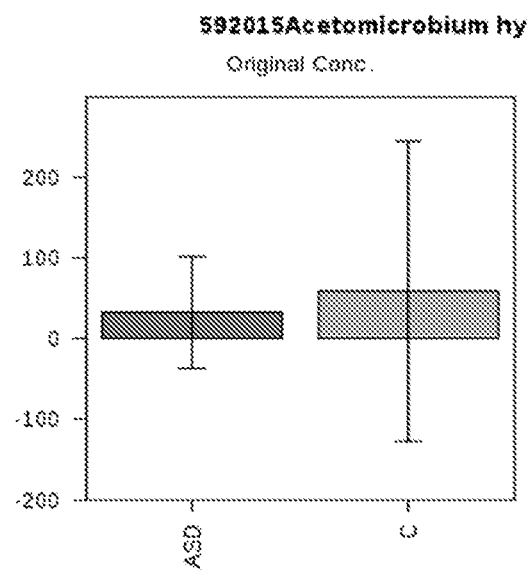
FIGS. 8A, B, C, D show box plots of selected taxon differences between ASD and TD children.
Figure 8B:
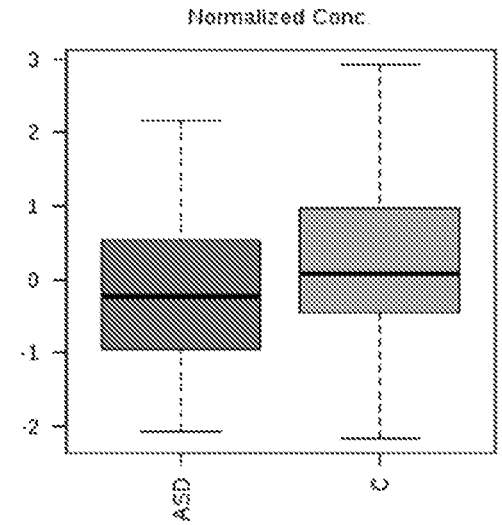
Figure 8C:
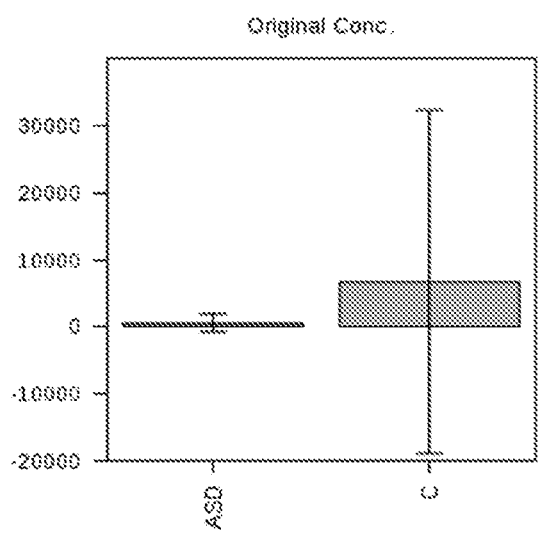
Figure 8D:
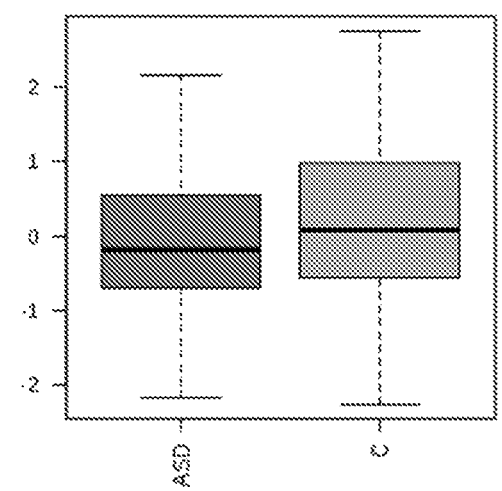
Figure 9A:
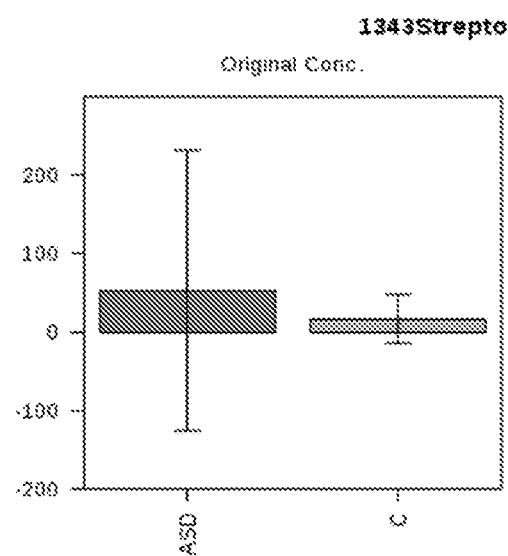
FIGS. 9A, B, C, D show box plots of selected taxon differences between ASD and TD children.
Figure 9B:
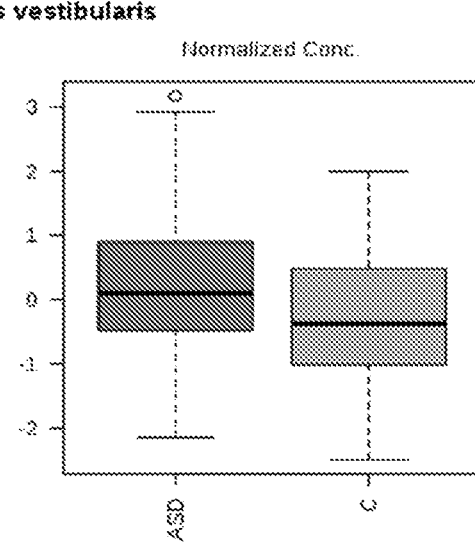
Figure 9C:
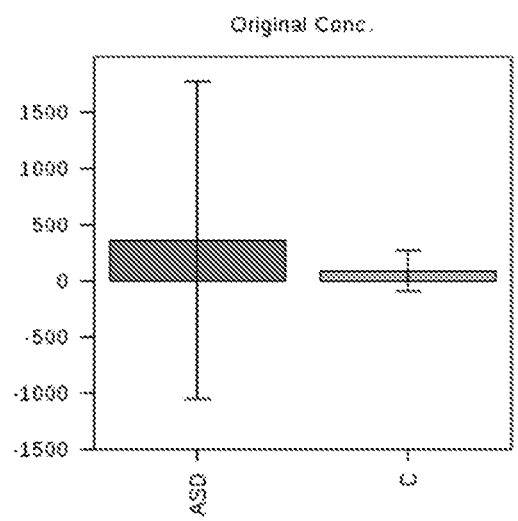
Figure 9D:
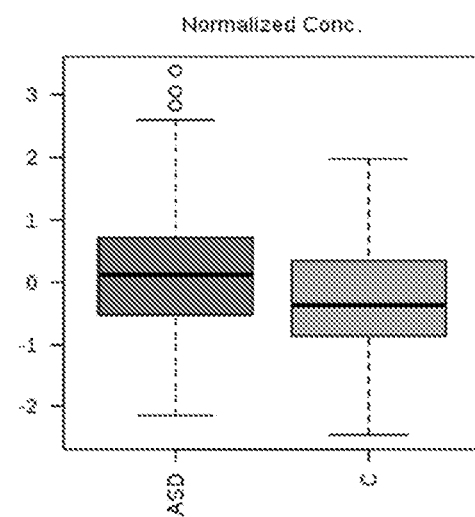
Figure 10A:
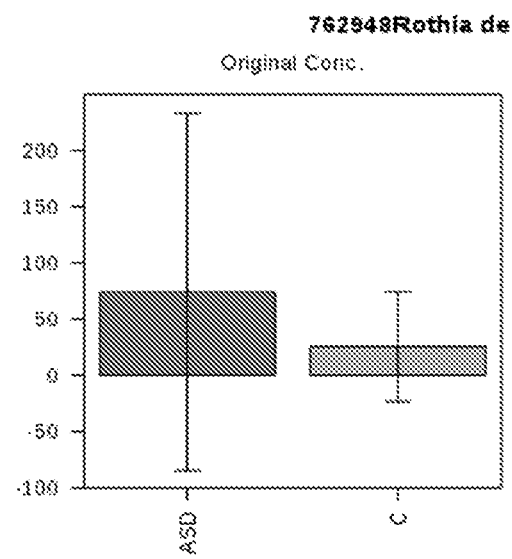
FIGS. 10A, B, C, D show box plots of selected taxon differences between ASD and TD children.
Figure 10B:
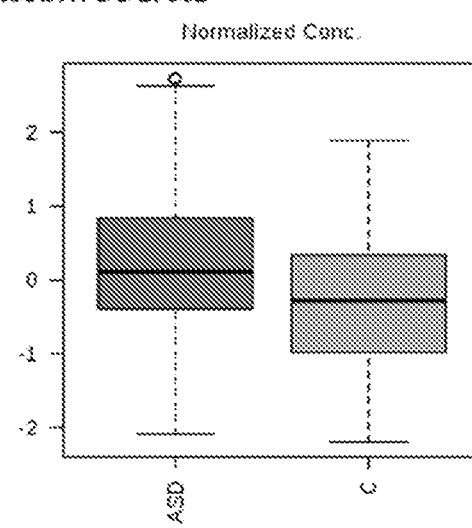
Figure 10C:
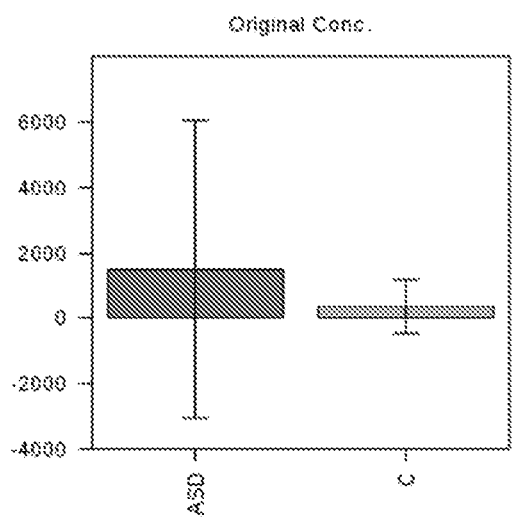
Figure 10D:
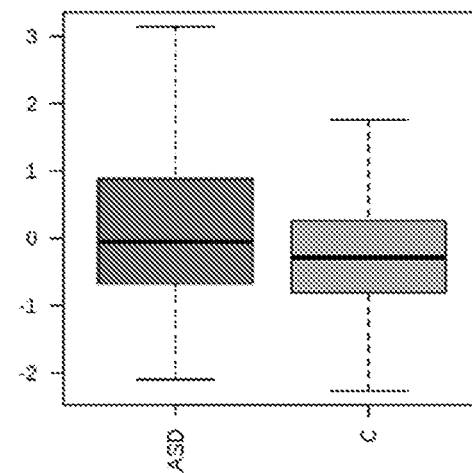
Figure 11:
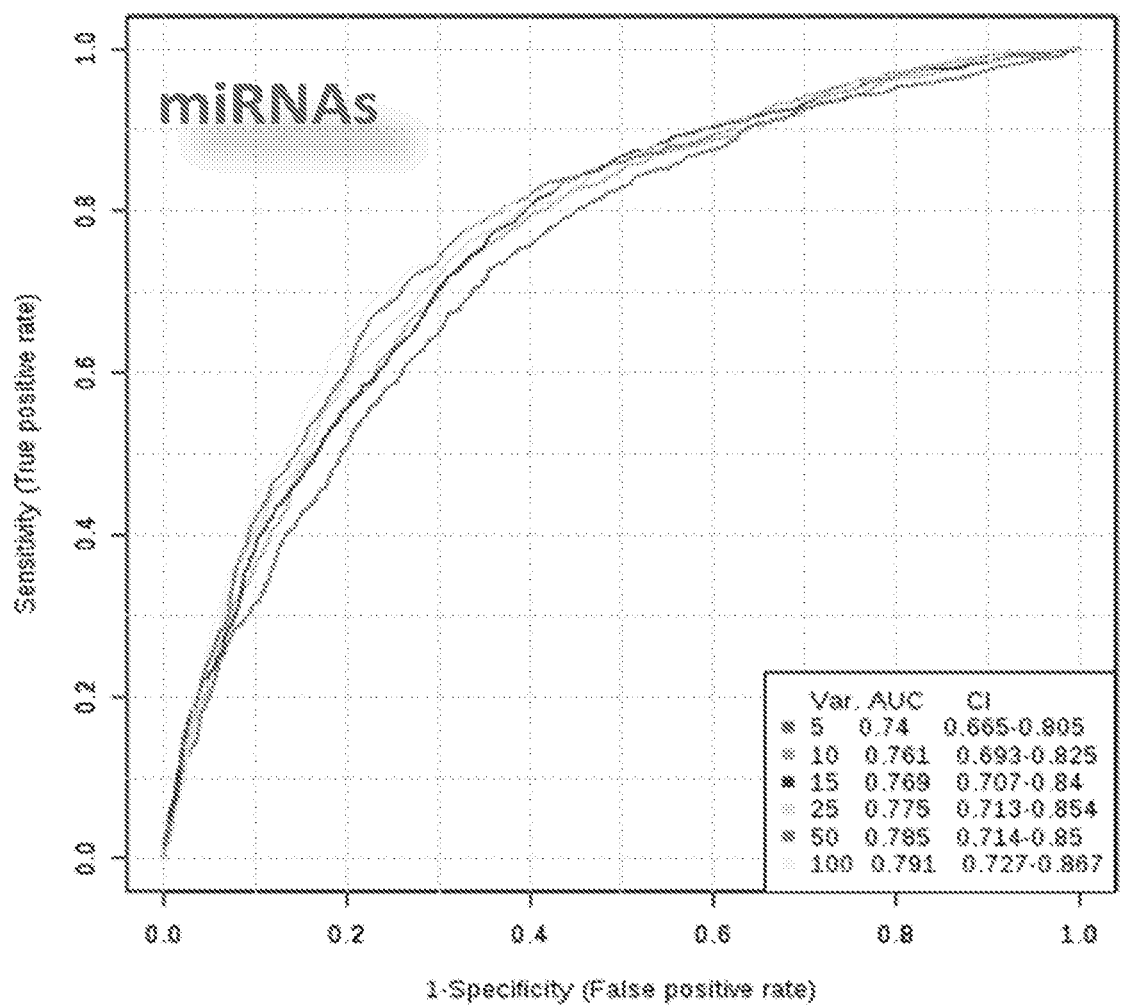
FIG. 11 shows the receiver operator characteristic (ROC) curve and area under the curve (AUC) for logistic regression classification of miRNA from ASD and TD children during training/discovery.
Figures 12A, 12B:
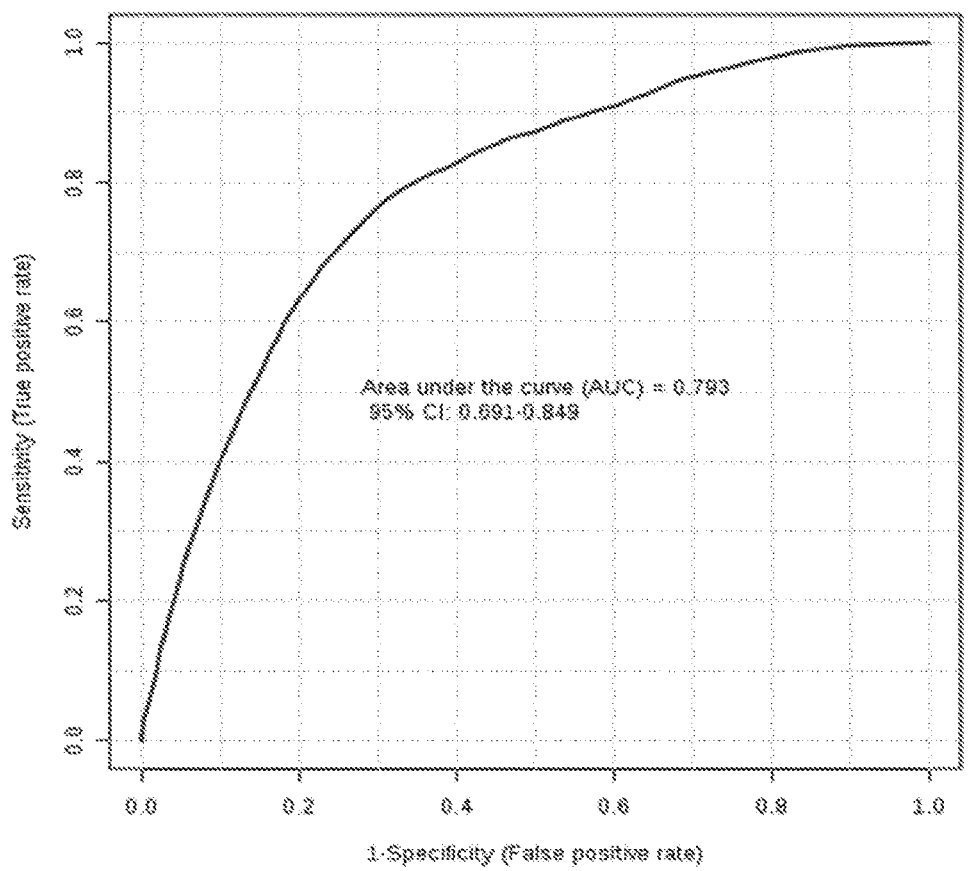
FIGS. 12A-B show the ROC curve, AUC, sensitivity and specificity for logistic regression classification of miRNAs and ratios of miRNAs from ASD and TD children during cross-validation.
Figure 13:
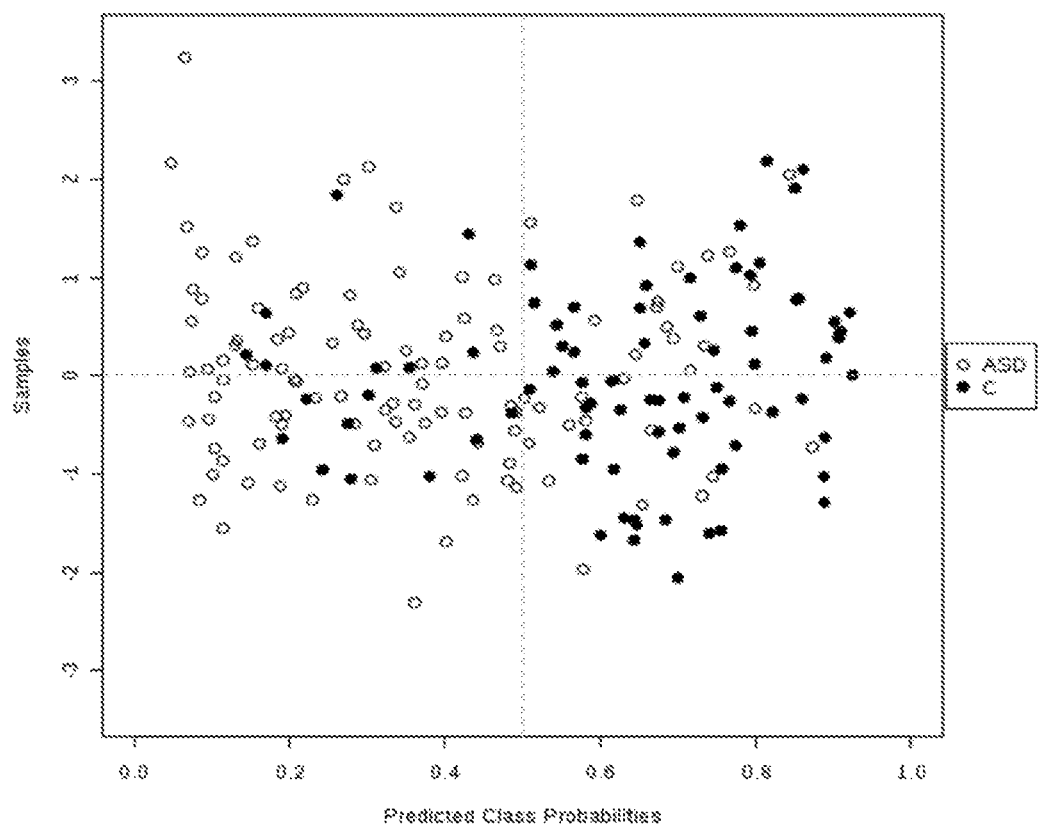
FIG. 13 shows predicted class probabilities of ASD and TD samples from logistic regression with taxons.
Figures 14A, 14B:
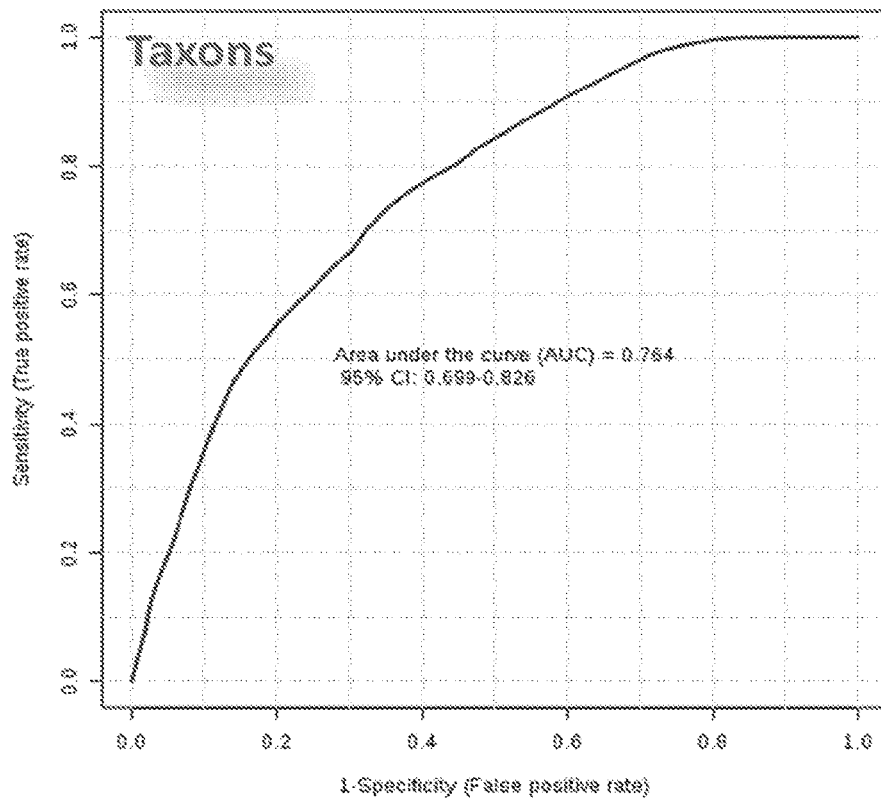
FIGS. 14A-B show ROC, AUC, sensitivity and specificity for logistic regression classification with taxons between ASD and TD children.
Figures 15, 16:
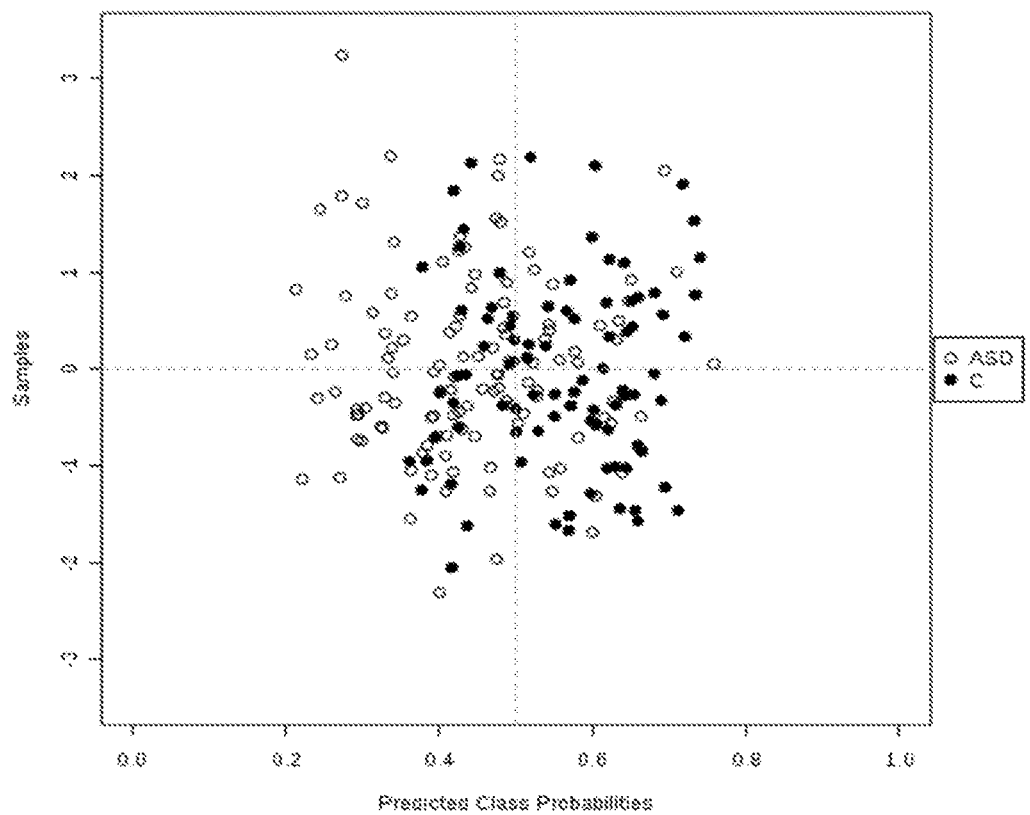
FIG. 15 shows predicted class probabilities of samples from logistic regression classification of 11 taxon ratios.
FIG. 16 shows confusion matrix and summary table for logistic regression model with 8 of the significantly different miRNAs, 10 significantly different taxons, plus age and gender. This model classified >90% of ASD and >80% of TD children correctly (86.6% overall).
Figure 17:
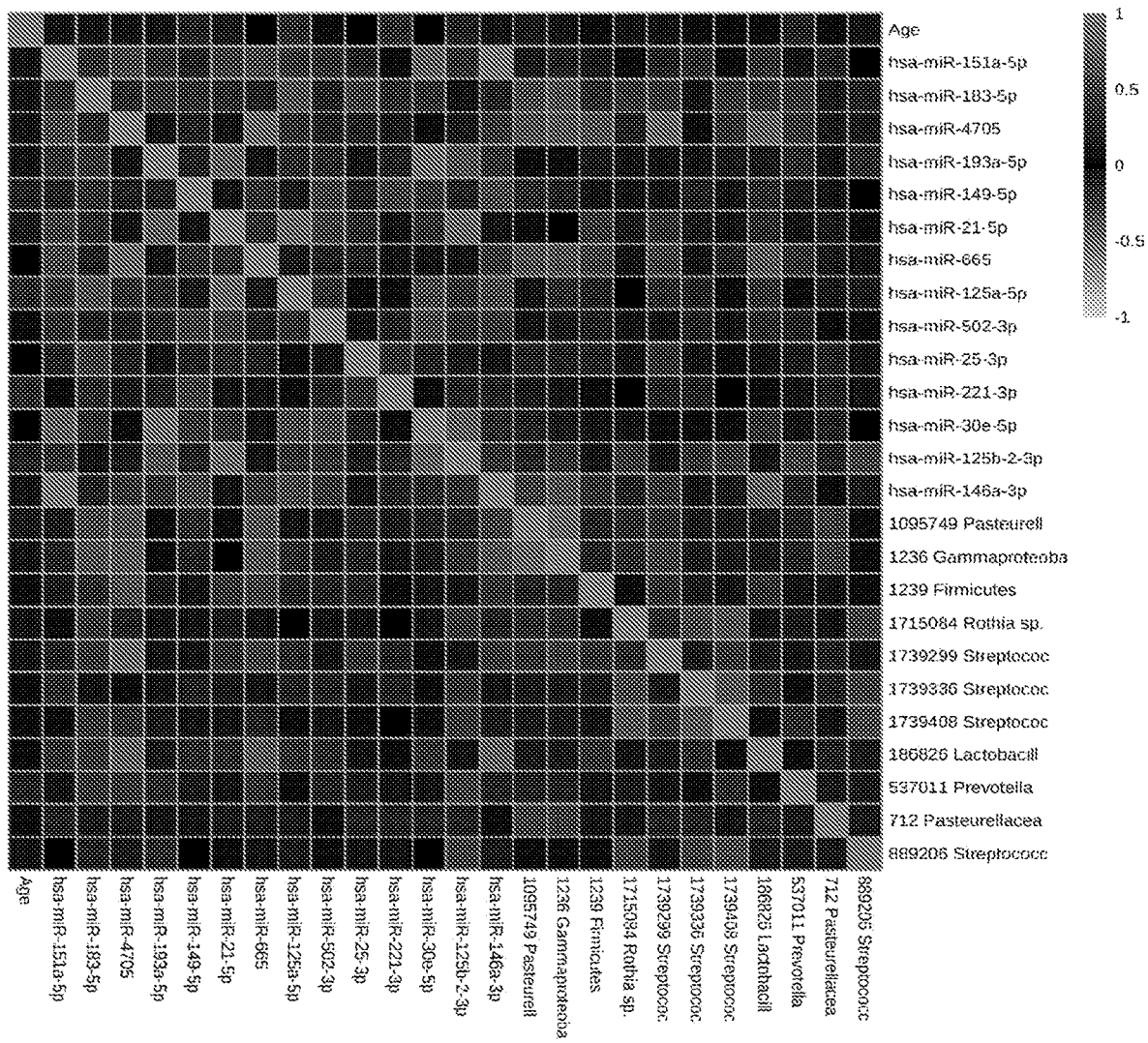
FIG. 17 shows Spearman correlation matrix of top different miRNA and taxon variables as well as age.

All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

This application provides methods to differentiate between subjects with autism spectrum disorder (ASD) and typically developing (TD) or developmentally delayed (DD) subjects using miRNA and/or microbiome levels detected in saliva samples and patient information. The method can be used to monitor the progress of ASD and guide its treatment. RNA-seq, qPCR, or other methods determine counts and abundance of miRNA or microbiomes. MicroRNA and/or microbiome sequencing data are refined by normalization to expression levels or abundance of time-invariant miRNAs and/or microbial RNAs to control for time of sample collection or to compensate for circadian fluctuations in these levels. Multivariate logistic regression and nonlinear classification techniques are further used to select a panel of miRNAs and microbiomes that accurately differentiate between subjects with ASD, DD, and TD in subjects with an unknown ASD status. These panels of miRNAs and microbiomes may be developed into a RNA assay kit.

Saliva is a slightly alkaline secretion of water, mucin, protein, salts, and often a starch-splitting enzyme (as ptyalin) that is secreted into the mouth by salivary glands, lubricates ingested food, and often begins the breakdown of starches. Saliva is released by the submandibular gland, parotid gland, and/or sublingual glands and saliva release may be stimulated by the sympathetic and/or parasympathetic nervous system activity. Saliva released primarily by sympathetic or paracympathetic induction may be used to isolate microRNAs.

Saliva may be collected by expectoration, swabbing the mouth, passive drool, or by other methods known in the art. In some embodiments it may be withdrawn from a salivary gland.

In some embodiments, a saliva sample may be further purified, for example, by centrifugation or filtration. For example, it may be filtered through a 0.22 micron or 0.45 micron membrane, and all membrane sizes in between, and the separated components used to recover microRNAs.

In other embodiments, proteins or enzymes that degrade microRNA may be removed, inactivated or neutralized in a saliva sample.

microRNA or miRNA is a small non-coding RNA molecule containing about 22 nucleotides, which is found in plants, animals and some viruses, that functions in RNA silencing and post-transcriptional regulation of gene expression (see Ambros et al., 2004; Bartel et al., 2004). MicroRNAs affect expression of the majority of human genes, including CLOCK, BMAL1, and other circadian genes. Notably, miRNAs are released by cells that make them and circulate throughout the body in all extracellular fluids where they interact with other tissues and cells. Recent evidence has shown that human miRNAs even interact with the population of bacterial cells that inhabit the lower gastrointestinal tract, termed the gut microbiome. Moreover, circadian changes in the gut microbiome have recently been established.

A miRNA standard nomenclature system uses the prefix "miR" followed by a dash and a number, the latter often indicating order of naming. For example, miR-120 was named and likely discovered prior to miR-241. A capitalized "miR-" refers to the mature form of the miRNA, while the uncapitalized "mir-" refers to the pre-miRNA and the pri-miRNA, and "MIR" refers to the gene that encodes them. Some miRNAs from human are denoted with the prefix "hsa-".

miRNA elements. Extracellular transport of miRNA via exosomes and other microvesicles and lipophilic carriers is an established epigenetic mechanism for cells to alter gene expression in nearby and distant cells. The microvesicles and carriers are extruded into the extracellular space, where they can dock and enter cells, and block the translation of mRNA into proteins (Hu et al., 2012). In addition, the microvesicles and carriers are present in various bodily fluids, such as blood and saliva (Gallo et al., 2012), enabling us to measure epigenetic material that may have originated from the central nervous system (CNS) simply by collecting saliva. In fact, the inventors believe that many of the detected miRNAs in saliva are secreted into the oral cavity via sensory nerve afferent terminals and motor nerve efferent terminals that innervate the tongue and salivary glands and thereby provide a relatively direct window to assay miRNAs which might be dysregulated in the CNS of individuals with ASD. Epigenetic data includes data about miRNAs.

microbiome elements. There is growing evidence for the role of the gut-brain axis in ASD and it has even been suggested that abnormal microbiome profiles propel fluctuations in centrally-acting neuropeptides and drive autistic behavior (Mulle et al., 2013).

Based on these studies and extensive preliminary data, the inventors have hypothesized that components of the oral microbiome may correlate with the diagnosis of ASD and/or specific behavioral symptoms. As the microbiome can be simultaneously detected using our salivary RNA diagnostic technology, the inventors have evaluated whether inclusion of components of the microbiome would improve diagnostic accuracy for ASD. This ability to jointly monitor the miRNA and microbiome elements of the microtranscriptome gains additional significance in view of recent data that miRNA levels can strongly fluctuate in concert with the host microbiome (Dalmasso et al., 2011). Moreover, other recent studies have revealed that alterations in the gut microbiome can affect the expression of brain miRNAs in mice, along with the production of anxiety symptoms. Thus, the interaction of the host miRNA elements and the GI microbiome elements and their joint effects on the brain and behavior comprises a key component of our current biomarker discovery path.

Salivary miRNA and microbiome elements are differentially expressed in children with ASD compared with TD controls and children with non-ASD developmental delays (DD). Differentially expressed miRNAs in the saliva are expressed in the developing brain (Ziats et al., 2014) and are functionally related to neurodevelopment (Mundalil et al., 2014). Two questions have been asked by the inventors: (1) whether the identified panel of biomarkers has sufficient sensitivity and specificity to be useful molecular diagnostic tools for ASD, and (2) What does the miRNA and microbiome profile look like at the time of initial ASD diagnosis and can it be used to differentiate children with ASD from children with typical developmental patterns? The inventors refined their technique for saliva collection and improved the software/statistical pipeline for RNA processing. As a result, it has become possible to measure both human and non-human RNA within a single sample. This approach has allowed the inventors to define a panel of 16 ratios involving 10 miRNAs and 3 microbial species that robustly differentiated 92 children with ASD from 54 typically developing children (ages 2-6 years) with 83.5% accuracy in a training set and 83.4% accuracy in an identically sized naïve holdout validation set. A secondary analysis demonstrated that the inventors could accurately distinguish ASD children from DD children, using a somewhat different set of molecular markers, and achieve comparable sensitivity and specificity. The methods disclosed by the inventors also comprise selecting a set miRNAs, and a set of microbial taxons that can be combined with appropriate weighting coefficients, or used in ratios, to generate a prediction of association with ASD.

Sex and several other biological factors of relevance are considered as potential modifiers of outcome for the utility of our diagnostic tools. As one example, it is known that ASD affects approximately 5 times more males than females. Nevertheless, it is absolutely essential that any molecular diagnostic tool that has been developed by the inventors is equally accurate for both males and females. A broad range of clinical, biological and neuropsychological variables are collected at each site on all subjects and specifically examined in all statistical models. Such variables include age, sex, ethnicity, birth age, birth weight, perinatal complications, current weight, body mass index, current oropharyngeal status (allergic rhinitis, sinus infection, cold/flu, fever, dental carries), sleep disorders, gastrointestinal issues, diet, current medications, chronic medical issues, immunization status, medical allergies, dietary restrictions, early intervention services, hearing deficits, visual deficits, surgical history, and family psychiatric history. Rigorous neuropsychological evaluation of the children using standardized, age-appropriate and validated measures of autism symptomology (ADOS-2), adaptive behavior (Vineland-III), and general cognitive and motor development (Mullen Scales of Early Learning) is also performed. Many children may also have an M-CHAT-R result that is entered in the record. The results of the invntors' molecular studies are directly compared with all of these in an unbiased manner to determine the specific magnitude of any interacting effects or to test for the presence of associations in the data that might be of interest. The inventors also used a set or a group of patient data to input to the algorithm.

miRNA isolation from biological samples such as saliva and their analysis may be performed by methods known in the art, including the methods described by Yoshizawa, et al., *Salivary MicroRNAs and Oral Cancer Detection*, Methods Mol. Biol., 2013; 936: 313-324 or by using commercially available kits, such as mirVana™ miRNA Isolation Kit).

Variable Importance in Projection (VIP) scores estimate the importance of each variable in a projection used in a PLS model and are often used for variable selection. A variable with a VIP Score close to or greater than 1 (one) can be considered important in given model.

In the recent study, the inventors have examined the relationship of microRNA (miRNA) levels to diurnal variations. The inventors have hypothesized that a portion of the miRNAs that target circadian genes would show strong circadian rhythms themselves. Because miRNAs can circulate throughout the body in all extracellular fluids, the measurements were conducted in human saliva. An additional reason to use saliva samples was to enable analysis of the relationship of miRNAs to the levels and diversity of microbes present in the human mouth, termed the microbiome. Previous research in the lower GI tract has shown a strong relationship between host miRNAs and the resident bacteria. Moreover, circadian changes in the gut microbiome have been established. Consequently, one objective of the inventors was to obtain evidence for correlated changes in a subset of circadian oscillating miRNAs and microbes. U.S. Provisional application 62/475,705 filed Mar. 23, 2017, and PCT/US18/23336, filed Mar. 20, 2018, are incorporate herein by reference in their entirety.

Eleven human subject volunteers participated in the initial study and provided saliva samples at various times of day on repeated days. Identification and quantification of saliva miRNA and microbial content was performed using next generation sequencing (NGS), real time PCR, or otherwise followed by a statistical analysis. The inventors have first used a two-way analysis of variance (ANOVA) in two independent sample sets to identify miRNAs and microbes that varied significantly according to the time of collection but not the day of collection (which could have been strongly affected by daily variation in routines). A subset of these miRNAs and microbes were then used in a third sample set to predict the time of collection using a multivariate regression. The results indicated that human saliva contained approximately 400 miRNAs and 2000 microbes that were reliably quantified. Of these, strong and predictable changes with time of collection were apparent for 19 distinct miRNAs and many microbes. A model was developed from the miRNA data in the first two sample sets that was able to predict time of collection in the third sample set within a 15% margin of error. The microbial data also showed a strong correlation with time of collection in the first two sample sets, but was not as accurate at predicting collection time in the third sample set. Also highly significant correlations between several of the miRNAs and microbes were observed. Interestingly, a bioinformatic analysis of the best time predictor miRNAs indicated that most target at least one or more circadian genes, in addition to genes involved in brain and immune function. Taken together, the inventors' data suggest a previously unknown relationship between saliva miRNA and microbe content as well as temporal influences (i.e., temporal variations) on miRNAs (and/or microbes) themselves. The systems and methods described herein to normalize epigenetic data (sequencing data or other data) that experience temporal variations may be used in any suitable application where temporal variations may affect the data. In an example, the systems and methods describes herein may be used in applications to detect the onset of medical conditions and/or changes in medical conditions—more specifically, to detect onset and/or changes in neurological disorders such as autism, sleep disorders and traumatic brain injury (TBI). An objective of the inventors was to investigate the utility of salivary microRNAs for differentiating children with ASD from peers with typical development (TD) and non-autistic developmental delay (DD). Another objective was to explore microRNA patterns among ASD phenotypes. Another objective of the inventors was to investigate the utility of oral microbiome for differentiating children with ASD from peers with typical development (TD) and non-autistic developmental delay (DD). Another objective of the inventors was to investigate strength of the relationships between miRNA and microbiome as a quick, accurate, and objective screening tool for ASD. In one embodiment, normalization of epigenetic sequence data to account for temporal variations is provided.

In one embodiment, data on miRNAs, microbiomes and patient information were used, with a temporal normalization where required, were used to diagnose, prognoze and/or differentiate ASD from TD and DD. In another embodiment, the progression of a disease such as ASD and/or related disorders was evaluated. In another embodiments, defined sets of miRNAs and/or microbiobes from a person to be screened were used to compare agains that of a known normal. In one embodiment, C-DNA was used to detect the RNAs and taxon nucleic acids. In another embodiment, probes and micorarrays were used to detect the RNAs and taxon nucleic acids. The temporal normalization was used for various embodiments in screening, diagnosing, prognosing, and/or differentiating ASD.

These and other objects and embodiments of the present invention will become more apparent in conjunction with the following detailed description of the preferred embodiments, either alone or in combinations thereof.

1. A method of comparing epigenetic and/or microbiome data for a subject suspected of having Autism Spectrum Disorder ("ASD") or developmental delay not known to be related to ASD ("DD"), or a subject that exhibits or is likely to exhibit symptoms of ASD or said developmental delay, to one or more healthy control-subjects or a compendium of healthy control subjects, wherein each healthy control-subject is known not to have ASD or DD, the method comprising:

determining a read-count of one or more microRNAs ("miRNA") and/or one or more microbial transcriptomic sequences in a biological sample taken from a subject, normalizing epigenetic data and/or microbial data of the subject to account for inter-sample count variations, wherein count normalization uses one or more invariant miRNAs or other invariant RNAs to represent data in proportion to their relative abundance, determining the time of day that the biological sample was taken, applying a time-of-day normalization to the count normalized miRNA and microbial transcriptomic sequence data by using the time-of-day to further normalize the subject's miRNA and microbial RNA abundance levels relative to time-of-day, and comparing the count and time-of-day normalized abundance levels of the one or more miRNAs and/or microbial RNAs against the count and time-of-day normalized abundance levels of one or more control miRNAs and/or one or more control microbial RNAs from one or more healthy control-subjects or a compendium of healthy control-subjects, wherein an increase or decrease in the abundance of the one or more of the subject's miRNAs and/or microbial RNAs as compared to the same one or more miRNAs and/or microbial RNAs from one or more healthy control-subjects or a compendium of healthy control-subjects or one or more developmentally delayed control-subjects or a compendium of developmentally delayed control-subjects, is indicative that the subject may have ASD or exhibits or is likely to exhibit ASD-related symptoms or that the subject may have DD or exhibits or is likely to exhibit DD-related symptoms. The increase or decrease in miRNA or microbial RNA may be compared to values from one or more healthy control subjects, one or more subjects with apparently typical development, one or more subjects with ASD, or one or more subjects with DD. When values from more than one subject are used as controls an averaged value may be used. Control subjects may be selected or matched for age, sex, or genetic background.

The method of embodiment 1 may be practiced in conjunction with one or more limitations described by embodiments 2-31.

2. A method for detecting or diagnosing an autism spectrum disorder ("ASD") comprising:

(a) determining an abundance or concentration level(s) of one or more micro RNAs ("miRNAs") in a saliva sample taken from a human subject, and (b) comparing the determined abundance or concentration level(s) of the one or more miRNAs against normal level(s) of the same one or more miRNAs, wherein the normal (or control) level is that found in a subject, an average from two of more subjects, not having an ASD; or abundance or concentration level(s) determined in the subject prior to appearance of one or more symptoms of an ASD, and (c) selecting a subject having an abnormal level of said one or more miRNAs as having, or as being at higher risk for having, an ASD;

wherein the one or more miRNAs is at least one selected from the group consisting hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, hsa-miR-146a-3p; miR-502, miR-502-3p, miR-502-5p, miR-125a, miR-125a-3p, miR-149-5p, miR-149, miR-149-3p, miR-193, miR-193-3p, miR-4705-3p, miR-4705-5p, miR-99b, miR-99b-3p, miR-99b-5p, miR-340-5p, miR-340, miR-340-3p, miR-183, miR-183-3p, miR-665-3p, miR-665-5p, miR 3074, miR-3074-3p, miR-3074-5p; miR-28-3p, miR-148a-5p, miR-151a-3p, mIR-125b-5p, miR-130b-3p, miR-92a, let-7d-3p, mir-598, miR-374c-5p, miR-374b-5p, miR-29c-3p, miR-1972, miR-675-3p, miR-7706, miR-500a-3p, miR-374a-5p, miR-190a-5p, let-7e-5p; miR-620, miR-1277-5p; miR-584-5p, let-7a-5p, mir-944, and miR-655; and/or those miRNA which share the seed sequences as the above listed miRNAs. In complementary or alternative embodiments, an increase or decrease in miRNA or microbial RNA may be compared to values from one or more healthy control subjects, one or more subjects with apparently typical development, one or more subjects with ASD, or one or more subjects with DD. When values from more than one subject are used as controls an averaged value may be used. Control subjects may be selected or matched for age, sex, or genetic background.

3. The method of embodiment 2, wherein said miRNA abundance levels are normalized to an abundance level, or average abundance level, of one or more housekeeping genes whose RNA abundance level is substantially invariant; and/or wherein said miRNA levels are normalized to compensate for diurnal or circadian fluctuations in the abundance of the one or more miRNA levels, normalized to compensate for fluctuations in the abundance of the one or more miRNAs due to food intake or exercise that raises the heart rate; or adjusted to compensate for differences in age, sex or genetic background.

4. The method of embodiment 2 or 3, wherein (a) determining a concentration of one or more miRNAs is done by RNA sequencing ("RNA-seq"), qPCR, a miRNA array, or multiplex miRNA profiling. (http://www.abcam.com/kits/review-of-mirna-assay-methods-qpcr-arrays-and-sequencing).

5. The method of embodiment 2, 3 or 4, wherein the at least one miRNA is selected from the group consisting of hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, and hsa-miR-146a-3p; and/or those miRNA which share the seed sequences as the above listed miRNAs.

6. The method of embodiment 2, 3, or 4, wherein the at least one miRNA is selected from the group consisting of miR-502, miR-502-3p, miR-502-5p, miR-125a, miR-125a-5p, miR-125a-3p, miR-149-5p, miR-149, miR-149-3p, miR-193a-5p, miR-193, miR-193-3p, miR-4705, miR-4705-3p, miR-4705-5p, miR-99b, miR-99b-3p, miR-99b-5p, miR-340-5p, miR-340, miR-340-3p miR-183-5p, miR-183, miR-183-3p, miR-665, miR-665-3p, miR-665-5p, miR 3074, miR-3074-3p, and miR-3074-5p; and/or those miRNA which share the seed sequences as the above listed miRNAs.

7. The method of embodiment 2, 3 or 4, wherein the at least one miRNA is selected from the group consisting of miR-28-3p, miR-148a-5p, miR-151a-3p, miR-149-5p, miR-125a-5p, mTR-125b-5p, miR-130b-3p, miR-92a, let-7d-3p, mir-598, miR-374c-5p, miR-374b-5p, miR-29c-3p, miR-1972, miR-675-3p, miR-7706, miR-500a-3p, miR-374a-5p, miR-190a-5p, and let-7e-5p; and/or those miRNA which share the seed sequences as the above listed miRNAs.

8. The method of embodiment 2, 3, or 4, wherein the at least one miRNA is selected from the group consisting of miR-665, miR-4705, miR-620, and miR-1277-5p; and/or those miRNA which share the seed sequences as the above listed miRNAs.

9. The method of embodiment 2, 3 or 4, wherein the at least one miRNA is selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or those miRNA which share the seed sequences as the above listed miRNAs.

10. The method of embodiment 2, 3 or 4, wherein the at least one miRNA is selected from the group consisting of miR-665, miR-4705, miR-620, and miR-1277-5p; and/or is at least one selected from the group consisting of miR-4705, miR-620, miR-1277-5p, miR-125a, and miR-193a-5p; and/or those miRNA which share the seed sequences as the above listed miRNAs.

11. The method of embodiment 2, 3 or 4, wherein the at least one miRNA is selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or is at least one selected from the group consisting of miR-655, miR-28-3p, miR-584-5p, let-7a-5p, miR-944, miR-148a-5p, miR-151a-3p, miR-125b-2-3p and miR-7706; and/or those miRNA which share the seed sequences as the above listed miRNAs.

13. The method of embodiment 2, 3 or 4, wherein the at least one miRNA is selected from the group consisting of miR-374c-5p, miR-29c-3p, or miR-190a-5p; and/or at least one selected from the group consisting of miR-28-3p, miR-148a-5p, miR-151a-3p, miR-125b-5p, miR-92a, mir-1972, and miR-7706; and/or those miRNA which share the seed sequences as the above listed miRNAs.

13. The method of embodiment 2, 3 or 4, wherein the at least one miRNA is selected from the group consisting of miR-665, miR-4705, miR-620, and miR-1277-5p; and/or selected from the group consisting of miR-665, miR-4705, miR-620, miR-1277-5p, let-7a-5p and miR-944; and/or those miRNA which share the seed sequences as the above listed miRNAs.

14. The method of embodiment 2, 3 or 4, wherein the at least one miRNA is selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or at least one selected from the group consisting of miR-125a, miR-193a-5p, miR-28-3p, miR-584-5p, miR-148a-5p, miR-151a-3p, miR-125b-2-3p, and miR-7706; and/or those miRNA which share the seed sequences as the above listed miRNAs.

15. The method of embodiment 2, 3 or 4, wherein the at least one miRNA is selected from the group consisting of miR-665, miR-4705, miR-620, and miR-1277-5p; and/or at least one selected from the group consisting of miR-665, miR-4705, miR-620, miR-1277-5p, let-7a-5p, and miR-944; and/or those miRNA which share the seed sequences as the above listed miRNAs.

16. The method of embodiment 2, 3 or 4, wherein the at least one miRNA is selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or at least one selected from the group consisting of miR-125a, miR-193a-5p, miR-28-3p, miR-584-5p, miR-148a-5p, miR-151a-3p, miR-125b-2-3p, and miR-7706; and/or those miRNA which share the seed sequences as the above listed miRNAs.

17. The method of embodiment 2, 3 or 4, wherein the at least one miRNA is selected from the group consisting of miR-374c-5p, miR-29c-3p, and miR-190a-5p; and/or at least one of miR-149-5p, miR-125a-5p, miR-130b-3p, let-7d-3p, miR-598, miR-374b-5p, miR-675-3p, miR-500a-3p, miR-374a-5p, and let-7e-5p; and/or those miRNA which share the seed sequences as the above listed miRNAs.

18. The method of any one of embodiments 2-17, wherein the saliva sample is taken from the human subject at a particular time of day and the concentration level(s) of miRNAs in said sample are compared to normal miRNA values in saliva taken at the same time of day under otherwise identical conditions.

19. The method of any one of embodiments 2-17, wherein the saliva sample is taken from the human subject at a different time of day than the time of day at which the normal level(s) of miRNAs were determined, further comprising adjusting or normalizing the value of the miRNA level(s) determined in the saliva sample to compensate for diurnal or circadian fluctuations in miRNA level(s).

20. The method of embodiment any one of embodiments 2-17, wherein the saliva sample is taken from the human subject at a different time of day than the time of day at which the normal level(s) of miRNAs were determined, further comprising adjusting or normalizing the value of the miRNA level(s) determined in the saliva sample to compensate for diurnal or circadian fluctuations in miRNA level(s) using a regression model or other statistical analysis; or to compensate for age, sex, or genetic background.

21. The method of any one of embodiments 2-20, wherein the saliva sample is taken within 1 hour of waking, before brushing or rinsing the mouth, before eating or drinking, and/or before exercise that elevates heart rate.

22. The method of any one of embodiments 2-21, wherein said selecting comprises selecting a subject having abnormal levels of four or more of said miRNAs, and, optionally calculating a Pearson correlation coefficient of said abnormal miRNA levels with likelihood of at least one symptom of an ASD.

23. The method of any one of embodiments 2-21, wherein said selecting comprises selecting a subject having abnormal levels of ten or more of said miRNAs, and, optionally calculating a Pearson correlation coefficient of said abnormal miRNA levels with likelihood of at least one symptom of an ASD.

24. The method of any one of embodiments 2-23, further comprising determining an abundance level of RNA(s) in said subject from one or more salivary microbes selected from the group consisting of *Prevotella timonensis*, *Streptococcus vestibularis*, *Enterococcus faecalis*, *Acetomicrobium hydrogeniformans*, *Streptococcus* sp. HMSC073D05, *Rothia dentocariosa*, *Prevotella marshii*, *Prevotells* sp. HMSC073D09, *Propionibacterium acnes*, and *Campylobacter* or a microbe having a genome that is at least 90, 95, 96, 97, 98, 99, 99.5 or 100% similar or identical thereto; and comparing the abundance level(s) of the microbial RNAs against normal level(s) of the same one or more microbial RNAs, wherein the normal (or control) abundance level is that found in a subject, an average from two of more subjects, not having an ASD; or concentration level(s) determined in the subject prior to appearance of one or more symptoms of a condition, disorder, or disease associated with an abnormal diurnal or circadian rhythm; and further selecting a subject having an abnormal abundance of said one or more microbial RNAs as having or as being at higher risk for having an ASD. Further information about these microbes may be accessed at https://_jgi.doe.gov/ or at http://_www.uniprot.org/proteomes/ both of which are incorporated by reference.

Nucleotide Basic Local Alignment Search Tool (BLASTn) may be used to identify a polynucleotide sequence having at least 70%, 75%, 80%, 85%, 87.5%, 90%, 92.5%, 95%, 97.5%, 98%, 99% sequence identity to a reference polynucleotide. A representative BLASTn setting optimized to find highly similar sequences uses an Expect Threshold of 10 and a Wordsize of 28, max matches in query range of 0, match/mismatch scores of 1/-2, and linear gap cost. Low complexity regions may be filtered/masked. Default settings are described by and incorporated by reference to http://blast.ncbi.nlm.nih.gov/Blast.cgi?PROGRAM=blastn&BLAST_PROGRAMS=megaBlast&PAGE_TYPE=BlastSearch&SHOW_DEFAULTS=on&LINK_LOC=blasthome (last accessed Mar. 19, 2018)(incorporated by reference).

25. The method of any one of embodiments 2-24, wherein determining salivary miRNA levels or determining microbial RNA abundance level(s) is done by RNA sequencing (RNA-seq). (https://_en.wikipedia.org/wiki/RNA-Seq).

26. The method of embodiment 25, wherein the sequencing data raw read counts are quantile-normalized, mean-centered, and divided by the standard deviation of each variable; data are normalized to account for inter-sample count variations; and/or wherein data are normalized to abundance of one or more invariant miRNAs to describe relative and/or absolute abundance levels; and optionally further statistically analyzing the normalized data.

27. The method of any one of embodiments 2-26, further comprising treating a subject having at least one abnormal level of miRNA with a regimen that reduces the at least one abnormal salivary level of one or more miRNAs and/or reduces one or more abnormal microbial RNA abundance levels.

28. The method of embodiment 27, further comprising obtaining saliva samples on at least two different points in time from the subject and determining efficacy of a treatment regimen when said second or subsequent saliva sample has miRNA level(s) and/or microbial RNA abundance levels closer to normal.

29. The method of any one of embodiments 2-26, further comprising treating a subject selected as having or as being at higher risk for having an ASD with a regimen that reduces at least one abnormal salivary abundance of one or more miRNAs or one or more microbial RNA abundance levels, wherein said regimen comprises administering one or more of surgical therapy, drug therapy, a miRNA or miRNA antagonist therapy, antimicrobial therapy, diet or nutritional therapy, physical therapy, phototherapy, psychotherapy, behavior therapy, or an alternative medical therapy.

30. A miRNA assay kit for detecting miRNAs and/or microbial RNA comprising one, two or more probes or primers complementary to or otherwise suitable for amplification and/or detection of at least one miRNA selected from the group consisting hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, hsa-miR-146a-3p; miR-502, miR-502-3p, miR-502-5p, miR-125a, miR-125a-3p, miR-149-5p, miR-149, miR-149-3p, miR-193, miR-193-3p, miR-4705-3p, miR-4705-5p, miR-99b, miR-99b-3p, miR-99b-5p, miR-340-5p, miR-340, miR-340-3p, miR-183, miR-183-3p, miR-665-3p, miR-665-5p, miR 3074, miR-3074-3p, miR-3074-5p; miR-28-3p, miR-148a-5p, miR-151a-3p, miR-125b-5p, miR-130b-3p, miR-92a, let-7d-3p, mir-598, miR-374c-5p, miR-374b-5p, miR-29c-3p, miR-1972, miR-675-3p, miR-7706, miR-500a-3p, miR-374a-5p, miR-190a-5p, let-7e-5p; miR-620, miR-1277-5p; miR-584-5p, let-7a-5p, mir-944, and miR-655; and/or those miRNA which share the seed sequences as the above listed miRNAs; and optionally: one or more sample collection tools, one or more sample collection containers, one or more reagents for amplification and/or detection and/or quantification of said miRNAs and/or microbial RNA, one or more positive or negative controls, one or more reaction substrates or platforms, packaging material(s) and/or instructions for use.

31. A method for identifying a concentration of at least one miRNA that correlates with at least one symptom of an ASD comprising:
   (a) collecting saliva samples from one or more subjects,
   (b) sequencing miRNA in said samples,
   (c) identifying differently abundant miRNAs by counting sequencing reads per miRNA, normalizing sequence read data, and comparing normalized sequence read counts among saliva samples taken at different times,
   (d) normalizing sequence read data to RNA expression of a housekeeping gene or miRNA (which exhibits invariant abundance or to an averaged RNA abundance from two or more housekeeping genes,
   (e) calculating a Pearson correlation coefficient for data obtained describing concentration levels of one or more miRNAs and one or more RNA abundance levels from a microorganism found in saliva and at least one symptom of an ADS, (f) selecting one or more miRNAs as having an abnormal abundance level that correlates with at least one symptom of an ASD; and (g) optionally, determining target genes for miRNAs using DIANA miRpath or other software.

Other compatible, complementary or alternative embodiments of the invention include the following:

32. A method of comparing epigenetic and/or microbiome data for a subject suspected of having Autism Spectrum Disorder (ASD) or developmental delay not known to be related to ASD ("DD"), or a subject that exhibits or is likely to exhibit symptoms of ASD or said developmental delay to one or more healthy control-subjects or a compendium of healthy control subjects the method comprising:

determining a read-count of one or more microRNAs (miRNA) and/or one or more microbial transcriptomic sequences in a biological sample taken from a subject, normalizing epigenetic data and/or microbial transcriptomic sequence data of the subject to account for inter-sample count variations, wherein count normalization that uses one or more invariant miRNAs or other invariant RNAs, represent data in proportion to their relative abundance, determining the time of day that the biological sample was taken, applying a time-of-day normalization to the count normalized miRNAs and microbial RNAs by using the time-of-day to further normalize the subject's miRNA and microbial RNA abundance levels relative to time-of-day, and comparing the count and time-of-day normalized abundance levels of the one or more miRNAs and/or microbial RNAs against the count and time-of-day normalized abundance levels of one or more control miRNAs and/or one or more control microbial RNAs from one or more healthy control-subjects or a compendium of healthy control-subjects, wherein an increase or decrease in the abundance levels of the one or more of the subject's miRNAs and/or microbial RNAs, as compared to the same one or more miRNAs and/or microbial RNAs from one or more healthy control-subjects or a compendium of healthy control-subjects or one or more developmentally delayed control-subjects or a compendium of developmentally delayed control-subjects is indicative that the subject may have ASD or exhibits or is likely to exhibit ASD-related symptoms or is indicative that the subject may have DD or exhibits or is likely to exhibit DD-related symptoms. In complementary or alternative embodiments, an increase or decrease in miRNA or microbial RNA may be compared to values from one or more healthy control subjects, one or more subjects with apparently typical development, one or more subjects with ASD, or one or more subjects with DD. When values from more than one subject are used as controls an averaged value may be used. Control subjects may be selected or matched for age, sex, or genetic background.

33. The method of embodiment 32, wherein a positive or negative difference in the abundance levels of the one or more of the subject's miRNAs and/or microbial RNAs as compared to the same one or more miRNAs and/or microbial RNAs from one or more healthy control-subjects or a compendium of healthy control-subjects is indicative of severity of the ASD-related symptoms, or one or more developmentally delayed control-subjects or a compendium of developmentally delayed control-subjects.

34. The method of embodiment 32, wherein the miRNAs are selected from a group consisting of hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, hsa-miR-146a-3p and/or those miRNA which share the seed sequences as the above listed miRNAs.

35. The method of embodiment 32, wherein the microbes identified by microbial RNAs are selected from a group consisting of Taxonomy ID 1095749 *Pasteurella bettyae* CCUG 2042, Taxonomy ID 1236 Gammaproteobacteria, Taxonomy ID 1239 Firmicutes, Taxonomy ID 1715084 *Rothia* sp. HMSC065C03, Taxonomy ID 1739299 *Streptococcus* sp. HMSC056C01, Taxonomy ID 1739336 *Streptococcus* sp. HMSC073D05, Taxonomy ID 1739408 *Streptococcus* sp. HMSC072G04, Taxonomy ID 186826 Lactobacillales, Taxonomy ID 537011 *Prevotella copri* DSM 18205, Taxonomy ID 712 Pasteurellaceae, Taxonomy ID 889206 *Streptococcus* vestibularis ATCC 49124 and/or those microbes which are mutations of or which are functional homologs of the above listed microbes, such as those having genomes that are at least 90, 95, 96, 97, 98, 99, 99.5 or 100% similar or identical thereto. BLASTN may be used to identify a polynucleotide or genomic sequence having at least 70%, 75%, 80%, 85%, 87.5%, 90%, 92.5%, 95%, 97.5%, 98%, 99% sequence identity to a reference polynucleotide such as those having at least 90, 95, 96, 97, 98 or 99% genomic identity to the microbes described above.

36. The method of embodiment 32, wherein the biological sample is saliva, cerebral spinal fluid, blood, serum, plasma, urine, feces, mucosal excretions, tears or tissue.

37. The method of embodiment 32, wherein the abundance levels of one or more miRNAs and/or microbes are determined by a real time PCR or next generation sequencing.

38. A method of monitoring the progression of a disorder or disease state in a subject, the method comprising:

analyzing at least two biological samples from the same subject taken at different time points to determine a count and time-of-day normalized abundance levels of one or more miRNAs and/or microbes in each of the at least two biological samples, and comparing the determined levels of the one or more miRNAs and/or microbes over time to determine a change over time of the subject's count and time-of-day normalized abundance levels of the one or more specific miRNAs and/or microbes;

wherein an increase or decrease in the count and time-of-day normalized abundance levels of the one or more miRNAs and/or microbes over time is indicative of a progression of ASD or ASD-related symptoms in the subject, and/or wherein a positive or negative difference in the abundance levels of the count and time-of-day normalized abundance levels of the one or more miRNAs and/or microbes over time is/are indicative of the progression of ASD or ASD-related symptoms in the subject.

39. The method of embodiment 38, wherein the miRNAs are selected from the group consisting of hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, and hsa-miR-146a-3p, and/or those miRNA which share the seed sequences as the above listed miRNAs.

40. The method of embodiment 38, wherein the microbes identified by RNAs are selected from a group consisting of Taxonomy ID 1095749 *Pasteurella bettyae* CCUG 2042, Taxonomy ID 1236 Gammaproteobacteria, Taxonomy ID 1239 Firmicutes, Taxonomy ID 1715084 *Rothia* sp.

HMSC065CO3, Taxonomy ID 1739299 *Streptococcus* sp. HMSC056C01, Taxonomy ID 1739336 *Streptococcus* sp. HMSC073D05, Taxonomy ID 1739408 *Streptococcus* sp. HMSC072G04, Taxonomy ID 186826 Lactobacillales, Taxonomy ID 537011 *Prevotella copri* DSM 18205, Taxonomy ID 712 Pasteurellaceae, Taxonomy ID 889206 *Streptococcus vestibularis* ATCC 49124 and/or those microbes which are mutations of or which are functional homologs of the above listed microbes.

41. The method of embodiment 38, wherein the biological sample is saliva, cerebral spinal fluid, blood, serum, plasma, urine, feces, mucosal excretions, tears or tissue.

42. The method of embodiment 38, wherein the abundance levels of one or more miRNAs and/or microbes are determined by a real-time PCR or next generation sequencing.

43. A method of detecting a miRNA sequence or a plurality of miRNA sequences in a biological sample of a subject, comprising:
obtaining a biological sample from the subject;
creating a double-stranded, complementary DNA sequence (cDNA) for each of one or more miRNA sequences selected from the group consisting of hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, and hsa-miR-146a-3p, and/or those miRNA which share the seed sequences as the above listed miRNAs; and
detecting the presence, absence or relative quantity of cDNA, wherein the presence, absence or relative quantity of cDNA is indicative of the presence, absence or relative quantity of the complementary miRNA sequences.

44. A method of detecting a miBIOME sequence or a plurality of miBIOME sequences in a biological sample of a subject, the method comprising:
obtaining a biological sample from the subject;
creating a double-stranded, complementary DNA sequence (cDNA) for each of one or more microbial RNA sequences selected from microbes belonging to the group consisting of Taxonomy ID 1095749 *Pasteurella bettyae* CCUG 2042, Taxonomy ID 1236 Gammaproteobacteria, Taxonomy ID 1239 Firmicutes, Taxonomy ID 1715084 *Rothia* sp. HMSC065CO3, Taxonomy ID 1739299 *Streptococcus* sp. HMSC056C01, Taxonomy ID 1739336 *Streptococcus* sp. HMSC073D05, Taxonomy ID 1739408 *Streptococcus* sp. HMSC072G04, Taxonomy ID 186826 Lactobacillales, Taxonomy ID 537011 *Prevotella copri* DSM 18205, Taxonomy ID 712 Pasteurellaceae, and Taxonomy ID 889206 *Streptococcus vestibularis* ATCC 49124; and
detecting the presence, absence or relative quantity of cDNA, wherein the presence, absence or relative quantity of cDNA is indicative of the presence, absence or relative quantity of the complementary miBIOME sequences.

45. The method of embodiment 44, wherein the biological sample is saliva, cerebral spinal fluid, blood, serum, plasma, urine, feces, mucosal excretions, tears, or tissue.

46. The method of embodiment 44, wherein the biological sample is a first biological sample taken at a first time point and the cDNA is a first cDNA, the method further comprising:
obtaining a second biological sample from said subject at a second time point;
creating a second cDNA for each of one or more miRNA sequences selected from the group consisting of hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, and hsa-miR-146a-3p;
creating a second cDNA for each of one or more microbial RNA sequences selected from microbes belonging to the group consisting of Taxonomy ID 1095749 *Pasteurella bettyae* CCUG 2042, Taxonomy ID 1236 Gammaproteobacteria, Taxonomy ID 1239 Firmicutes, Taxonomy ID 1715084 *Rothia* sp. HMSC065CO3, Taxonomy ID 1739299 *Streptococcus* sp. HMSC056C01, Taxonomy ID 1739336 *Streptococcus* sp. HMSC073D05, Taxonomy ID 1739408 *Streptococcus* sp. HMSC072G04, Taxonomy ID 186826 Lactobacillales, Taxonomy ID 537011 *Prevotella copri* DSM 18205, Taxonomy ID 712 Pasteurellaceae, and Taxonomy ID 889206 *Streptococcus vestibularis* ATCC 49124;
and detecting the presence, absence or relative quantity of the second cDNA, wherein the presence, absence or relative quantity of the second cDNA in said biological sample from said second time point is indicative of the presence, absence or relative quantity of the complementary miRNA sequences and/or microbial sequences at the second time point; and optionally tracking the progression of ASD and/or ASD-related symptoms by comparing results from the first time point to results from the second time point.

47. A kit for determining whether a subject has ASD and/or ASD-related symptoms, the kit comprising: a probe set comprising 2 or more miRNA probes having ribonucleotide sequences corresponding to ribonucleotide sequences of miRNAs selected from the group consisting of hsa-miR-151a-5p, hsa-miR-183-5p, hsa-miR-4705, hsa-miR-193a-5p, hsa-miR-149-5p, hsa-miR-21-5p, hsa-miR-665, hsa-miR-125a-5p, hsa-miR-502-3p, hsa-miR-25-3p, hsa-miR-221-3p, hsa-miR-30e-5p, hsa-miR-125b-2-3p, and hsa-miR-146a-3p, and/or those miRNA which share the seed sequences as the above listed miRNAs.

48. The kit of embodiment 47, further comprising a solid support attached to the probe set.

49. The kit of embodiment 47, further comprising at least one of the following: (a) one randomly-generated ribonucleotide sequence used as a negative control; (b) at least one oligonucleotide sequence derived from a housekeeping gene, used as a standardized control for total RNA degradation; and (c) at least one randomly-generated ribonucleotide sequence used as a positive control.

50. A microarray comprising at least 10, preferably at least 15, more preferably at least 20 probes comprising nucleotide sequences corresponding to sequences of miRNAs.

51. The microarray of embodiment 50, wherein at least some of the miRNAs are selected from the group consisting of miR-502, miR-502-3p, miR-502-5p, miR-125a, miR-125a-5p, miR-125a-3p, miR-149-5p, miR-149, miR-149-3p, miR-193a-5p, miR-193, miR-193-3p, miR-4705, miR-4705-3p, miR-4705-5p, miR-99b, miR-99b-3p, miR-99b-5p, miR-340-5p, miR-340, miR-340-3p miR-183-5p, miR-183, miR-183-3p, miR-665, miR-665-3p, miR-665-5p, miR 3074, miR-3074-3p, and miR-3074-5p, and/or those miRNA which share the seed sequences as the above listed miRNAs, on a support.

52. The microarray of embodiment 50 or 51, comprising:
a set of at least probes comprising nucleotide sequences corresponding to sequences of miRNAs selected from the group consisting of miR-502, miR-502-3p, miR-502-5p, miR-125a, miR-125a-5p, miR-125a-3p, miR-149-5p, miR-149, miR-149-3p, miR-193a-5p, miR-193, miR-193-3p, miR-4705, miR-4705-3p, miR-4705-5p, miR-99b, miR- 99b-3p, miR-99b-5p, miR-340-5p, miR-340, miR-340-3p miR-183-5p, miR-183, miR-183-3p, miR-665, miR-665-3p, miR-665-5p, miR 3074, miR-3074-3p, and miR-3074-5p, and/or those miRNA which share the seed sequences as the above listed miRNAs, and optionally a set of probes comprising nucleotide sequences capable of detecting and quantifying at least one microbial genetic sequence present in the saliva sample, wherein the at least one microbial sequence is from at least one organism selected from the group consisting of *Prevotella timonensis, Streptococcus vestibularis, Enterococcus faecalis, Acetomicrobium hydrogeniformans, Streptococcus* sp. HMSC073D05, *Rothia dentocariosa, Prevotella marshii, Prevotells* sp. HMSC073D09, *Propionibacterium acnes*, and *Campylobacter*.

53. A method of detecting miRNA abundance profiles in a subject being analyzed for an autism spectrum disorder (ASD), the method comprising:

detecting profile alterations of micro RNAs (miRNA) in a sample obtained from the subject, preferably the sample is a saliva sample, compared to a miRNA profile of a healthy individual or individual with non-ASD developmental delay, wherein the miRNA profile comprises at least 10, preferably at least 15, more preferably at least 20 miRNAs.

54. The method of embodiment 53, further comprising detecting a profile of microbial genetic sequences present in a saliva sample of the subject compared to a profile of microbial RNA from saliva of a healthy individual or individual with non-ASD developmental delay.

55. The method of embodiment 53, wherein some of the miRNAs are at least one selected from the group consisting of miR-502, miR-502-3p, miR-502-5p, miR-125a, miR-125a-5p, miR-125a-3p, miR-149-5p, miR-149, miR-149-3p, miR-193a-5p, miR-193, miR-193-3p, miR-4705, miR-4705-3p, miR-4705-5p, miR-99b, miR-99b-3p, miR-99b-5p, miR-340-5p, miR-340, miR-340-3p miR-183-5p, miR-183, miR-183-3p, miR-665, miR-665-3p, miR-665-5p, miR 3074, miR-3074-3p, and miR-3074-5p, and/or those miRNA which share the seed sequences as the above listed miRNAs.

56. The method of embodiment 54, wherein the microbes identified by RNA sequences comprises at least two selected from the group of microbes consisting of *Prevotella timonensis, Streptococcus vestibularis, Enterococcus faecalis, Acetomicrobium hydrogeniformans, Streptococcus* sp. HMSC073D05, *Rothia dentocariosa, Prevotella marshii, Prevotells* sp. HMSC073D09, *Propionibacterium acnes*, and *Campylobacter*.

57. A method of treating an autism spectrum disorder in a subject, the method comprising treating the subject with one or more of a behavior therapy, a communication therapy, a diet therapy, a medication therapy, and an alternative medical therapy, wherein the subject is identified for treating the autism spectrum disorder by the method of any one of claims 53-56.

58. The method of embodiment 57, wherein the autism spectrum disorder comprises a deficit in at least one of social communication, social interaction, repetitive patterns of behavior as classified in the diagnostic and statistical manual of mental disorders, fifth edition (DSM-5, 2013).

59. A microarray comprising a set of probes comprising nucleotide sequences capable of detecting and quantifying at least one microbial genetic sequence present in a saliva sample that are correlative to autism spectrum disorder.

60. The microarray of embodiment 59, further comprising a set of at least 10, preferably at least 15, more preferably at least 20 probes comprising nucleotide sequences corresponding to sequences of miRNAs that are correlative to autism spectrum disorder.

61. A method detecting miRNA abundance profiles in a subject being analyzed for an autism spectrum disorder (ASD), the method comprising: detecting a profile of microbial genetic sequences present in a saliva sample of the subject compared to a profile of mBIOME from saliva of a healthy individual or an individual with non-ASD developmental delay.

62. A method for detecting or diagnosing ASD comprising:

detecting one or more miRNAs associated with ASD in saliva of a subject, detecting or diagnosing ASD when said miRNA is present in an amount significantly below or above that of a subject who does not have an ASD; and optionally treating the subject for ASD.

63. The method of embodiment 62, wherein detecting or diagnosing comprises detecting an abnormal level of one or more microRNAs associated with difficulties with oral-motor and/or oral-sensory processing.

64. The method of embodiment 63, wherein the oral-motor processing is speech apraxia and/or the oral-sensory processing is food texture sensitivity.

65. The method of embodiment 62, wherein detecting or diagnosing comprises detecting an abnormal level of one or more microRNAs associated with difficulties with axonal guidance, neurotrophic signaling, GABAergic synapse, or nicotine addiction.

66. The method of embodiment 62, wherein detecting or diagnosing comprises detecting an abnormal level of one or more microRNAs associated with difficulties with social affect or with restricted/repetitive behavior.

67. The method of embodiment 62, wherein the one or more microRNAs comprises at least one selected from the group consisting of miR-28-3p, miR-148a-5p, miR-151a-3p, miR-149-5p, miR-125a-5p, mIR-125b-5p, miR-130b-3p, miR-92a, let-7d-3p, mir-598, miR-374c-5p, miR-374b-5p, miR-29c-3p, miR-1972, miR-675-3p, miR-7706, miR-500a-3p, miR-374a-5p, miR-190a-5p, and let-7e-5p.

68. The method of embodiment 62, wherein an increased level of one or more microRNA compared to microRNA levels in a TD or DD subject is associated with ASD wherein an increased level of one or more microRNA compared to microRNA levels in a TD or DD subject is associated with ASD and wherein the increased level of at least one microRNA selected from the group consisting of miR-665, miR-4705, miR-620, and miR-1277-5p is detected.

69. The method of embodiment 62, wherein a decreased level of one or more microRNA compared to microRNA levels in a TD or DD subject is associated with ASD.

70. The method of embodiment 62, wherein a decreased level of one or more microRNA compared to microRNA levels in a normal subject is associated with ASD wherein a decreased level of one or more microRNA compared to microRNA levels in a TD or DD subject is associated with ASD and wherein the decreased level of at least one microRNA selected from the group consisting of miR-125a, miR-193a-5p, miR-28-3p, miR-584-5p, let-7a-5p, miR-944, miR-148a-5p, miR-151a-3p, miR-125b-2-3p and miR-7706 is detected.

71. The method of embodiment 62, comprising detecting or diagnosing ASD when at least one miRNA is selected from the group consisting of miRNAs present in an amount above that of a subject who does not have ASD and at least one miRNA selected from the group consisting of miRNAs present in an amount below that of a subject who does not have ASD.

72. The method of embodiment 62, comprising detecting or diagnosing ASD when a ratio of a normalized value of at least one miRNA present in an amount above that in a subject without ASD to a normalized value of at least one miRNA present in an amount below that in a subject without ASD ranges from at least 0.1, 0.2, 0.5, 1, 2, 3, 4, 5, 6, 7, 8, 9 to 10 and all intervening and intermediate values, wherein the ratio is based on a normalized value determined by dividing the amount of miRNA by the amount of miRNA in a subject not having ASD.

73. The method of embodiment 62, further comprising differentially detecting or diagnosing ASD from DD by detecting an increase in one or more of the miRNAs selected from the group consisting of miR-665, miR-4705, miR-620, and miR-1277-5p; and/or a decrease in one or more of the microRNAs selected from the group consisting of miR-4705, miR-620, miR-1277-5p, miR-125a, and miR-193a-5p.

74. The method of embodiment 62, further comprising differentially detecting or diagnosing ASD from DD by detecting a decrease in one or more of the miRNAs selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or an increase in one or more of the miRNAs selected from the group consisting of miR-655, miR-28-3p, miR-584-5p, let-7a-5p, miR-944, miR-148a-5p, miR-151a-3p, miR-125b-2-3p and miR-7706.

75. The method of embodiment 62, further comprising differentially detecting or diagnosing ASD from DD by detecting at least one of mir-374c-5p, miR-29c-3p, or miR-190a-5p; and at least one of miR-28-3p, miR-148a-5p, miR-151a-3p, miR-125b-5p, miR-92a, mir-1972, or miR-7706.

76. The method of embodiment 62, further comprising differentially detecting or diagnosing ASD from TD by detecting an increase in one or more of the microRNAs selected from the group consisting of miR-665, miR-4705, miR-620, and miR-1277-5p; and/or a decrease in one or more of the microRNAs selected from the group consisting of miR-665, miR-4705, miR-620, miR-1277-5p, let-7a-5p and miR-944.

77. The method of embodiment 62, further comprising differentially detecting or diagnosing ASD from TD by detecting a decrease in one or more of the miRNAs selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or an increase in one or more of the miRNAs selected from the group consisting of miR-125a, miR-193a-5p, miR-28-3p, miR-584-5p, miR-148a-5p, miR-151a-3p, miR-125b-2-3p, and miR-7706.

78. The method of embodiment 62, further comprising differentially detecting or diagnosing ASD from TD by detecting an increase in one or more of the miRNAs selected from the group consisting of miR-665, miR-4705, miR-620, and miR-1277-5p; and/or a decrease in one or more of the miRNAs selected from the group consisting of miR-665, miR-4705, miR-620, miR-1277-5p, let-7a-5p, and miR-944.

79. The method of embodiment 62, further comprising differentially detecting or diagnosing ASD from TD by detecting a decrease in one or more of the miRNAs selected from the group consisting of miR-125a, miR-193a-5p, miR-28-3p, miR-584-5p, let-7a-5p, miR-944, miR-148a-5p, miR-151a-3p, miR-125b-2-3p and miR-7706; and/or an increase in one or more of the miRNAs selected from the group consisting of miR-125a, miR-193a-5p, miR-28-3p, miR-584-5p, miR-148a-5p, miR-151a-3p, miR-125b-2-3p, and miR-7706.

80. The method of embodiment 62, further comprising differentially detecting or diagnosing ASD and excluding TD by detecting at least one of mir-374c-5p, miR-29c-3p, and miR-190a-5p; and at least one of miR-149-5p, miR-125a-5p, miR-130b-3p, let-7d-3p, miR-598, mir374b-5p, miR-675-3p, mir-500a-3p, miR-374a-5p, and let-7e-5p.

81. The method of embodiment 62, wherein the saliva is collected with a swab. 82. The method of embodiment 62, wherein the subject is at least 0, 1, 2, 3, 4, 5, 6, 7, 8, 9, 10, 11, or 12 months, or 1, 2, 3, 4, 5, 6, 7, 8, 9, 10, 11, 12, 13, 14, 15, 16, 17, 18, 19, 20, 21, 22, 23, 24, or 25 years old.

83. A method for differentially detecting or diagnosing DD from TD in a subject who does not have ASD, the method comprising:

detecting a decrease in an amount of one or more of miRNAs selected from the group consisting of miR-125a-5p and miR 584-5p; and/or an increase in an amount of let-7a-5p and miR-944, thereby detecting a subject having DD; and optionally treating the subject for DD; or detecting a decrease in an amount of one or more of miRNAs selected from the group consisting of miR-665, let-7a-5p, and miR-944; and/or an increase in an amount of miR-125a-5p and miR-193a-5p, thereby detecting a subject having TD; and optionally withdrawing the subject from a treatment for DD.

84. A composition having two or more probes that detect micro-RNAs associated with ASD, DD, or TD.

85. A kit for detection of miRNAs in saliva comprising one, two or more probes that recognize miRNAs and optionally, excipients, buffers, platforms, containers, indicators, packing materials or instructions for use.

86. A method for monitoring brain development, brain repair, or brain rejuvenation in a subject, the method comprising:

detecting one or more miRNAs associated with brain development, brain repair, or brain rejuvenation in saliva of the subject and prognosing brain development, brain repair, or brain rejuvenation when said miRNA is present in an amount significantly below or above that of a control subject who is not undergoing brain development, brain repair, or brain rejuvenation, and optionally selecting to initiate, continue, change, or discontinue treatment.

87. The method of embodiment 86, wherein prognosing comprises detecting an abnormal level of one or more miRNAs associated with desired brain development, brain repair or brain rejuvenation.

88. A method of normalizing epigenetic sequence data to account for temporal variations in microRNA (miRNA) abundance, the method comprising:

determining read-counts of one or more miRNAs in a biological sample taken from a subject, normalizing epigenetic data of the subject to account for inter-sample read-count variations, wherein the read-count normalization uses one or more invariant miRNAs, determining time of day that the biological sample was taken, and applying an algorithm to the read-count normalized miRNAs, wherein the algorithm uses the time-of-day to normalize the subject's miRNA abundance levels relative to time-of-day.

89. A method of comparing epigenetic sequencing data for a subject with a suspected disorder or disease, to one or more healthy control-subjects or a compendium of healthy control subjects, each healthy control-subject being known not to have ASD, the method comprising:

normalizing the subject's epigenetic sequence data to account for read-count variations, further normalizing the epigenetic sequence data to account for temporal variations in abundance, comparing the read-count and time-of-day normalized abundance levels of the one or more of the subject's miRNAs against read-count and time-of-day normalized abundance levels of the same one or more miRNAs from one or more healthy control-subjects or a compendium of healthy control-subjects, wherein an increase or decrease in the abundance levels of the one or more of the subject's miRNAs against the same one or more miRNAs from one or more healthy control-subjects or a compendium of healthy control-subjects is indicative that the subject may have a disorder or disease state.

90. The method of embodiment 89, wherein the miRNAs are selected from the group consisting of Group A circadian-varying microRNAs (circaMiRs) and/or those miRNAs which share the seed sequences of the Group A circaMiRs.

91. The method of embodiment 89, wherein the miRNAs are selected from the group consisting of both Group A circaMiRs and Group B circaMiRs and/or those miRNAs which share the seed sequences of the Group A circaMiRs and Group B circaMiRs.

92. The method of embodiment 89, wherein the subject is suspected to have ASD-related symptoms.

93. The method of embodiment 89, wherein the biological sample is saliva, cerebral spinal fluid, blood, serum, plasma, urine, feces, mucosal excretions, tears or tissue.

94. A method of monitoring progression of a disorder or disease state in a subject, the method comprising:

analyzing at least two biological samples from the subject taken at different time points to determine a read-count and time-of-day normalized abundance levels of one or more specific miRNAs in each of the at least two biological samples, and comparing the determined levels of the one or more specific miRNAs over time to determine if the subject's read-count and time-of-day normalized abundance levels of the one or more specific miRNAs is changing over time, wherein an increase or decrease in the read-count and time-of-day normalized abundance levels of the one or more specific miRNAs over time is indicative that the subject's disorder or disease state is improving or deteriorating.

95. The method of embodiment 94, wherein the miRNAs subject to time-of-day normalization are selected from the group consisting of Group A circaMiRs and/or those miRNA which share the seed sequences of the Group A circaMiRs.

96. The method of embodiment 94, wherein the miRNAs subject to time-of-day normalization are selected from the group consisting of Group A circaMiRs and Group B circaMiRs and/or those miRNA which share the seed sequences of the Group A circaMiRs and Group B circaMiRs.

97. The method of embodiment 94, wherein the biological sample is saliva, cerebral spinal fluid, blood, serum, plasma, urine, feces, mucosal excretions, tears or tissue.

98. The method of embodiment 94, wherein the subject is suspected to have ASD-related symptoms.

99. A method of normalizing epigenetic sequence data to account for temporal variations in microbiome genetic sequence abundance, the method comprising:

determining read-counts of one or more microbial genetic sequence abundance in a biological sample taken from a subject, normalizing the subject's epigenetic sequence data to account for inter-sample read-count variations, wherein the read-count normalization uses one or more invariant miRNAs, determining time of day that the biological sample was taken, and applying an algorithm to the read-count normalized microbial abundance, wherein the algorithm uses the time-of-day to normalize the subject's microbial abundance levels relative to time-of-day.

100. A method of comparing the epigenetic sequence for a subject with a disorder or disease state, to one or more healthy control-subjects or a compendium of healthy control subjects, each healthy control-subject being known not to have the disorder or disease, the method comprising:

normalizing subject's epigenetic sequence data to account for read-count variations, further normalizing the epigenetic sequence data to account for temporal variations in abundance, comparing read-counts and time-of-day normalized abundance levels of the one or more of the subject's microbial RNA abundance against read-counts and time-of-day normalized abundance levels of the same one or more microbes from one or more healthy control-subjects or a compendium of healthy control-subjects, wherein an increase or decrease in the abundance levels of the one or more of the subject's microbial RNAs against the same one or more microbial RNAs from one or more healthy control-subjects or a compendium of healthy control-subjects is indicative that the subject may have the disorder or disease state.

101. The method of embodiment 100, wherein the microbial RNAs are selected from the group consisting of Group C microbial RNAs.

102. The method of embodiment 100, wherein the biological sample is saliva, cerebral spinal fluid, blood, serum, plasma, urine, feces, mucosal excretions, tears or tissue.

103. The method of embodiment 100, wherein the subject is suspected to have ASD-related symptoms.

104. A method of monitoring the progression of a disorder or disease state, in a subject, the method comprising:

analyzing at least two biological samples from the subject taken at different time points to determine read-counts and time-of-day normalized abundance levels of one or more specific microbial RNAs in each of the at least two biological samples, and comparing the determined levels of the one or more specific microbial RNAs over time to determine if the subject's read-counts and time-of-day normalized abundance levels of the one or more specific miRNAs is changing over time, wherein an increase or decrease in the read-counts and time-of-day normalized abundance levels of the one or more specific microbial RNAs over time is indicative that the subject's disorder or disease state is improving or deteriorating.

105. The method of embodiment 104, wherein the microbial RNAs subject to time-of-day normalization are selected from the group consisting of Group C microbial RNAs.

106. The method of embodiment 104, wherein the biological sample is saliva, cerebral spinal fluid, blood, serum, plasma, urine, feces, mucosal excretions, tears or tissue.

107. The method embodiment 104, wherein the subject is suspected to have ASD-related symptoms.

108. A method of detecting a miRNA and/or a microbial RNAs sequence or a plurality of miRNAs and/or microbial RNA sequences in a first biological sample, the method comprising:

obtaining a biological sample from a subject;

creating a double-stranded, complementary DNA sequence (cDNA) for each of one or more miRNA or microbial RNA sequences selected from Group A circaMiRs, Group B circaMiRs and Group C microbial RNAs; and detecting the presence, absence or relative quantity of cDNAs, wherein the presence, absence or relative quantity of cDNA is indicative of the presence, absence or relative quantity of the complementary miRNA or microbial RNA sequences.

109. The method embodiment 108, wherein the first biological sample is saliva, cerebral spinal fluid, blood, serum, plasma, urine, feces, mucosal excretions, tears or tissue.

110. A method of detecting a miRNA and/or a microbial RNA sequence or a plurality of miRNAs and/or microbial RNA sequences in a second biological sample, the method comprising:

obtaining a biological sample from said subject at a second time point;

creating a double-stranded, complementary DNA sequence (cDNA) for each of one or more miRNA or microbial RNA sequences selected from Group A circaMiRs, Group B circaMiRs and Group C miBiomes; and detecting the presence, absence or relative quantity of cDNAs, wherein the presence, absence or relative quantity of cDNA in said biological sample from said second time point is indicative of the presence, absence or relative quantity of the complementary miRNA or miBiome sequence(s) at the second time point; and tracking the progression of a disorder or disease by comparing the results from the first time point to the results from the second time point.

111. The method of embodiment 110, wherein the biological sample collected at a second time point is saliva, cerebral spinal fluid, blood, serum, plasma, urine, feces, mucosal excretions, tears or tissue.

112. The method of embodiment 110, wherein the subject is suspected to have ASD-related symptoms.

113. A method for detecting an alteration in a temporal rhythm comprising:

detecting at least one abnormal or altered pattern of miRNA or microbial RNA levels in saliva compared to a control value from one or more normal subjects, and selecting a subject having at least one abnormal or altered pattern of amounts of miRNA or microbial RNA; and, optionally, selecting a subject having ASD or ASD-related symptoms associated with an altered temporary rhythm, and optionally, administering a treatment that reduces or resynchronizes the at least one abnormal or altered pattern of amounts of the miRNA or microbial RNA.

114. The method of embodiment 113, wherein the abnormal or altered pattern in an amount of one or more miRNAs is detected.

Generally, the present invention further provides that a positive or negative difference in the abundance levels of the subject's miRNAs and/or miBIOMEs, as compared to the same miRNAs and/or microbial RNAs from one or more healthy control-subjects or a compendium of healthy control-subjects is indicative of severity of the ASD-related symptoms.

In various embodiments, abundance levels of miRNAs and/or microbial RNAs could be determined by a real time PCR, next generation sequencing, or other applicable methods.

In various embodiments, a biological sample could be one or more of saliva, cerebral spinal fluid, blood, serum, plasma, urine, feces, mucosal excretions, tears, and tissue. A biological sample could be of a human subject.

The detecting miRNA sequences and microbial RNA sequence, as described above, could be conducted in the same embodiment.

In one embodiment, an objective of the inventors was to provide a method of treating an autism spectrum disorder in a subject, comprising treating the subject with one or more of a behavior therapy, a communication therapy, a diet therapy, a medication therapy, and an alternative medical therapy, wherein the subject is identified for treating the autism spectrum disorder by the methods described above. Exemplary conditions, subject's the autism spectrum disorder may include, but are not limited to, a deficit in at least one of social communication, social interaction, repetitive patterns of behavior as classified in the diagnostic and statistical manual of mental disorders, fifth edition (2013).

In another embodiment, a method for detecting or diagnosing ASD comprises detecting at least one miRNA associated with ASD in saliva of a subject, detecting or diagnosing ASD when said miRNA is present in an amount significantly below or above that of a subject who does not have an ASD; and optionally treating the subject for ASD.

In one embodiment, an increased or decreased level of one or more miRNAs compared to miRNA levels in a normal subject is associated with ASD. An increased level of one or more miRNAs selected from the group consisting of miR-665, miR-4705, miR-620, and miR-1277-5p is detected. A decreased level of at least one miRNA selected from the group consisting of miR-125a, miR-193a-5p, miR-28-3p, miR-584-5p, let-7a-5p, miR-944, miR-148a-5p, miR-151a-3p, miR-125b-2-3p and miR-7706 is detected.

Another objective was to provide a microarray comprising a set of probes comprising nucleotide sequences capable of detecting and quantifying at least one microbial genetic sequence present in a saliva sample that are correlative to or predictive of autism spectrum disorder. In one embodiment, the microarray further comprises a set of at least 10, 11, 12, 13, 14, 15, 16, 17, 18, 19 or at least 20 probes comprising nucleotide sequences corresponding to sequences of miRNAs that are correlative to autism spectrum disorder.

Having generally described this invention, a further understanding can be obtained by reference to certain specific examples which are provided herein for purposes of illustration only, and are not intended to be limiting unless otherwise specified.

EXAMPLES

Example 1

An objective of this study was, among others, to determine how well differences in salivary miRNA can distinguish ASD and NS children, to determine how well differences in the oral microbiome can distinguish ASD and NS children, to quantify the strength of the relationship between the miRNAs and microbiome, and to examine the functional consequences of the top findings.

Methods

Subjects

Parental consent was obtained for all subjects. A total of 258 samples were collected from children aged 2-6, with either a confirmed ASD diagnosis, a diagnosis of Developmental Delay (DD) or Typically Developing (DD) Healthy Controls. Comprehensive medical and demographic information was obtained using detailed questionnaires, the Vineland Adaptive Behavior Scales (2nd Edition), and the Autism Diagnostic Observation Schedule (2nd Edition).

TABLE 1

| Group | N | M | F | % M | Age | SleepDx | Height % | Weight % | Collection Time | Allergies/ Asthma | Eczema/ Atopia | GI DX |
|---|---|---|---|---|---|---|---|---|---|---|---|---|
| ASD | 122 | 109 | 13 | 89% | 4.1 | 35 (28.7%) | 62.8 | 63.0 | 12:17PM | 35 (34.3%) | 11 (10.8%) | 10 (9.8%) |
| Control | 91 | 53 | 38 | 58% | 3.4 | 3 (3.7%) | 49.8 | 49.0 | 1:00PM | 19 (26.0%) | 11 (15.1%) | 0 (0%) |
| Dev Delay | 45 | 30 | 15 | 67% | 3.8 | 9 (20.9%) | 47.2 | 53.0 | 1:00PM | 10 (27.0%) | 5 (13.5%) | 3 (8.1%) |
|  | 258 | 192 | 66 | 74.5 | 3.75 | 40 (18.9%) | 56.7 | 56.9 | 12:39PM | 64 (30.2%) | 27 (12.7%) | 13 (6.1%) |

ASD diagnosis = clinical DSM-5 criteria, ADOS,
Developmental delay diagnosis = ICD-10 coding not meeting DSM-5 criteria for ASD,
Developmental status qualified with the Vineland Adaptive Behavior Scales-3,
Saliva collected once, at enrollment
Non-fasting state
Oral tap-water rinse
Sub-lingual and parotid glands
no restriction on time of collection.

Next Generation Sequencing

Identification and quantification of saliva miRNA and microbiome abundance were performed using next generation sequencing (NGS) on a NextSeq® 500 instrument at the SUNY Molecular Analysis Core (SUNYMAC) at Upstate Medical University. Alignment of NGS reads was performed to the miRbase21 database using the Shrimp®2 algorithm in Partek Flow software to identify mature miRNAs. Additional alignment of reads was performed to the Human Microbiome Database, using K-SLAM.

Data Analysis

The focus in this study was on the ASD and Control children. miRNA data and microbiome data were separately normalized to control for differences in total read number and subjected to quantile normalization. Normalized values were screened for sphericity prior to statistical analysis using principal component analysis (PCA). Data were filtered to eliminate those with more than 60% missingness and extreme outlier samples removed based on the PCA results. A non-parametric Mann-Whitney test was initially used to screen for the most robust miRNAs and microbiome taxon IDs with a significant effect of Diagnosis. The top significant miRNAs and taxon 1Ds were then used in diagnostic classification models and to generate a correlation matrix. miRNAs that showed the strongest predictive utility were subjected to functional analysis using Diana Tools miRpath®. The results are shown in FIGS. 1-17.

Saliva miRNA and microbiome taxon variables demonstrate the ability to distinguish children with ASD from typically developing controls, with cross-validating accuracy approximating 75-80%. When combined, the best miRNA and taxon classifiers performed at an overall accuracy level exceeding 86%, including more than 90% accuracy for ASD children. Many miRNAs and taxon classifiers exhibit significant correlations with each other. The top miRNA classifiers target mRNAs that enriched in several key biological pathways of interest for ASD, including Amphetamine Addiction, Axon Guidance, Oxytocin Signaling. See Table 6.

TABLE 2

ASD Microbiome List

| Taxonomy ID | Microbiome |
|---|---|
| Taxonomy ID 1095749 | Pasteurella bettyae CCUG 2042 |
| Taxonomy ID 1236 | Gammaproteobacteria |
| Taxonomy ID 1239 | Firmicutes |
| Taxonomy ID 1715084 | Rothia sp. HMSC065C03 |

TABLE 2-continued

ASD Microbiome List

| Taxonomy ID | Microbiome |
|---|---|
| Taxonomy ID 1739299 | Streptococcus sp. HMSC056C01 |
| Taxonomy ID 1739336 | Streptococcus sp. HMSC073D05 |
| Taxonomy ID 1739408 | Streptococcus sp. HMSC072G04 |
| Taxonomy ID 186826 | Lactobacillales |
| Taxonomy ID 537011 | Prevotella copri DSM 18205 |
| Taxonomy ID 712 | Pasteurellaceae |
| Taxonomy ID 889206 | Streptococcus vestibularis ATCC 49124 |

TABLE 3

ASD miRNA List

|  | miRNA |
|---|---|
| 1 | hsa-miR-151a-5p, |
| 2 | hsa-miR-183-5p, |
| 3 | hsa-miR-4705, |
| 4 | hsa-miR-193a-5p, |
| 5 | hsa-miR-149-5p, |
| 6 | hsa-miR-21-5p, |
| 7 | hsa-miR-665, |
| 8 | hsa-miR-125a-5p, |
| 9 | hsa-miR-502-3p, |
| 10 | hsa-miR-25-3p, |
| 11 | hsa-miR-221-3p, |
| 12 | hsa-miR-30e-5p, |
| 13 | hsa-miR-125b-2-3p, |
| 14 | hsa-miR-146a-3p |

TABLE 4

Saliva miRNA altered in autism

| miRNA | Fold Change | P-value |
|---|---|---|
| miR-502-3p | 0.7166 | 1.4E−6 |
| miR-125a-5p | 0.6976 | 2.2E−6 |

TABLE 4-continued

Saliva miRNA altered in autism

| miRNA | Fold Change | P-value |
|---|---|---|
| miR-149-5p | 0.7447 | 0.0001 |
| miR-193a-5p | 0.7509 | 0.0001 |
| miR-4705 | 13.4810 | 0.0002 |
| miR-99b-5p | 0.7179 | 0.0003 |
| miR-340-5p | 1.3128 | 0.0003 |
| miR-183-5p | 1.4913 | 0.0004 |
| miR-665 | 1.3643 | 0.0004 |
| miR-3074-5p | 0.7355 | 0.0011 | miRNAs without a -3p or -5p designation are pre-miR-NAs. Mature forms are also included in the list (may not be listed). For example, miR-665 is also included as miR-665-3p and miR-665-5p, miR-502-3p also included muR-502 and miR-502-5p. The same is for the rest of miRNA described herein.

Obtained data were quantile normalized and mean centered.

TABLE 5

| | FC | log$_2$(FC) | p. value | #NAME |
|---|---|---|---|---|
| hsa-miR-502-3p | 0.71657 | −0.48083 | 1.43E−06 | 5.8461 |
| hsa-miR-125a-5p | 0.69757 | −0.5196 | 2.25E−06 | 5.6475 |
| hsa-miR-149-5p | 0.7447 | −0.42527 | 5.48E−05 | 4.2611 |
| hsa-miR-193a-5p | 0.7509 | −0.41331 | 0.000143 | 3.8442 |
| hsa-miR-4705 | 13.481 | 3.7529 | 0.00017 | 3.7686 |
| hsa-miR-99b-5p | 0.71786 | −0.47823 | 0.000298 | 3.5265 |
| hsa-miR-340-5p | 1.3128 | 0.39261 | 0.000314 | 3.5024 |
| hsa-miR-183-5p | 1.4913 | 0.57654 | 0.00038 | 3.42 |
| hsa-miR-665 | 1.3643 | 0.44817 | 0.00041 | 3.3875 |
| hsa-miR-3074-5p | 0.7355 | −0.44321 | 0.001104 | 2.9571 |
| hsa-miR-4436b-3p | 1.3324 | 0.41402 | 0.001923 | 2.7161 |
| hsa-miR-6739-5p | 1.5567 | 0.63845 | 0.004878 | 2.3118 |
| hsa-miR-142-3p | 1.5855 | 0.66498 | 0.007421 | 2.1295 |
| hsa-miR-941 | 0.73276 | −0.4486 | 0.010078 | 1.9966 |
| hsa-miR-4454 | 1.5773 | 0.6575 | 0.01159 | 1.9359 |
| hsa-miR-3613-5p | 1.6135 | 0.69018 | 0.015795 | 1.8015 |
| hsa-miR-143-3p | 1.4562 | 0.54219 | 0.016232 | 1.7896 |
| hsa-miR-454-3p | 1.3203 | 0.40081 | 0.040824 | 1.3891 |
| hsa-let-7g-5p | 1.3991 | 0.48451 | 0.06314 | 1.1997 |
| hsa-miR-378c | 1.9658 | 0.97511 | 0.08286 | 1.0817 |

TABLE 6

Functional Analysis of miRNA

| # KEGG pathway | p-value | # genes | # miRNAs |
|---|---|---|---|
| 1. Amphetamine addition (hsa05031) | 0.000105231540272 | 29 | 13 |
| 2. MAPK signaling pathway (hsa04010) | 0.000695871720742 | 97 | 14 |

TABLE 6-continued

Functional Analysis of miRNA

| # KEGG pathway | p-value | # genes | # miRNAs |
|---|---|---|---|
| 3. Adrenergic signaling in cardiomyocytes (hsa04261) | 0.00073601512659 | 58 | 13 |
| 4. Regulation of actin cytoskeleton (hsa04810) | 0.000783789134254 | 82 | 13 |
| 5. Axon guidance (hsa04360) | 0.00265983298081 | 55 | 12 |
| 6. Oxytocin signaling pathway (hsa04921) | 0.00329587958232 | 62 | 13 |
| 7. Hippo signaling pathway (hsa04390) | 0.00607639308645 | 42 | 12 |
| 8. GABAergic synapse (hsa04727) | 0.00607639308645 | 31 | 12 |
| 9. PI3K-Akt signaling pathway (hsa04151) | 0.00607639308645 | 116 | 13 |
| 10. Platelet activation (hsa04611) | 0.00607639308645 | 49 | 13 |

KEGG Pathway
cAMP signaling (p = 0.0009, 48 genes)
Amphetamine addiction (p = 0.0009, 17 genes)
MAPK signaling (p = 0.0009, 56 genes)
Axon guidance (p = 0.0017, 32 genes)
Dopaminergic synapse (p = 0.0024, 32 genes)
Oxytocin signaling (p = 0.017, 31 genes)
Genes with micro-T-cds score >0.8 aligned in DIANA mirPATH

TABLE 7

Oral microbioma altered in autism

| | Fold Change | P-value |
|---|---|---|
| *Prevotella timonensis* | 0.2048 | 2.61E−05 |
| *Streptococcus vestibularis* | 2.272 | 0.0002 |
| *Enterococcus faecalis* | 0.3884 | 0.0003 |
| *Acetomicrobium hydrogeniformans* | 0.4860 | 0.0017 |
| *Streptococcus* sp. HMSC073D05 | 2.471 | 0.0026 |
| *Rothia dentocariosa* | 2.010 | 0.0038 |
| *Prevotella marshii* | 0.2658 | 0.0104 |
| *Prevotella* sp. HMSC073D09 | 0.2034 | 0.0150 |
| *Propionbacterium acnes* | 3.361 | 0.0192 |
| *Campylobacter* | 3.376 | 0.0222 |

A Logistic Regression analysis accounting for age and gender revealed 8 miRNA, 10 microbiota, and 86% accuracy.

TABLE 8

Logistic Classification Table for Dx

| | Predicted ASD | Predicted C | Percent Correct |
|---|---|---|---|
| Observed ASD | 108 | 11 | 90.76% |
| Observed C | 16 | 66 | 80.49% |
| Overall | | | 86.57% |

TABLE 9

| | FC | log$_2$(FC) | p. value | |
|---|---|---|---|---|
| 679189 *Prevotella timonensis* CRIS 5C-B1 | 0.20475 | −2.2881 | 2.61E−05 | 4.5838 |
| 1236 Gammaproteobacteria | 0.66645 | −0.58544 | 0.00014413 | 3.8412 |
| 1343 *Streptococcus vestibularis* | 2.2722 | 1.1841 | 0.00019153 | 3.7178 |
| 889206 *Streptococcus vestibularis* ATCC 49124 | 1.3129 | 0.39273 | 0.00028546 | 3.5445 |
| 1134787 *Enterococcus faecalis* ERV129 | 0.3884 | −1.3644 | 0.00034255 | 3.4653 |
| 1739299 *Streptococcus* sp. HMSC056C01 | 0.52708 | −0.92391 | 0.00082339 | 3.0844 |
| 1095749 *Pasteurella bettyae* CCUG 2042 | 0.70115 | −0.51221 | 0.00097188 | 3.0124 |

TABLE 9-continued

| | FC | log$_2$(FC) | p. value | |
|---|---|---|---|---|
| 471872*Streptococcus infantarius* subsp. *infantarius* ATCC BAA-102 | 1.4953 | 0.58044 | 0.0013351 | 2.8745 |
| 742727*Bacteroides oleiciplenus* YIT 12058 | 0.63971 | −0.6445 | 0.001598 | 2.7964 |
| 592015*Acetomicrobium hydrogeniformans* ATCC BAA-1850 | 0.48601 | −1.0409 | 0.0017159 | 2.7655 |
| 1739276*Achromobacter* sp. HMSC070F04 | 0.56824 | −0.81543 | 0.0020386 | 2.6907 |
| 904293*Streptococcus downei* F0415 | 1.3785 | 0.46313 | 0.002111 | 2.6755 |
| 1739336*Streptococcus* sp. HMSC073D05 | 2.4705 | 1.3048 | 0.0025587 | 2.592 |
| 888728*Haemophilus aegyptius* ATCC 11116 | 0.62003 | −0.68958 | 0.0030225 | 2.5196 |
| 762948*Rothia dentocariosa* ATCC 17931 | 2.0999 | 1.0703 | 0.0037931 | 2.421 |
| 749547*Escherichia coli* MS 187-1 | 1.471 | 0.55682 | 0.004008 | 2.3971 |
| 1125722*Porphyromonas gingivalis* W50 | 0.71125 | −0.49158 | 0.0060599 | 2.2175 |
| 1095733*Streptococcus parasanguinis* F0449 | 1.5667 | 0.64768 | 0.0084794 | 2.0716 |
| 186826Lactobacillales | 0.62219 | −0.68457 | 0.0091924 | 2.0366 |
| 862515*Prevotella marshii* DSM 16973 JCM 13450 | 0.26581 | −1.9115 | 0.010448 | 1.981 |
| 1227270*Porphyromonas gingivalis* F0569 | 0.76227 | −0.39162 | 0.012081 | 1.9179 |
| 1715104*Rothia* sp. HMSC064D08 | 1.8359 | 0.87648 | 0.012162 | 1.915 |
| 816*Bacteroides* | 0.73525 | −0.44369 | 0.013714 | 1.8628 |
| 638301*Granulicatella adiacens* ATCC 49175 | 1.3867 | 0.47167 | 0.013848 | 1.8586 |
| 905067*Streptococcus parasanguinis* F0405 | 0.75614 | −0.40327 | 0.013848 | 1.8586 |
| 547042*Bacteroides coprophilus* DSM 18228 JCM 13818 | 0.56724 | −0.81797 | 0.014209 | 1.8474 |
| 1739260*Rothia* sp. HMSC067H10 | 1.8119 | 0.85749 | 0.014256 | 1.846 |
| 117563*Granulicatella* | 1.3651 | 0.44901 | 0.014483 | 1.8391 |
| 1159093 *Streptococcus pneumoniae* PNI0076 | 0.69603 | −0.52277 | 0.01472 | 1.8321 |
| 1739459*Prevotella* sp. HMSC073D09 | 0.20344 | −2.2974 | 0.014957 | 1.8252 |
| 543Enterobacteriaceae | 1.4359 | 0.52198 | 0.015198 | 1.8182 |
| 537011*Prevotella copri* DSM 18205 | 0.60356 | −0.72843 | 0.015541 | 1.8085 |
| 976Bacteroidetes | 0.58111 | −0.78313 | 0.015873 | 1.7993 |
| 1127690*Actinomyces* sp. oral taxon 181 str. F0379 | 1.5126 | 0.59704 | 0.01589 | 1.7989 |
| 765087*Propionibacterium acnes* HL083PA1 | 3.3606 | 1.7487 | 0.019178 | 1.7172 |
| 563194*Pediococcus acidilactici* 7_4 | 0.60742 | −0.71924 | 0.020088 | 1.6971 |
| 1338*Streptococcus intermedius* | 1.9832 | 0.9878 | 0.021035 | 1.6771 |
| 500635*Mitsuokella multacida* DSM 20544 | 1.7556 | 0.81196 | 0.021622 | 1.6651 |
| 1313 *Streptococcus pneumoniae* | 0.73746 | −0.43937 | 0.022104 | 1.6555 |
| 194*Campylobacter* | 3.3764 | 1.7555 | 0.022156 | 1.6545 |
| 1134791*Enterococcus faecalis* ERV41 | 0.62983 | −0.66696 | 0.023825 | 1.623 |
| 1739462*Rothia* sp. HMSC036D11 | 2.4011 | 1.2637 | 0.023826 | 1.623 |
| 556269*Oxalobacter formigenes* OXCC13 | 0.474 | −1.077 | 0.023826 | 1.6229 |
| 1739308*Rothia* sp. HMSC065G12 | 2.3586 | 1.2379 | 0.02397 | 1.6203 |
| 1715123*Haemophilus* sp. HMSC071C11 | 0.73313 | −0.44786 | 0.024999 | 1.6021 |
| 450748*Propionibacterium* sp. 5_U_42AFAA | 8.2952 | 3.0523 | 0.025074 | 1.6008 |
| 1715088*Rothia* sp. HMSC058E10 | 2.1301 | 1.0909 | 0.025604 | 1.5917 |
| 1073372*Streptococcus parasanguinis* CC87K | 1.7094 | 0.77347 | 0.026536 | 1.5762 |
| 13 04*Streptococcus salivarius* | 3.3374 | 1.7387 | 0.03276 | 1.4847 |
| 157687*Leptotrichia wadei* | 1.4922 | 0.57742 | 0.033331 | 1.4772 |
| 883167*Streptococcus intermedius* F0413 | 1.5395 | 0.62242 | 0.034203 | 1.4659 |
| 1715034*Rothia* sp. HMSC071F11 | 2.6758 | 1.42 | 0.036212 | 1.4411 |
| 563032*Rothia dentocariosa* M567 | 1.8044 | 0.85155 | 0.036316 | 1.4399 |
| 1127695*Selenomonas* sp. oral taxon 138 str. F0429 | 1.7807 | 0.83242 | 0.039189 | 1.4068 |
| 1073377*Aeromonas hydrophila* SSU | 0.75211 | −0.41099 | 0.04042 | 1.3934 |
| 575590Bacteroidetes oral taxon 274 str. F0058 | 0.035411 | −4.8196 | 0.040761 | 1.3898 |
| 1739381 *Streptococcus* sp. HMSC072D03 | 0.76709 | −0.38253 | 0.040873 | 1.3886 |
| 1159084*Streptococcus pneumoniae* PCS125219 | 0.72843 | −0.45713 | 0.041563 | 1.3813 |
| 888807*Streptococcus sanguinis* SK1 NCTC 7863 | 0.72986 | −0.45431 | 0.043812 | 1.3584 |
| 1127699*Prevotella saccharolytica* F0055 | 0.70446 | −0.50541 | 0.044787 | 1.3489 |
| 419005*Prevotella amnii* | 0.69973 | −0.51513 | 0.046286 | 1.3346 |
| 1035191*Brevundimonas diminuta* 470-4 | 0.60681 | −0.72069 | 0.049015 | 1.3097 |
| 1739518*Rothia* sp. HMSC065D02 | 1.7958 | 0.84462 | 0.049952 | 1.3015 |

Saliva contains both miRNA and microbiome elements. Those elements have functional relationships with brain development pathways. Salivary microbiome and miRNA profiles were altered in children with ASD. Those profiles can be used to accurately differentiate children with ASD from typically developing controls.

Example 2

It was hypothesized that differential expression of brain-related miRNA may be detected in the saliva of ASD subjects, predictive of ASD classification, and related to neurodevelopmental measures of adaptive behavior. This could result in a rapid, simple, non-invasive ASD diagnostic. In a pilot study testing this hypothesis, miRNAs differently expressed in ASD patients, compared with age- and sex-matched controls, were discovered.

It was further found that these miRNAs were expressed in developing brain and functionally related to neurodevelopment.

Figure 18:
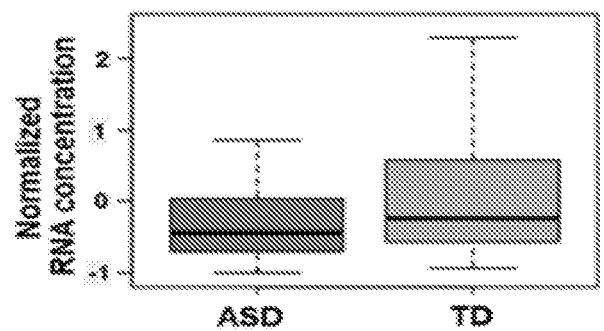
FIG. 18 shows a box plot of normalized *Lactobacillus* levels in ASD (n=120) and TD (n=85) subjects (p=0.002).

In addition to the presence of miRNAs in saliva, the inventors have ascertained that a considerable portion of the RNA in saliva samples was, in fact, not of human origin. After further investigation, this finding enabled to determine that the salivary RNA NGS data could be reliably mined to fully characterize the complete salivary microtranscriptome, which comprises miRNA and microbiome elements, including host miRNA and all resident and transcriptionally active bacteria, viruses, fungi, archae, and yeast. Furthermore, the inventors have found that these comprehensive oral microtranscriptomes of children with ASD were different than that of typically developing children, and that several of the oral miRNA and microbiome elements exhibited highly robust correlations in transcript levels, as illustrated in FIG. 18 for *Lactobacillus* which was significant different in 120 AS and 85 TD subjects (p=0.002) and associated with levels of miR-151a-5p (p=1.05e-4).

Overall, the inventors have completed the ascertainment and analysis of the samples from 188 ASD children and 116 typically developing (TD) controls. Half of these samples were used in pursuit of the goals of developing a diagnostic algorithm. Thus, subjects used to train the algorithm consisted of 94 ASD children between the ages of 2-6 with a diagnosis confirmed by clinical consensus per DSM 5 standards, and 58 age- and gender-matched TD controls. Notably, children with any $1^{st}$ degree relatives with ASD were excluded from the control group, and children with a known syndromic phenotype (i.e., Rett Syndrome, Tuberous Sclerosis, Angelman Syndrome, Fragile X, 22qDS) were excluded from both groups. Collections primarily took place at the time of previously-scheduled well-child pediatric visits for healthy TD controls, or clinical visits to the Penn State Hershey Medical Center Developmental Pediatrics Clinic and SUNY Upstate's Center for Development, Behavior, and Genetics, Family Behavior Analysis Clinic, or Margaret L. Williams Developmental Evaluation Center for ASD children. Various medical, demographic, and neuropsychological data were collected at the time of sample collection, including age, gender, ethnicity, birth age, birth weight, perinatal complications, body mass index, current oropharyngeal status (allergic rhinitis, sinus infection, cold/flu, fever, dental carries), sleep disorders, gastrointestinal issues, diet, current medications, chronic medical issues, immunization status, medical allergies, dietary restrictions, early intervention services, hearing deficits, visual deficits, surgical history, and family psychiatric history.

Saliva was collected in a non-fasting state after a brief water rinse using an ORAcollect® RNA collection kit (DNA Genotek; Ottawa, Canada) and stored at room temperature until processing by the SUNY Molecular Analysis Core (SUNYMAC) laboratory under the direction of Dr. F. Middleton. Salivary RNA was isolated according to the DNA Genotek RNA purification protocol using TRI Reagent LS, followed by a second round of purification using the RNeasy® mini column (Qiagen). The yield and quality of the RNA samples were assessed using the Agilent Bioanalyzer prior to library construction with the Illumina TruSeq® Small RNA Sample Prep protocol (Illumina; San Diego). Multiplexed samples were run on an Illumina NextSeq® 500 instrument at a targeted depth of 10 million reads per sample. After demultiplexing and filtering to remove PCR duplicates and poor quality reads, as well as trimming of index and adapter sequences, the resulting FASTQ® files (containing sequences found in each sample along with quality scores for each base) were examined for quality metrics.

After eliminating poor quality reads (mean q score <30) and samples whose RNA read content was >1.5 s.d. from the group mean in four quality metrics (total read count, % unique reads, % GC content, and average quality score), the remaining reads and samples were used in two different downstream workflows to map host miRNA and microbiome elements as follows: (1) Whole genome alignment of the reads was performed to build hg38 of the human genome reference sequence using the SHRiMP2® aligner in the Partek Flow environment (Partek; St. Louis, Mo.). Total miRNA counts within each sample were then quantified to the mature and precursor sequences in the miRBase21 database; (2) Microbial RNA alignment was performed to the NCBI Microbiome genomic database using a custom configuration of the K-SLAM® software package; (3) Filtering of miRNAs and microbiome elements was performed to only consider mapped entities with >10 reads in at least 10% of the combined set of samples; (4) quantile normalization of miRNA data and microbiome data was performed separately; (5) differential expression and multivariate classification analyses were performed on the miRNA and microbiome data using Partek Flow, NCSS11, and the R tools developed in Microbiome Analyst and Metaboanalyst applications to identify the miRNA and microbiome that best distinguish ASD and TD children, or ASD and DD children, controlling for the effects of age, gender, and other potential confounds. During the differential expression analysis, correction for multiple testing was performed using the Benjamini-Hochberg False Discovery Rate (FDR) algorithm. The miRNAs with the greatest differential expression across groups were combined into multivariate Logistic Regression Classification models, with 100-fold Monte-Carlo cross-validation performed during training using balanced subsampling of ½ of the samples and calculation of whole model sensitivity and specificity with an Area Under the Curve (AUC) for the Receiver Operating Characteristic (ROC) curve generated for 5, 10, 15, 20 and 25 different miRNAs, miRNA: miRNA ratios, and microbiome elements. The best overall performing features were then identified from both sets of data and used in construction of a joint miRNA/microbiome classifier that was evaluated in a hold-out sample.

The systems-level analysis of consensus miRNA findings was performed using the proprietary Core Analysis workflow of the Qiagen Ingenuity® Pathway Analysis (IPA) software to identify brain-specific pathways and networks, and to predict the activation or inhibition of specific miRNA targets, as well as PICrUS® and KEGG® tools for the microbiome data. The inventors have complemented the IPA analyses with a pathway enrichment analysis using the mirPath® v.3 analysis package of the DIANA TOOLS® suite.

Figure 19:
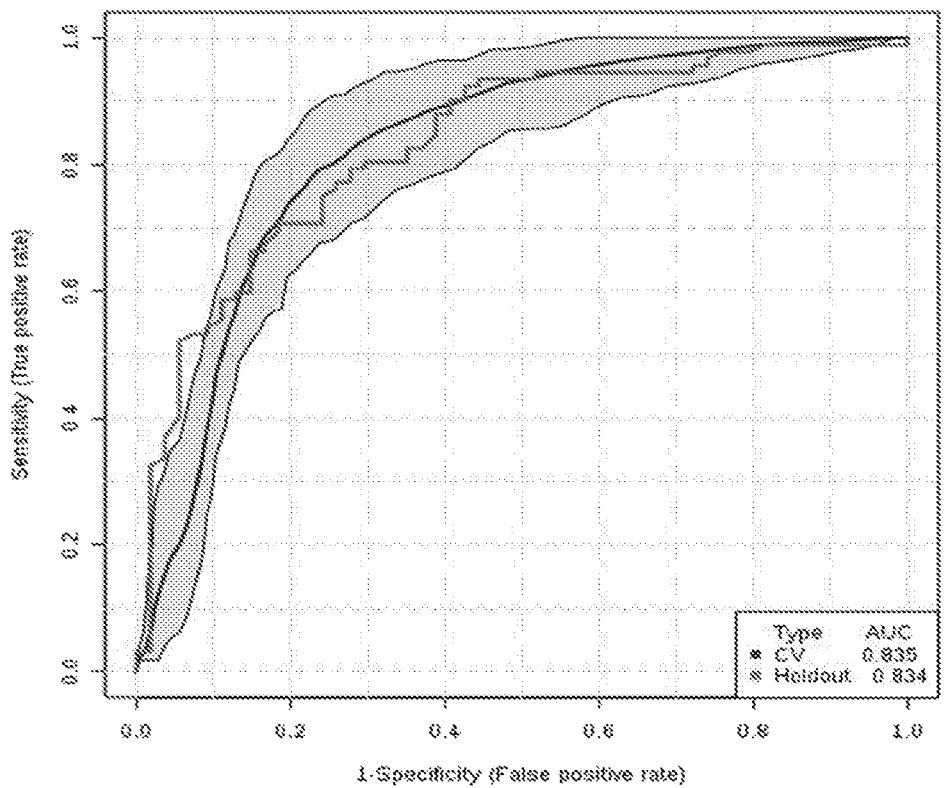
FIG. 19 shows ROC curve and AUC of logistic regression model classifying ASD vs. Typically Developing Controls. 16 ratios involving 10 miRNAs and 3 microbiota yielded an area under the curve (AUC) of 0.835 for the cross-validated (CV) training analysis and 0.834 for the holdout analysis.

After rigorous QC filtering, the inventors obtained 188 samples from children with ASD, 116 from those with typical development (TD), and 62 from those who were developmentally delayed (DD; diagnosed by ICD-10 coding not meeting DSM-5 criteria for ASD). Using logistic regression and controlling for sex and sleep disturbance, we found 16 ratios involving 10 miRNAs and 3 microbial species (see Table 10). In the initial analysis of 92 children with ASD and 54 TD children to develop and train the algorithm, the ratios predicted ASD with 83.5% accuracy. Using the same ratios and beta coefficients to test the algorithm in a group of 92 children with ASD and 54 TD children (Aim 2), the accuracy was essentially identical at 83.4% accuracy (see FIG. 19).

TABLE 10

Top-ranked miRNA and microbiota for classification of ADS v. TD controls

|  | Fold Change | P-value |
|---|---|---|
| miRNA |  |  |
| miR-502-3p | 0.717 | 1.4E–6 |
| miR-125a-5p | 0.698 | 2.2E–6 |
| miR-149-5p | 0.745 | 0.0001 |
| miR-193a-5p | 0.750 | 0.0001 |
| miR-4705 | 13.481 | 0.0002 |
| miR-99b-5p | 0.718 | 0.0003 |
| miR-340-5p | 1.313 | 0.0003 |
| miR-183-5p | 1.491 | 0.0004 |
| miR-665 | 1.364 | 0.0004 |
| miR-3074-5p | 0.736 | 0.0011 |
| Bacterium |  |  |
| *Prevotella timonensis* | 0.205 | 2.61E–05 |

TABLE 10-continued

Top-ranked miRNA and microbiota for classification of ADS v. TD controls

|  | Fold Change | P-value |
|---|---|---|
| *Prevotella marshii* | 0.266 | 0.0104 |
| *Prevotella* sp. HMSC073D09 | 0.203 | 0.0150 |

Figure 20:
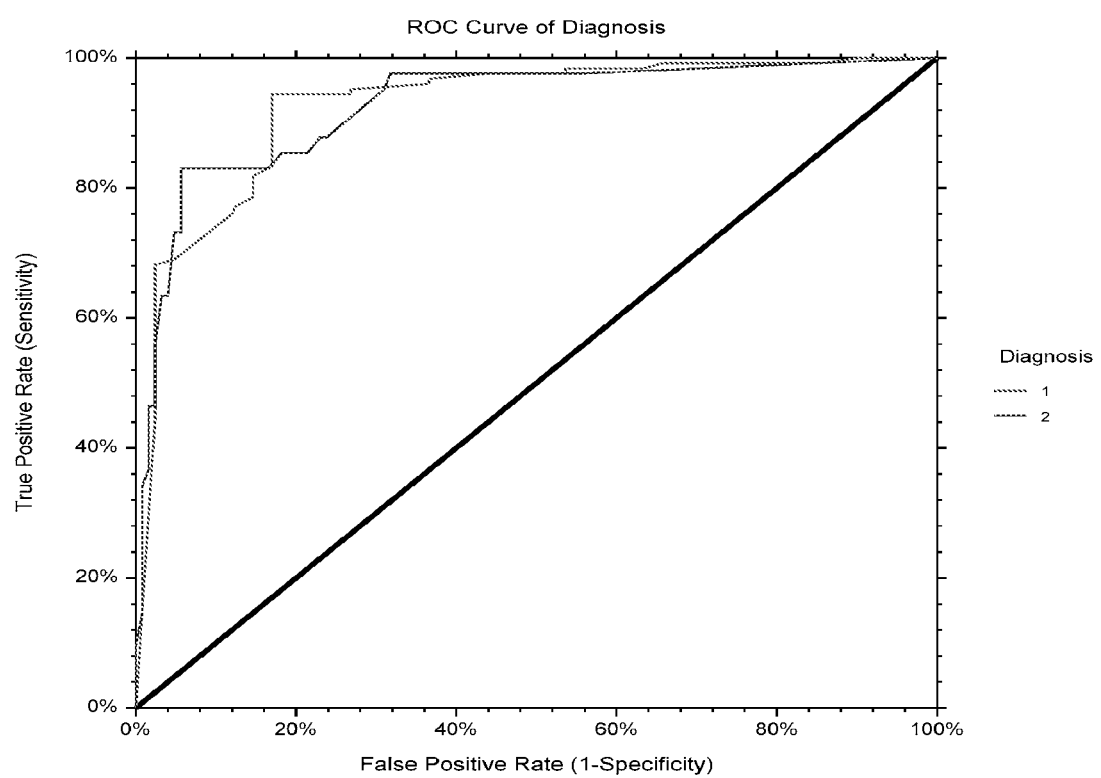
FIG. 20 shows ROC curve of a logistic regression classifier between ASD and Developmental Delay children. Using 13 miRNAs and 8 microbiome elements and age, a training set analysis yielded an overall accuracy >91%, and a ⅓ holdout analysis of naïve samples yielded 75.0% accuracy.

The inventors have determined that benefit of the presented molecular diagnostic was in having the ability to not only distinguish ASD from TD children, but also ASD from DD children. To this end, the inventors have developed an optimal panel of individual miRNA and microbiome biomarkers that could accomplish this task. Using logistic regression analysis comparing these subjects while accounting for possible effects of age, BMI, sex, sleep disorder, food allergies, and GI problems, the inventors have produced a model with 91% classification accuracy in the training set (accuracy 94% for ASD, 80.5% for DD) with an AUC>0.92 utilizing a panel of 13 miRNAs, 8 microbiome elements and age (see FIG. 20). In the hold-out validation sample (representing 1/3 of the overall samples), the same model achieved an overall accuracy >75% (84% for ASD, but only ~50% for DD).

Pathway Analysis.

To provide context for the top miRNAs that were identified in the biomarker screening, these were subjected to pathway enrichment analyses in DIANA TOOLS® miRpath. This analysis revealed several brain-related KEGG groups were targeted by salivary biomarker miRNAs. Most notable in these KEGG pathways were neurodevelopmental and neurotrans neurotransmission groups as well as Oxytocin signaling group. Top-Ranked Target Gene KEGG Pathway: cAMP signaling (p=0.0009, 48 genes); Amphetamine addiction (p=0.0009, 17 genes); MAPK signaling (p=0.0009, 56 genes); Axon guidance (p=0.0017, 32 genes); Dopaminergic synapse (p=0.0024, 32 genes); Oxytocin signaling (p=0.017, 31 genes).

Complementing the miRNA analysis, the data to identify the most predictive individual bacteria for any evidence of functional clustering were examined. The inventors have noted trends for decreased levels of *Prevotella* and *Enterococcus* as well as increased *Streptococcus, Rothia* and *Camplylobacter* species in the saliva of ASD children compared to TD controls.

TABLE 11

Microbiota Host Relationships of altered bacterial elements

| Decreased in ASD | *Prevotella timonensis*: gram negative anaerobe; rarely opportunistic pathogen<br>*Prevotella* sp. HMSC073D09: may comprise up to 50% of the childhood gut microbiome and be promoted by a carbohydrate/fiber diet. |
|---|---|
| Increased in ASD | *Enterococcus faecalis*: intestinal, toxin-producing organism capable of genetic transfer and implicated in UTI, bacteremia, and endocarditis<br>*Streptococcus vestibularis*: gram positive cocci negative cocci from vestibular mucosa of human oral cavity. Generally non-pathogenic.<br>*Rothia dentocariosa*: gram positive rod implicated in dental carries and rarely endocarditis. Case reports of meningitis. |

(NCBI Genome, De Filippo et al., 2010).

Some of these findings are similar to results from fecal studies in ASD subjects.

In summary, saliva contains both miRNA and microbiome elements, and the profiles of both are altered in patients with ASD. Further, these profiles can be used to accurately differentiate children with ASD, and this accuracy endures in naïve hold-out samples. Finally, the data from saliva strongly implicate brain-related miRNAs and target gene pathways that appear to be particularly relevant for ASD as well as findings from other microbiome studies performed in fecal samples from ASD subjects.

Example 3

Figure 21A:
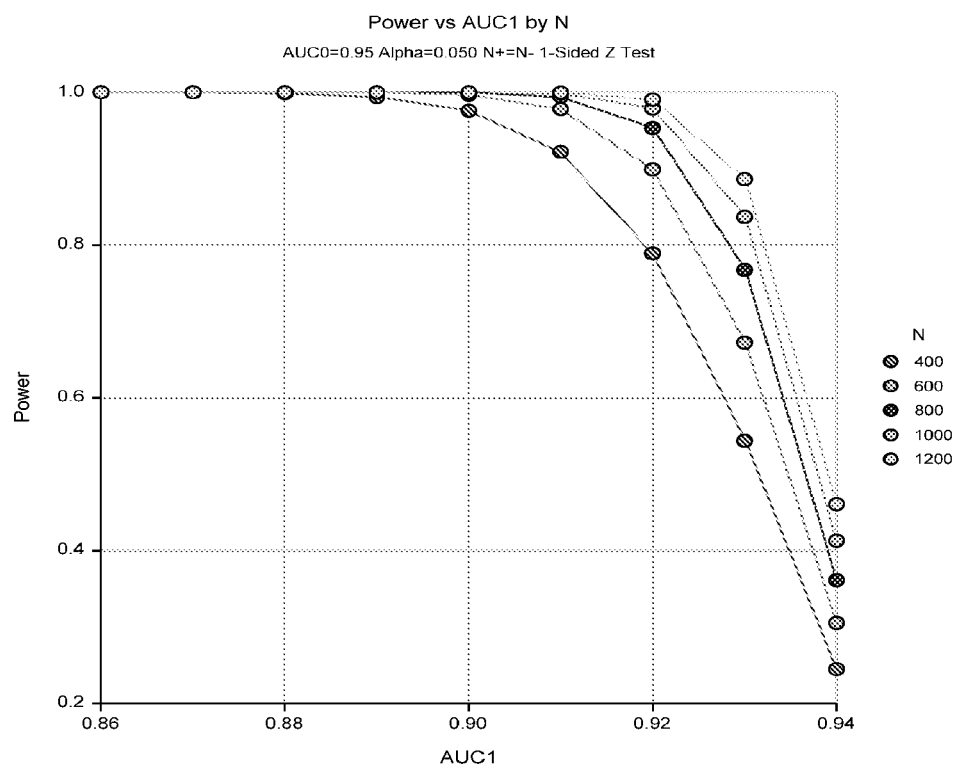
FIGS. 21A-B show Power and sample size estimates based on non-inferiority of planned AUC analysis (A) and interrater reliability (Cohen's kappa coefficient) of a three group classification test (B). These calculations are based on the methods described in Hanley and McNeil (1983) Obuchowski and McClish (1997) and Fleiss, Lein and Palk (2003).
Figure 21B:
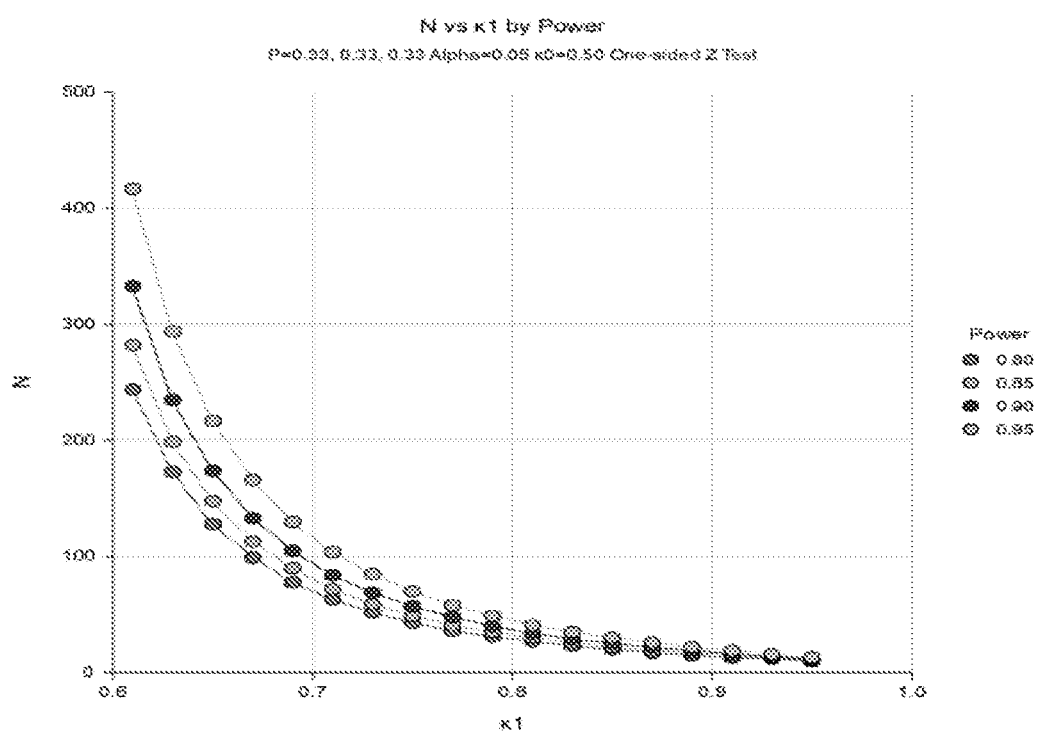

An example in which a larger sample size, comprised of ASD, DD, and TD children, was used, with methods similar to that above. The sample size was 400, to yield a power of approximately 94% for a three group classification test (see FIG. 21 A-B).

Example 4

Blinded samples of salivary miRNA are purified according to the DNA Genotek RNA purification protocol using TRI Reagent LS, followed by a second round of purification using the RNeasy mini column (Qiagen). The yield and quality of the RNA samples are assessed using the Agilent Bioanalyzer prior to library construction with the Illumina TruSeq® Small RNA Sample Prep protocol (Illumina; San Diego, Calif.). Multiplexed samples are runned on an Illumina NextSeq® instrument at SUNY Upstate at 3-5 million reads per sample. After demultiplexing the samples based on the barcode indexes, filtering to remove PCR duplicates and poor-quality reads, and trimming of index and adapter sequences the resulting FASTQ files (containing all the sequences found in each sample along with quality scores for each base) are examined for quality metrics. After eliminating poor quality sequences (quality score <30), the remaining reads are used in two different downstream workflows to map host miRNA and microbial RNA as follows: 1) Whole genome alignment of the reads is performed to build hg38 of the human genome reference sequence using Partek Flow software (Partek; St. Louis, Mo.) and the SHRiMP2® aligner. Total miRNA counts within each sample are then quantified to the mature and precursor sequences in the mirBASE21 database. 2) Microbial RNA alignment is performed to the NCBI Microbiome genomic database using K-SLAM software.

Example 5

An example in which the logistic regression model uses ratios of patient data, miRNAs, and microbiome data from the samples in Example 4.

TABLE 12

Combined Logistic Regression parameters and AUROCC values and factors for CTRL vs ASD.

| NAME | Estimate | | z value | Pr(>|z|) | Odds |
|---|---|---|---|---|---|
| Sleep dist/hsa-miR-598-3p | −16110.1 | 642850 | −0.025 | 0.98 | 0 |
| hsa-miR-598-3p/365046*Ramlibacter tataouinensis* TTB310 | −34093.3 | 1360501 | −0.025 | 0.98 | 0 |
| Sleep dist/837*Porphyromonas gingivalis* | −100856 | 1240155 | −0.081 | 0.935 | 0 |
| Sleep dist/869309*Streptococcus pneumoniae* SPNA45 | −212147 | 1246673 | −0.17 | 0.865 | 0 |
| 365046*Ramlibacter tataouinensis* TTB310/285473 *Streptomyces rubrolavendulae* | 0.147 | 0.622 | 0.237 | 0.813 | 1.16 |
| hsa-miR-125b-2-3p/365046*Ramlibacter tataouinensis* TTB310 | 686836.9 | 1328064 | 0.517 | 0.605 | Inf |
| Sleep dist/hsa-miR-222-3p | −4.897 | 6.986 | −0.701 | 0.483 | 0.01 |
| Sleep dist/471*Acinetobacter calcoaceticus* | −953775 | 1158359 | −0.823 | 0.41 | 0 |
| 365046*Ramlibacter tataouinensis* TTB310/471*Acinetobacter calcoaceticus* | 1267716 | 1539640 | 0.823 | 0.41 | Inf |
| hsa-miR-151a-3p/Sleep dist | −350383 | 420269.7 | −0.834 | 0.404 | 0 |
| hsa-miR-151a-3p/365046*Ramlibacter tataouinensis* TTB310 | 754996 | 905628.6 | 0.834 | 0.404 | Inf |
| hsa-miR-125b-2-3p/1678128*Limnohabitans* sp. 63ED37-2 | 1247110 | 1230999 | 1.013 | 0.311 | Inf |
| hsa-miR-125b-5p/Sleep dist | −5.601 | 4.955 | −1.13 | 0.258 | 0 |
| Sleep dist/hsa-miR-6499-5p | 1.402 | 1.208 | 1.16 | 0.246 | 4.06 |
| hsa-miR-151a-5p/Sleep dist | 577276.8 | 482234.1 | 1.197 | 0.231 | Inf |
| hsa-miR-151 a-5p/365046*Ramlibacter tataouinensis* TTB310 | −1257242 | 1050273 | −1.197 | 0.231 | 0 |
| 869309*Streptococcus pneumoniae* SPNA45/1678128*Limnohabitans* sp. 63ED37-2 | 2142164 | 1615518 | 1.326 | 0.185 | Inf |
| hsa-miR-148b-3p/Sleep dist | −842761 | 584565.3 | −1.442 | 0.149 | 0 |
| hsa-miR-148b-3p/365046*Ramlibacter tataouinensis* TTB310 | 1812942 | 1257508 | 1.442 | 0.149 | Inf |
| 365046*Ramlibacter tataouinensis* TTB310/869309*Streptococcus pneumoniae* SPNA45 | 2504292 | 1687251 | 1.484 | 0.138 | Inf |
| Sleep dist/hsa-miR-874-3p | −2.367 | 1.56 | −1.517 | 0.129 | 0.09 |
| hsa-miR-125b-2-3p/Sleep dist | −911870 | 586241.7 | −1.555 | 0.12 | 0 |
| 365046*Ramlibacter tataouinensis* TTB310/837*Porphyromonas gingivalis* | −4014135 | 2038589 | −1.969 | 0.049 | 0 |
| hsa-miR-149-5p/Sleep dist | 1870719 | 846441.9 | 2.21 | 0.027 | Inf |
| hsa-miR-149-5p/3 65046*Ramlibacter tataouinensis* TTB310 | −4021587 | 1819638 | −2.21 | 0.027 | 0 |

TABLE 12-continued

Combined Logistic Regression parameters and AUROCC values and factors for CTRL vs ASD.

| NAME | Estimate | | z value | Pr(>|z|) | Odds |
|---|---|---|---|---|---|
| Sleep dist/hsa-miR-22-3p | 16.427 | 6.961 | 2.36 | 0.018 | 13616668 |
| hsa-miR-148a-5p/Sleep dist | 1926285 | 811946.1 | 2.372 | 0.018 | Inf |
| hsa-miR-148a-5p/365046*Ramlibacter tataouinensis* TTB310 | −4155739 | 1751666 | −2.372 | 0.018 | 0 |
| 1678128*Limnohabitans* sp. 63ED37-2/837*Porphyromonas gingivalis* | 4218173 | 1723142 | 2.448 | 0.014 | Inf |
| Sex 0M/1678128*Limnohabitans* sp. 63ED37-2 | −2.96 | 1.183 | −2.502 | 0.012 | 0.05 |
| Sleep dist/1168034*Draconibacterium orientale* | 6704900 | 2493480 | 2.689 | 0.007 | Inf |
| 365046*Ramlibacter tataouinensis* TTB310/1168034*Draconibacterium orientale* | −8952426 | 3329312 | −2.689 | 0.007 | 0 |
| (Intercept) | 2.202 | 0.704 | 3.129 | 0.002 | — |
| 365046*Ramlibacter tataouinensis* TTB310 | −103.467 | 32.396 | −3.194 | 0.001 | 0 |

Figure 22:
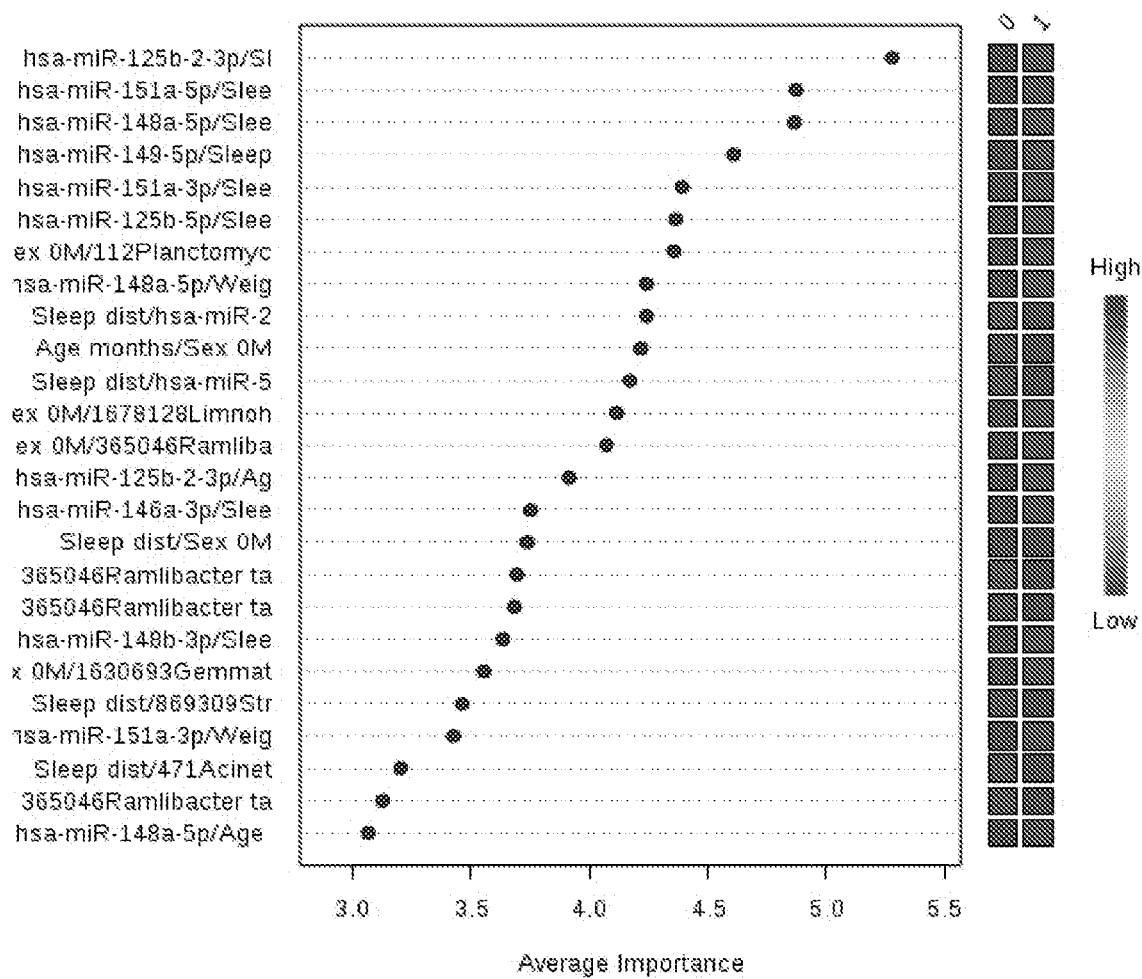
FIG. 22 shows the variable importance of different ratios of miRNAs, taxa, and patient features in differentiating between ASD and TD children. Color/gray scale panel on the right indicates if the ratios are higher or lower in TD (0) or ASD (1) children.

The average importance is shown in FIG. 22.

TABLE 13

| Confusion Matrix (Cross-Validation) | | | Confusion Matrix (Hold-out) | | |
|---|---|---|---|---|---|
| — | 00 | 1 | — | 0 | 1 |
| 0 | 44 | 19 | 0 | 36 | 16 |
| 1 | 10 | 73 | 1 | 18 | 76 |

Performance of Logistic Regression Model:

| — | AUC | Sensitivity | Specificity |
|---|---|---|---|
| Training/Discovery | 0.982 (0.975~0.989) | 0.970 (0.958~0.981) | 0.895 (0.868~0.922) |
| 10-fold Cross-Validation | 0.823 (0.750~0.896) | 0.848 (0.848~0.921) | 0.704 (0.582~0.825) |

Logistic Regression Model with Selected Compounds:

logit(P) = log(P/(1 − P)) = 2.202 + 1267716.438 365046*Ramlibacter tataouinensis* TTB310/471*Acinetobacter calcoaceticus* − 8952426.416 365046*Ramlibacter tataouinensis* TTB310/1168034*Draconibacterium orientale* + 2504291.92 365046*Ramlibacter tataouinensis* TTB310/869309*Streptococcus pneumoniae* SPNA45 − 1257241.598 hsa-miR-151a-5p/365046*Ramlibacter tataouinensis* TTB310 − 4021587.004 hsa-miR-149-5p/365046*Ramlibacter tataouinensis* TTB310 + 6704899.6 Sleep dist/1168034*Draconibacterium orientale* + 1247110.195 hsa-miR-125b-2-3p/1678128*Limnohabitans* sp. 63ED37-2 + 1812941.821 hsa-miR-148b-3p/365046*Ramlibacter tataouinensis* TTB310 − 953774.819 Sleep dist/471*Acinetobacter calcoaceticus* − 100856.014 Sleep dist/837*Porphyromonas gingivalis* − 4014134.845 365046*Ramlibacter tataouinensis* TTB310/837*Porphyromonas gingivalis* + 686836.889 hsa-miR-125b-2-3p/365046*Ramlibacter tataouinensis* TTB310 − 2.96 Sex 0M/1678128*Limnohabitans* sp. 63ED37-2 + 754996.025 hsa-miR-151a-3p/365046*Ramlibacter tataouinensis* TTB310 − 4155738.926 hsa-miR-148a-5p/365046*Ramlibacter tataouinensis* TTB310 − 5.601 hsa-miR-125b-5p/Sleep dist + 1.402 Sleep dist/hsa-miR-6499-5p + 16.427 Sleep dist/hsa-miR-22-3p − 16110.12 Sleep dist/hsa-miR-598-3p + 577276.776 hsa-miR-151a-5p/Sleep dist − 842761.42 hsa-miR-148b-3p/Sleep dist + 1870719.469 hsa-miR-149-5p/Sleep dist − 350383.237 hsa-miR-151a-3p/Sleep dist − 911869.897 hsa-miR-125b-2-3p/Sleep dist + 1926285.356 hsa-miR-148a-5p/Sleep dist − 4.897 Sleep dist/hsa-miR-222-3p + 4218172.551 1678128*Limnohabitans* sp. 63ED37-2/837*Porphyromonas gingivalis* − 212146.69 Sleep dist/869309*Streptococcus pneumoniae* SPNA45 − 34093.301 hsa-miR-598-3p/365046*Ramlibacter tataouinensis* TTB310 + 0.147 365046*Ramlibacter tataouinensis* TTB310/285473*Streptomyces rubrolavendulae* + 2142163.968 869309*Streptococcus pneumoniae* SPNA45/1678128*Limnohabitans* sp. 63ED37-2 − 103.467 365046*Ramlibacter tataouinensis* TTB310 − 2.367 Sleep dist/hsa-miR-874-3p, where P is Pr(y = 1|x). The best threshold (or Cutoff) for the predicted P is 0.43.
Original Label: 0/1 --> Labels in Logistic Regression: 0/1
Note)
The class/response value is recommended as (Case: 1 and Control: 0)

Example 6

An example in which a non-linear statistical learning method (e.g., Random Forest) was employed using microbiome and miRNA data.

TABLE 14

| | |
|---|---|
| 1168034*Draconibacterium orientale* | Random Forest |
| 1678128*Limnohabitans* sp. 63ED37-2 | |
| 285473*Streptomyces rubrolavendulae* | |
| 365046*Ramlibacter tataouinensis* TTB310 | |
| 471*Acinetobacter calcoaceticus* | |
| 837*Porphyromonas gingivalis* | |
| 869309*Streptococcus pneumoniae* SPNA45 | |
| hsa-miR-125b-2-3p | |
| hsa-miR-125b-2-3p | |
| hsa-miR-125b-5p | |
| hsa-miR-148a-5p | |
| hsa-miR-148b-3p | |

Figure 23:
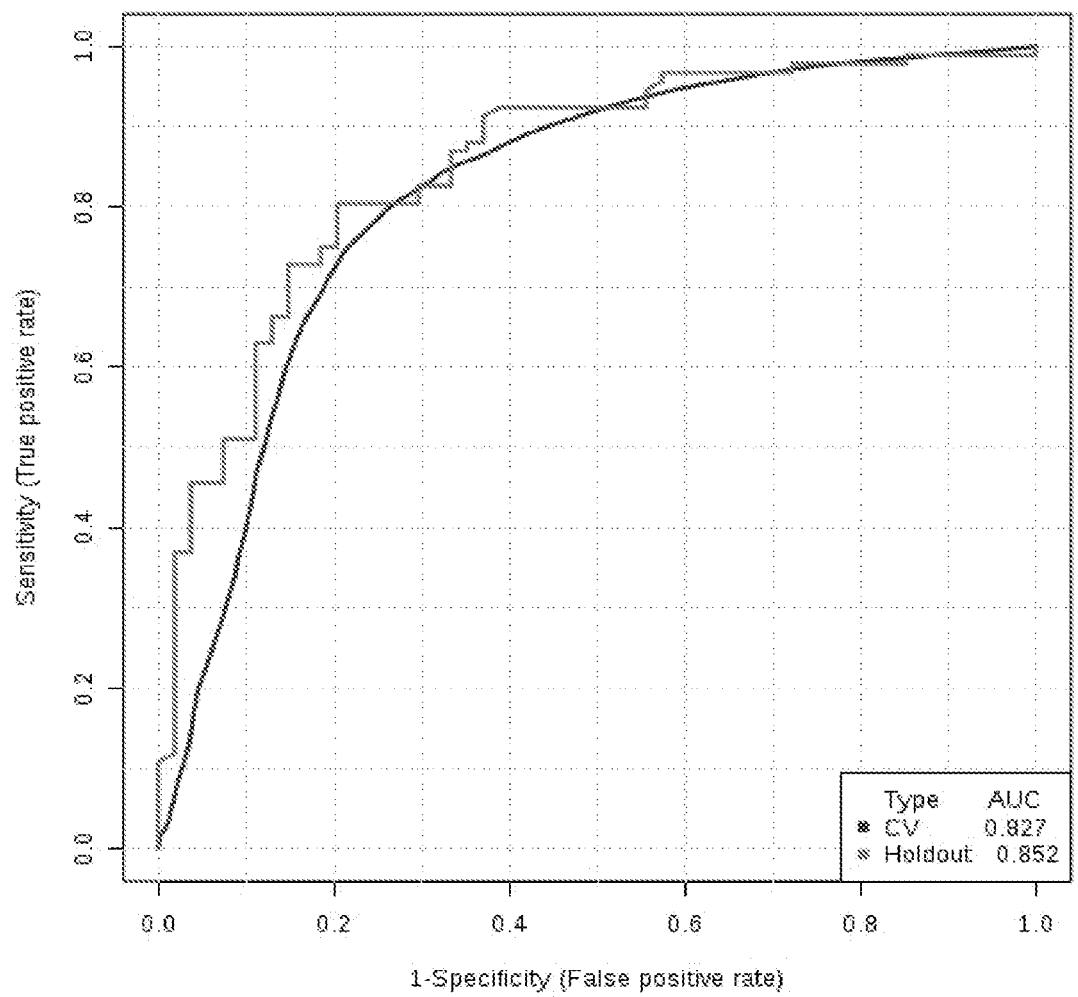
FIG. 23 shows an ROC curve and AUC for an example random forest classifier using a combination of miRNAs and microbiome taxa.

TABLE 14-continued hsa-miR-149-5p
hsa-miR-151a-3p
hsa-miR-151a-5p
hsa-miR-222-3p
hsa-miR-22-3p
hsa-miR-598-3p
hsa-miR-6499-5p
hsa-miR-874-3p
Sex 0M
Sleep dist 1-Sensitivity (false positive rate) v. Sensitivity (true positive rate) is shown in FIG. 23.

Example 7

An example in which a logistic regression classifier used scaled (z-score) ratios of patient data, miRNAs, and microbial data.

TABLE 15

| z value | Pr(>|z|) | Odds | Random Forest |
|---|---|---|---|
| −1.086 | 0.278 | — | |
| 1.669 | 0.095 | Inf | |
| −1.229 | 0.219 | 0 | |
| −0.609 | 0.542 | 0 | |
| −0.232 | 0.816 | 0.92 | |
| −0.096 | 0.923 | 0.97 | |
| −2.187 | 0.029 | 0.87 | |
| −2.784 | 0.005 | 0.2 | |
| −0.094 | 0.925 | 0.99 | |
| 0.525 | 0.6 | 1.29 | |
| 0.826 | 0.409 | 1.56 | |
| −1.055 | 0.292 | 0.58 | |
| −1.669 | 0.095 | 0 | |
| 0.609 | 0.542 | Inf | |
| −1.294 | 0.196 | 0.96 | |
| 1.229 | 0.219 | Inf | |
| 2.51 | 0.012 | 1.07 | |

Performance of Logistic Regression Model:

| | AUC | Sensitivity | Specificity |
|---|---|---|---|
| Training/Discovery | 0.905 (0.888~0.922) | 0.795 (0.767~0.822) | 0.844 (0.811~0.876) |
| 10-fold Cross-Validation | 0.840 (0.773~0.907) | 0.772 (0.772~0.858) | 0.778 (0.667~0.889) |

Logistic Regression Model with Selected Compounds:

logit(P) = log(P/(1 − P)) = −5.281 + 88261.597 hsa-miR-148a-5p/Sleep dist − 59821.789 hsa-miR-125b-2-3p/Sleep dist − 28441.813 hsa-miR-151a-3p/Sleep dist − 0.082 hsa-miR-149-5p/Sleep dist − 0.035 Sleep dist/hsa-miR-598-3p − 0.14 Sex 0M/365046*Ramlibacter tataouinensis* TTB310 − 1.606 Sleep dist/hsa-miR-22-3p − 0.011 Sleep dist/hsa-miR-6499-5p + 0.254 hsa-miR-125b-5p/Sleep dist + 0.443 hsa-miR-148b-3p/Sleep dist − 0.543 hsa-miR-151a-5p/Sleep dist − 88263.782 hsa-miR-148a-5p/365046*Ramlibacter tataouinensis* TTB310 + 28441.992 hsa-miR-151a-3p/365046*Ramlibacter tataouinensis* TTB310 − 0.044 Sex 0M/1678128*Limnohabitans* sp. 63ED37-2 + 59821.943 hsa-miR-125b-2-3p/365046*Ramlibacter tataouinensis* TTB310 + 0.072 365046*Ramlibacter tataouinensis* TTB310/837*Porphyromonas gingivalis*, where P is Pr(y = 1|x). The best threshold (or Cutoff) for the predicted P is 0.66.
Original Label: 0/1 --> Labels in Logistic Regression: 0/1
Note)
The class/response value is recommended as (Case: 1 and Control: 0)

Figure 24:
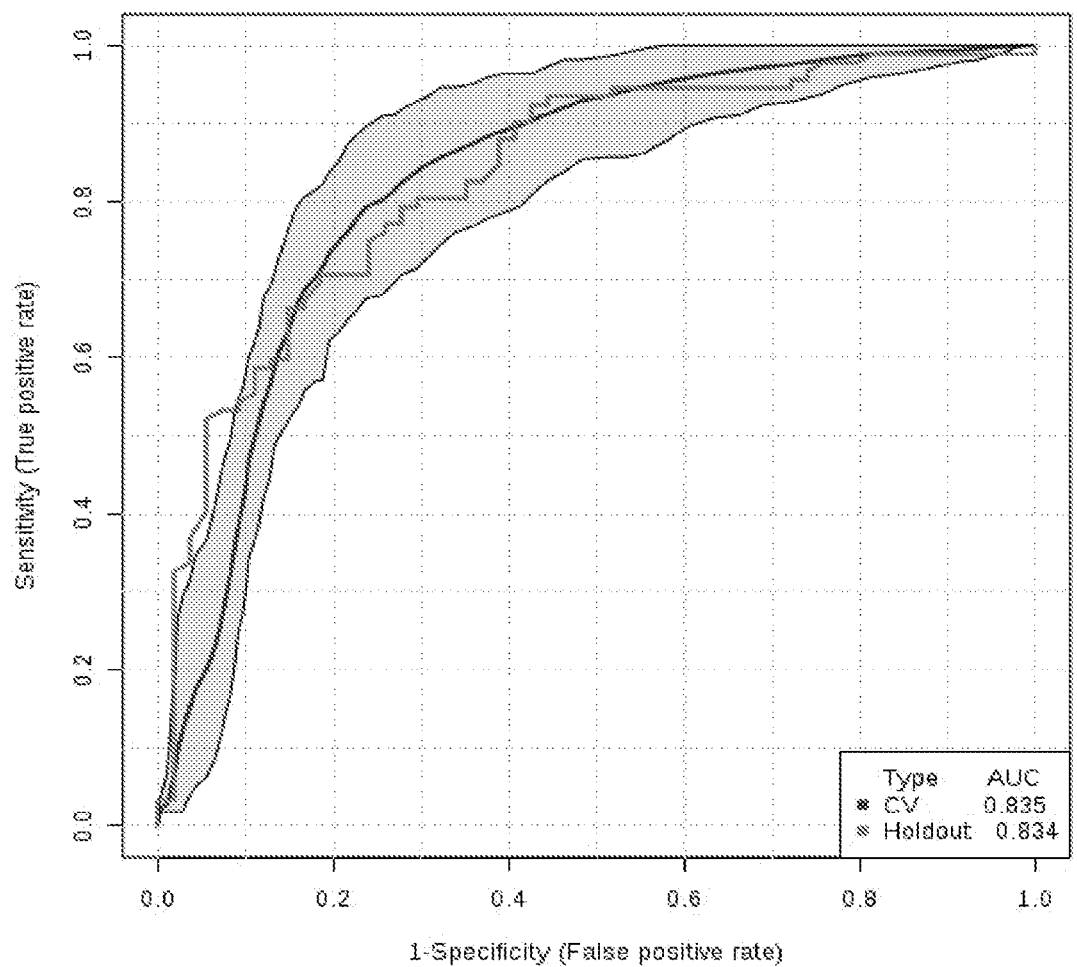
FIG. 24 shows an ROC curve and AUC for an example logistic regression classifier.

1-Sensitivity (false positive rate) v. Sensitivity (true positive rate) is shown in FIG. 24.

Example 8

An example in which ratios of miRNAs and ratios of microbiome data were inputs to a statistical learning model.

TABLE 16

| Estimate | Std. Error | z value | Pr(>\|z\|) | Odds | — |
|---|---|---|---|---|---|
| (Intercept) | −2.447 | 13.482 | −0.182 | 0.856 | — |
| hsa-miR-125b-2-3p/hsa-miR-186-5p | −114713 | 130266.1 | −0.881 | 0.379 | 0 |
| hsa-miR-186-5p/hsa-miR-28-3p | −104204 | 87908.31 | −1.185 | 0.236 | 0 |
| hsa-miR-151a-3p/hsa-miR-222-3p | 71241.92 | 102691.2 | 0.694 | 0.488 | Inf |
| hsa-miR-125b-2-3p/hsa-miR-22-3p | −103191 | 98117.26 | −1.052 | 0.293 | 0 |
| hsa-miR-148a-5p/hsa-miR-186-5p | −55025.7 | 108235.4 | −0.508 | 0.611 | 0 |
| hsa-miR-15b-5p/hsa-miR-944 | −336662 | 123629.8 | −2.723 | 0.006 | 0 |
| hsa-miR-148a-5p/hsa-miR-27b-3p | 279155 | 134966 | 2.068 | 0.039 | Inf |
| hsa-miR-125b-2-3p/hsa-miR-27b-3p | 336696.6 | 148976.7 | 2.26 | 0.024 | Inf |
| hsa-miR-125b-2-3p/hsa-miR-24-3p | −2.361 | 1.788 | −1.32 | 0.187 | 0.09 |
| hsa-miR-151a-3p/hsa-miR-186-5p | 42938.04 | 102984.8 | 0.417 | 0.677 | Inf |
| hsa-miR-148a-5p/hsa-miR-15b-5p | −224125 | 130622.2 | −1.716 | 0.086 | 0 |
| hsa-miR-15b-5p/hsa-miR-378i | 48818.38 | 104234.4 | 0.468 | 0.64 | Inf |
| hsa-miR-151a-3p/hsa-miR-27b-3p | −217369 | 118358.9 | −1.837 | 0.066 | 0 |
| hsa-miR-125b-2-3p/hsa-miR-15b-5p | 40484.1 | 86783.74 | 0.466 | 0.641 | Inf |
| hsa-miR-27b-3p/hsa-miR-944 | 336662.6 | 123630.1 | 2.723 | 0.006 | Inf |
| hsa-let-7a-5p/hsa-miR-186-5p | 1.643 | 1.632 | 1.007 | 0.314 | 5.17 |
| hsa-miR-222-3p/hsa-miR-378i | −88038.6 | 107353.6 | −0.82 | 0.412 | 0 |
| hsa-miR-27b-3p/hsa-miR-378i | 61818.56 | 108371.7 | 0.57 | 0.568 | Inf |
| hsa-miR-125b-2-3p/hsa-miR-30a-5p | 1.755 | 1.282 | 1.37 | 0.171 | 5.78 |
| hsa-miR-151a-3p/hsa-miR-22-3p | 103190.2 | 98117.13 | 1.052 | 0.293 | Inf |
| hsa-miR-125b-2-3p/hsa-miR-222-3p | −159277 | 115540.7 | −1.379 | 0.168 | 0 |
| hsa-miR-125b-2-3p/hsa-miR-23a-3p | −0.345 | 0.807 | −0.428 | 0.669 | 0.71 |
| hsa-miR-1307-5p/hsa-miR-378i | 1.319 | 0.886 | 1.489 | 0.136 | 3.74 |
| hsa-miR-15b-5p/hsa-miR-28-3p | 104202.4 | 87908.01 | 1.185 | 0.236 | Inf |
| 291183*Lacinutrix*/1367847*Paracoccus aminophilus* JCM 7686 | −0.11 | 0.064 | −1.712 | 0.087 | 0.9 |
| 291183*Lacinutrix*/272942*Rhodobacter capsulatus* SB 1003 | −0.021 | 0.062 | −0.338 | 0.736 | 0.98 |
| hsa-miR-186-5p/hsa-miR-378i | −22599.2 | 117411 | −0.192 | 0.847 | 0 |

Logistic Regression Model with Selected Compounds:

logit(P) = log(P/(1 − P)) = −2.447 − 114713.017 hsa-miR-125b-2-3p/hsa-miR-186-5p − 104204.334 hsa-miR-186-5p/hsa-miR-28-3p + 71241.921 hsa-miR-151a-3p/hsa-miR-222-3p − 103191.136 hsa-miR-125b-2-3p/hsa-miR-22-3p − 55025.655 hsa-miR-148a-5p/hsa-miR-186-5p − 336661.91 hsa-miR-15b-5p/hsa-miR-944 + 279154.976 hsa-miR-148a-5p/hsa-miR-27b-3p + 336696.569 hsa-miR-125b-2-3p/hsa-miR-27b-3p − 2.361 hsa-miR-125b-2-3p/hsa-miR-24-3p + 42938.039 hsa-miR-151a-3p/hsa-miR-186-5p − 224124.934 hsa-miR-148a-5p/hsa-miR-15b-5p + 48818.384 hsa-miR-15b-5p/hsa-miR-378i − 217368.672 hsa-miR-151a-3p/hsa-miR-27b-3p + 40484.1 hsa-miR-125b-2-3p/hsa-miR-15b-5p + 336662.558 hsa-miR-27b-3p/hsa-miR-944 + 1.643 hsa-let-7a-5p/hsa-miR-186-5p − 88038.633 hsa-miR-222-3p/hsa-miR-378i + 61818.56 hsa-miR-27b-3p/hsa-miR-378i + 1.755 hsa-miR-125b-2-3p/hsa-miR-30a-5p + 103190.202 hsa-miR-151a-3p/hsa-miR-22-3p − 159277.11 hsa-miR-125b-2-3p/hsa-miR-222-3p − 0.345 hsa-miR-125b-2-3p/hsa-miR-23a-3p + 1.319 hsa-miR-1307-5p/hsa-miR-378i + 104202.432 hsa-miR-15b-5p/hsa-miR-28-3p − 0.11 291183*Lacinutrix*/1367847*Paracoccus aminophilus* JCM 7686 − 0.021 291183*Lacinutrix*/272942*Rhodobacter capsulatus* SB 1003 − 22599.205 hsa-miR-186-5p/hsa-miR-378i, where P is Pr(y = 1|x). The best threshold (or Cutoff) for the predicted P is 0.16.
Original Label: 1/2 --> Labels in Losistic Regression: 0/1
Note)
The class/response value is recommended as (Case: 1 and Control: 0)

TABLE 17

Confusion matrix (cross-validation)

|  | ASD | DD |
|---|---|---|
| ASD | 67 | 7 |
| DD | 25 | 21 |

TABLE 18

Confusion matrix (hold-out)

|  | ASD | DD |
|---|---|---|
| ASD | 80 | 21 |
| DD | 12 | 7 |

Figure 25:
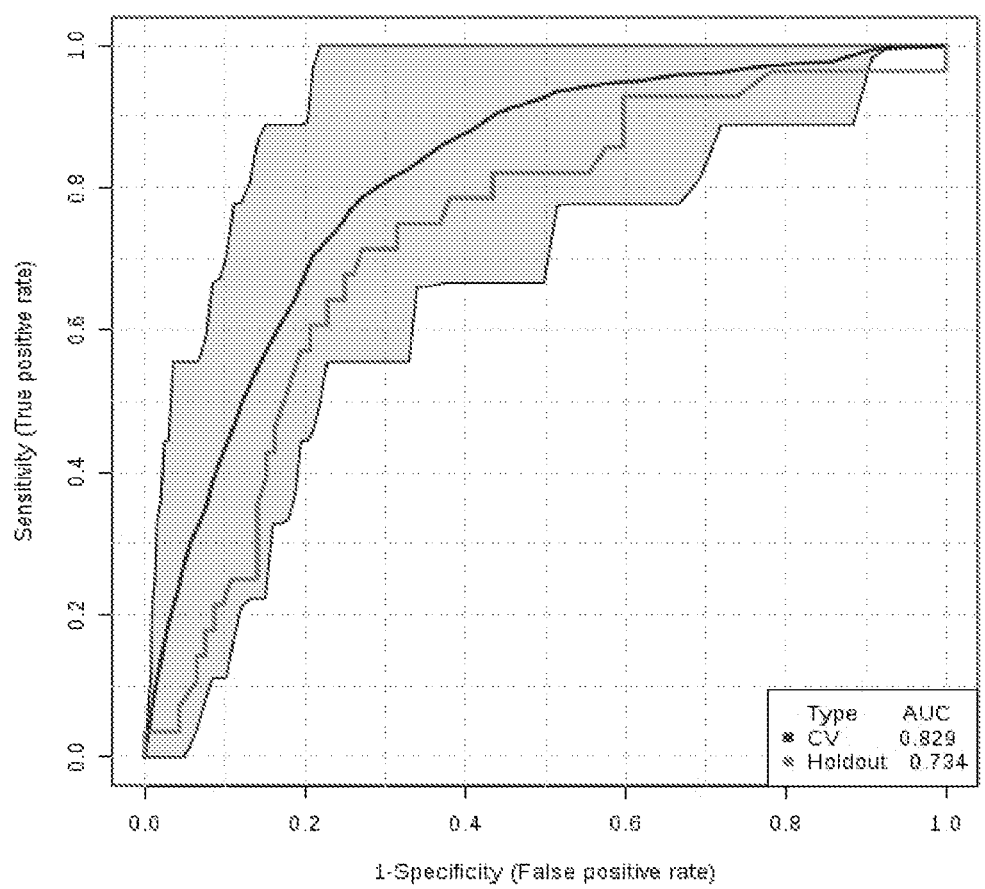
FIG. 25 shows an ROC curve and AUC for an example logistic regression classifier between ASD and DD children incorporating ratios of miRNAs and ratios of microbiome RNAs.

1-Sensitivity (false positive rate) v. Sensitivity (true positive rate) is shown in FIG. 25.

Example 9

MiRNA in ASD: 12 studies have identified 219 miRNAs with differential expression, 34 miRNAs (16%) overlap across multiple studies, and 27 miRNA were changed in the same direction.

TABLE 19

Direction of Change in Different Biomaterials
DIRECTION OF CHANGE IN DIFFERENT BIOMATERIALS

| miRNA ID | CNS | Blood | Saliva | Lympoblast | Olfactory |
|---|---|---|---|---|---|
| miR-7-5p | ↑↓ | | ↑ | | |
| miR-10a-5p | ↑ | | | ↑ | |
| miR-15a-5p | ↓ | ↓ | | | |
| miR-15b-5p | ↓ | ↓ | | | |
| miR-19b-3p | ↑ | ↑↓ | | | |
| miR-21-3p | ↑↑ | | | | |
| miR-23a-3p | ↑↓ | | ↓ | ↓↑ | |
| miR-27a-3p | ↓ | ↑ | ↓ | | |
| miR-30e-5p | | | ↓ | ↓↑ | |
| miR-92a-3p | | ↓ | | ↓ | |
| miR-92b-3p | ↓ | | | ↓ | |
| miR-93 | ↓ | | | ↓ | |
| miR-103a-3p | | ↓ | | ↓ | |
| miR-106b-5p | ↑ | ↑ | | ↑ | |
| miR-132 | | | | ↑↑ | |
| miR-140-3p | ↑ | | ↑ | | |
| miR-146a-5p | ↑ | | | ↑ | ↑ |
| miR-146b | ↑ | | | ↑ | |
| miR-155-5p | ↑↑ | | | | |
| miR-199-5p | | ↓↑ | | ↓ | |
| miR-199b-5p | | | | ↑↑ | |
| miR-219-5p | ↑ | | | ↑ | |
| miR-320a | ↑ | ↓ | | ↓ | |
| miR-335-3p | ↑ | | ↑ | | |
| miR-338-5p | ↑ | | | ↑ | |
| miR-451a | ↑ | ↓ | | ↓ | |
| miR-494 | ↑ | ↑ | | | |
| overlap: | 23.1 | 19.0 | 42.8 | 25.8 | 25.0 |

Figure 26A:
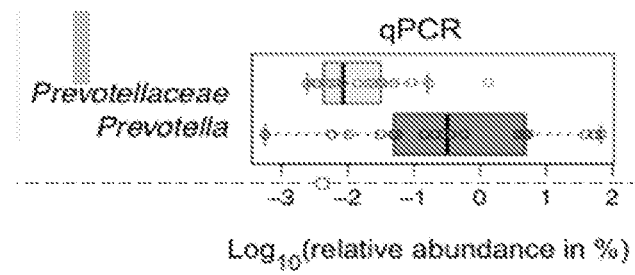
FIG. 26A shows the abundance of Prevotellacaea and *Prevotella* in qPCR analysis.
Figure 26B:
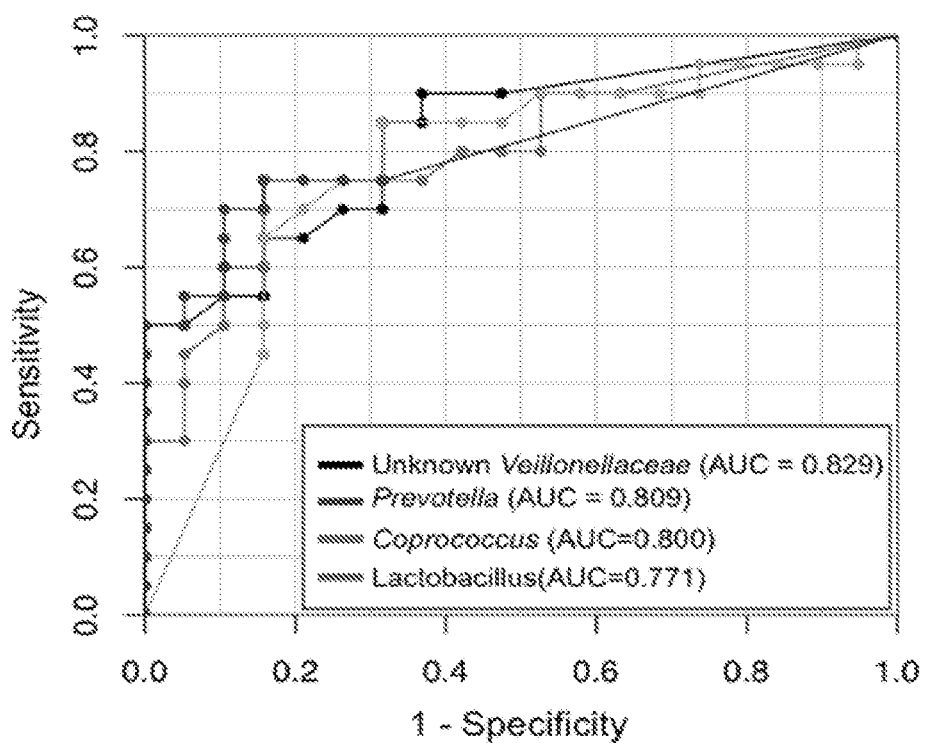
FIG. 26B shows the ROC and AUC of classification models using individual core oral microbiome taxa.

Gut microbiome is altered in autism (Kang et al., 2013):
20 autism v. 20 CTRL,
Fecal 16S rDNA,

*Prevotella* correlated with autism symptoms but not diet. FIGS. 26A-B.

Example 10

Methods

This cross-sectional, observational, case control study was approved by the Independent Review Boards at the Penn State College of Medicine and the State University of New York Upstate Medical University. Written informed consent was obtained from the parents of all children who participated in the study.

Participants

Children ages 2-6 years (n=346) were enrolled in the study. Participants were divided into three groups (ASD, n=180; TD, n=106; DD, n=60) based on developmental status. ASD was defined by clinician consensus diagnosis, using criteria specified in the Diagnostic and Statistical Manual of the American Psychiatric Association, 5$^{th}$ Edition (DSM-5). TD participants included children with negative ASD screening on the Modified Checklist for Autism in Toddlers-Revised (MCHAT-R), and who met typical developmental milestones on standardized physician assessment (e.g. survey of wellbeing in young children; parents' evaluation of developmental status). The DD group included children with an ICD-10 diagnosis of atypical development (e.g. expressive speech delay, intellectual disability, behavioral concern) who did not meet DSM-5 criteria for ASD on clinician assessment. Children with feeding tube dependence, active tooth decay, fever, upper respiratory infection, or currently taking oral antibiotics were excluded from all groups. Children with a family history of ASD in a first degree relative or a chronic medical condition requiring routine care by a pediatric specialist were excluded from the TD group. Phenotypic sub-group analysis compared ASD children with attention deficit hyperactivity disorder (ADHD; n=43), or GI disturbance (n=39) to ASD children without the given condition. ADHD was identified through parental survey and confirmed by ICD-10 diagnosis when possible. GI disturbance was defined as constipation, reflux, chronic abdominal pain, food sensitivities, or recurrent diarrhea reported by parental survey and confirmed through chart-review.

Data Collection

Parents of all participants were administered a child medical/demographic survey and the Vineland Adaptive Behavior Scale (VABS), 2$^{nd}$ edition at the time of enrollment. Most of the ASD (n=138) and DD participants (n=21) were administered the autism diagnostic observation schedule (ADOS), 2$^{nd}$ edition, or previous assessment scores were documented through chart review when available. ADOS administration was performed by a trained certified health professional. The participant characteristics that were collected included: 1) demographic information (age, sex, ethnicity, body mass index); 2) oral/GI factors (time of collection, time of last meal, time of last tooth brushing, probiotic use, history of GI disturbance, medical/food allergies, dietary restrictions); and 3) medical history (birth age, birth delivery route, birth weight, asthma status, vaccination status). These factors were selected based on potential relevance to the profile of the oral microbiome.

Sample Collection and RNA Analysis

Saliva was collected from each participant at the time of enrollment. Following an oral water rinse, an ORAcollect® swab (DNA Genotek, Ottawa Canada) was used to obtain saliva from the sublingual and parotid regions of the mouth in a non-fasting state, at least 15 minutes after the most recent consumption of food or drink. Swabs were stored at −20 C prior to processing at the State University of New York Upstate Molecular Analysis Core Facility. Salivary RNA was extracted using a standard Trizol technique and the RNeasy mini column (Qiagen, Valencia Calif.). Yield and quality of RNA was checked with an Agilent Bioanalyzer prior to library construction and quantification with next generation sequencing. Multiplexed samples were processed on a NextSeq® 500 Instrument (Illumina, San Diego, Calif.) at a targeted depth of 10 million single end 50 base reads per sample. After adapter trimming and QC analysis, RNA reads were aligned to the Human Microbiome Database using k-SLAM software. Sequence alignment with the k-mer method was used for comprehensive taxonomic classification and identification of microbial genes, as previously described. Only taxons with raw read counts of 10 or more in at least 20% of samples were interrogated for differential abundance. Individual RNA transcripts were not subjected to analysis. Instead, we interrogated the pathways and ontologies represented by the community of microbial transcripts through cross-referencing the Kyoto Encyclopedia of Genes and Genomes (KEGG) microbial database using Microbiomanalyst software. This database consists of 82 KEGG Ontology (KO) Pathway sets, 11 KEGG Metabolism sets, and 20 Clusters of Orthologous Groups (COG) Function sets. Mapping was limited to those transcripts present at raw read counts of 5 or more in at least 10% of samples. Both taxonomic and pathway level data were analyzed for differences between groups following quantile normalization, using Metaboanalyst software to perform non-parametric comparisons of the observed abundance counts between groups. These data sets will be made publicly available on the NCBI Sequence Read Archive following acceptance for publication.

Statistical Analysis

Differences in medical, demographic, and neuropsychological characteristics between ASD and TD or DD groups were assessed with a two-tailed Student's t-test, with significant differences defined by an uncorrected p<0.05. Taxons with the greatest abundance (present in the largest concentrations) and prevalence (present in the largest number of samples) were reported at the species and phylum levels. The Shannon alpha diversity index and Bray-Curtiss index of beta diversity (homogeneity of group dispersions method) were calculated from the taxonomic profiles and compared across the three groups. Differential taxon expression across all participants was visualized with a multivariate partial least squares discriminant analysis (PLS-DA) and variable importance in projection was determined for each taxon. Individual taxon differences among the three groups were investigated with non-parametric Kruskal-Wallis testing, followed by post-hoc between group comparisons (ASD:TD; or ASD:DD) with a Mann-Whitney U test. Differences in KEGG pathway transcripts between diagnostic groups were evaluated using a one way Analysis of Variance (ANOVA) with an FDR correction for multiple testing set at q<0.05). Post-hoc testing was performed between all 3 groups using a Tukey's Honestly Significantly Difference (HSD) test.

Taxon associations with a predefined set of ASD endophenotypes were assessed as follows: 1) Taxon differences between ASD participants with/without GI disturbance; and with/without ADHD were examined with a non-parametric Mann-Whitney U test. 2) ASD participants were divided into three adaptive behavior groups (0-, 1-, or 2-standard deviations below the mean value of 100) for Communication, Socialization, and Activities of Daily Living subscales of the VABS and between groups taxonomic differences were assessed with non-parametric Kruskal-Wallis testing. 3) Relationships between autistic behavior measures on the ADOS (Social Affect, Restrictive/Repetitive Behavior, and Total Score) and oral taxon activity were assessed with Pearson's correlations. Factors with Benjamini-Hochberg False Discovery Rate (FDR) correction <0.05 were reported for each phenotype-taxonomic comparison.

Relationships between oral taxons and clinical characteristics were assessed with Pearson's correlation (for continuous variables) or Spearman's rank test (for dichotomous variables). Diagnostic accuracies of taxon levels in the oral microbiome were assessed with a multivariate logistic regression analysis, comparing 1) ASD:TD; 2) ASD:DD; and 3) GI disturbance phenotypes across diagnoses. Classification accuracy was visualized with a receiver operating characteristic (ROC) curve, using the first 50% of samples from each group (chosen at random) and a 10-fold cross-validation procedure. The remaining 50% of samples were used to validate the predictive model for each comparison. Area under the curve (AUC) was calculated and 95% confidence intervals were reported.

Results

Participant Characteristics

The ASD group (n=180) had a mean age of 53 (±16) months, was 85% male, and was 59% Caucasian (Table 1). TD participants (n=106) were, on average, 10 months younger (43±16 months), were 60% male, and were 63% Caucasian. The DD group (n=60) had an average age of 50 (±13) months, was 70% male, and was 67% Caucasian. There was no difference in average collection time between ASD (12:29 PM±2:48), TD (12:21 PM±2:43), and DD (12:43 PM±2:43) subjects. There was also no difference between groups in time since last meal, or time since last tooth brushing. Only 3% of ASD and DD children were taking a probiotic, compared with 0% of TD children. ASD participants had higher rates of GI disturbance (22%) than the TD group (3%), but not the DD group (20%). More ASD participants had a food or medicine allergy (21%) than TD (9%) and DD (8%) participants, but they had similar rates of dietary restrictions. There was no difference between groups in birth weight, though children in the ASD group had higher rates of cesarean section (19%) than TD (9%) and DD (8%) participants. There were no differences between groups in rates of asthma or vaccination. The ASD group had lower mean VABS scores on the Socialization (73±13) and Activities of Daily Living (75±14) domains relative to TD and DD groups. Average VABS communication score in the ASD group (72±18) differed from TD participants (103±15), but not DD participants (76±17). ASD subjects had higher total ADOS scores on the Social Affect domain (13±5) and the Restrictive and Repetitive Behavior domain (3±1) relative to DD participants (6±4; and 2±1, respectively).

TABLE 20

Participant Characteristics

| Clinical Characteristics | ASD (n = 180) | TD (n = 106) | DD (n = 60) |
|---|---|---|---|
| Demographics | | | |
| Age, mean (SD), years | 53 (16) | 43 (16)* | 50 (13) |
| Male (%), No. | 154 (86) | 64 (60)* | 43 (70)* |
| Caucasian (%), No. | 107 (59) | 67 (63) | 40 (67) |
| Body mass index (SD), kg/m$^2$ | 16.5 (2.8) | 16.4 (2.0) | 17.0 (3.1) |
| Oral/GI Factors | | | |
| Time of collection (SD) | 12:29 (2:48) | 12:21 (2:43) | 12:43 (2:38) |
| Time since last meal (SD), hrs | 3 (3) | 3 (3) | 2 (2) |
| Time of last tooth brush (SD), hrs | 8 (5) | 5 (4) | 5 (3) |
| Food/medical allergies (%), No. | 38 (21) | 9 (9)* | 5 (8)* |
| Dietary restrictions (%), No. | 25 (14) | 8 (8) | 11 (18) |
| Probiotic use (%), No. | 5 (3) | 0 (0) | 2 (3) |
| GI disturbance (%), No. | 39 (22) | 3 (3)* | 12 (20) |
| Medical Characteristics | | | |
| Cesarean section (%), No. | 35 (19) | 9 (9)* | 5 (8)* |
| Birth weight (SD), kg | 3.3 (0.9) | 3.2 (0.7) | 3.2 (1.2) |
| Asthma (%), No. | 18 (10) | 8 (8) | 10 (17) |
| Fully vaccinated (%), No. | 169 (94) | 97 (92) | 58 (97) |

TABLE 20-continued

Participant Characteristics

| Clinical Characteristics | ASD (n = 180) | TD (n = 106) | DD (n = 60) |
|---|---|---|---|
| Neuropsychiatric Characteristics | | | |
| ADHD (%), No. | 43 (23) | 10 (9)* | 17 (24) |
| Vineland Communication (SD) | 72 (18) | 103 (15)* | 76 (17) |
| Vineland Socialization (SD) | 73 (13) | 107 (17)* | 80 (19)* |
| Vineland ADL (SD) | 75 (14) | 104 (18)* | 81 (18)* |
| ADOS Social Affect (SD) | 13 (5) | — | 6 (4)* |
| ADOS RRB (SD) | 3 (1) | — | 2 (1)* |

Characteristics with significant ($p < 0.05$) between group differences on Student's two-tailed t-test are denoted with asterisks.
Vineland domain standard scores are shown (where a score of 100 is average).
Autism Diagnostic Observation Schedule (ADOS) total scores are shown.
Abbreviations: Autism spectrum disorder (ASD); typically developing (TD); non-autistic developmental delay (DD); gastrointestinal (GI); attention-deficit hyperactivity disorder (ADHD); activities of daily living (ADL); restricted and repetitive behavior (RRB).

Microbial Diversity Profiles

Among all samples, there was an average of 790,031 taxonomic reads per sample. The mean read count did not differ between ASD (785,766), TD (823,480), and DD (738,335) groups. Taxonomic reads were filtered to include only the taxons with counts of >10 in >20% of samples. Of the 753 taxons meeting these criteria, 41 were present in all samples.

Figure 27:
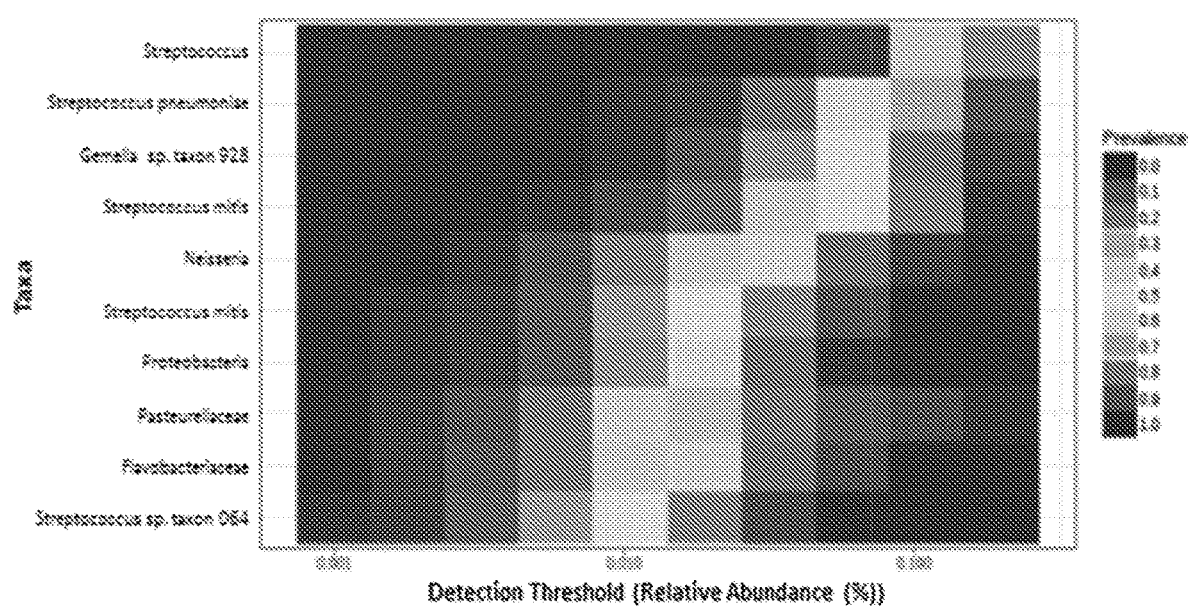
FIG. 27 shows the prevalence and abundance of core oral microbiome taxa. The 10 oral taxons with the highest transcriptional activity across all participants (n=346) are shown. Relative abundance (x-axis) for all 10 taxons exceeded 0.5% of the oral microbiome, and each taxa was present in counts of 10 or more in at least 70% of samples (prevalence, shown in red-blue scale/gray scale).
Figures 28A, 28B:
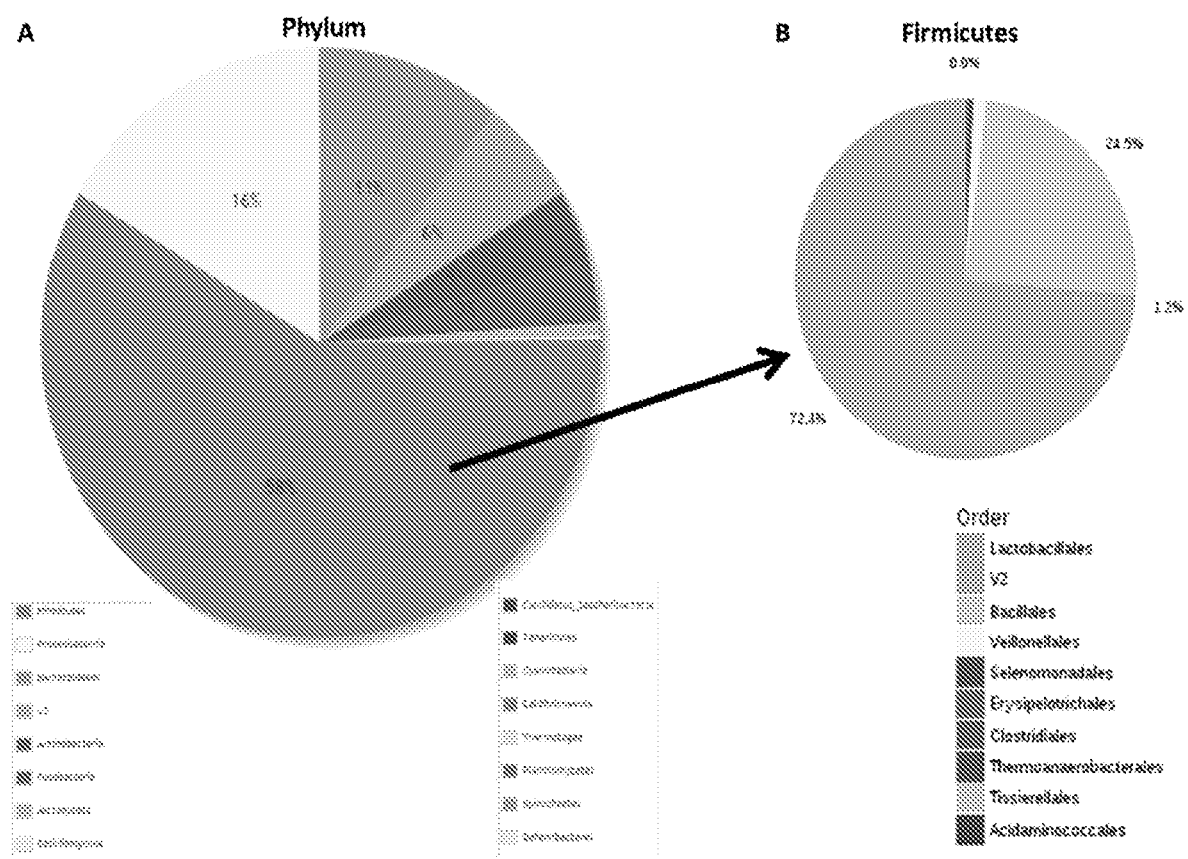
FIGS. 28A-B show the core oral phyla. Abundance of oral transcripts at the phylum level across all participants (n=346) are shown as percentage of the total (A). Firmicutes (58%) was the most abundant phylum, followed by Proteobacteria (16%) and *Bacteroides* (11%). Among the Firmicutes phylum (B) lactobacillales was most abundant (72.4%) order, followed by Bacillales (24.5%).
Figure 29A:
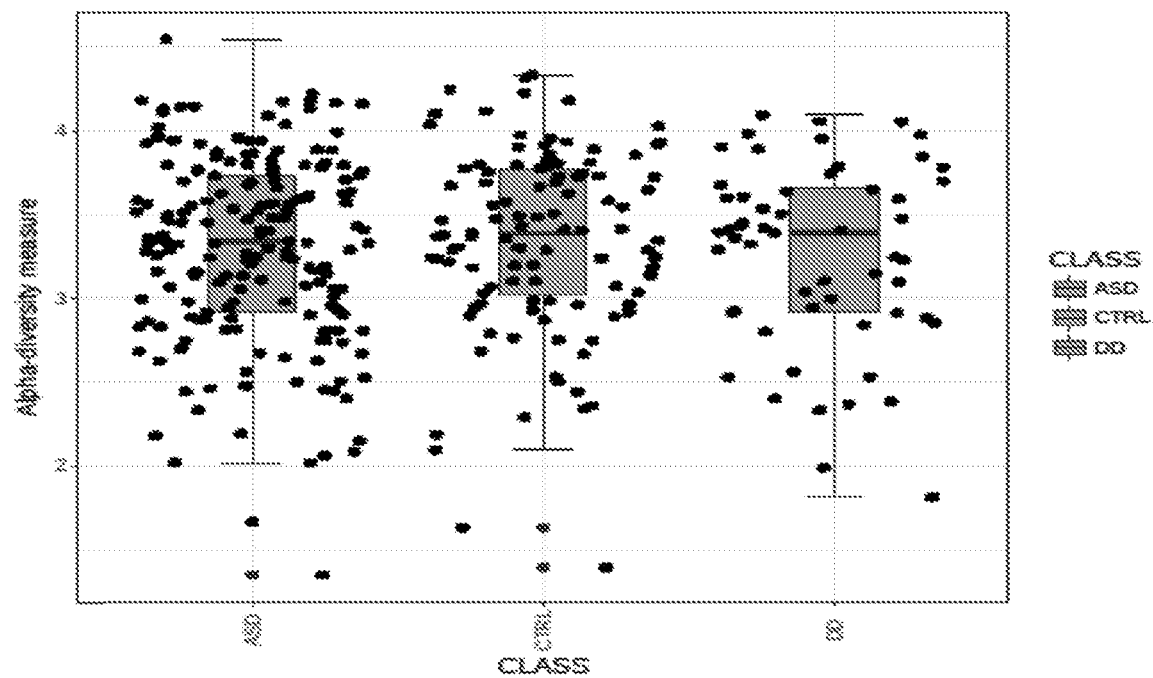
FIGS. 29A-B show no difference in Shannon alpha-diversity between ASD, TD, and DD groups at the species (p=0.60; F=1.01) (A) or phylum levels (p=0.48; F=0.73) (B).
Figure 29B:
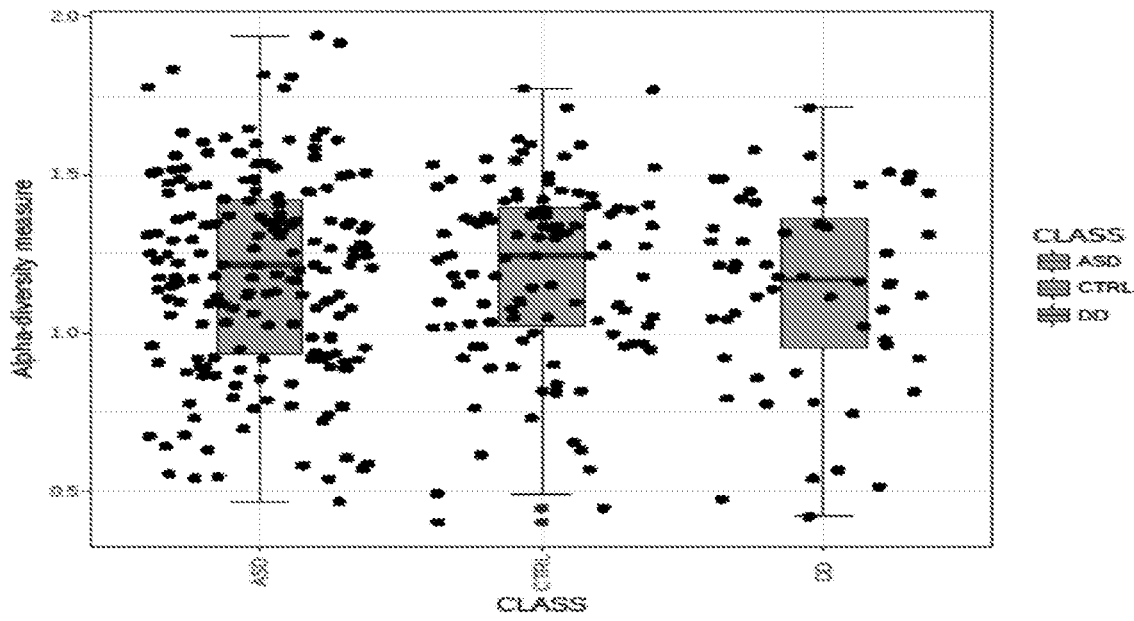
Figure 30:
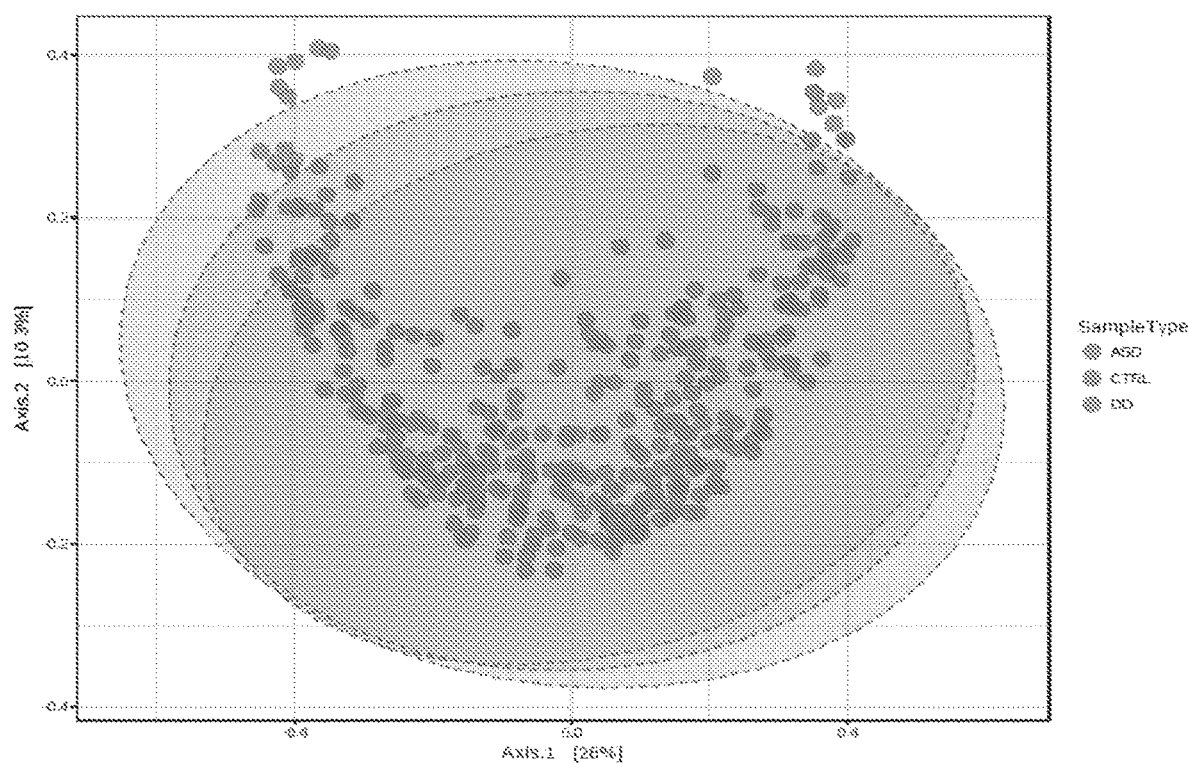
FIG. 30 shows Bray-Curtis beta-diversity. Microbial diversity between participants was calculated using a homogeneity of group dispersions technique for ASD (red/gray scale; n=180), TD (green/gray scale; n=106), and DD (blue/gray scale; n=60) groups. There was a significant difference (p=0.04, F=3.25) between the groups, with the greatest between-samples diversity in the TD group. This two-dimensional plot accounts for 38.3% of the variance among participants. 95% confidence intervals are shown by the colored/gray scale ovals.

The core, oral microbiome (defined as taxons present in >70% of samples with relative abundance >0.5%) included ten taxons (FIG. 27): *Streptococcus* ($3.9 \times 10^7$ total raw reads), *Streptococcus pneumoniae* ($2.0 \times 10^7$), *Gemella* sp. oral taxon 928 ($3.5 \times 10^7$), *Streptococcus mitis* ($2.0 \times 10^7$), *Neisseria* ($9.2 \times 10^6$), *Streptococcus mitis* B6 ($7.3 \times 10^6$), Proteobacteria ($5.1 \times 10^6$), Pasteurellacae ($6.0 \times 10^6$), Flavobacteriaceae ($5.6 \times 10^6$), and *Streptococcus* sp. oral taxon 064 ($3.6 \times 10^6$). The most abundant oral phyla among all samples was Firmicutes (58% of reads), followed by Proteobacteria (16%) and *Bacteroides* (11%; FIG. 28A). The most prominent taxonomic orders within the Firmicutes phylum were Lactobacillales (72% of reads) and Bacillales (25%; FIG. 28B). There was no difference in Shannon alpha-diversity between ASD, TD, and DD groups at the species (p=0.60; F=1.01; FIG. 29A), or phylum levels (p=0.48; F=0.73; FIG. 29B). Bray-Curtis beta-diversity, measured with a homogeneity of group dispersions technique, demonstrated significant differences (p=0.04, F=3.25) between ASD, TD, and DD groups with the greatest between-sample diversity visualized in the TD group (FIG. 30).

Microbial Differences

Differences between ASD, TD, and DD groups were explored at the phylum and species levels with a non-parametric Kruskal-Wallis test. There were 12 taxons with significant differences (FDR<0.05) between ASD, TD, and DD groups (Table 21).

TABLE 21

Taxon differences between ASD, TD, and DD groups at the species level

| | 3 Group Comparison | | | ASD v TD | | ASD v DD | |
|---|---|---|---|---|---|---|---|
| Taxon | $\chi^2$ | P | FDR | FC | FDR | FC | FDR |
| *Ramlibacter tataouinensis* TTB310 | 42.4 | 6.28E−10 | 4.73E−07 | 0.85 | 0.0009 | 0.61 | 0.18 |
| *Limnohabitans* sp. 63ED37-2 | 33.3 | 6.04E−08 | 2.27E−05 | 1.05 | 0.01 | 0.69 | 0.26 |
| *Gemmata* sp. SH-PL17 | 30.7 | 2.11E−07 | 5.29E−05 | 0.86 | 0.052 | 0.73 | 0.19 |
| *Flavobacterium psychrophilum* | 23.6 | 7.37E−06 | 0.0014 | 1.28 | 0.24 | 0.62 | 0.12 |
| *Flavobacterium* sp. PK15 | 22.8 | 1.13E−05 | 0.0017 | 0.80 | 0.56 | 0.41 | 0.058 |
| Planctomycetales | 22.0 | 1.64E−05 | 0.0021 | 1.21 | 0.049 | 0.97 | 0.65 |
| *Comamonas testosteroni* TK102 | 19.7 | 5.19E−05 | 0.0056 | 0.87 | 0.26 | 0.69 | 0.12 |
| *Chamaesiphon minutus* PCC 6605 | 19.4 | 6.22E−05 | 0.0058 | 1.07 | 0.38 | 0.62 | 0.12 |
| *Mucilaginibacter* sp. PAMC 26640 | 19.2 | 6.89E−05 | 0.0058 | 0.17 | 0.0009 | 0.59 | 0.97 |
| Cyanobacteria | 18.0 | 0.0001 | 0.0093 | 2.38 | 0.06 | 1.07 | 0.50 |
| *Kingella kingae* | 16.4 | 0.0003 | 0.0188 | 1.69 | 0.31 | 0.65 | 0.17 |
| *Enterococcus faecalis* OG1RF | 15.2 | 0.0005 | 0.0317 | 1.45 | 0.26 | 2.27 | 0.058 |

Species with significant (False detection rate (FDR) < 0.05) differences among autism spectrum disorder (ASD), typically developing (TD), and non-autistic developmental delay (DD) groups on Kruskal-Wallis testing are shown.
Fold changes (FC) among ASD:TD and ASD:DD groups are listed.

Four of these taxons displayed differential expression (FDR<0.05) between ASD and TD groups on Mann Whitney U-test. Two taxons were elevated in children with ASD (*Limnohabitans* sp. 63ED37-2, p=0.01; *Planctomycetales*, p=0.049) and two were decreased (*Ramlibacter tataouinensis* TTB310, p=0.0009; *Mucilaginibacter* sp. PAMC 26640, p=0.0009). No taxons showed significant differences (FDR<0.05) between ASD and DD children. Phylum differences were observed between the three diagnostic groups (FIG. 31) for Planctomycetes ($\chi2$=31.0, FDR=3.2E-06), Cyanobacteria ($\chi2$=14.8, FDR=0.005), and Calditrichaeota ($\chi2$=9.6, FDR=0.04). These differences resulted largely from ASD/TD variation (Table 22).

TABLE 22

| Phylum | 3-group comparison | | | ASD v TD | | ASD v DD | |
|---|---|---|---|---|---|---|---|
| | $\chi2$ | P | FDR | FC | FDR | FC | FDR |
| Actinobacteria | 0.7615 | 0.68335 | 0.77446 | 1.0712 | 0.96948 | 1.1384 | 0.91752 |
| Ascomycota | 3.5146 | 0.17251 | 0.48119 | 4.2859 | 0.50415 | 2.3652 | 0.91752 |
| Bacteroidetes | 6.5385 | 0.038034 | 0.16165 | 0.88975 | 0.051132 | 0.89655 | 0.91752 |
| Basidiomycota | 3.7448 | 0.15375 | 0.48119 | 1.1986 | 0.43487 | 1.3719 | 0.64367 |
| Calditrichaeota | 9.5594 | 0.008399 | 0.047592 | 0.56309 | 0.026096 | 2.3959 | 0.98704 |
| Candidatus_Saccharibacteria | 3.2376 | 0.19814 | 0.48119 | 0.79465 | 0.241 | 0.7693 | 0.91752 |
| Cyanobacteria | 14.815 | 0.000607 | 0.005157 | 1.6542 | 0.005896 | 1.0573 | 0.91752 |
| Deferribacteres | 1.034 | 0.59631 | 0.72409 | 0.98884 | 0.59555 | 0.001077 | 0.91752 |
| FB ratio | 1.8422 | 0.39808 | 0.67673 | 1.4088 | 0.55472 | 2.2932 | 0.91752 |
| Firmicutes | 2.1653 | 0.33869 | 0.63975 | 0.95487 | 0.42843 | 1.003 | 0.98704 |
| Fusobacteria | 1.3183 | 0.51729 | 0.72409 | 0.94041 | 0.55472 | 1.1881 | 0.91752 |
| Planctomycetes | 30.97 | 1.88E-07 | 3.20E-06 | 1.2792 | 0.001085 | 0.032498 | 0.023851 |
| Proteobacteria | 1.0801 | 0.58271 | 0.72409 | 1.0456 | 0.55472 | 1.025 | 0.91752 |
| Spirochaetes | 0.49661 | 0.78012 | 0.79932 | 1.2524 | 0.66151 | 1.2837 | 0.91752 |
| Tenericutes | 0.448 | 0.79932 | 0.79932 | 1.2159 | 0.59555 | 1.2293 | 0.98704 |
| Thermotogae | 2.7043 | 0.25868 | 0.5497 | 1.088 | 0.42843 | 0.11733 | 0.91752 |
| V3 | 1.5085 | 0.47037 | 0.72409 | 1.2756 | 0.55472 | 0.92724 | 0.91752 |

3 group comparisons utilize non-parametric Kruskal-Wallis ANOVA.
2 group comparisons utilize Mann-Whitney U Test.
All p-values are False Detection Rate (FDR) adjusted.
Abbreviations: fold change (FC), autism spectrum disorder (ASD); typical development (TD); developmental delay (DD)

Only Planctomycetes differed between ASD and both TD (Fold change=1.28, FDR=0.001) and DD groups (FC=0.03; FDR=0.02). Notably, no changes were observed in the Firmicutes:*Bacteroides* ratio of the ASD group, though *Bacteroides* displayed nominally lower expression in ASD versus TD participants (FC=0.89, FDR=0.051). A partial least squares discriminant analysis (PLS-DA) was used to visualize differences in taxonomic profiles at the species level between ASD, TD, and DD groups in two dimensions. A model accounting for 4% of the variance between groups resulted in partial separation of ASD, TD, and DD participants (FIG. 32A). The 20 taxons most critical for the differential group projection are shown (FIG. 32B). Of these 20 taxons, 14 demonstrate relative reductions in ASD samples and three are increased in saliva of ASD participants relative to TD and DD groups.

Microbiome Variations Among ASD Phenotypes

Variations among microbiome elements at the phylum and taxon level were explored among common ASD phenotypes (Table 23).

TABLE 23

Differential phyla and species profiles among ASD phenotypes

| ASD Phenotypes | Phyla (#) | Species (#) |
|---|---|---|
| Medical Traits | | |
| With (n = 39) and without (n = 141) GI Disturbance | 0 | 28 |
| With (n = 70) and without (n = 110) ADHD | 0 | 0 |

TABLE 23-continued

Differential phyla and species profiles among ASD phenotypes

| ASD Phenotypes | Phyla (#) | Species (#) |
|---|---|---|
| Adaptive Behavior (binned into groups of 0, 1, or 2 standard deviations below mean) | | |
| Communication (n = 38, 43, 64) | 1<br>Caldotrichea, $\chi2$ = 9.7, FDR = 0.039 | 5<br>*Acinetobacter*, $\chi2$ = 23.0, FDR = 0.0019<br>*Micrococcus luteus*, $\chi2$ = 21.5, FDR = 0.0033<br>*Moraxella*, $\chi2$ = 18.2, FDR = 0.014<br>*Porphyromonas*, $\chi2$ = 15.3, FDR = 0.049<br>Pasteurellaceae bacterium, =15.1, FDR = 0.049 |
| Socialization (n = 25, 61, 59) | 0 | 0 |
| Activities of daily living (n = 35, 64, 46) | 0 | 0 |
| Autistic Characteristics | | |
| Social Affect Score | 1<br>Actinobacteria, R = 0.24, FDR = 0.036 | 0 |
| Restrictive/Repetitive Behavior Score | 0 | 4<br>*Moraxella bovoculi*, R = 0.40, FDR = 0.0003<br>*Streptococcus mitis*, R = 0.35, FDR = 0.005<br>*Riemerella anatipestifer*, R = 0.34, FDR = 0.005<br>*Chryseobacterium* sp. IHB B 17019, R = 0.31, FDR = 0.030 |
| Total ADOS Score | 0 | 0 |

Comparison of phyla and species level data among autism spectrum disorder (ASD) phenotypes was completed for medical traits, adaptive behavior, and autistic characteristics.
ASD subjects with/without gastrointestinal disturbance; and with/without attention deficit hyperactivity disorder (ADHD) were compared by Mann Whitney U-Test.
The number of phyla/species differences are listed for each comparison.
Adaptive behaviors (measured by Vineland Adaptive Behavior Scale - $2^{nd}$ edition) were defined as 0-, 1-, or 2- standard deviations below the mean score (100) and microbial differences were compared across groups with a non-parametric Kruskal-Wallis test.
Autistic traits were quantified with the Autism Diagnostic Observation Schedule - $2^{nd}$ edition, and associations with oral microbiome levels were determined with Pearson Correlation analysis.
Individual phylum/species differences are denoted, with the exception of species differences among GI phenotypes, which can be found in Table 24.

Differential expression among ASD subjects with/without ADHD, and with/without GI disturbance was investigated with a non-parametric Mann-Whitney approach. There were no taxons or phyla with differential expression among ASD children with and without ADHD. There were no phyla and 28 taxons with significant differences (FDR<0.05) between ASD patients with and without GI disturbance (Table 24).

TABLE 24

Taxon Differences between ASD patients with and without GI disturbance

| Taxon | log2FC | P values | FDR | T-Stat |
|---|---|---|---|---|
| *Jonesia denitrificans* DSM 20603 | −1.0104 | 0.000157 | 0.039645 | 1661.5 |
| *Fusobacterium nucleatum* subsp. *animalis* | 1.2847 | 0.000138 | 0.039645 | 1651.5 |
| Negativicutes | 0.83074 | 0.000149 | 0.039645 | 1656.5 |
| *Arthrobacter* | 1.4619 | 0.000362 | 0.041513 | 1722.5 |
| *Acidipropionibacterium acidipropionici* | 0.57234 | 0.000235 | 0.041513 | 1692.5 |
| *Tropheryma whipplei* TW08/27 | 0.75715 | 0.000377 | 0.041513 | 1725.5 |
| *Micrococcus luteus* NCTC 2665 | 0.49797 | 0.000383 | 0.041513 | 1728 |
| *Cellulomonas fimi* ATCC 484 | 0.72778 | 0.000445 | 0.042158 | 1745.5 |
| *Riemerella anatipestifer* RA-CH-1 | 1.1463 | 0.000835 | 0.042824 | 1787 |
| *Arthrobacter* sp. YC-RL1 | 0.57269 | 0.000878 | 0.042824 | 1808.5 |
| *Campylobacter pinnipediorum* subsp. *pinnipediorum* | 1.0493 | 0.000883 | 0.042824 | 1797.5 |
| *Trueperella pyogenes* | 1.2003 | 0.00096 | 0.042824 | 1809 |
| *Gordonia* | 0.88984 | 0.000717 | 0.042824 | 1777 |
| *Veillonella parvula* DSM 2008 | 0.40963 | 0.000948 | 0.042824 | 1797 |
| [*Eubacterium*] *eligens* ATCC 27750 | 0.73588 | 0.000836 | 0.042824 | 1790.5 |
| *Campylobacter gracilis* | 1.4945 | 0.000679 | 0.042824 | 1771 |
| *Selenomonas* | 1.73 | 0.000623 | 0.042824 | 1764 |
| *Pelosinus fermentans* JBW45 | −0.38341 | 0.001108 | 0.042977 | 1811.5 |

TABLE 24-continued

Taxon Differences between ASD patients with and without GI disturbance

| Taxon | log2FC | P values | FDR | T-Stat |
|---|---|---|---|---|
| *Fusobacterium nucleatum* subsp. *animalis* 7 1 | 0.50384 | 0.001162 | 0.042977 | 1814 |
| [*Clostridium*] saccharolyticum WM1 | 0.89781 | 0.001191 | 0.042977 | 1816 |
| *Fusobacterium* | 0.84978 | 0.001161 | 0.042977 | 1813.5 |
| *Fusobacterium nucleatum* subsp. *vincentii* 3 127 | 0.89022 | 0.001275 | 0.043929 | 1821.5 |
| *Brachybacterium faecium* DSM 4810 | 0.89829 | 0.001449 | 0.045756 | 1833 |
| *Mycobacterium sinense* | 0.6082 | 0.001418 | 0.045756 | 1840 |
| Micrococcales | −0.11514 | 0.001617 | 0.049018 | 1841 |
| Actinobacteria | 0.44833 | 0.001842 | 0.049863 | 1852 |
| *Fusobacterium nucleatum* subsp. *animalis* 21 1A | 0.9138 | 0.00178 | 0.049863 | 1849.5 |
| *Beutenbergia cavernae* DSM 12333 | 0.52426 | 0.00179 | 0.049863 | 1852 |

Three of these taxons were down-regulated in ASD children with GI disturbance and 25 were up-regulated. None of the 28 taxons overlapped with those identified in ASD:TD and ASD:DD comparisons. Domain standard scores for adaptive behaviors (Communication, Socialization, and Activities of Daily Living) were characterized as 0-, 1-, or 2-standard deviations below the mean value (100) and phyla/taxon differences across ASD participants were identified with a Kruskal-Wallis test. There was one phyla (Claditrichaeota) and five taxons with differences across ASD Communication groups (*Acinetobacter, Micrococcus luteus, Moraxella, Porphyromonas*, and Pasterurellaceae bacterium). There were no differences across Socialization, or Activities of Daily Living phenotypes at the phyla or taxon level. Relationships of microbiome elements with Restrictive/Repetitive Behavior, Socialization, and Total Scores on ADOS were interrogated using a Pearson correlation. At the phylum level, actinobacteria levels were significantly correlated (R>0.20, FDR<0.05) with ADOS Social Affect (R=0.24; FDR=0.036) and ADOS total scores (R=0.25; FDR=0.019). There were no phyla correlated with ADOS Restrictive/Repetitive Behavior Scores. At the taxon level, there were 4 elements correlated with ADOS Restrictive/Repetitive Behavior Scores (*Moraxella bovoculi, Streptococcus mitis, Riemerella anatipestifer*, and *Chryseobacterium* sp. IHB B 17019). There were no taxons correlated with ADOS Socialization or Total Scores.

Relationship of Oral Microbiome Elements and Clinical Characteristics

There were no significant (R>0.20; FDR<0.05) relationships between clinical characteristics and individual phylum levels on Spearman Rank (dichotomous variables) or Pearson correlation analysis (continuous variables). Individual taxons showed relationships with age, body mass index, time of collection, time since last meal, and time since last tooth brushing (Table 25).

TABLE 25

Relationship between oral taxons and clinical characteristics

| Clinical characteristic | Taxon | R | FDR |
|---|---|---|---|
| Age | *Sideroxydans lithotrophicucus* ES1 | −0.23 | 4.5E−4 |
| | *Klebsiella pneumoniae* | 0.21 | 0.012 |
| | *Snodgrassella alvi* B2 | −0.21 | 0.018 |
| | *Riemerella anatipestifer* Yb2 | −0.20 | 0.022 |
| Sex | — | — | — |
| Ethnicity | — | — | — |
| Body mass index | *Streptococcus pneumoniae* ST556 | 0.34 | 4.5E−8 |
| | *Streptococcus pneumoniae* Taiwan 19F-14 | 0.29 | 1.0E−5 |
| | *Streptococcus pneumoniae* PCS8235 | 0.23 | 2.0E−5 |
| | *Streptococcus infantarius* subsp. CJ18 | 0.21 | 6.4E−5 |
| Collection time | *Streptococcus pneumoniae* SPNA45 | 0.26 | 0.0014 |
| | *Streptococcus pseudopneumoniae* IS7493 | 0.26 | 0.0014 |
| | *Streptococcus pneumoniae* OXC141 | 0.25 | 0.0023 |
| | *Streptococcus oralis* | 0.24 | 0.0035 |
| | *Snodgrassella alvi* wkB2 | −0.24 | 0.0037 |
| | *Streptococcus pneumoniae* TIGR4 | 0.24 | 0.0037 |
| | *Streptococcus pneumoniae* 70585 | 0.23 | 0.0057 |
| | *Streptococcus pneumoniae* PCS8235 | 0.23 | 0.0071 |
| | *Streptococcus pneumoniae* Hungary 19A-6 | 0.22 | 0.0077 |
| | *Streptococcus pneumoniae* R6 | 0.22 | 0.0081 |
| | *Haemophilus influenzae* 86-028NP | 0.22 | 0.0082 |
| | *Porphyromonas* | −0.22 | 0.0083 |
| | *Streptococcus pneumoniae* gamPNI0373 | 0.22 | 0.0095 |
| | *Streptococcus* sp. oral taxon 064 | 0.21 | 0.0095 |
| | *Streptococcus pneumoniae* Taiwan19F-14 | 0.21 | 0.0095 |
| | *Bacteroides caecimuris* | −0.21 | 0.013 |
| | *Streptococcus pneumoniae* ATCC 700669 | 0.21 | 0.014 |
| | *Streptococcus pneumoniae* D39 | 0.20 | 0.016 |
| | *Tannerella forsythia* KS16 | −0.20 | 0.016 |
| | *Sideroxydans lithotrophicus* ES-1 | −0.20 | 0.017 |
| | *Streptococcus pneumoniae* | 0.20 | 0.018 |

TABLE 25-continued

Relationship between oral taxons and clinical characteristics

| Clinical characteristic | Taxon | R | FDR |
|---|---|---|---|
| Time since last meal | *Planococcus maritimus* | 0.28 | 0.0061 |
| | *Brevibacillus laterosporus* LMG 15441 | 0.26 | 0.016 |
| | *Actinomyces meyeri* | 0.24 | 0.027 |
| Last tooth brush | *Candida dubliniensis* CD36 | 0.43 | 0.048 |
| Food/medical allergies | — | — | — |
| Dietary restrictions | — | — | — |
| Probiotic use | — | — | — |
| Cesarean section | — | — | — |
| Birth weight | — | — | — |
| Asthma | — | — | — |
| Vaccination status | — | — | — |

Relationships between species level data and clinical/demographic characteristics are shown.
Pearson analysis was employed for continuous variables and Spearman Rank analysis was used for dichotomous variables.

None of the taxons associated with clinical features overlapped with taxons identified as "altered" in ASD patients, or among ASD endophenotypes. The largest number of taxon associations (21) was found with time of saliva collection, and 15 of these taxons were from the *Streptococcus* genus. The strongest correlation was found between time since last toothbrush and *Candida dubliniensis* CD36 (R=0.43; FDR=0.048). Notably, dietary restrictions, food/medicine allergies, probiotic use, and vaccination status showed no correlations with oral taxonomic concentrations.

Classification Accuracy

Figure 33A:
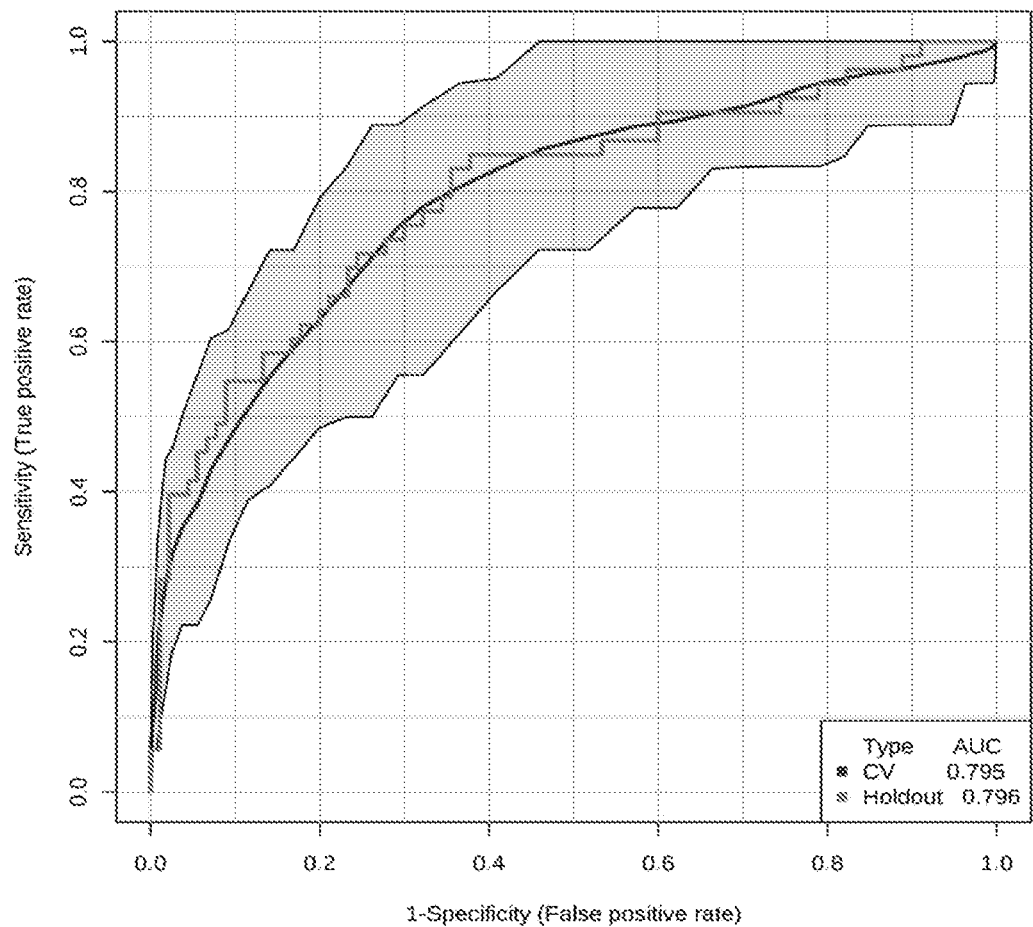
FIGS. 33A, B, C show that Transcriptional activity of oral taxons differentiates ASD participants. (A) this panel of taxons demonstrated nearly identical performance in the hold-out set, identifying 73/90 ASD children and 33/53 TD children (AUC=0.796); (B) three ratios performed similarly in the hold-out set of naïve samples, identifying 82/90 ASD children and 21/30 DD children (AUC=0.765); (C) in the hold-out set, this panel of taxons identified 7/20 ASD children with GI disturbance and 67/71 children without GI disturbance (AUC=0.857).
Figure 33B:
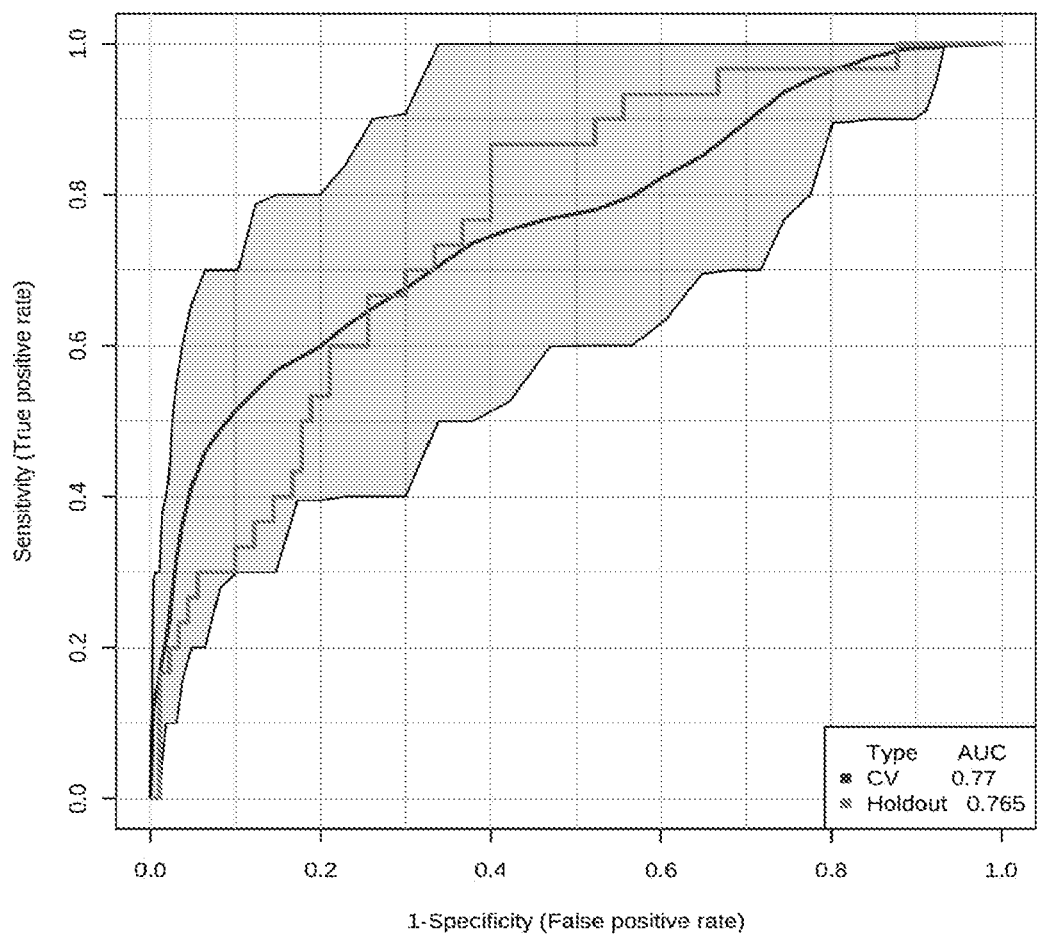
Figure 33C:
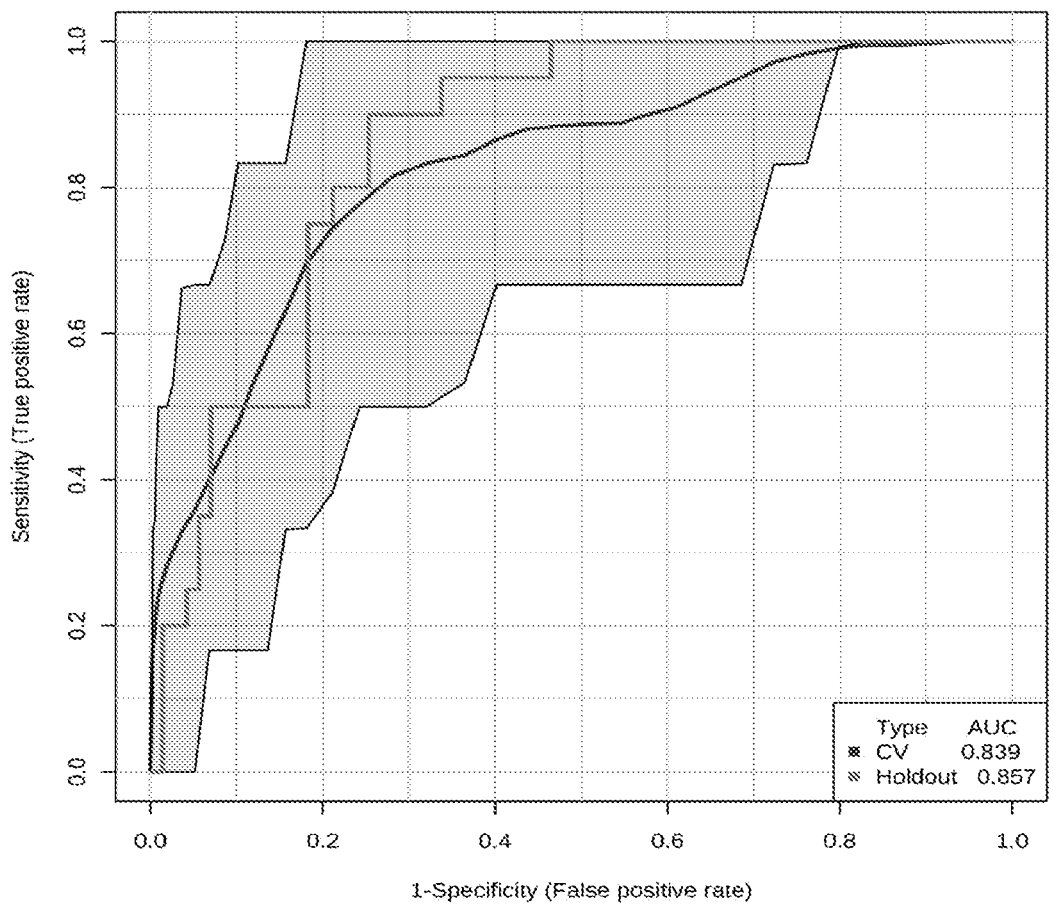

The utility of individual taxons to identify ASD status and GI phenotype was explored with a multivariate logistic regression analysis and classification accuracy was visualized by receiver operator characteristic (ROC) curve analysis. For each comparison, 50% of the participants in each group were used to identify ratios between taxons with predictive accuracy which were then tested in the remaining 50% of naïve "hold-out" samples. Five ratios, involving eight taxons (*Mucilaginibacter/Ramlibacter tataouinensis, Sphingomonadales/Planctomycetales, Alphaproteobacteria/Cyanobacteria, Alphaproteobacteria/Limnohabitans, Ramlibacter tataouinensis/Thiobacillus dentrificans*) correctly identified 66/90 ASD participants and 38/53 TD participants in the training set, demonstrating an AUC of 0.795 (95% CI: 0.711-0.872). This panel of taxons demonstrated nearly identical performance in the hold-out set (FIG. 33A), identifying 73/90 ASD children and 33/53 TD children (AUC=0.796). Three ratios, involving five taxons (*Chamaesiphon minutus/Lactococcus lactis, Pseudomonadaceae/Lactococcus lactis, Flavobacterium* sp. PK15/Burkholderiales) correctly identified 64/90 ASD children and 20/30 DD children in the training set, demonstrating an AUC of 0.770 (95% CI: 0.643-0.867). These three ratios performed similarly in the hold-out set of naïve samples, identifying 82/90 ASD children and 21/30 DD children (AUC=0.765) (FIG. 33B). Taxon levels also demonstrated utility for differentiating ASD children with GI disturbance from ASD children without GI disturbance. Three ratios, involving five taxons (*Meisseria meningitides* M04-240196/*Sideroxydans lithotrophicus* ES-1, *Neurospora crassa* OR 74A/*Acidipropionibacterium acidipropionici, Enterobacterales/Neurospora crassa* OR 74A) correctly identified 17/19 ASD children with GI disturbance and 51/70 ASD children without GI disturbance in the training set (AUC=0.839; 95% CI: 0.759-0.958). In the hold-out set, this panel of taxons identified 7/20 ASD children with GI disturbance and 67/71 children without GI disturbance (AUC=0.857) (FIG. 33C).

Metabolomic Pathway Profiling

The functional properties of microbial RNA transcripts measured in the oropharynx were investigated through alignment to the KEGG microbial database. KEGG pathways were filtered to include those with five or more alignments in at least 10% of the samples and quantile normalized. This resulted in 113 total KEGG pathway sets. Among the 113 pathways, seven demonstrated differential abundance (FDR<0.05) between ASD, TD, and DD groups (Table 26).

TABLE 26

Metabolic pathways differentially regulated in the oral microbiome of ASD, TD, and DD children

| KEGG Pathway | $\chi^2$ | P value | FDR | Mann-Whitney |
|---|---|---|---|---|
| Energy metabolism | 24.8 | 4.17E−06 | 0.00047 | ASD > TD |
| | | | | ASD > DD |
| Translation ribosomal structure and biogenesis | 18.2 | 0.0001 | 0.0062 | ASD > TD |
| | | | | ASD > DD |
| Pyrimidine metabolism | 15.8 | 0.0003 | 0.013 | ASD < TD |
| | | | | ASD < DD |
| Lysine degradation | 15.3 | 0.0005 | 0.013 | ASD > TD |
| Nucleotide metabolism | 14.5 | 0.0007 | 0.016 | ASD < TD |
| | | | | ASD < DD |
| Carbon metabolism | 12.6 | 0.0018 | 0.030 | ASD > TD |
| | | | | ASD > DD |

TABLE 26-continued

Metabolic pathways differentially regulated in
the oral microbiome of ASD, TD, and DD children

| KEGG Pathway | $\square^2$ | P value | FDR | Mann-Whitney |
|---|---|---|---|---|
| Nucleotide transport and metabolism | 12.6 | 0.0018 | 0.030 | ASD < TD<br>ASD < DD |

Non-parametric Kruskal-Wallis testing was used to interrogate 113 KEGG pathways for differences in representation among the oral microbiome in children with autism spectrum disorder (ASD), typical development (TD), or non-autistic developmental delay.
KEGG pathways with false detection rate (FDR) < 0.05 are shown.
A Mann-Whitney test was used as a post-hoc contrast between the groups.

KEGG pathways with differential representation included Microbial Energy Metabolism, Translation Ribosome Structure and Biogenesis, Pyrimidine Metabolism, Lysine Degradation, Nucleotide Metabolism, Carbon Metabolism, and Nucleotide Transport and Metabolism (FIG. 34A-H).

Discussion

To our knowledge this study comprised the largest investigation of the microbiome in children with ASD, and the first to utilize oropharyngeal samples. It has established distinct oral micro-transcriptomic profiles in ASD children relative to both typically developing peers and non-autistic peers with developmental delay. These taxonomic patterns have shown some overlap with previous reports of the gut microbiome, but also identified novel changes, unique to the oropharynx.

Like the gut, the oropharynx is a site of significant pathology in ASD. Children with ASD experience increased rates of motor (speech apraxia) and sensory (food texture and taste) dysfunction. In addition, the oropharynx represents the sole point of entry to the GI tract and a major site of host-environment interaction. Sensory and motor innervation of the oropharynx by five cranial nerves (V, VII, IX, X, and XII) provides major linkages between the oropharynx and central nervous system and a plausible exchange pathway for the gut-brain axis (which also exerts major influences via cranial nerve X). Thus, it is not surprising that particular micro-transcriptome profiles are enhanced in ASD children with GI disturbance. Notably, we found that several of these "alterations" are also associated with specific autistic features. For example, *Micrococcus luteus* levels are decreased in both ASD children with GI disturbance and ASD children with adaptive communication scores more than two standard deviations below the mean. Similarly, levels of *Riemerella anatipestifer* and Actinobacteria demonstrated correlations with measures of restricted/repetitive behavior, and social affect, respectively, and were "altered" in children with GI disturbance. Such trends are particularly striking when considering that ASD phenotypes unrelated to the GI tract (ADHD) showed no differences in microbiome profiles at the phylum or species levels.

In the context of recent studies that have highlighted the genetic contributions to ASD, it is unlikely that microbial shifts represent the sole driver of autistic behavior. However, alterations in the microbiome have been linked with atypical social, communicative, and repetitive behavior in animal models. One mechanism for this link may be metabolomic disruptions. Here, it was shown that the microbial RNA profiles disrupted in children with ASD (relative to DD and TD peers) differentially target metabolic pathways in the oropharynx. It is well established that microbial activity in the GI tract plays an important role in the metabolism of compounds essential to host nutrition. Here, the inventors have identified up-regulation of microbial RNAs related to Lysine Degradation in the oropharynx of children with ASD. Lysine is a ketogenic amino acid whose degradation results in glutamate production. Glutamate is a key neurotransmitter involved in learning and memory, and increased levels have been reported both in plasma and the central nervous system of patients with ASD. Evidence of increased Energy Metabolism and Carbon Metabolism transcripts in the oral microbiota of ASD children relative to TD and DD children was also found. The KEGG Energy Metabolism entry actually includes a set of subcategories (Oxidative phosphorylation, Photosynthesis, Carbon fixation, Methane metabolism, Nitrogen metabolism and Sulfur metabolism). Of these, further inspection strongly suggested that the increase in Energy Metabolism was being driven in ASD children by increased expression of bacterial transcripts involved in Oxidative phosphorylation (1.6 fold) and Methane metabolism (1.2 fold).

A second mechanism by which host-microbial interactions may lead to altered social behavior is through subclinical pathology. For example, here we report alterations in oral Cyanobacteria in children with ASD at the phylum (FIG. 31), and species (Table 21) level, and show that levels of Cyanobacteria may be used to differentiate children with autism from typically developing peers. Cyanobacteria are water-borne pathogens that produce cyanotoxins that can lead to serious illness, including GI disturbance, hay fever, and pruritis. The cyanobacteria neurotoxin β-N-methyl-amino-L-alanine (BMAA) has been proposed to contribute to neurodegenerative conditions such as Parkinson's and Alzheimer's diseases. In addition, Son et al. (2015) have previously reported disruptions in cyanobacteria levels in the fecal microbiome of children with ASD relative to neurotypical siblings.

Clinical Implications

The unique micro-transcriptome profiles found in the oropharynx of children with ASD provides an objective tool for screening, diagnosing, or classifying patients. The inventors have shown herein that the levels of eight oral taxons might distinguish children with ASD from typically developing peers, while a unique panel of five taxons classifies ASD and DD subjects with nearly 80% accuracy. The inventors have demonstrated that microRNA levels in saliva may differentiate children with ASD from healthy controls. It is intriguing to consider that some perturbations in salivary microRNA may be driven by host interactions with the microbiome. Given the role of microRNA as an intercellular signaling molecule and its importance in normal brain development, microbial-microRNA cross-talk may be one mechanism by which the gut-brain-axis functions.

Large scale individual profiling of the microbiome also highlights a potential avenue for therapeutic targets. Several previous studies have demonstrated changes in autistic behavior with anti-microbial or probiotic interventions. These studies successfully reset the gut microbiota using untargeted approaches. Given the heterogeneity of taxonomic features that become evident when large numbers of ASD children are studied alongside specific measures of behavioral features, it seems that a more targeted approach is in order. For instance, based on these findings, probiotics targeted at the restoration of *Micrococcus* species in autistic children with GI disturbance and communication difficulties may provide individualized benefit. Alternatively, antibiotics selected to specifically target *Riemerella* species in ASD children with GI difficulties and repetitive behaviors might be of clinical utility. Perhaps the greatest benefit to the oral microbiome approach is it allows easily repeated microbiome collections on-demand, over time, so that one can track changes in these microbial communities in response to targeted therapy.

Limitations

It is impossible to control for every variable that could conceivably influence the oral microbiome across ASD, TD, and DD groups. The present study included a rigorous collection of relevant factors (Table 20) so that the results could be interpreted with full transparency. It is worth noting that the only oral/GI factors that differed between ASD, TD, and DD groups were GI disturbance rates, and food/medical allergy rates, and the latter was not associated with expression patterns of any oral taxons. One oral taxon (*Riemerella anatipestifer* Yb2) associated with GI disturbance (Table 24) was also weakly associated with age (Table 25), and a second oral taxon (*Sideroxydans lithotrophicucus* ES1) with utility for detecting GI disturbance among ASD subjects was also associated with age and collection time. Thus, it is possible that several microbial factors identified in the present study are confounded by changes in the GI tract over time. Longitudinal analyses of the oral microbiome among developing children is useful in elucidating these relationships.

A second factor to consider when comparing results of the present study to previous literature is the use of high throughput metatranscriptomic sequencing, rather than a 16S rRNA approach. In the current study, the resulting values provide a direct measure of transcriptional activity within the microbiome from different species and taxa, rather than simply microbial abundance. This approach allows for a functional interrogation of RNA properties through KO databases, but also makes comparisons to previous literature somewhat difficult. Thus, patterns of microbial disturbance previously reported in the fecal microbiome may be missed with this approach if abundance did not translate directly to transcriptional activity (i.e., the bacteria in those studies were not actively transcribing gene products).

Conclusions

There is mounting evidence that the GI microbiome is disrupted in children with ASD. The current study has shown that this disruption might extend to the oropharynx, influencing the transcriptional activity of the microbial community. Such shifts appear to be associated with ASD co-morbidities (such as GI disturbance), as well as social and repetitive behaviors. The mechanism for this relationship may result from alterations of microbial metabolism, or through pathogenic microbial-host relationships. In the meantime, oral taxonomic and functional profiling may provide utility as objective markers of ASD phenotype.

Example 11

Participants.

This multi-center, cross-sectional, prospective, case-control study included 396 children, ages 2-6 years, receiving well child or developmental specialist care at the Penn State College of Medicine, or SUNY Upstate Medical University. The 2-6 year age-group was chosen to include children at the earliest ages of ASD diagnosis, when screening and diagnostic biomarkers would be of most clinical benefit. Recruitment occurred at academic, outpatient, primary and tertiary care clinics between October, 2015 and August, 2017. There were 197 children with ASD, 128 children with TD, and 71 children with DD enrolled for salivary RNA sequencing and clinical assessment. Nearly equal numbers of ASD, TD, and DD participants were recruited from each site. Comparison of TD and DD control groups with ASD participants allowed for identification of screening and diagnostic miRNA biomarker candidates, respectively. ASD status was defined by Diagnostic and Statistics Manual (DSM)-5 diagnosis, confirmed by physician assessment within the previous 12 months, and supported by evaluation with the Autism Diagnostic Observation Schedule (ADOS)-II (or other standardized assessment tool such as the Checklist for Autism Spectrum Disorder, the Autism Diagnostic Interview—Revised, or the Childhood Autism Rating Scale). TD status was defined by history of negative autism screening on the MCHAT-R and documentation of typical development at a pediatric well child visit within the previous 12 months. DD status was defined by a clinical deficit in gross motor, fine-motor, expressive communication, receptive communication, or socialization that was identified by standardized screening (Survey of Wellbeing in Young Children, MCHAT-R, or Parents Evaluation of Developmental Status) at a regularly scheduled visit, but did not meet DSM-5 criteria for ASD. Participants were age- and sex-matched across ASD, DD, and TD groups through targeted recruitment. Exclusion criteria for all groups included feeding-tube dependence, active periodontal disease, upper respiratory infection, fever, confounding neurological (i.e. cerebral palsy, epilepsy) or sensory (i.e. blindness, deafness) impairment, and wards of the state. TD participants with a family history of ASD in a first degree relative, or a chronic medical condition requiring daily medication or pediatric specialist care were also excluded.

Participant Characterization.

For all participants, extensive medical and demographic characterization was performed, including: age, sex, ethnicity, birth age, birth weight, perinatal complications, current weight, body mass index, oropharyngeal status (e.g. allergic rhinitis), dietary restrictions, medications, chronic medical issues, immunization status, medical allergies, early intervention services, surgical history, and family psychiatric history. Given the prevalence of attention deficit hyperactivity disorder (ADHD) (Gargaro et al., 2011) and gastrointestinal (GI) disturbance (Molloy et al., 2003) among children with ASD, survey questions were included to identify these two common medical co-morbidities. GI disturbance was defined by presence of constipation, diarrhea, abdominal pain, or reflux on parental report, ICD-10 chart review, or use of stool softeners/laxatives in the child's medication list. ADHD was defined by parental report, or ICD-10 chart review. Adaptive skills in communication, socialization, and daily living activities were measured in all participants using the Vineland Adaptive Behavior Scale (VABS)-II and standardized scores were reported. Evaluation of autism symptomology (ADOS-II) was completed when possible for ASD and DD participants (n=164). Social affect (SA), restricted repetitive behavior (RRB) and total ADOS-II scores were recorded.

the sublingual and parotid regions of the oral cavity over a 5-10 second period, taking care to avoid the teeth when possible (Hypertext Transfer Protocol Secure (https)://www.youtube.com/watch?v=AzCpHWqhRQs&feature=youtu.be).

Time of saliva collection was recorded, and swabs were kept at room temperature in stabilization solution for up to four weeks prior to storage at −20° C. Salivary miRNA was purified using a standard Trizol method, followed by a second purification with an RNeasy mini column (Qiagen, Germantown, Md.). The yield and quality of the RNA samples was assessed using the Agilent Bioanalyzer prior to library construction. RNA was sequenced at the SUNY Molecular Analysis Core at Upstate Medical University with an Illumina TruSeq® Small RNA Sample Prep protocol (Illumina; San Diego, Calif.). The targeted read depth for each sample was ten million reads, using 50 base pair single end reads on a NextSeq® 500 instrument (Illumina, San Diego, Calif.). Reads for each sample were aligned to the hg38 build of the human genome in Partek Flow (Partek; St.

TABLE 27

Participants Characteristics

| Participant characteristics Characteristic | All groups (n = 381) | ASD (n = 187) | TD (n = 125) | DD (n = 69) |
|---|---|---|---|---|
| Demographics and anthropometries | | | | |
| Age, months (SD) | 51 (16) | 54 (15) | 47 (18)[a] | 50 (13) |
| Male, no. (%) | 285 (75) | 161 (86) | 76 (60)[a] | 48 (70)[a] |
| Caucasian, no. (%) | 274 (72) | 132 (71) | 95 (76) | 47 (69) |
| Body mass index, kg/m$^2$ (SD) | 18.9 (11) | 17.2 (7) | 21.2 (16) | 19.5 (10) |
| Clinical characteristics | | | | |
| Asthma, no. (%) | 43 (11) | 19 (10) | 10 (8) | 14 (20) |
| GI disturbance, no. (%) | 50 (13) | 35 (19) | 2 (2)[a] | 13 (19) |
| ADHD, no (%) | 74 (19) | 43 (23) | 10 (8)[a] | 21 (30) |
| Allergic rhinitis, no. (%) | 81 (21) | 47 (25) | 19 (15) | 15 (22) |
| Oropharyngeal factors | | | | |
| Time of collection, hrs (SD) | 13:00 (3) | 13:00 (3) | 13:00 (2) | 13:00 (3) |
| Time since last meal, hrs (SD) | 2.8 (2.5) | 2.9 (2.5) | 3.0 (2.9) | 2.1 (1.1)[a] |
| Dietary restrictions, no. (%) | 50 (13) | 28 (15) | 10 (8) | 12 (18) |
| Neuropsychiatric factors | | | | |
| Communication, VABS-II standard score (SD) | 83 (23) | 73 (20) | 103 (17)[a] | 79 (18)[a] |
| Socialization, VABS-II standard score (SD) | 85 (23) | 73 (15) | 108 (18)[a] | 82 (20)[a] |
| Activities of daily living, VABS-II standard score (SD) | 85 (20) | 75 (15) | 103 (15) | 83 (19)[a] |
| Social affect, ADOS-II score (SD) | — | 13 (5) | — | 5 (3)a |
| Restrictive/repetitive behavior, ADOS-II score (SD) | — | 3 (2) | — | 1 (1)a |
| ADOS-II total score (SD) | — | 16 (6) | — | 6 (4)a |

Saliva Collection and RNA Processing.

Saliva was collected from all children in a non-fasting state using a P-157 Nucleic Acid Stabilizing Swab (DNA Genotek; Ottawa, ON, Canada). Saliva was obtained from Louis, Mo.) with the SHRiMP2® aligner. Total miRNA counts within each sample were quantified with miRBase precursor and mature-microRNA v21. Poor quality reads (mean q score <30) were eliminated, and 15 samples with total mature miRNA read counts less than 20,000 were excluded. This resulted in a final comparison of 187 ASD, 69 DD, and 125 TD samples. Of the 2813 mature miRNAs aligned, the inventors interrogated 527 for differential expression among groups. The 527 miRNAs included: 1) those with robust expression (raw read counts greater than 10 in at least 10% of samples; n=375); and 2) those identified in previous ASD studies (17) and detectable in saliva (raw counts greater than 1 in 10% of samples; n=152). Prior to statistical analysis, read counts were quantile normalized, mean-centered, and divided by the standard deviation of each variable.

Statistical Analyses.

The primary outcome of this study was the identification of miRNA that could serve two clinical utilities: 1) as a diagnostic panel for differentiating ASD and DD participants (logistic regression analysis); and 2) as a screening panel for differentiating ASD and TD participants (logistic regression analysis). Differences in medical and demographic characteristics between ASD/TD, or ASD/DD groups were compared using a two-tailed Student's t-test. A non-parametric Kruskal-Wallis test and a partial least squared discriminant analysis (PLS-DA) were used to identify individual miRNA candidates for differentiating ASD/TD and ASD/DD groups. The miRNAs with significant differences between groups (false detection rate (FDR)<0.05), and/or PLS-DA weighted sum of absolute regression coefficients >2.0, were selected for biomarker testing. Biomarker exploration was performed with MetaboAnalyst R package (McGill University, Montreal, Canada, Hypertext Transfer Protocol (http://www.metaboanalyst.ca/faces/ModuleView.xhtml) using the biomarker workflow (Xia et al., 2009).

Multivariate logistic regression analysis with a 100-fold Monte-Carlo cross-validation procedure employed 50% of the samples as a training set to select two panels of miRNAs (ASD/TD and ASD/DD). The training set was used to determine threshold (cut-off) concentrations for miRNA/miRNA ratios, which were employed in lieu of individual miRNAs as a second control for variations in total miRNA concentration across individual participants. To avoid "overfitting" the model and to ensure that the miRNAs accurately differentiated ASD participants, each panel was tested in a naïve "hold-out" set, containing the remaining 50% of ASD/TD or ASD/DD samples.

Performance of each panel was evaluated using area under the curve (AUC) analysis from receiver operating characteristic (ROC) curves generated during training, cross-validation, and hold-out testing. An a-priori power analysis using a two-sided z-test at a significance level of 0.05 suggested this number of participants provided >90% power to conclude that the true AUC of each diagnostic algorithm was greater than 0.70 if the observed AUC was 0.80.

Associations between salivary miRNA concentrations and autism phenotypic characteristics were explored with Spearman's rank correlations (for dichotomous variables) or Pearson's correlations (for continuous variables), with FDR correction. The phenotypic characteristics of interest included: 1) adaptive behavior scores (VABS-II); 2) autistic traits (ADOS-II scores); and 3) medical co-morbidities (presence/absence of GI disturbance or ADHD). Relationships between salivary miRNA concentrations and confounding medical/demographic characteristics (i.e. age, sex, ethnicity, body mass index, asthma, allergic rhinitis, time of collection, time of last meal, dietary restrictions) were also evaluated with Pearson's or Spearman's rank correlations. Any miRNA-variable association in which R>[0.25] and FDR<0.05 was reported as significant.

Secondary analyses investigated the mRNA targets for two sets of miRNAs: 1) the miRNAs "altered" between ASD, TD, and DD groups based on the initial Kruskal-Wallis testing; and 2) the miRNAs associated with autistic features on ADOS testing. Functional analysis was performed for each miRNA set in DIANA mirPath v3 online software (Hypertext Transfer Protocol (http://snf-515788.vm.okeanos.grnet.gr/) http://string-db.org) (Vlachos et al., 2015). The microT-CDS algorithm was employed to identify species-specific gene targets for each miRNA. DIANA® mirPath identified KEGG pathways with significant (FDR<0.05) target enrichment using a Fisher's Exact Test. A list of high confidence mRNA targets (experimentally validated miRNA-mRNA interaction with microT-CDS score ≥0.975) was interrogated for protein-protein interaction networks using moderate stringency settings (interaction score >0.40) in String v10 software (Szklarczyk et al., 2015). Enrichment of mRNA target lists for the 961 autism-associated genes on the SFARI autism database (Hypertext Transfer Protocol Secure (https://gene.sfari.org/database/human-gene/) (Abrahams et al., 2013) was explored using a chi-square test with Yates' correction. The number of overlapping mRNAs was reported, along with enrichment relative to a random sampling of the ~20,000 coding mRNAs.

Participant Characteristics.

Two-tailed student's t-tests were used to compare demographic, medical, and oropharyngeal characteristics among ASD, TD, and DD groups (Table 26). The average age of ASD participants (54±15 months) was older (p=0.006) than TD participants (47±18 months), but not DD participants (50±13 months; p=0.076). The ASD group had a higher proportion of males (161/187; 86%) than the TD group (76/126; 60%; p=1.0E-6) and the DD group (48/69; 70%; p=0.015). Children with ASD had higher rates of GI disturbance (35/187; 19%) than TD children (2/125; 2%; p=5.4E-7), but not DD children (13/69; 19%; p=0.92). The ASD group also had higher rates of ADHD (43/187; 25%) than the TD group (10/125; 8%; p=0.0003), but not the DD group (21/69; 30%; p=0.26). There were no significant differences (p<0.05) among the three groups in the proportion of Caucasian children (274/381, 72%), the average body mass index (18.9±11 kg/m$^2$), rates of asthma (43/381, 11%), or allergic rhinitis (81/381, 21%), the time of saliva collection (13:00±3 hours), or the rates of dietary restrictions (50/381, 13%).

Neuropsychiatric characteristics were assessed with the VABS-II (adaptive behaviors; all 3 groups) and the ADOS-II (autistic features, ASD and DD groups only). Standard scores were compared among the three groups using two-tailed student's t-tests. Children with ASD had lower standardized communication scores (73±20) than TD (103±17; p=3.5E-27) and DD children (79±17; p=0.044). The ASD group also had lower mean scores in socialization (73±15) and activities of daily living (75±15) than the TD group (socialization=108±18, p=2.0E-33; activities of daily living=103±15, p=1.7E-29) and the DD group (socialization=82±20; p=0.006; activities of daily living=83±19, p=0.009). Children with ASD had higher mean scores on the social affect (13±5) and restricted/repetitive behavior (3±2) components of the ADOS-II than DD counterparts (social=5±3, p=2.0E-11; restricted/repetitive behavior=1±1, p=3.1E-9). This resulted in higher total ADOS-II scores for the ASD group (16±6) compared with the DD group (6±4, p=1.9E-13).

Expression of Salivary miRNA.

Figure 35:
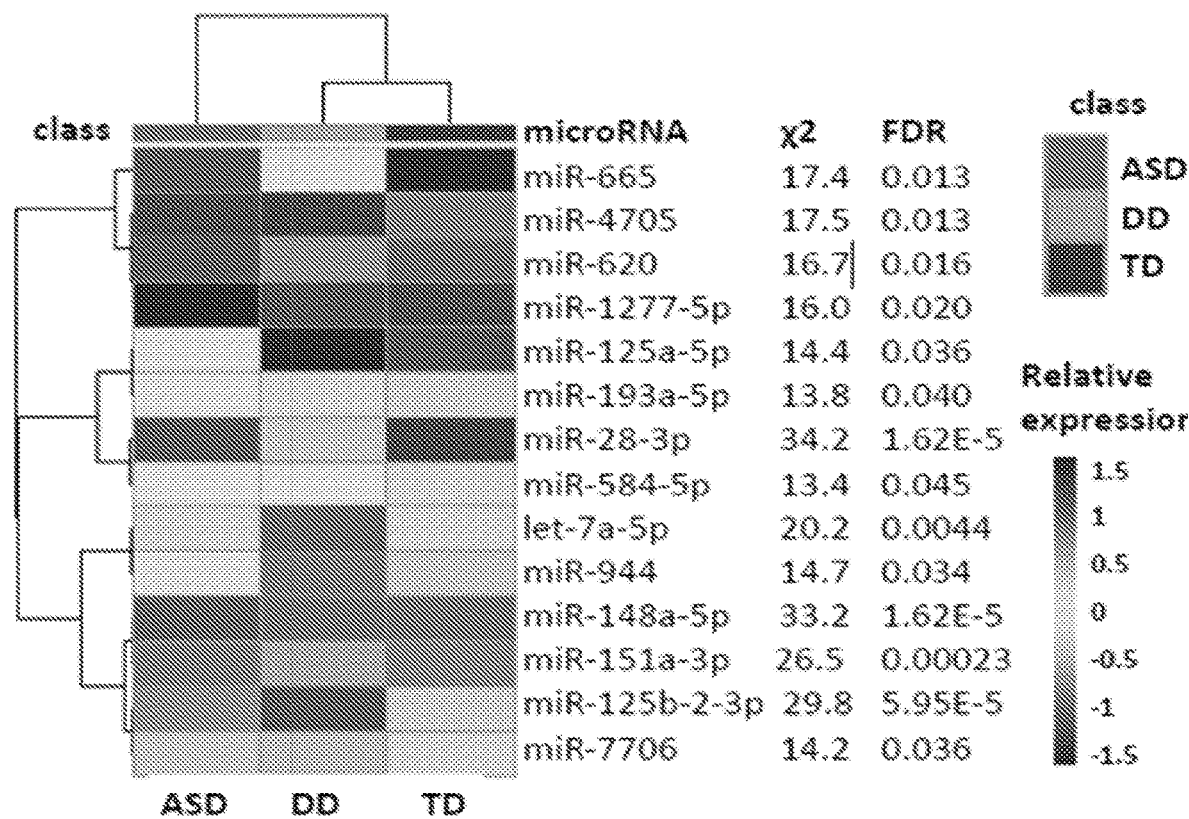
FIG. 35 Salivary miRNAs are differentially expressed across ASD, DD, and TD groups. The 14 miRNAs with differential abundance (FDR<0.05) across ASD (red/gray scale; n=187), DD (green/gray scale; n=69), and TD (blue/gray scale; n=125) participants on Kruskal-Wallis testing are shown, along with $\chi2$ statistics. Colored/gray scale boxes represent relative group abundance (measured by Pearson's distance metric) and miRNAs are clustered in the heatmap using a complete clustering algorithm.

Concentrations of 527 mature miRNAs were explored in the saliva of ASD, TD, and DD participants. Among these 527 miRNAs, 80 were present in the saliva of every participant. The miRNA with the highest salivary concentrations across all participants was miR-203a-3p, accounting for $1.14\times10^6$ of the total $8.44\times10^7$ raw read counts in the experiment (1.4%). Kruskal-Wallis non-parametric testing identified 14 miRNAs with significant (FDR<0.05) differences across ASD, TD, and DD groups (FIG. 35). The miRNA with the largest change was miR-28-3p ($\chi2=34.2$, FDR=1.62E-5), which demonstrated down-regulation in ASD children relative to TD and DD children. Four other miRNAs demonstrated relative down-regulation in the ASD group compared with both TD and DD groups (miR 148a-5p, miR-151a-3p, miR-125b-2-3p, and miR-7706). There were four miRNAs with relative up-regulation in the ASD group compared with TD and DD groups (miR-665, miR-4705, miR-620, and miR-1277-5p). Only one of these 14 miRNAs (miR-151a-3p) had been identified as "altered" in previous studies of miRNA expression in ASD patients (Mundalil et al., 2014).

Figure 36A:
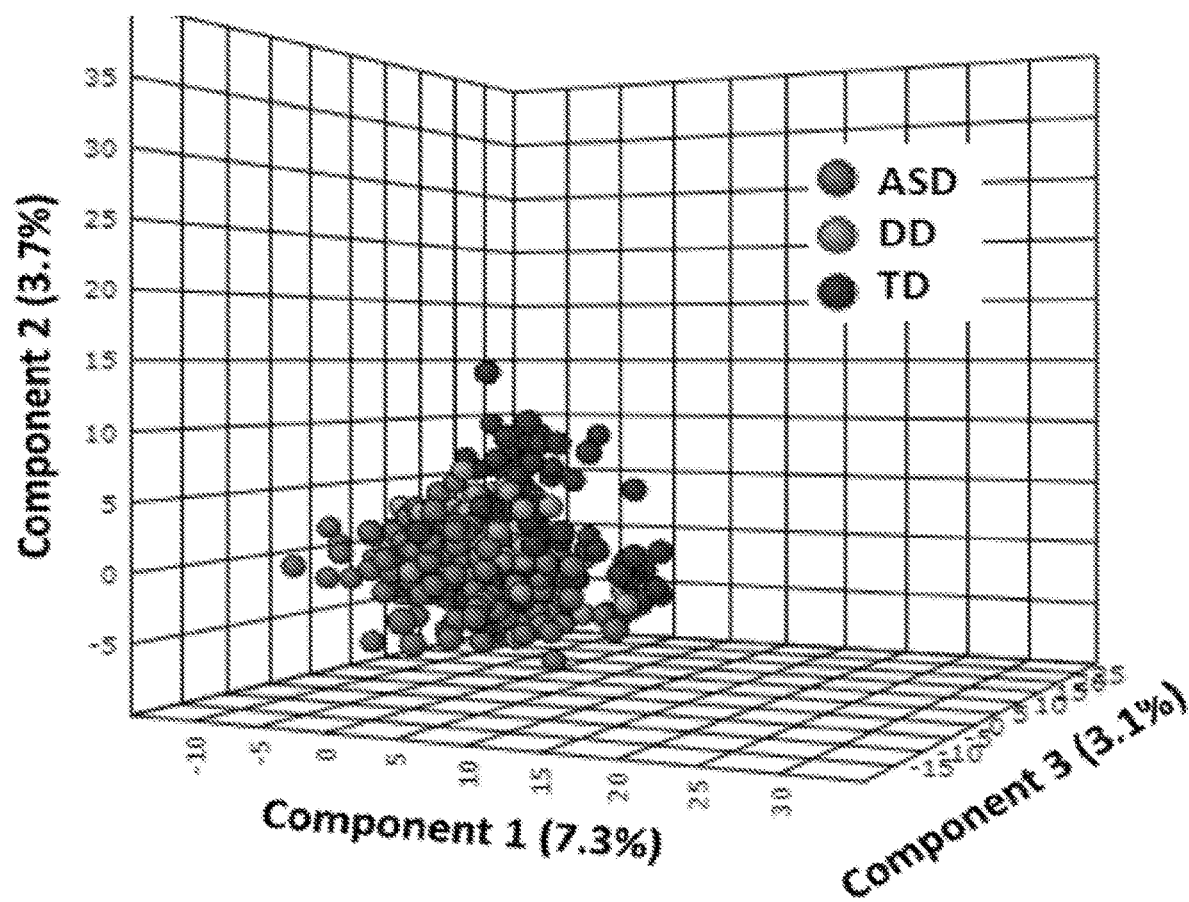
FIGS. 36A-B. (A) Salivary miRNA profiles separate ASD, DD, and TD groups. A partial least squares discriminant analysis (PLS-DA) was used to map all 381 children in three-dimensional space based on abundance of the 527 salivary miRNAs. The PLS-DA demonstrated nearly complete separation of children with autism spectrum disorder (ASD; red/gray scale dots; n=187) from children with typical development (TD; blue/gray scale dots; n=125) while accounting for 14.1% of the variance. There was incomplete spatial separation between ASD children and those with non-autistic developmental delay (DD; green/gray scale dots; n=69). (B) Salivary miRNA profiles separate ASD, DD, and TD groups. Variable importance in projection (VIP) scores was determined for the 527 individual miRNAs, and the 20 miRNAs with VIP>2.0 are shown. Color scales/gray scales demonstrate relative projection importance across ASD, TD, and DD groups. The miRNAs denoted with asterisks represent those identified in previous miRNA studies involving human patients.
Figure 36B:
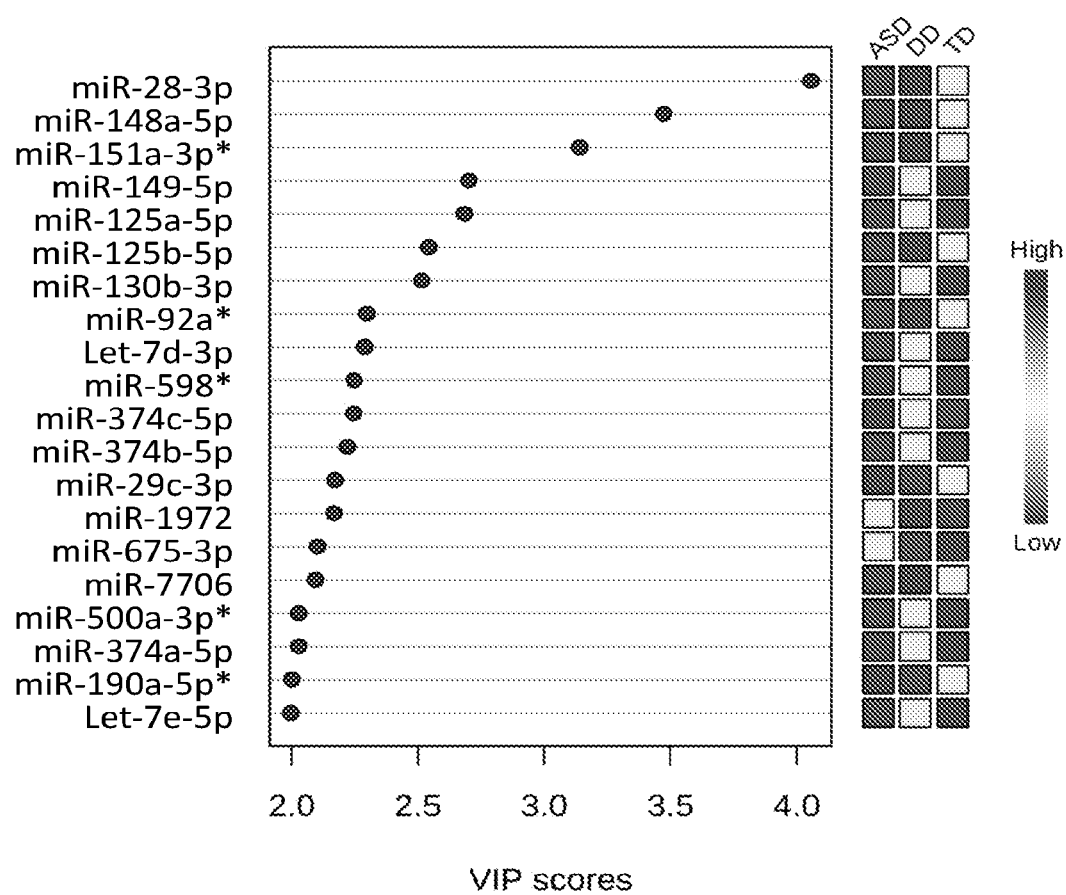

The utility of salivary miRNA profiles for identifying ASD-status was explored with PLS-DA. Individual participants were mapped in three-dimensional space using salivary miRNA profiles for the 527 miRNAs. This approach resulted in nearly complete separation of ASD and TD groups, with intermediate alignment of DD participants (FIG. 36A). It accounted for 14.1% of the variance in salivary miRNA expression among participants. Importance of individual miRNAs in participant PLSD-DA projection was determined by weighted sum of absolute regression coefficients (VIP). Twenty miRNAs displayed significant (VIP≥2.0) variable projection importance (FIG. 36B). Six of these 20 miRNAs overlapped with the 14 miRNAs identified on Kruskal-Wallis testing (miR-28-3p, miR-148a-5p, miR-7706, miR-151a-3p, miR-125a-5p, miR-125b-2-3p). Five of these 20 miRNAs overlapped with those identified in previous miRNA studies in human ASD subjects (miR-151a-3p (Mundalil et al., 2015), miR-92a-3p (Huang et al., 2015; Talebizadeh et al., 2008), miR-598-5p (Abu-Elneel et al., 2008), miR-500a-3p (Ghahramani et al., 2011), miR-190a-5p (Sarachana et al., 2010).

Classification Accuracy.

A logistic regression analysis with 100-fold cross validation procedure was used to build and test biomarker toolsets with potential utility in ASD screening (ASD vs. TD children) and diagnosis (ASD vs. DD children).

Half of the children in each group were selected at random and the 28 miRNAs identified on PLS-DA/Kruskal-Wallis testing were used to build a miRNA panel for differentiating ASD children from TD or DD peers. The established panels were then tested in a naïve hold-out set containing the remaining 50% of samples. In the comparison of ASD and TD participants, five ratios involving four miRNAs (while controlling for sex and presence of GI disturbance) successfully identified 74/93 ASD children and 42/62 TD children in the cross-validation set (AUC=0.788, 95% CI: 0.677-0.875; FIG. 37A). In the hold-out set, this panel correctly identified 76/94 children with ASD and 35/63 children with TD (AUC=0.744, 95% CI: 0.722-0.867). In the comparison of ASD and DD participants, four ratios involving four miRNAs (while controlling for age) successfully identified 60/93 children with ASD and 22/34 children with DD in the cross-validation set (AUC=0.714, 95% CI: 0.564-0.847; FIG. 37B). In the hold-out set, this panel correctly identified 84/94 children with ASD and 16/35 children with DD (AUC=0.803, 95% CI: 0.603-0.827).

Expression of Salivary miRNA Across ASD Phenotypes.

Salivary miRNA expression patterns were explored among ASD phenotypes. Presence of GI disturbance in ASD participants was significantly (R>[0.25], FDR<0.05) correlated with salivary levels of two miRNAs (miR-4700-3p, R=0.37, FDR=6.3E-5; miR-4485-3p, R=−0.27, FDR=0.043), one of which (miR-4700-3p) had been identified in previous ASD studies. Presence of ADHD was not correlated with salivary miRNA expression. There were five miRNAs correlated with standardized score on the socialization component of VABS-II testing (miR-152-3p, R=0.30, FDR=0.023; miR-379-5p, R=−0.30, FDR=0.023; miR-4781-3p, R=−0.28, FDR=0.038; miR-26a-5p, R=−0.28 FDR=0.039; miR-221-3p, R=0.28, FDR=0.039), two of which (miR-379-5p (Mor et al., 2015) and miR-221-3p (Wu et al., 2016; Nguyen et al., 2016) had been previously identified in ASD studies. There were no miRNAs correlated with communication or activities of daily living scores on VABS-II testing. Eight miRNAs were correlated with social affect on the ADOS-11 (miR-223-3p, R=0.34, FDR=0.0082; miR-142-3p, R=0.33, FDR=0.0082; miR-182-5p, R=−0.31, FDR=0.016; miR-142-5p, R=0.31, FDR=0.016; miR-125b-2-3p, R=−0.29, FDR=0.035; miR-181c-5p, R=0.29, FDR=0.036; miR-148b-3p, R=−0.29, FDR=0.036; miR-143-3p, R=0.28, FDR=0.044), six of which had been previously identified in ASD studies (miR-223-3p, miR-142-3p, miR-182-5p, miR-142-5p, miR-148b-3p (17)) and one of which was utilized in the ASD/DD classification panel in the present study (miR-125b-2-3p). Ten miRNAs correlated with restricted/repetitive behavior on the ADOS-II (miR-136-3p, R=0.52, FDR=1.7E-8; miR-8485, R=0.42, FDR=3.21E-5; miR-106a-5p, R=0.38, FDR=0.0005; miR-3679, R=0.36, FDR=0.0011; miR-573, R=0.33, FDR=0.0049; miR-6733-5p, R=0.30, FDR=0.022; miR-8061, R=0.29, FDR=0.026; miR-130a-3p, R=0.28, FDR=0.040; miR-766-5p, R=0.28, FDR=0.045; miR-431-5p, R=0.028, FDR=0.45) and four of these had been identified in previous ASD studies (miR-136-3p, miR-106a-5p, miR-130a-3p, and miR-431-5p (Hicks et al., 2016)). Notably, all 10 were positively correlated with restricted/repetitive behavior score. Finally, six miRNAs were correlated with total score on the ADOS-II (miR-223-3p, R=0.35, FDR=0.0043; miR-142-3p, R=0.34, FDR=0.0043; miR-142-5p, R=0.31, FDR=0.015, miR-182-5p, R=−0.31, FDR=0.021; miR-151a-3p, R=−0.28, FDR=0.049) and all six had been identified in previous ASD miRNA studies (Hicks et al., 2016)). One of these miRNAs (miR-151a-3p) was downregulated in ASD children relative to TD and DD participants, and displayed significant variable importance in PLS-DA group projection.

Influences of Clinical Characteristics on miRNA Expression.

Associations of salivary miRNA expression and clinical/demographic characteristics were assessed with Pearson's (continuous) or Spearman's Rank (dichotomous) correlation testing. There were no significant associations (R<[0.25], FDR<0.05) between expression of the 527 miRNAs and participant sex, ethnicity, body mass index, dietary restrictions, asthma status, or allergic rhinitis status. Time of saliva collection had largest number of miRNA associations of any of the medical/demographic variables tested (n=21). The strongest association was between miR-210-3p levels and time of saliva collection (R=−0.35; t-stat=−6.6; FDR=4.2E-8). One miRNA (miR-23b-3p) was associated with time since last meal (R=0.25; t-stat=4.2; FDR=0.012). Of the 22 miRNAs associated with time of collection or time since last meal, twelve had been identified as potential biomarkers in previous miRNA studies. None were "altered" in the saliva of ASD children in the current study. Given the importance of age in developing biomarker toolsets, it is worth noting that participant age was weakly (R<[0.25]), yet significantly (FDR<0.05) associated with 34 miRNAs. None of these miRNAs were utilized in the current biomarker panels, but 15 had been identified as potential targets in previous ASD miRNA studies (Hicks et al., 2016).

This case-control study of 381 children (ages 2-6 years) identified 28 salivary miRNAs with varying levels among children with ASD, TD, or DD. Two distinct panels of miRNAs displayed diagnostic (ASD vs. DD) and screening potential (ASD vs. TD), while controlling for age, sex, and/or GI disturbance. A subset of salivary miRNAs was also associated with measures of adaptive or autistic behavior. Together, these groups of miRNAs targeted genes strongly related to neurodevelopment and implicated in ASD pathogenesis.

There are a number of potential mechanisms which may disrupt levels of miRNAs in the oropharynx of ASD children. Certainly, dietary restrictions in children with ASD (Schreck et al., 2004) may alter the salivary miRNA milieu. However, the current study found no associations between saliva miRNA levels and the presence of dietary restrictions, and only two miRNAs were strongly associated with GI disturbance. In addition, there was no difference in the rate of dietary restrictions between ASD, DD, and TD groups. A second potential mechanism for salivary miRNA disruption could be differences in dental hygiene, given the resistance of many children with ASD to teeth brushing (Nguyen et al., 2016). For this reason, this study specifically excluded children with active dental infections or decay. There are certainly alterations in the oral microbiome of children with ASD (Vuong et al., 2017) which may drive a portion of salivary miRNA changes, but microbiome differences are largely unrelated to the bacteria implicated in dental caries (Struzycka et al., 2014).

Another source of salivary miRNA includes the four cranial nerves which innervate the mouth, regulating somatic and autonomic functions. Children with ASD experience difficulties with oral-motor (speech apraxia (Tierney et al., 2012) and oral-sensory (food texture sensitivity (Cermak et al., 2010) processing. The cranial nerves which guide these processes may have "altered" patterns of miRNA expression. Brain-relatedness of the salivary miRNAs identified in this study is supported by the functions of their mRNA targets, which include axonal guidance, neurotrophic signaling, GABAergic synapse, and nicotine addiction. For example, miR-148a-5p (utilized in both the diagnostic and screening panels of the current study) targets seven mRNAs involved in axon guidance, and two of these (SLIT3 and SRGAP3) are autism candidate genes (Abrahams et al., 2013). The SLIT3 protein product acts as a molecular guidance cue in axonal outgrowth by interacting with the protein product of another autism candidate gene, ROBO1 (Greaves et al., 2015). It is notable that ROBO1 is a target of miR-944, another of the 14 miRNAs associated with ASD-status in the present study. Remarkably, miR-944 and miR-148a-5p are highly correlated in both salivary concentration (FIG. 35) and function (FIG. 38). Thus, alterations in these two miRNAs may act in concert to disrupt axon guidance, leading to an ASD phenotype. This may explain, in part, why levels of miR-148b (a homolog of miR-148a) are highly correlated with social affect and total autistic symptoms on ADOS-II testing.

Other targets include mRNAs associated with prion diseases, morphine addiction, PI3K-Akt-signalling, Wnt signalling, glioma, endocannabinoid signalling, and circadian entrainment.

The glymphatic system represents yet another potential route for salivary entry of brain-related miRNAs. The anatomical proximity of the perivascular drainage spaces in the glymphatic system to the oropharynx creates a prospective avenue for gut-brain cross-talk and miRNA transfer (Hicks et al., 2017). In light of the pronounced diurnal activity displayed by the glymphatic system (Jessen et al., 2015), indirect support for this transfer may lie in the surprising correlations between salivary miRNA levels and time of collection. In addition, the mRNA targets of ASD-associated miRNAs show enrichment for circadian-related pathways, and disordered sleep is a common medical phenotype among children with ASD (Miano et al., 2016).

The relevance of salivary miRNA levels to autistic behavior is underscored by the large number of salivary miRNAs associated with measures of autism symptoms on the ADOS-II. Previous studies have described several of these miRNAs as "altered" in ASD patients relative to healthy controls (Hicks et al., 2016), but the sample size of the current investigation provides power to sufficiently explore their patterns of expression among ASD phenotypes. Here the inventors identified eight miRNAs associated with social affect and ten miRNAs associated with restricted/repetitive behavior. One of these miRNAs (miR-106a-5p) has been previously identified in three separate studies of post-mortem brain (Abu-Elneel et al., 2008), blood (Mundalil et al., 2014), and lymphoblasts (Sarachana et al., 2010) from ASD patients. Like miR-148a-5p, miR-106a-5p targets several mRNAs involved in axon guidance (n=20) (Vlachos et al., 2015), and four of these (SEMA5A, NTNG1, SRGAP3, and MAPK1) are autism candidate genes (Abrahams et al., 2013). Thus, miR-106a-5p may induce autistic behavior in an incremental fashion, by targeting key transcripts in brain development. In this setting, measurement of miR-106a-5p (and other similar ADOS-associated miRNAs) may provide some prognostic utility, or serve as a biomarker of therapeutic response.

This study also identified two panels of miRNAs with diagnostic and screening potential for ASD status. In naïve hold-out sets the diagnostic panel (ASD vs. DD) demonstrated 89% sensitivity and 46% specificity, while the screening panel (ASD vs. TD) demonstrated 81% sensitivity and 56% specificity. The accuracy of these tools is similar to the subjective measures currently employed (e.g. MCHAT-R (Charman et al., 2016)) with the added benefit of being fast, objective, and non-invasive. However, emerging biomarker work in eye-tracking (Frazier et al., 2016; Loth et al., 2016), imaging (Wolff et al., 2012), genetic (Veenstra-VanderWeele et al., 2012), and electrophysiologic markers (Peters et al., 2013) have also shown considerable promise for identifying ASD status. ASD evaluation may also involve a multi-factorial approach employing each of these components in concert.

None of the miRNAs identified in previous studies (Hicks et al., 2016) demonstrated robust ability to identify ASD status in the current cohort. This may be because blood and lymphoblast miRNAs are not reliably transferred to (or expressed in) saliva, or it may reflect inability to translate findings from smaller cohorts to a large heterogeneous population of autistic children. It is also notable that many previously identified miRNA biomarkers (n=11) demonstrated associations with time of collection, a factor that has not been routinely considered in ASD miRNA investigations. Given recent findings that a significant proportion of serum-based miRNAs demonstrate diurnal variation[44], these findings likely apply to blood-based biomarkers as well. Further studies examining the interaction between miRNA expression and circadian rhythm could be important in understanding the role of these molecules in sleep-wake cycles, and provide valuable information in the development of miRNA biomarkers for clinical application. Importantly, none of the miRNAs utilized in the current ASD diagnostic/screening panels were significantly associated with collection time and there were no differences in collection time between the ASD, TD, and DD cohorts in this study.

Surprisingly there was little overlap between the salivary miRNAs identified in our pilot investigation (Hicks, Ignacio, et al., 2016), and those identified in the present study. This may have resulted from three important differences in study protocols; 1) The pilot study used expectorated saliva, while this investigation collected saliva with a swab technique. This change was made because children with ASD have difficulty producing expectorant on command. It may have led to differences in ratios of cell-derived and (vesicle) carrier-derived miRNA. 2) The pilot study involved children 5-14 years of age, while the current study enrolled participants 2-6 years. This change was made to capture children at the age when ASD diagnosis is first made and screening/diagnostic testing is most needed (Zwaigenbaum et al., 2015). It may have influenced a subset of miRNAs with age-related expression. 3) The pilot study targeted children with "high functioning" ASD (average ADOS-II score=10.6±4.1), while this large follow-up study included all children with ASD regardless of severity (average ADOS-II score=16±6). Given that salivary miRNA expression is associated with levels of autistic symptoms (measured by ADOS-II) it is likely that expanding the current study to include a heterogeneous population of children with ASD led to changes in observable between-group differences.

There are numerous medical and demographic factors that must be considered when identifying and testing physiologic biomarkers. The prospective nature of the current study allows us to control for many of these factors by employing identical collection, storage, and sample processing techniques across groups. The inventors also attempted to match groups based on relevant factors such as age, gender, ethnicity, body mass index, and time of collection. Unfortunately, complete matching of all of these factors is nearly impossible and the current cohort displays group differences in age and sex. However, it is worth noting that the age range utilized in the present study (2-6 years) is extremely tight compared with many biomarker studies and the resulting age difference between ASD and TD groups (7 months) is unlikely to have significant bearing on miRNA expression. In addition, none of the miRNA biomarkers identified in this study demonstrated significant correlations with age or sex, and these demographic variables were controlled for in the multivariate regression analysis.

This study provides large-scale evidence that salivary miRNA may be used to differentiate children with autism from peers with typical development, or non-autistic developmental delay. It shows that levels of salivary miRNAs are correlated with measures of adaptive and autistic behaviors and that these miRNAs target pathways implicated in ASD-pathogenesis. Future investigations prospectively validating salivary miRNA panels in younger cohorts will be critical to clinical implementation. Additional characterization of the factors that may influence salivary miRNA expression will also be crucial.

Example 12

The hypothesis for this experiment was that a portion of the miRNAs that exhibit strong circadian rhythms targets known circadian genes and oscillate in association with specific microbes.

Methods

Eleven human subject volunteers participated in the study and provided saliva samples at various times of day on repeated days in three different rounds of sample collection. Saliva was collected via a swab and prepared using a salivary preparation kit.

In an example where saliva was collected as the biological sample, the purification process, if used, could include purifying salivary RNA in accordance with, for example, the Oragene RNA purification protocol using TRI Reagent LS, a TriZol purification method, or similar method. The Oragene purification protocol generally includes multiple parts. In the first part, a sample is shaken vigorously for 8 seconds or longer and the sample is incubated in the original vial at 50° C. for one hour in a water bath or for two hours in an air incubator. In the second part, a 250-500 µL aliquot of saliva is transferred to a microcentrifuge tube, the microcentrifuge tube is incubated at 90° C. for 15 minutes and cooled to room temperature, the microcentrifuge tube is incubated on ice for 10 minutes, the saliva sample is centrifuged at maximum speed (>13,000×g) for 3 minutes, the clear supernatant is transferred into a fresh microcentrifuge tube and the precipitate is discarded, two volumes of cold 95% EtOH is added to the clear supernatant and mixed, the supernatant mixture is incubated at −20° C. for 30 minutes, the microcentrifuge tube is centrifuged at maximum speed, the precipitate is collected while the supernatant is discarded, the precipitate is dissolved in 350 µL of buffer RLT, and 350 µL of 70% EtOH is added to the dissolved pellet mixture and mixed by vortexing. The first two parts may be followed by the Qiagen RNeasy cleanup procedure.

The purification process may further include a second purification step of, for example, purifying the saliva sample using a RNeasy mini spin column by Qiagen. The purification of a biological sample may include any suitable number of steps in any suitable order. Purification processes may also differ based on the type of a biological sample collected from the subject. The yield and quality of the purified biological sample may be assessed via a device such as an Agilent Bioanalyzer, for example, to determine if the yield and quality of RNA is above a predetermined threshold.

Collection 1: 8 am & 8 pm samples collected on days 1, 3, and 7.

Collection 2: 8 am, 12 pm, 4 pm, & 8 pm samples on days 1, 5, 10 & 15.

Collection 3: 12 non-repeated times throughout the day on days 1 and 2.

Identification and quantification of saliva miRNA and microbial content was performed using next generation sequencing (NGS) on a NextSeq 500 instrument at the SUNY Molecular Analysis Core (SUNYMAC) at Upstate Medical University, following the TruSeq® Small RNA Library Preparation Kit protocol (Illumina, San Diego, Calif.). Alignment of the NGS reads was performed to the miRbase21 database using the SHRRiMP2® algorithm in Partek Flow software to identify mature miRNAs. Mapping of microbiome reads was performed using Kraken software and OneCodex® software to identify only microbes that were consistently found in both. The term "reads" or "read-counts" should be understood to apply to any method for adjusting miRNA or microbiome expression data to account for variations between samples, such as using the expression levels of certain control miRNAs or metabolites that are always present at a predictable level in saliva to normalize the levels of all miRNAs in the samples so they can be compared more accurately.

In an alternative embodiment, fluorescence methods may be used to determine miRNA and/or microbiome levels. In an example, separate groups of ligands targeting some or all of the target miRNA described herein may be anchored in groups on a substrate. The target miRNA and microbiome sequences may be tagged with a fluorescent tag (or non-fluorescent dye) either before or after it binds to the ligand. In this application, relative intensity at each ligand group may be a measure of quantity of miRNA and/or microbiome present. This method may be implemented on a chip-type assay. Other suitable chip-type-assays may be used to determine miRNA and/or microbiome levels.

Statistical Analysis

A two-way analysis of variance (ANOVA) was performed in the Collection 1 and 2 sample sets to identify miRNAs and microbes that varied significantly according to collection time but not the day of collection (which could have been strongly affected by daily variation in routines). A subset of these miRNAs and microbes were then used in a third sample set to assess the accuracy of prediction for the time of collection using multivariate linear regression. miRNAs that showed the strongest circadian oscillations were termed circaMiRs and examined for being predicted regulators of a total of 139 annotated circadian genes using Ingenuity Pathway Analysis (IPA) software. circaMiRs targeting circadian genes were then examined for evidence of association with the strongest circadian-oscillating microbes using Pearson correlation analysis. The functions of the genes targeted by circaMiRs were examined for their specific biological functions using IPA and miRpath software.

Results

Preliminary results showed that a difference in statistics (e.g., variance, total variance, or average variance) related to epigenetic data (e.g., miRNA and/or microbiome) and/or a difference in level of expression (e.g., read count, fluorescence, etc.) of epigenetic data may be used to distinguish between healthy subjects (children and/or adults) and subjects suffering from a particular disease, disorder, or condition. The particular diseases or disorders distinguishable based on the systems and methods described herein may be, without limitation, autism spectrum disorder (ASD), sleep disorders, and/or traumatic brain injury. In some embodiments, certain subjects (e.g., ASD patients) may have a lower average variance relative to normal, healthy subjects. In other embodiments, certain subjects may have a higher average variance relative to normal, healthy subjects.

Figure 39:
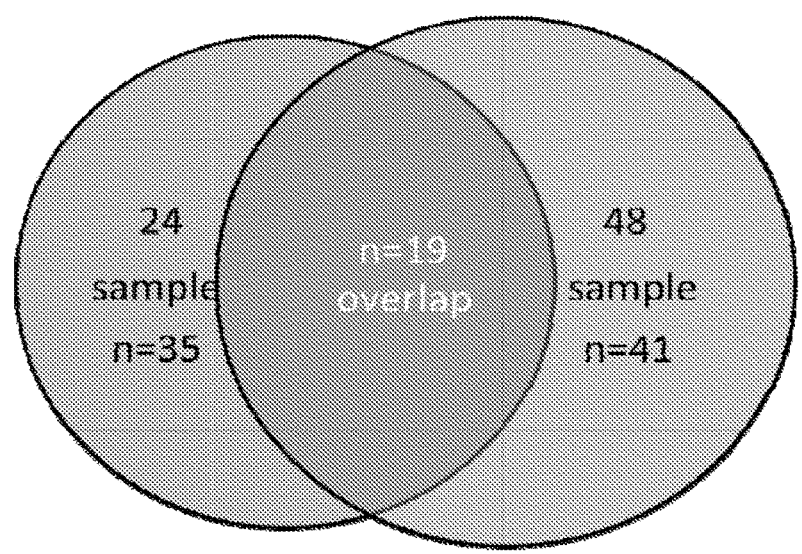
FIG. 39 shows a Venn diagram of overlapping miRNAs from analysis of 24 samples in Collection 1 and 48 samples in Collection 2 for circadian analysis.

24 sample data set: A total of 35 miRNAs showed a highly-significant effect of collection time (FDR<0.001) and no effect of day of collection;

48 sample data set: A total of 41 mi miRNAs showed a highly-significant effect of collection time (FDR<0.001) and no effect of day of collection;

19 miRNAs were commonly changed in both and examined for the ability to predict collection time in a third data set as shown in FIG. 39.

circaMiR Time Prediction

TABLE 28

Accuracy of 19 circaMiRs to predict collection time.

| | Multiple R | P value | Margin of Error |
|---|---|---|---|
| Collection 1 | 0.990 | 0.003929 | 12.9% |
| Collection 2 | 0.878 | 0.000031 | 18.1% |
| Collection 3 | 0.875 | 0.000040 | 26.0% |
| (no 4 am) | 0.938 | $2.28e^{-10}$ | 15.7% |

Microbe Findings

TABLE 29

List of 11 microbes most related to collection time.

| Taxon | | Sample Collection 1 | | | Sample Collection 2 | | |
|---|---|---|---|---|---|---|---|
| ID | Taxon name | Day | Time | Interaction | Day | Time | Interaction |
| 1510155 | Falconid herpesvirus 1 | 0.7246 | 0.0003 | 0.1104 | 0.9999 | 0.0009 | 0.9982 |
| 553174 | *Prevotella melaninogenica* ATCC 25845 | 0.8213 | 0.0011 | 0.1693 | 0.9999 | 0.0359 | 0.9982 |
| 862965 | *Haemophilus parainfluenzae* T3T1 | 0.2276 | 0.0061 | 0.2426 | 0.9999 | 0.0045 | 0.9982 |
| 479436 | *Veillonella parvula* DSM 2008 | 0.7246 | 0.0076 | 0.1069 | 0.9999 | 0.0001 | 0.9982 |
| 458233 | *Macrococcus caseolyticus* JCSC5402 | 0.0830 | 0.0338 | 0.1302 | 0.9999 | 0.0381 | 0.9982 |
| 190304 | *Fusobacterium nucleatum* subsp. *nucleatum* ATCC 25586 | 0.9782 | 0.0127 | 0.1069 | 0.9999 | 0.0350 | 0.9982 |
| 724 | *Haemophilus* | 0.5928 | 0.0127 | 0.2426 | 0.9999 | 0.0139 | 0.9982 |
| 469604 | *Fusobacterium nucleatum* subsp. *vincentii* 3136A2 | 0.7246 | 0.0209 | 0.1069 | 0.9999 | 0.0187 | 0.9982 |
| 11855 | Mason-Pfizer monkey virus | 0.5439 | 0.0213 | 0.4616 | 0.9999 | 0.0046 | 0.9982 |
| 360107 | *Campylobacter hominis* ATCC BAA-381 | 0.9713 | 0.0359 | 0.2413 | 0.9999 | 0.0084 | 0.9982 |
| 838 | *Prevotella* | 0.7246 | 0.0482 | 0.2844 | 0.9999 | 0.0037 | 0.9982 |

Microbial Time Prediction

TABLE 30

Accuracy of 11 microbes to predict collection time.

|  | Multiple R | P value | Margin of Error |
|---|---|---|---|
| Collection 1 | 0.927 | 0.00139 | 24.5% |
| Collection 2 | 0.858 | $1.73e^{-7}$ | 19.38% |
| Collection 3 | 0.709 | 0.003175 | 33.99% |
| (no 4 am) | 0.865 | $8.03e^{-7}$ | 20.7% |

Other Functions of circaMiRs

TABLE 31

Biological pathways containing genes targeted by circaMiRs

| Kyoto Encyclopedia of Genes and Genomes (KEGG) Pathways | p-value | # genes | # miRNAs |
|---|---|---|---|
| Fatty acid biosynthesis | 4.6e–11 | 5 | 6 |
| Proteoglycans in cancer | 3.1e–08 | 94 | 17 |
| Prion diseases | 4.8e–07 | 10 | 9 |
| Hippo signaling pathway | 2.0e–06 | 71 | 17 |
| FoxO signaling pathway | 8.0e–06 | 70 | 16 |
| Signaling pathways regulating pluripotency of stem cells | 8.0e–06 | 68 | 17 |
| Renal cell carcinoma | 1.1e–05 | 39 | 17 |
| Glutamatergic synapse | 7.9e–05 | 52 | 17 |
| Prostate cancer | 7.9e–05 | 47 | 17 |
| Pathways in cancer | 8.0e–05 | 159 | 17 |
| Glioma | 8.7e–05 | 33 | 15 |
| Adrenergic signaling in cardiomyocytes | 8.7e–05 | 61 | 17 |
| Estrogen signaling pathway | 0.00013 | 46 | 16 |
| Thyroid hormone signaling pathway | 0.00014 | 57 | 16 |
| Rap1 signaling pathway | 0.00016 | 91 | 17 |
| Regulation of actin cytoskeleton | 0.00027 | 94 | 17 |
| PI3K-Akt signaling pathway | 0.00044 | 136 | 17 |
| Focal adhesion | 0.00044 | 91 | 17 |
| mTOR signaling pathway | 0.00055 | 34 | 15 | circaMiR and Microbiome are Presented in Tables 32 and 33:

TABLE 32

Groups A and B circaMiRNAs

|  | Group A circaMiRs | Group B circaMiRs |
|---|---|---|
| 1 | hsa-miR-106b-3p | hsa-let-7a-5p |
| 2 | hsa-miR-128-3p | hsa-let-7d-3p |
| 3 | hsa-miR-130a-3p | hsa-miR-101-3p |
| 4 | hsa-miR-15a-5p | hsa-miR-10b-5p |
| 5 | hsa-miR-192-5p | hsa-miR-125b-2-3p |
| 6 | hsa-miR-199a-3p | hsa-miR-1307-5p |
| 7 | hsa-miR-199b-3p | hsa-miR-140-3p |
| 8 | hsa-miR-203a-3p | hsa-miR-142-3p |
| 9 | hsa-miR-221-3p | hsa-miR-143-3p |
| 10 | hsa-miR-26a-5p | hsa-miR-148b-3p |
| 11 | hsa-miR-26b-5p | hsa-miR-16-5p |
| 12 | hsa-miR-3074-5p | hsa-miR-181a-5p |
| 13 | hsa-miR-30e-3p | hsa-miR-181c-5p |
| 14 | hsa-miR-320a | hsa-miR-186-5p |
| 15 | hsa-miR-345-5p | hsa-miR-191-5p |
| 16 | hsa-miR-375 | hsa-miR-193a-5p |
| 17 | hsa-miR-423-3p | hsa-miR-200b-3p |
| 18 | hsa-miR-92a-3p | hsa-miR-205-5p |
| 19 | hsa-miR-93-5p | hsa-miR-215-5p |
| 20 |  | hsa-miR-21-5p |
| 21 |  | hsa-miR-223-3p |
| 22 |  | hsa-miR-22-3p |
| 23 |  | hsa-miR-23a-3p |
| 24 |  | hsa-miR-23b-3p |
| 25 |  | hsa-miR-24-3p |
| 26 |  | hsa-miR-25-3p |
| 27 |  | hsa-miR-29a-3p |
| 28 |  | hsa-miR-30d-5p |
| 29 |  | hsa-miR-320b |
| 30 |  | hsa-miR-361-5p |
| 31 |  | hsa-miR-363-3p |
| 32 |  | hsa-miR-374a-3p |
| 33 |  | hsa-miR-423-5p |
| 34 |  | hsa-miR-425-5p |
| 35 |  | hsa-miR-532-5p |
| 36 |  | hsa-miR-574-3p |
| 37 |  | hsa-miR-629-5p |
| 38 |  | hsa-miR-98-5p |

TABLE 33

Group C miBiome

| Taxon ID | Taxon name |
|---|---|
| 1510155 | Falconid herpesvirus 1 |
| 553174 | *Prevotella melaninogenica* ATCC 25845 |
| 862965 | *Haemophilus parainfluenzae* T3T1 |
| 479436 | *Veillonella parvula* DSM 2008 |
| 458233 | *Macrococcus caseolyticus* JCSC5402 |
| 190304 | *Fusobacterium nucleatum* subsp. *nucleatum* ATCC 25586 |
| 724 | *Haemophilus* |
| 469604 | *Fusobacterium nucleatum* subsp. *vincentii* 3136A2 |
| 11855 | Mason-Pfizer monkey virus |
| 360107 | *Campylobacter hominis* ATCC BAA-381 |
| 838 | *Prevotella* |

Tables 32-33 list circaMiRs and microbiomes that may be used to distinguish healthy subjects from subjects having a disease or disorder using the methods described herein. Moreover, other miRNAs sharing the same seed sequences as any of the miRNAs in the above tables may be used to distinguish a healthy subject from a subject having a particular disease or disorder.

Figure 40:
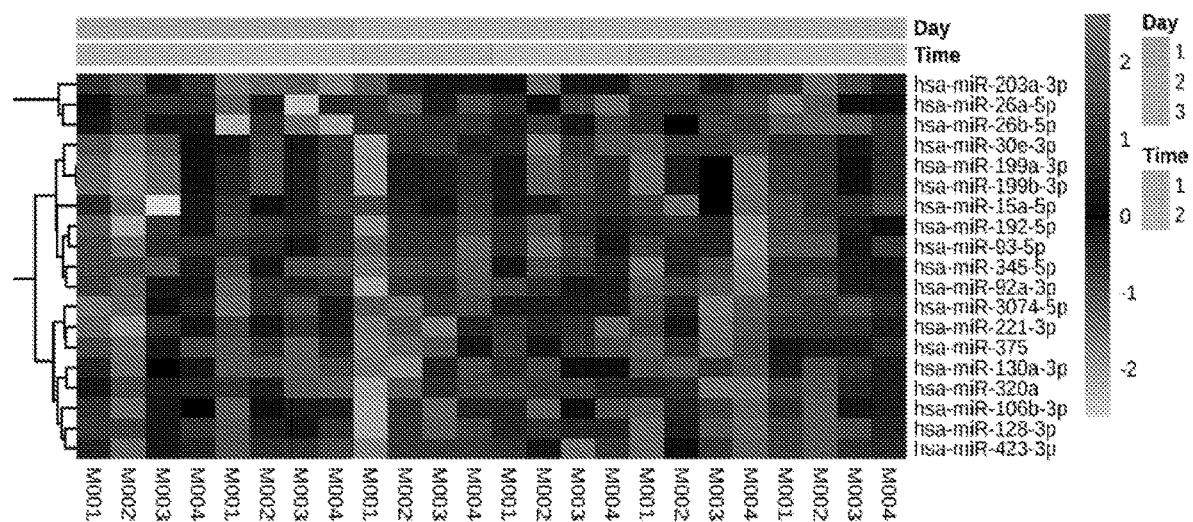
FIG. 40 shows a heat map clustering of abundance data for the 19 overlapping miRNAs in the circadian analysis changed according to collection time in 24 samples from 4 subjects across 3 days of sampling (days 1, 3, 7) at a frequency of 2 times/day (8 am, 8 pm).
Figure 41:
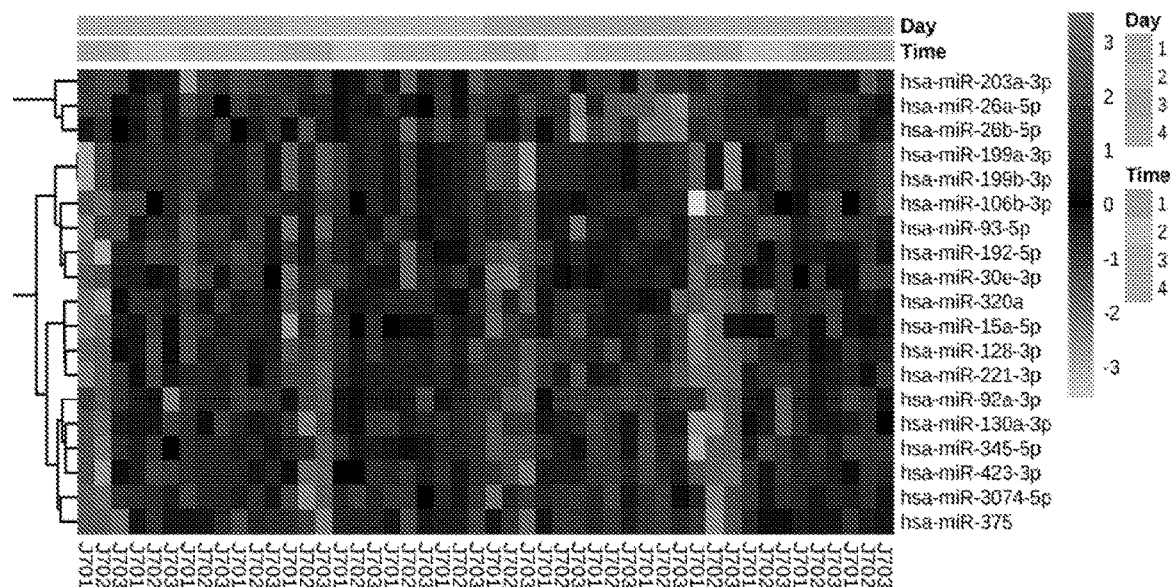
FIG. 41 shows a heat map clustering of abundance data for the 19 overlapping miRNAs in the circadian analysis changed according to collection time in 48 samples from 3 subjects across 4 days of sampling (days 1, 5, 10, 15) at a frequency of 4 times/day (8 am, 12 pm, 4 pm, 8 pm).
Figure 42:
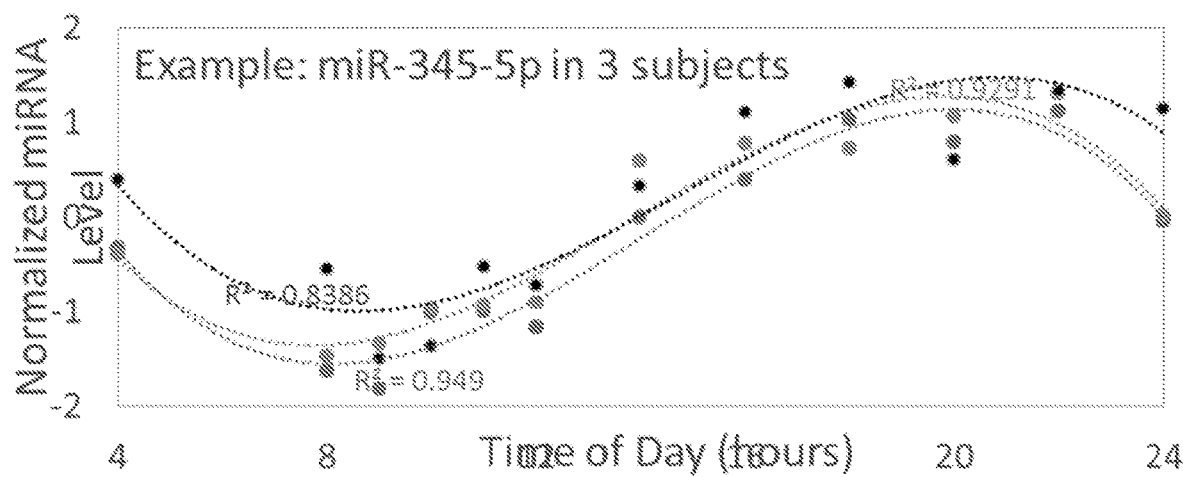
FIG. 42 shows normalized data for 1 of the top 19 miRNAs shown for 3 of the subjects in Collection 3 (collected at various times).
Figure 43:
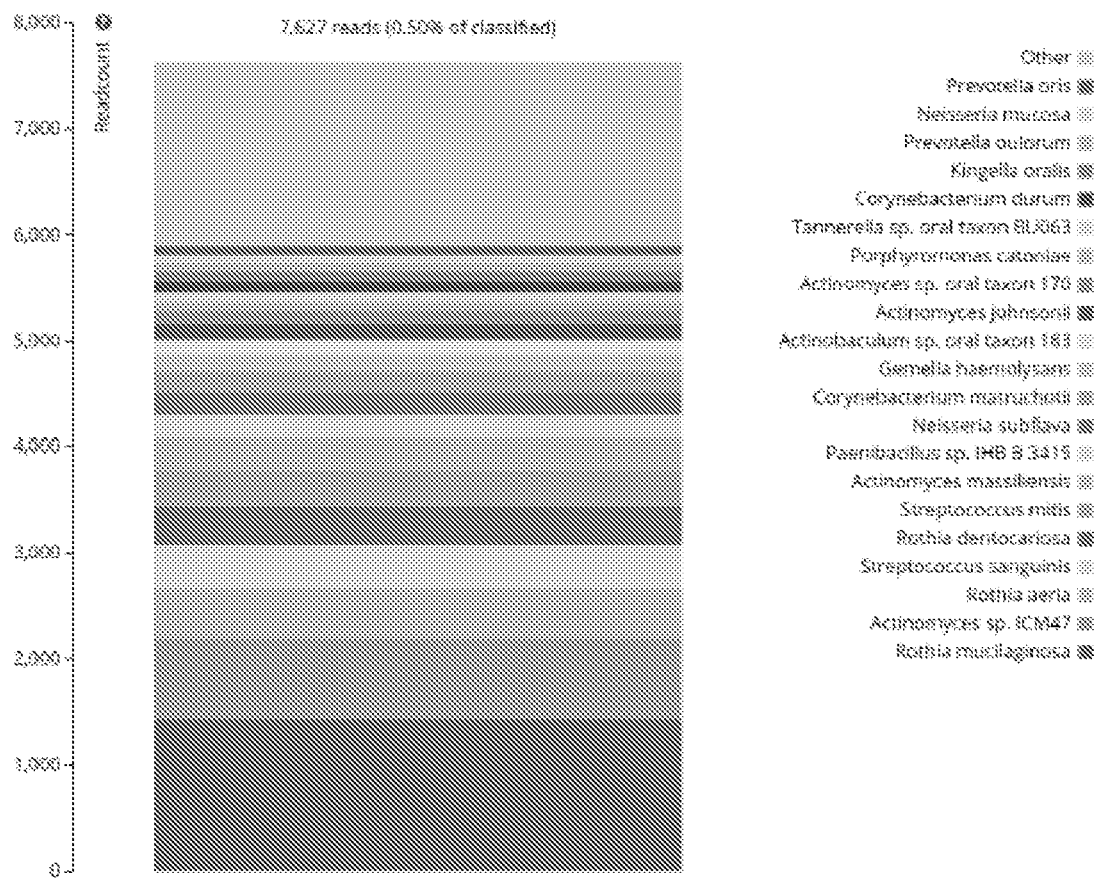
FIG. 43 shows absolute abundance of species in the microbiome of one of the subjects in Collection 3.
Figure 44:
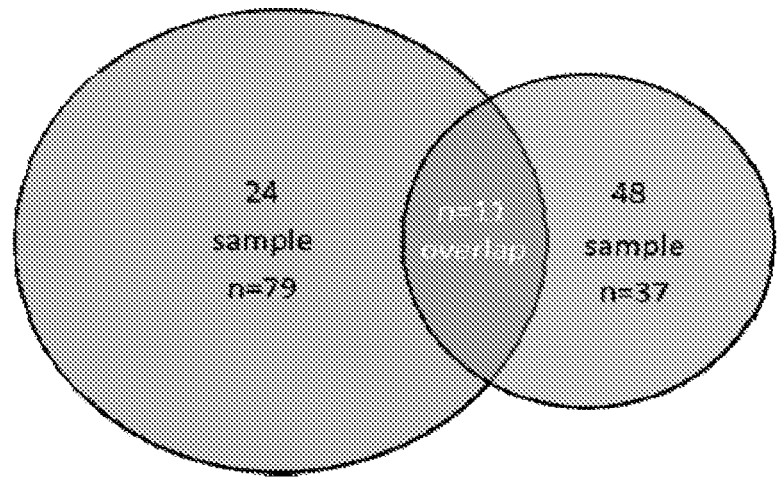
FIG. 44 shows a Venn diagram of overlapping significantly changed microbes from analysis of Collection 1 and 2 samples for the circadian analysis.
Figure 45B:
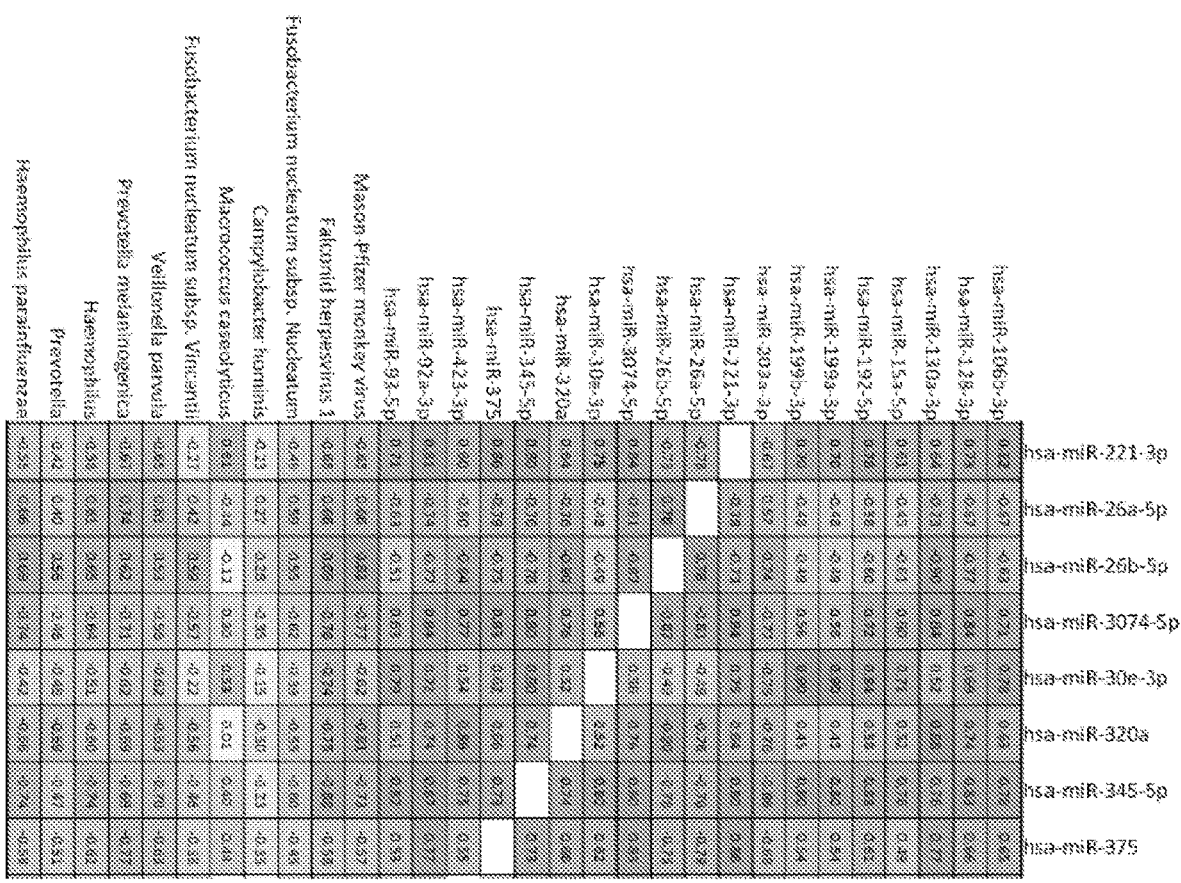
FIGS. 45A, B, C, D show a Pearson correlation matrix of circadian microbes and circadian-varying miRNAs (circaMiRs). Note the presence of several large correlations between the circaMiRs and microbes (lower left, upper right).
Figure 45C:
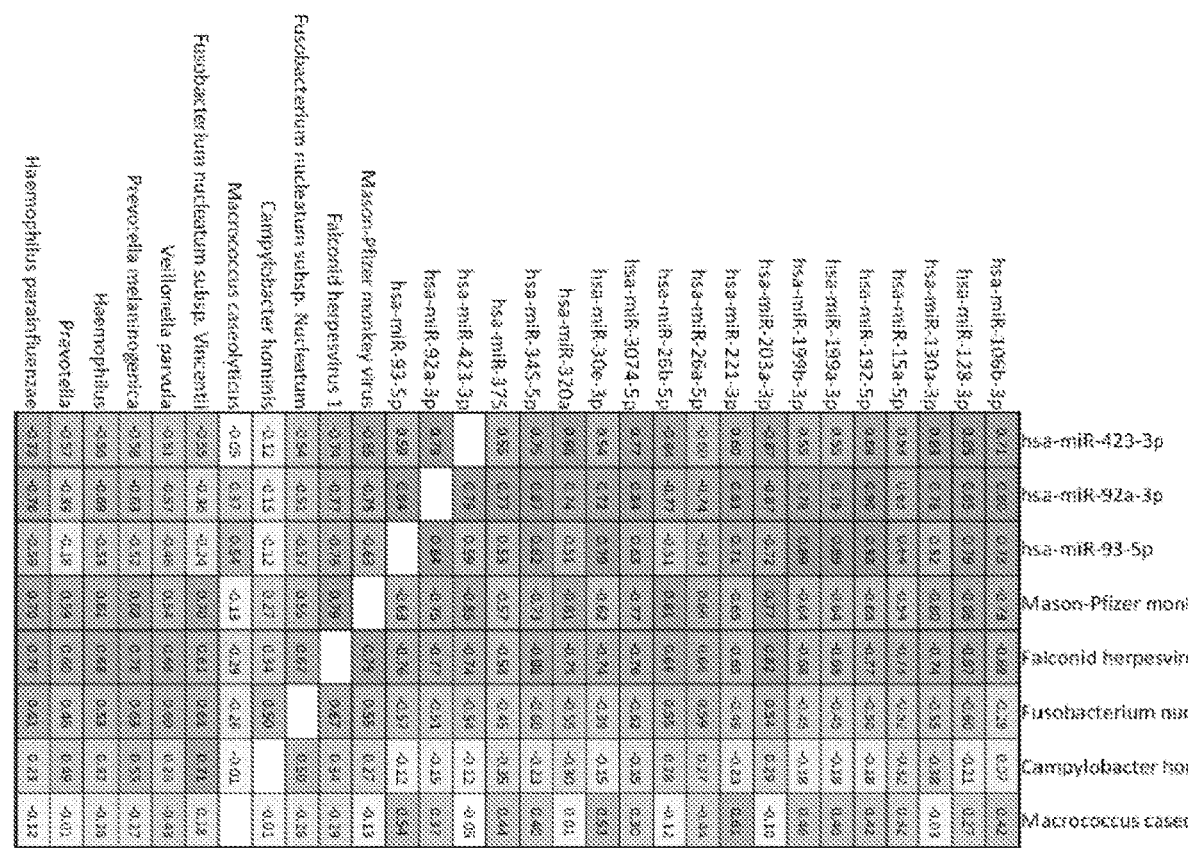
Figure 45D:
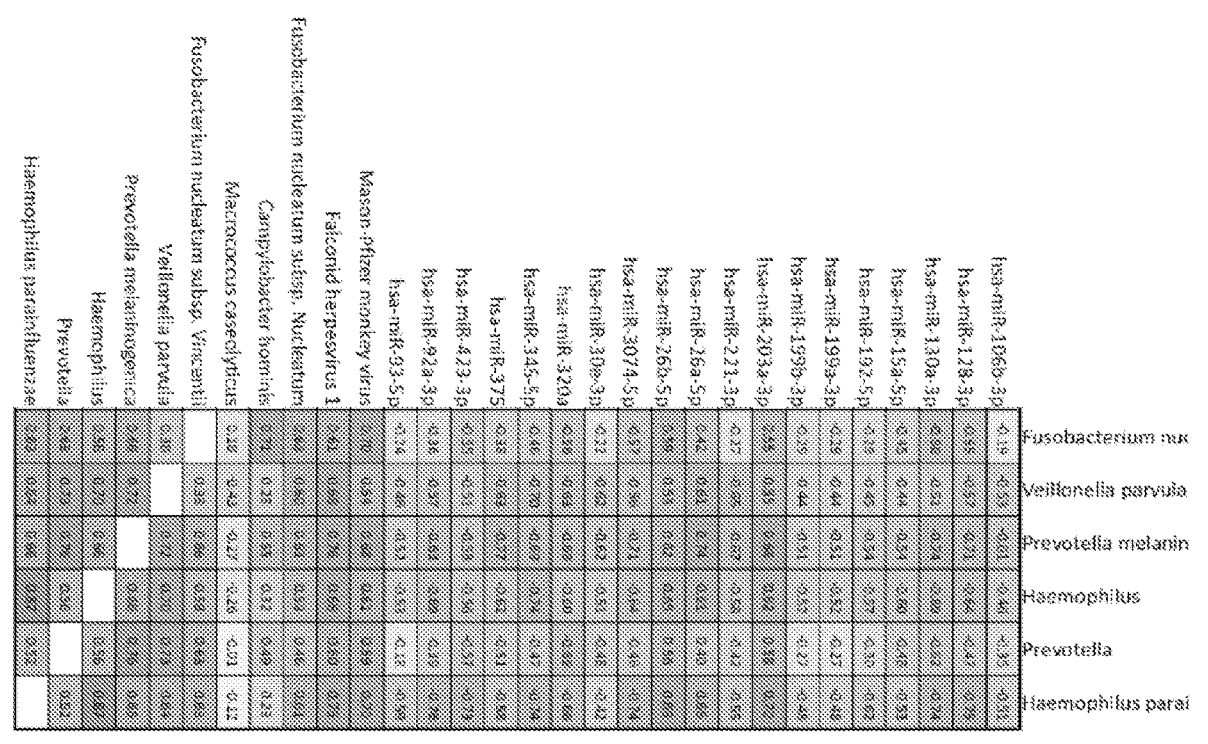

A heat map clustering of expression data for the 19 miRNAs changed according to collection time in 24 samples from 4 subjects across 3 days of sampling (days 1, 3, 7) at a frequency of 2 times/day (8 am, 8 pm) is shown in FIG. 40. A heat map clustering of expression data for the 19 miRNAs changed according to collection time in 48 samples from 3 subjects across 4 days of sampling (days 1, 5, 10, 15) at a frequency of 4 times/day (8 am, 12 pm, 4 pm, 8 pm) is shown in FIG. 41. Normalized data for 1 of the top 19 miRNAs shown for 3 of the subjects in Collection 3 (collected at various times) is shown in FIG. 42. Absolute abundance of species in the microbiome of one of the subjects in Collection 3 is shown in FIG. 43. A Venn diagram of overlapping significantly changed microbes from analysis of Collection 1 and 2 samples is shown in FIG. 44. A Pearson correlation matrix of circadian microbes and circaMiRs is shown in FIGS. 45A-D (note the presence of several large correlations between the circaMiRs and microbes (lower left, upper right)).

CONCLUSIONS

Portions of the saliva miRNA and microbiome levels show strong circadian patterns. This observation is highly novel and has not been previously described. There are highly significant correlations between several of the saliva miRNAs and microbes. Most saliva circaMiRs target at least one or more circadian genes, in addition to genes involved in brain, metabolic and cancer function.

Furthermore, the present disclosure contemplates a kit suitable for determining whether a subject has a disease, disorder, or condition including 2 or more miRNA probes of a probe set. Each miRNA probe may include a ribonucleotide sequence corresponding to a specific miRNA described herein. In an implementation, the kit further may include a solid support attached to the 2 or more miRNA probes. In an implementation, the kit may further include at least one of the following: (a) one randomly generated miRNA sequence adapted to be used as a negative control; (b) at least one oligonucleotide sequence derived from a housekeeping gene, used as a standardized control for total RNA degradation; or (c) at least one randomly-generated sequence used as a positive control. Alternatively, a probe set may include miRNA probes having ribonucleotide sequences corresponding to DNA sequences from particular microbiomes described herein.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

Numerous modification and variations on the present invention are possible in light of the above teachings. It is therefore to be understood that within the scope of the appended claims, the invention may be practiced otherwise than as specifically described herein.

All publications, patent applications, patents, and other references mentioned herein are incorporated by reference in their entirety. Further, the materials, methods, and examples are illustrative only and are not intended to be limiting, unless otherwise specified.

LITERATURE

1. Zwaigenbaum L, Bauman M L, Fein D, Pierce K, Buie T, Davis P A, et al. Early Screening of Autism Spectrum Disorder: Recommendations for Practice and Research. Pediatrics. 2015; 136(Supplement 1):S41-S59.
2. Dawson G, Rogers S, Munson J, Smith M, Winter J, Greenson J, et al. Randomized, Controlled Trial of an Intervention for Toddlers With Autism: The Early Start Denver Model. Pediatrics. 2010; 125(1):e17-e23.
3. Macari S L, Campbell D, Gengoux G W, Saulnier C A, Klin A J, Chawarska K. Predicting developmental status from 12 to 24 months in infants at risk for Autism Spectrum Disorder: a preliminary report. J Autism Dev Disord 2012; 42:2636-47.
4. Modified Checklist for Autism in Toddlers, Revised (M-CHAT-R™). Autism Speaks, 2015. (Accessed Dec. 28, 2015, at Hypertext Transfer Protocol Secure://WorldWideWeb. autismspeaks.org/what-autism/diagnosis/screen-your-child.)
5. Robins D L. Screening for autism spectrum disorders in primary care settings. Autism 2008; 12:537-56.
6. Goldani A A, Downs S R, Widjaja F, Lawton B, Hendren R L. Biomarkers in autism. Front Psychiatry, 2014; 5:100.
7. Dawson M, Gernsbacher M A. Effectiveness of intensive autism programmes. Lancet 2010; 375:722-3; author reply 3.
8. MontereyBayForum. All that glitters is not gold—use of the ADOS akin to fool's gold assessing for autism. In: Monterey Bay Forum 2012.
9. Wilkinson L A. Best Practice Review: The Autism Diagnostic Observation Schedule (ADOS). In: Best Practices Autism; 2012.
10. Durkin M S, Maenner M J, Newschaffer C J, et al. Advanced parental age and the risk of autism spectrum disorder. Am J Epidemiol 2008; 168:1268-76.
11. Huang T N, Hsueh Y P. Brain-specific transcriptional regulator T-brain-1 controls brain wiring and neuronal activity in autism spectrum disorders. Front Neurosci 2015; 9:406.
12. Saeedi Saravi S S, Dehpour A R. Potential role of organochlorine pesticides in the pathogenesis of neurodevelopmental, neurodegenerative, and neurobehavioral disorders: A review. Life Sci 2015.
13. Mohamed Fel B, Zaky E A, El-Sayed A B, et al. Assessment of Hair Aluminum, Lead, and Mercury in a Sample of Autistic Egyptian Children: Environmental Risk Factors of Heavy Metals in Autism. Behav Neurol 2015; 2015:545674.
14. Schmidt R J, Tancredi D J, Ozonoff S, et al. Maternal periconceptional folic acid intake and risk of autism spectrum disorders and developmental delay in the CHARGE (CHildhood Autism Risks from Genetics and Environment) case-control study. Am J Clin Nutr 2012; 96:80-9.
15. Talbott E O, Marshall L P, Rager J R, Arena V C, Sharma R K, Stacy S L. Air toxics and the risk of autism spectrum disorder: the results of a population based case-control study in southwestern Pennsylvania. Environ Health 2015; 14:80.
16. Liu D, Zhan J Y, Shao J. [Environmental risk factors for autism spectrum disorders in children]. Zhongguo Dang Dai Er Ke Za Zhi 2015; 17:1147-53.
17. Geschwind D H. Genetics of autism spectrum disorders. Trends Cogn Sci 2011; 15:409-16.
18. Rosenberg R E, Law J K, Yenokyan G, McGready J, Kaufmann W E, Law P A. Characteristics and concordance of autism spectrum disorders among 277 twin pairs. Arch Pediatr Adolesc Med 2009; 163:907-14.
19. Constantino J N, Todorov A, Hilton C, et al. Autism recurrence in half siblings: strong support for genetic mechanisms of transmission in ASD. Mol Psychiatry 2013; 18:137-8.
20. Xu L M, Li J R, Huang Y, Zhao M, Tang X, Wei L. AutismKB: an evidence-based knowledgebase of autism genetics. Nucleic Acids Res 2012; 40:D1016-22.
21. Chahrour M H, Yu T W, Lim E T, et al. Whole-exome sequencing and homozygosity analysis implicate depolarization-regulated neuronal genes in autism. PLoS Genet 2012; 8:e1002635.
22. Hui Z, Yongchao Z, Yongqing Z. Recent progresses in molecular genetics of autism spectrum disorders. Yi Chuan 2015; 37:845-54.
23. Wisniowiecka-Kowalnik B, Kastory-Bronowska M, Stankiewicz P. [Genetic bases of autism spectrum disorders]. Med Wieku Rozwoj 2013; 17:207-23.
24. Li J, You Y, Yue W, et al. Genetic Evidence for Possible Involvement of the Calcium Channel Gene CACNA1A in Autism Pathogenesis in Chinese Han Population. PLoS One 2015; 10:e0142887.
25. Hall L, Kelley E. The contribution of epigenetics to understanding genetic factors in autism. Autism. 2014; 18(8):872-81.
26. Follert P, Cremer H, Beclin C. MicroRNAs in brain development and function: a matter of flexibility and stability. Front Mol Neurosci. 2014; 7:5.
27. Abu-Elneel K, Liu T, Gazzaniga F S, et al. Heterogeneous dysregulation of microRNAs across the autism spectrum. Neurogenetics 2008; 9:153-61.
28. Ghahramani Seno M M, Hu P, Gwadry F G, et al. Gene and miRNA expression profiles in autism spectrum disorders. Brain Res 2011; 1380:85-97.
29. Talebizadeh Z, Butler M G, Theodoro M F. Feasibility and relevance of examining lymphoblastoid cell lines to study role of microRNAs in autism. Autism Res 2008; 1:240-50.
30. Sarachana T, Zhou R, Chen G, Manji H K, Hu V W. Investigation of post-transcriptional gene regulatory networks associated with autism spectrum disorders by microRNA expression profiling of lymphoblastoid cell lines. Genome Med 2010; 2:23.
31. Hicks S D, Middleton F A. A Comparative Review of microRNA Expression Patterns in Autism Spectrum Disorder. Front Psychiatry 2016; 7:176.
32. Banerjee-Basu S, Larsen E, Muend S. Common microRNAs Target Established ASD Genes. Front Neurol 2014; 5:205.
33. Baron C A, Liu S Y, Hicks C, Gregg J P. Utilization of lymphoblastoid cell lines as a system for the molecular modeling of autism. J Autism Dev Disord 2006; 36:973-82.

34. Hicks S D, Johnson J, Carney M C, Bramley H, Olympia R P, Loeffert A C, et al. Overlapping MicroRNA Expression in Saliva and Cerebrospinal Fluid Accurately Identifies Pediatric Traumatic Brain Injury. J Neurotrauma. 2017.
35. Sun E, Shi Y. MicroRNAs: Small molecules with big roles in neurodevelopment and diseases. Exp Neurol. 2015; 268:46-53.
36. Ander B P, Barger N, Stamova B, Sharp F R, Schumann C M. Atypical miRNA expression in temporal cortex associated with dysregulation of immune, cell cycle, and other pathways in autism spectrum disorders. Mol Autism. 2015; 6:37.
37. Mor M, Nardone S, Sams D S, Elliott E. Hypomethylation of miR-142 promoter and upregulation of microRNAs that target the oxytocin receptor gene in the autism prefrontal cortex. Mol Autism. 2015; 6:46.
38. Sarachana T, Zhou R, Chen G, Manji H K, Hu V W. Investigation of post-transcriptional gene regulatory networks associated with autism spectrum disorders by microRNA expression profiling of lymphoblastoid cell lines. Genome Med. 2010; 2(4):23.
39. Ghahramani Seno M M, Hu P, Gwadry F G, Pinto D, Marshall C R, Casallo G, et al. Gene and miRNA expression profiles in autism spectrum disorders. Brain Res. 2011; 1380:85-97.
40. Hicks S D, Middleton F A. A Comparative Review of microRNA Expression Patterns in Autism Spectrum Disorder. Front Psychiatry. 2016; 7:176.
41. Mundalil Vasu M, Anitha A, Thanseem I, Suzuki K, Yamada K, Takahashi T, et al. Serum microRNA profiles in children with autism. Mol Autism. 2014; 5:40.
42. Obuchowski N A, McClish D K. Sample size determination for diagnostic accuracy studies involving binormal ROC curve indices. Stat Med. 1997; 16:1529-42.
43. Gallo A, Tandon M, Alevizos I, Illei G G. The majority of microRNAs detectable in serum and saliva is concentrated in exosomes. PLOS One 2012; 7:e30679.
44. Rodier P M, Ingram J L, Tisdale B, Nelson S, Romano J. Embryological origin for autism: developmental anomalies of the cranial nerve motor nuclei. J Comp Neurol 1996; 370:247-61.
45. Mulle, J. G., Sharp, W. G., & Cubells, J. F., The gut microbiome: a new frontier in autism research, Current Psychiatry Eeports, 15(2), 337 (2013).
46. Adams, James B., et al. Gastrointestinal flora and gastrointestinal status in children with autism—comparisons to typical children and correlation with autism severity. BMC gastroenterology 11.1 (2011): 22.
47. Kang, D. W., Park, J. G., Ilhan, Z. E., Wallstrom, G., LaBaer, J., Adams, J. B., & Krajmalnik-Brown, R. (2013). Reduced incidence of *Prevotella* and other fermenters in intestinal microflora of autistic children. PloS one, 8(7), e68322.
48. McElhanon B O, McCracken C, Karpen S, Sharp W G. Gastrointestinal symptoms in autism spectrum disorder: a meta-analysis. Pediatrics 2014; 133:872-83.
49. Luna R A, Magee A, Runge I X, Venkatachalam A, RubioGonzales M, Versalovic J. A Case Study of the Gut Microbiome in ASD: Correlation of Microbial Profiles with GI and Behavioral Symptoms. In: International Meeting for Autism Research (IMFAR). Baltimore, Md.; 2016.
50. Strati F, Cavalieri D, Albanese D, et al. New evidences on the altered gut microbiota in autism spectrum disorders. Microbiome 2017; 5:24.
51. Ledford J R, Gast D L. Feeding problems in children with autismspectrum disorders: a review. Focus Autism Other Dev Disabl. 2006; 21:153-66.
52. Sharp W G, Jaquess D L, Luckens C T. Multi-method assessment of feeding problems among children with autism spectrum disorders. Res Autism Spectr Disord. 2012; 7:56-65.
53. Hill A P, Zuckerman K E, Fombonne E. Obesity and Autism. Pediatrics. 2015 Oct. 1:peds-2015.
54. Pang, K. H. and Croaker, G. D. H., Constipation in children with autism and autistic spectrum disorder. Pediatric surgery international, 2011; 27(4):353-358.
55. Hediger M L, et al. Reduced bone cortical thickness in boys with autism or autism spectrum disorder. J Autism Dev Disord. 2008; 38:848-56.
56. Buffington, Shelly A., et al. Microbial reconstitution reverses maternal diet-induced social and synaptic deficits in offspring. Cell 165.7 (2016): 1762-1775.
57. Kang, D. W., Adams, J. B., Gregory, A. C., Borody, T., Chittick, L., Fasano, A., . . . & Pollard, E. L. (2017).
58. Dalmasso, G., Nguyen, H. T. T., Yan, Y, Laroui, H., Charania, M. A., Ayyadurai, et al., Microbiota modulate host gene expression via microRNAs. PLoS One, 6(4), e19293 (2011).
59. Ziats M N, Rennert O M. Identification of differentially expressed microRNAs across the developing human brain. Mol Psychiatry 2014; 19:848-52.
60. De Filippo C, Cavalieri D, Di Paola M, Ramazzotti M, Poullet J B, Massart S, Collini S, Pieraccini G, Lionetti P, Impact of diet in shaping gut microbiota revealed by a comparative study in children from Europe and rural Africa, Proc Natl Acad Sci USA. 2010 Aug. 17; 107(33).
61. Kang D-W, Park J G, Ilhan Z E, Wallstrom G, LaBaer J, Adams T B, et al. (2013) Reduced Incidence of *Prevotella* and Other Fermenters in Intestinal Microflora of Autistic Children. PLoS ONE 8(7): e68322.
62. Gargaro B A, Rinehart N J, Bradshaw J L, Tonge B J, Sheppard D M. Autism and ADHD: how far have we come in the comorbidity debate? Neurosci Biobehav Rev. 2011; 35(5):1081-8.
63. Molloy C A, Manning-Courtney P. Prevalence of chronic gastrointestinal symptoms in children with autism and autistic spectrum disorders. Autism. 2003; 7(2):165-71.
64. Xia J, Psychogios N, Young N, Wishart D S. MetaboAnalyst: a web server for metabolomic data analysis and interpretation. Nucleic Acids Res. 2009; 37(Web Server issue):W652-60.
65. Vlachos I S, Zagganas K, Paraskevopoulou M D, Georgakilas G, Karagkouni D, Vergoulis T, et al. DIANA-miRPath v3.0: deciphering microRNA function with experimental support. Nucleic Acids Res. 2015; 43(W1): W460-6.
66. Szklarczyk D, Franceschini A, Wyder S, Forslund K, Heller D, Huerta-Cepas J, et al. STRING v10: protein-protein interaction networks, integrated over the tree of life. Nucleic Acids Res. 2015; 43(Database issue):D447-52.
67. Huang F, Long Z, Chen Z, Li J, Hu Z, Qiu R, et al. Investigation of Gene Regulatory Networks Associated with Autism Spectrum Disorder Based on MiRNA Expression in China. PLoS One. 2015; 10(6):e0129052.
68. Wu Y E, Parikshak N N, Belgard T G, Geschwind D H. Genome-wide, integrative analysis implicates microRNA dysregulation in autism spectrum disorder. Nat Neurosci. 2016; 19(11):1463-76.
69. Nguyen L S, Lepleux M, Makhlouf M, Martin C, Fregeac J, Siquier-Pernet K, et al. Profiling olfactory stem cells from living patients identifies miRNAs relevant for autism pathophysiology. Mol Autism. 2016; 7:1.
70. Hicks S D, Middleton F A. A Comparative Review of microRNA Expression Patterns in Autism Spectrum Disorder. Front Psychiatry. 2016; 7:176.
71. Schreck K A, Williams K, Smith A F. A comparison of eating behaviors between children with and without autism. J Autism Dev Disord. 2004; 34(4):433-8.
72. Vuong H E, Hsiao E Y. Emerging Roles for the Gut Microbiome in Autism Spectrum Disorder. Biol Psychiatry. 2017; 81(5):411-23.
73. Struzycka I. The oral microbiome in dental caries. Pol J Microbiol. 2014; 63(2):127-35.
74. Tierney C D, Kurtz M, Souders H. Clear as mud: another look at autism, childhood apraxia of speech and auditory processing. Curr Opin Pediatr. 2012; 24(3):394-9.
75. Cermak S A, Curtin C, Bandini L G. Food selectivity and sensory sensitivity in children with autism spectrum disorders. J Am Diet Assoc. 2010; 110(2):238-46.
76. Jessen N A, Munk A S, Lundgaard I, Nedergaard M. The Glymphatic System: A Beginner's Guide. Neurochem Res. 2015; 40(12):2583-99.
77. Miano S, Giannotti F, Cortesi F. Sleep disorders and autism spectrum disorder: Springer International Publishing; 2016. 111-28 p.
78. Charman T, Baird G, Simonoff E, Chandler S, Davison-Jenkins A, Sharma A, et al. Testing two screening instruments for autism spectrum disorder in UK community child health services. Dev Med Child Neurol. 2016; 58(4):369-75.
79. Frazier T W, Klingemier E W, Beukemann M, Speer L, Markowitz L, Parikh S, et al. Development of an Objective Autism Risk Index Using Remote Eye Tracking. Journal of the American Academy of Child & Adolescent Psychiatry. 2016; 55(4):301-9.
80. Loth E, Spooren W, Ham L M, Isaac M B, Auriche-Benichou C, Banaschewski T, et al. Identification and validation of biomarkers for autism spectrum disorders. Nat Rev Drug Discov. 2016; 15(1):70-3.
81. Wolff J J, Gu H, Gerig G, Elison J T, Styner M, Gouttard S, et al. Differences in white matter fiber tract development present from 6 to 24 months in infants with autism. Am J Psychiatry. 2012; 169(6):589-600.
82. Veenstra-VanderWeele J, Blakely R D. Networking in autism: leveraging genetic, biomarker and model system findings in the search for new treatments. Neuropsychopharmacology. 2012; 37(1):196-212.
83. Peters J M, Taquet M, Vega C, Jeste S S, Fernandez I S, Tan J, et al. Brain functional networks in syndromic and non-syndromic autism: a graph theoretical study of EEG connectivity. BMC Med. 2013; 11:54.
84. Ambros et al., The functions of animal microRNAs, Nature, 431 (7006):350-5 (Sep. 16, 2004).
85. Bartel et al., MicroRNAs: genomics, biogenesis, mechanism, and function, Cell, 116 (2): 281-97 (Jan. 23, 2004).
86. Son J S, Zheng L J, Rowehl L M, Tian X, Zhang Y, Zhu W, et al. (2015) Comparison of Fecal Microbiota in Children with Autism Spectrum Disorders and Neurotypical Siblings in the Simons Simplex Collection. PLoS ONE 10(10): e0137725.
87. Greaves E, Collins F, Esnal-Zufiaurre A, Giakoumelou S, Home A W, Saunders P T. Estrogen receptor (ER) agonists differentially regulate neuroangiogenesis in peritoneal endometriosis via the repellent factor SLIT3. Endocrinology. 2014; 155(10):4015-26.
88. Hicks S D, Johnson J, Carney M C, Bramley H, Olympia R P, Loeffert A C, et al. Overlapping MicroRNA Expression in Saliva and Cerebrospinal Fluid Accurately Identifies Pediatric Traumatic Brain Injury. J Neurotrauma., 2018 Jan. 1; 35(1):64-72. doi: 10.1089/neu.2017.5111. Epub 2017 Oct. 27.

The invention claimed is:

1. A method for detecting or diagnosing an autism spectrum disorder (ASD) comprising
    (a) determining abundance or concentration level(s) of one or more micro-RNAs (miRNAs) in a saliva sample taken from a human subject, and
    (b) comparing the determined abundance or concentration level(s) of the one or more miRNAs against normal level(s) of the same one or more miRNAs, wherein the normal level is that found in a subject or an average from two or more subjects not having an ASD, and
    (c) selecting a subject having an abnormal level of said one or more miRNAs as having, or as being at higher risk for having ASD, and
    (d) treating the selected subject with a regimen effective for treating autism, wherein said regimen comprises administering one or more treatment selected from the group consisting of drug therapy, antimicrobial therapy, diet or nutritional therapy, physical therapy, phototherapy, psychotherapy, behavior therapy, or an alternative medical therapy; wherein the one or more miRNAs is at least one selected from the group consisting of miR-502-3p, miR-125a-5p, miR-149-5p, miR-193a-5p, miR-4705, miR-99b-5p, miR-340-5p, miR-183-5p, miR-665, and miR-3074-5p.

2. The method of claim 1, wherein said miRNA expression levels are normalized to an abundance level, or average abundance level of one or more housekeeping genes whose RNA expression is substantially invariant; and/or adjusted to compensate for differences in age, sex, or genetic background.

3. The method of claim 1, wherein said one or more miRNAs additionally includes one or more miRNA selected from the group consisting of miR-151a-5p, miR-21-5p, miR-665, miR-25-3p, miR-221-3p, miR-30e-5p, mir-125b-2-3p, and miR-146a-3p.

4. The method of claim 1, wherein said one or more miRNAs additionally includes one or more miRNA selected from the group consisting of miR-502-5p, miR-125a-3p, miR-149-3p, miR-193-3p, miR-4705-3p, miR-4705-5p, miR-99b-3p, miR-340-3p, miR-183-3p, miR-665-3p, miR-665-5p, and miR-3074-3p.

5. The method of claim 1, wherein said one or more miRNAs additionally includes one or more miRNA selected from the group consisting of miR-28-3p, miR-148a-5p, miR-151a-3p, miR-125b-5p, miR-130b-3p, miR-92a, let-7d-3p, mir-598, miR-374c-5p, miR-374b-5p, miR-29c-3p, miR-1972, miR-675-3p, miR-7706, miR-500a-3p, miR-374a-S5p, miR-190a-Sp, and let-7e-5p.

6. The method of claim 1, wherein said one or more miRNAs additionally includes one or more miRNA selected from the group consisting of miR-620, and miR-1277-5p.

7. The method of claim 1, wherein said one or more miRNAs additionally includes one or more miRNA selected from the group consisting of miR-28-3p, miR-584-5p, let-7a-5p, miR-944, miR-148a-5p, miR-151a-3p, miR-125b-2-3p and miR-7706.

8. The method of claim 1, wherein said one or more miRNAs additionally includes one or more miRNA selected from the group consisting of miR-620, and miR-1277-5p, miR-620, miR-1277-5p, and miR-193a-5p.

9. The method of claim 1, wherein said one or more miRNAs additionally includes one or more miRNA selected from the group consisting of miR-28-3p, miR-584-5p, let-7a-5p, miR-944, miR-148a-5p, miR-151a-3p, miR-125b-2-3p and miR-7706, miR-125b-2-3p and miR-7706.

10. The method of claim 1, wherein said one or more miRNAs additionally includes one or more miRNA selected from the group consisting of mir-374c-5p, miR-29c-3p, or miR-190a-5p, miR-28-3p, miR-148a-5p, miR-151a-3p, miR-125b-5p, miR-92a, mir-1972, and miR-7706.

11. The method of claim 1, wherein said one or more miRNAs additionally includes one or more miRNA selected from the group consisting of miR-620, miR-1277-5p, let-7a-5p and miR-944.

12. The method of claim 1, wherein said one or more miRNAs additionally includes one or more miRNA selected from the group consisting of miR-28-3p, miR-584-5p, let-7a-5p, miR-944, miR-148a-5p, miR-151a-3p, miR-125b-2-3p and miR-7706.

13. The method of claim 1, wherein said one or more miRNAs additionally includes one or more miRNA selected from the group consisting of miR-620, and miR-1277-5p, let-7a-5p, and miR-944.

14. The method of claim 1, wherein said one or more miRNAs additionally includes one or more miRNA selected from the group consisting of miR-28-3p, miR-584-5p, let-7a-5p, miR-944, miR-148a-5p, miR-151a-3p, miR-125b-2-3p, miR-7706.

15. The method of claim 1, wherein said one or more miRNAs additionally includes one or more miRNA selected from the group consisting of mir-374c-5p, miR-29c-3p, and miR-190a-5p, miR-130b-3p, let-7d-3p, miR-598, mir374b-5p, miR-675-3p, mir-500a-3p, miR-374a-5p, and let-7d-5p.

16. The method of claim 1, wherein the saliva sample is taken from the human subject at a particular time of day and the concentration level(s) of miRNAs in said sample are compared to normal miRNA values in saliva taken at the same time of day under otherwise identical conditions.

17. The method of claim 1, wherein the saliva sample is taken within 1 hour of waking, before brushing or rinsing the mouth, before eating or drinking, and/or before exercise that elevates heart rate.

18. The method of claim 1, wherein said selecting comprises selecting a subject having abnormal levels of four or more of said miRNAs, and, calculating a Pearson correlation coefficient of said abnormal miRNA levels with likelihood of at least one symptom of an ASD.

19. The method of claim 1, wherein said selecting comprises selecting a subject having abnormal levels of two or more of said miRNAs, and, calculating a Pearson correlation coefficient of said abnormal miRNA levels with likelihood of at least one symptom of an ASD.

* * * * *